(12) United States Patent
Capone et al.

(10) Patent No.: US 12,264,179 B2
(45) Date of Patent: *Apr. 1, 2025

(54) EPSTEIN-BARR VIRUS ANTIGEN CONSTRUCTS

(71) Applicant: GLAXOSMITHKLINE BIOLOGICALS SA, Rixensart (BE)

(72) Inventors: Stefania Capone, Rome (IT); Antonella Folgori, Rome (IT); Armin Lahm, Rome (IT); Benjamin Wizel, Rockville, MD (US)

(73) Assignee: GlaxoSmithKline Biologicals SA, Rixensart (BE)

( * ) Notice: Subject to any disclaimer, the term of this patent is extended or adjusted under 35 U.S.C. 154(b) by 0 days.

This patent is subject to a terminal disclaimer.

(21) Appl. No.: 18/358,350

(22) Filed: Jul. 25, 2023

(65) Prior Publication Data

US 2024/0076318 A1 Mar. 7, 2024

Related U.S. Application Data

(63) Continuation of application No. 16/770,963, filed as application No. PCT/IB2018/060101 on Dec. 14, 2018, now Pat. No. 11,773,139.

(60) Provisional application No. 62/608,038, filed on Dec. 20, 2017.

(51) Int. Cl.
| | |
|---|---|
| *C07K 14/005* | (2006.01) |
| *A61K 39/00* | (2006.01) |
| *A61K 39/245* | (2006.01) |
| *C12N 7/00* | (2006.01) |

(52) U.S. Cl.
CPC .......... *C07K 14/005* (2013.01); *A61K 39/245* (2013.01); *C12N 7/00* (2013.01); *A61K 2039/70* (2013.01); *C12N 2710/16222* (2013.01); *C12N 2710/16234* (2013.01); *C12N 2710/16271* (2013.01)

(58) Field of Classification Search
CPC .............. C07K 14/005; C07K 2319/00; A61K 39/245; A61K 2039/70; A61K 2039/5258; A61K 2039/545; A61K 2039/57; A61K 39/12; C12N 7/00; C12N 2710/16222; C12N 2710/16234; C12N 2710/16271; C12N 2710/10343; C12N 2710/16034; C12N 2710/24143; C12N 15/86; A61P 31/20; A61P 31/22; A61P 35/00
See application file for complete search history.

(56) References Cited

U.S. PATENT DOCUMENTS

| | | |
|---|---|---|
| 5,716,845 A | 2/1998 | Sugden |
| 2009/0130134 A1 | 5/2009 | Pancre |
| 2009/0202584 A1 | 8/2009 | Thomson et al. |
| 2009/0305324 A1 | 12/2009 | Kuzushima |
| 2009/0324630 A1 | 12/2009 | Jensen |
| 2014/0004081 A1 | 1/2014 | Cobbold |
| 2020/0276295 A1 | 9/2020 | Ogembo |
| 2020/0330587 A1 | 10/2020 | Kanekiyo |

FOREIGN PATENT DOCUMENTS

| | | |
|---|---|---|
| DE | 4427117 C1 | 10/1995 |
| JP | 2016523888 A | 8/2016 |
| JP | 2017523139 A | 8/2017 |
| WO | 2007/065215 A1 | 6/2007 |
| WO | 2007/097820 A2 | 8/2007 |
| WO | 2014/059489 A1 | 4/2014 |
| WO | 2015001361 A1 | 1/2015 |
| WO | 2015189425 A1 | 12/2015 |
| WO | 2016198621 A1 | 12/2016 |

OTHER PUBLICATIONS

Duraiswamy, et al., "Therapeutic LMP1 polyeptiope vaccine for EBV-associated Hodgkin disease and nasopharyngeal carcinoma." Blood, American Society of Hematology; 2003; pp. 3150-3156; 101(8).
Hui, et al., "Phase I Trial of Recombinant Modified Vaccinia Ankara Encoding Epstein-Barr Viral Tumor Antigens in Nasopharyngeal Carcinoma Patients." Cancer Research; 2013; pp. 1676-1688; vol. 73(6).
Khanna, et al., "Localization of Epstein-Barr Virus Cytotoxic T Cell Epitopes using Recombinant Vaccinia: Implications for Vaccine Development" The Journal of Experimental Medicine; 1992; pp. 169-176; vol. 176(1).
Smith, et al., "Functional Reversion of Antigen-Specific CD8+ T Cells from Patients with Hodgkin Lymphoma following In Vitro Stimulation with Recombinant Polyepitope." The Journal of Immunology; 2006; pp. 4897-4906; vol. 177(7).
Smith, et al., "Effective Treatment of Metastatic Forms of Esptein-Barr Virus-Associated Nasopharyngeal Carcinoma with a Novel Adenovirus-Based Adoptive Immunotherapy." Cancer Research; 2012; pp. 1116-1125; vol. 72(5).
Roy et al., "Simian Adenovirus 34, Complete Genome," GenBank: FJ025905.1. Dep. Mar. 8, 2012.
International Preliminary Report on Patentability, issued in PCT/IB2018/060101, dated Jun. 23, 2020, 7 pages.
International Search Report, issued in PCT/IB2018/060101, dated Mar. 29, 2019, 4 pages.

*Primary Examiner* — Rachel B Gill
(74) *Attorney, Agent, or Firm* — Christopher L. Wright

(57) ABSTRACT

The invention provides Epstein-Barr Virus antigen polynucleotides, polypeptides and vectors; as well as immunogenic compositions comprising the same. It includes the use of Epstein-Barr Virus antigen constructs to produce vaccines for treating and preventing Epstein-Barr Virus infections and Epstein-Barr Virus-associated diseases, such as multiple sclerosis, rheumatoid arthritis and systemic lupus erythematosus.

44 Claims, 11 Drawing Sheets

Specification includes a Sequence Listing.

A) EBV-Latent construct

B) EBV-Latent+Lytic construct

A) CalHV3-Latent construct

B) CalHV3-Latent+Lytic construct

C) Genetic adjuvanted CalHV3-Latent+Lytic construct

A) T-cell responses to EBV constructs in mice

B) T-cell responses to CalHV3 constructs in mice

A) Cumulative response to EBV-LLy antigens

B) Responses to single EBV-LLy antigens

EPSTEIN-BARR VIRUS ANTIGEN CONSTRUCTS

CROSS-REFERENCE TO RELATED APPLICATIONS

This application is a continuation of U.S. application Ser. No. 16/770,963, filed Jun. 9, 2020, which was filed pursuant to 35 U.S.C. § 371 as a United States National Phase Application of International Application No. PCT/162018/060101, filed Dec. 14, 2018, which claims priority from U.S. Provisional Application No. 62/608,038, filed Dec. 20, 2017, the entireties of each of which are hereby incorporated herein by reference.

STATEMENT OF GOVERNMENT INTEREST

This invention was created in the performance of a Cooperative Research and Development Agreement with the National Institutes of Health, an Agency of the Department of Health and Human Services. The Government of the United States has certain rights in this invention.

SEQUENCE LISTING

The instant application contains a Sequence Listing which has been submitted electronically in XML file format and is hereby incorporated by reference in its entirety. Said XML copy, created on Jul. 13, 2023, is named VU66487C1-US_SL.xml and is 307,250 bytes in size.

FIELD OF THE INVENTION

This invention is in the field of treating and preventing viral infections. In particular, the present invention relates to Epstein Barr Virus antigen constructs. It includes the use of Epstein-Barr Virus antigen constructs for treating and preventing Epstein-Barr Virus infections and Epstein-Barr Virus-associated diseases.

BACKGROUND

Epstein-Barr Virus (EBV), also known as human herpesvirus 4 (HHV-4), is one of the most common viruses in humans, infecting at least 90% of adults. EBV establishes asymptomatic latent infection in most infected individuals, but is also known as the primary causative agent of infectious mononucleosis.

More significantly, EBV infection is associated with certain types of malignancies (e.g., gastric carcinoma, nasopharyngeal carcinoma, Hodgkin's lymphoma, non-Hodgkin's lymphoma, Burkitt's lymphoma) as well as an increased risk of multiple sclerosis (MS), systemic lupus erythematosus (SLE), rheumatoid arthritis (RA) and Sjögren's syndrome.

Like other members of the herpesvirus family, EBV contains a double-stranded DNA genome of about 192 kilobases encoding about 85 genes. The EBV genome is encased in a protein nucleocapsid surrounded by a viral tegument. An outer envelope layer comprises lipids and surface glycoproteins which are thought to be involved in targeting the virus to its primary host cells, B lymphocytes and epithelial cells.

The EBV viral replication cycle is well-characterized. After initial infection of host cells, EBV enters a stage of active production of infectious virions, termed the lytic replication stage (or lytic stage). During the lytic stage, EBV gene expression is characterized by expression of one or more lytic gene products, including ZEBRA, BRLF1, BNLF2, BCRF1, and viral capsid antigens (VCAs), as well as envelope glycoproteins such as gp350 and gp110.

Following a period of lytic replication, EBV enters a state of persistent viral infection without active viral production, termed latency (or the latent phase). Latent EBV infection is accompanied by characteristic gene expression programs, including expression of one or more latent gene products such as EBNA1, EBNA2, EBNA3A, EBNA3B, EBNA3C, EBNA leader protein (EBNA-LP), LMP1, and/or LMP2. Latently-infected cells can be reactivated to lytic viral production by triggers which are not yet understood.

A number of EBV vaccine candidates have been evaluated in animal models and human trials. Most prophylactic vaccine candidates have focused on the major EBV envelope glycoprotein gp350 as the immunogen. Gu et al. reported that a recombinant live vaccinia virus expressing EBV gp350 elicited EBV neutralizing antibodies and modest protection in children, but not in adults. Gu et al., Dev. Biol. Stand. 1995; 84: 171-177. A recombinant gp350 vaccine was found not to protect against EBV infection, but reduced the occurrence of infectious mononucleosis. Sokal et al., J. Infect. Dis. 2007; 196(12):1749-1753.

Therapeutic EBV vaccine candidates have primarily targeted T-cell epitopes of EBV nuclear antigen-1 (EBNA1) and LMP2. For example, Taylor et al. have described a modified vaccinia virus Ankara (MVA) vector expressing a peptide fragment of EBNA1 fused to the full-length LMP2 protein. The so-called MVA-EL vaccine was reported to induce antigen-specific CD4+ and CD8+ T cell responses in early clinical trials. Taylor et al., J. Virol. January 2004, p. 768-778. Similarly, a recombinant human adenoviral vector expressing full length LMP2 protein was reported to induce antigen-specific T-cell responses in vitro and in in mice. Pan et al., Biochem Biophys Res Commun. 2006 Sep. 1; 347 (3):551-7.

Despite the clear need in the art, no EBV vaccine has yet been licensed for use in humans. Thus, there remains a need for an EBV vaccine for use in preventing EBV infection as well as in treating EBV-associated malignancies and EBV-associated diseases, such as multiple sclerosis.

SUMMARY OF THE INVENTION

The present inventors provide EBV antigen polypeptides, polynucleotides and vectors useful as components of immunogenic compositions for the induction of an immune response in a subject against Epstein-Barr Virus (EBV) infection; methods for their use in prevention and treatment of EBV infection and EBV-associated diseases; and processes for their manufacture.

There is provided a polynucleotide encoding an EBV antigen polypeptide comprising:
(a) at least one fragment of at least 8 amino acids of SEQ ID NO: 1,
(b) at least one fragment of at least 8 amino acids of SEQ ID NO: 6,
(c) at least one fragment of at least 8 amino acids of SEQ ID NO: 11, and
(d) at least one fragment of at least 8 amino acids of SEQ ID NO: 13; wherein the polynucleotide is operatively linked to one or more sequences which direct expression of said polypeptide in a host cell. In some embodiments, the polypeptide further comprises at least one fragment of at least 8 amino acids of SEQ ID NO: 21.

Also provided is a polynucleotide encoding an EBV antigen polypeptide comprising:
(a) at least two LMP1 fragments of at least 8 amino acids of SEQ ID NO: 1, wherein the LMP1 fragments are not adjacent to each other,
(b) at least two LMP2 fragments of at least 8 amino acids of SEQ ID NO: 6, wherein the LMP2 fragments are not adjacent to each other,
(c) at least two EBNA1 fragments of at least 8 amino acids of SEQ ID NO: 11, wherein the EBNA1 fragments are not adjacent to each other,
(d) at least two EBNA3A fragments of at least 8 amino acids of SEQ ID NO: 13, wherein the EBNA3A fragments are not adjacent to each other, and/or
(e) at least two ZEBRA fragments of at least 8 amino acids of SEQ ID NO: 21, wherein the ZEBRA fragments are not adjacent to each other;
wherein the polynucleotide is operatively linked to one or more sequences which direct expression of said polypeptide in a host cell.

Also provided is a polynucleotide as described above, wherein the EBV antigen polypeptide comprises:
(a) a first fragment of LMP1 consisting of SEQ ID NO: 2,
(b) a second fragment of LMP1 consisting of SEQ ID NO: 3,
(c) a third fragment of LMP1 consisting of SEQ ID NO: 4,
(d) a fourth fragment of LMP1 consisting of SEQ ID NO: 5,
(e) a first fragment of LMP2 consisting of SEQ ID NO: 7,
(f) a second fragment of LMP2 consisting of SEQ ID NO: 8,
(g) a third fragment of LMP2 consisting of SEQ ID NO: 9,
(h) a fourth fragment of LMP2 consisting of SEQ ID NO: 10,
(i) a first fragment of EBNA1 consisting of SEQ ID NO: 12,
(j) a first fragment of EBNA3A consisting of SEQ ID NO: 14,
(k) a second fragment of EBNA3A consisting of SEQ ID NO: 15,
(l) a third fragment of EBNA3A consisting of SEQ ID NO: 16,
(m) a fourth fragment of EBNA3A consisting of SEQ ID NO: 17,
(n) a fifth fragment of EBNA3A consisting of SEQ ID NO: 18,
(o) a sixth fragment of EBNA3A consisting of SEQ ID NO: 19, and
(p) a seventh fragment of EBNA3A consisting of SEQ ID NO: 20;
wherein the first, second, third and fourth LMP1 fragments are not adjacent to each other; the first, second, third and fourth LMP2 fragments are not adjacent to each other; and the first, second, third, fourth, fifth, sixth, and seventh EBNA3A fragments are not adjacent to each other. Optionally, the polypeptide further comprises: (a) a first fragment of ZEBRA consisting of SEQ ID NO: 22, and (b) a second fragment of ZEBRA consisting of SEQ ID NO: 23; wherein the first and second ZEBRA fragments are not adjacent to each other.

Also provided is a polynucleotide as described above, wherein the EBV antigen polypeptide is at least 80% identical to SEQ ID NO: 24 or SEQ ID NO: 26.

Also provided are vectors comprising the polynucleotides as described herein, including, for example, adenovirus vectors (e.g., non-human simian adenovirus vectors) and vaccinia virus vectors (e.g., modified vaccinia Ankara (MVA) vectors).

Also provided are EBV antigen polypeptides encoded by the polynucleotides and vectors as described herein, such as polypeptides at least 80% identical to SEQ ID NO: 24 or SEQ ID NO: 26.

Also provided are compositions comprising polynucleotides, vectors and polypeptides described herein; and a pharmaceutically acceptable excipient. Such compositions optionally comprise one or more adjuvants.

Also provided are uses of the polynucleotides, vectors, polypeptides and compositions as described herein, in the manufacture of a medicament for the treatment or prophylaxis of a disease caused by Epstein-Barr Virus infection.

Also described are methods of inducing an immune response in a subject comprising administering the polynucleotides, vectors, polypeptides and compositions as described herein to the subject.

Also provided are methods of treating or preventing an EBV-associated disease in a subject, comprising administering the polynucleotides, vectors, polypeptides and compositions as described herein to the subject. EBV-associated diseases include, for example, EBV-associated diseases (e.g., multiple sclerosis, rheumatoid arthritis and systemic lupus erythematosus).

Also provided are the polynucleotides, vectors, polypeptides and compositions as described herein, for use in the treatment or prophylaxis of a disease caused by Epstein-Barr Virus infection.

Also provided are methods of inducing an immune response in a subject comprising:
(a) administering an adenovirus comprising a polynucleotide encoding an
EBV antigen polypeptide as described herein, and
(b) administering a vaccinia virus comprising a polynucleotide encoding an
EBV antigen polypeptide as described herein;
wherein steps (a) and (b) are conducted in either order.

Also provided is a method of treating or preventing an EBV-associated disease in a subject, comprising:
(a) administering an adenovirus comprising a polynucleotide encoding an
EBV antigen polypeptide as described herein, and
(b) administering a vaccinia virus comprising a polynucleotide encoding an
EBV antigen polypeptide as described herein;
wherein steps (a) and (b) are conducted in either order.

DESCRIPTION OF THE DRAWINGS

FIG. 2A shows an EBV latent antigen construct (EBV-L), comprising immunogenic fragments derived from LMP2 (identified as a1 to a4), LMP1 (identified as b1 to b4), EBNA1 (identified as c1) and EBNA3A (identified as d1 to d7). FIG. 2B shows an EBV latent+lytic antigen construct (EBV-LLy), comprising immunogenic fragments derived from LMP1, LMP2, EBNA1, EBNA3A (all identified as in FIG. 2A) and ZEBRA (identified as e1 to e2). Regions of the polyvalent antigens with the same letter prefix (i.e., a, b, c, d, e) are derived from the same EBV protein.

Figure 3:
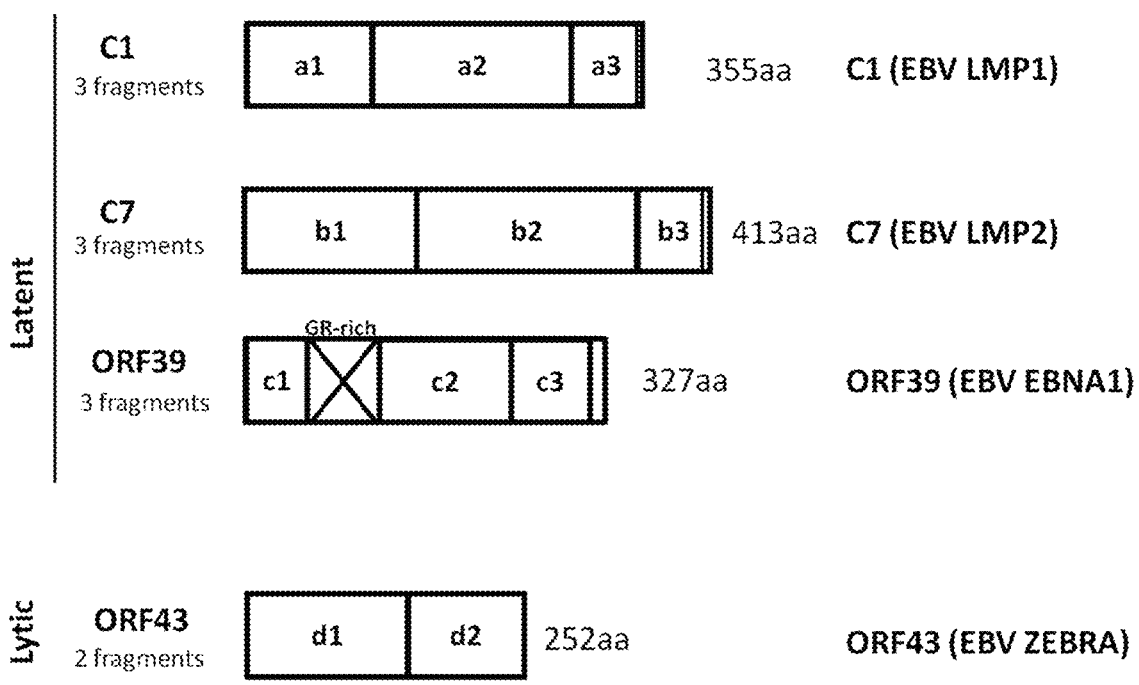

FIG. 3: Schematic representation of CalHV3 latent (C1, C7 and ORF39) and lytic (ORF43) proteins. Numbered regions indicate immunogenic fragments used to construct polyvalent CalHV3 antigen polypeptides. Alphanumeric identifiers (e.g., a1, a2, b1, b2) correspond to the fragments represented in polyvalent constructs shown in FIG. 4A-C. C1, C7, ORF39 and ORF43 antigens were selected because they are the putative marmoset (*Callithrix jacchus*) herpesvirus orthologs of EBV proteins LMP1, LMP2, EBNA1 and ZEBRA, respectively.

Figure 4A:
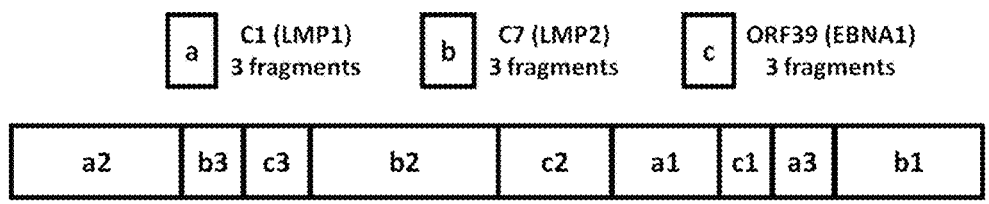
Figure 4B:
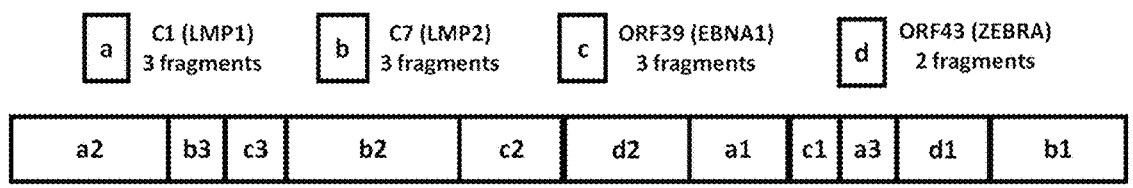
Figure 4C:
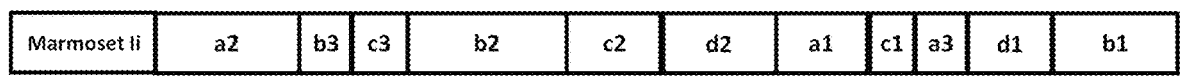

FIG. 4A-C: Schematic representation of polyvalent CalHV3 antigen constructs.

FIG. 4A shows a CalHV3 latent antigen construct (CalHV3-L), comprising immunogenic fragments derived from C1, C7 and ORF39. FIG. 4B shows a CalHV3 latent+lytic antigen construct (CalHV3-LLy), comprising immunogenic fragments derived from C1, C7, ORF39 and ORF43. FIG. 4C shows a CalHV3-LLy construct from FIG. 4B, fused to the marmoset MHC class II-associated invariant chain (Ii). Regions of the polyvalent antigens with the same letter prefix (i.e., a, b, c, d) are derived from the same CalHV3 protein.

Figure 5A:
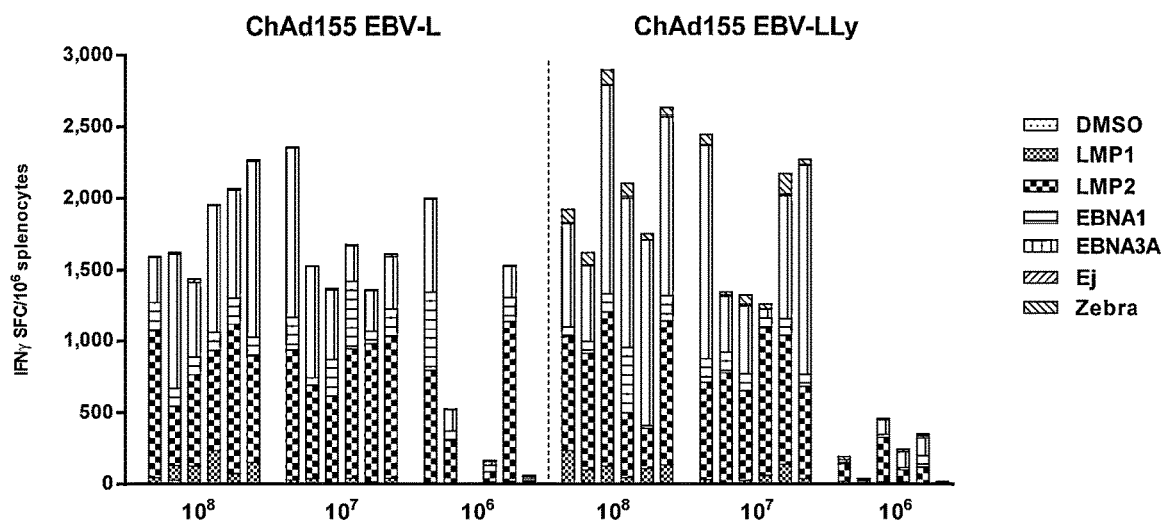

FIG. 5A: T-cell responses in mice immunized with adenoviral vectors encoding EBV antigen constructs at doses of $10^6$, $10^7$ and $10^8$ viral particles (vp). ChAd155-EBV-L and ChAd155-EBV-LLy elicited interferon gamma (IFNγ) secretion from splenocytes in a dose-dependent manner. T-cell activation in response to stimulation with peptide pools covering LMP1, LMP2, EBNA1 and EBNA3A was observed to each of the EBV latent antigens in both EBV-L and EBV-LLy immunized mice. T-cell responses to the EBV lytic protein, ZEBRA, were only detected in EBV-LLy immunized mice. No responses were detected to the EBV junctional peptides (Ej) or to DMSO (dimethyl sulfoxide), the peptide pool diluent, used as a negative control.

Figure 5B:
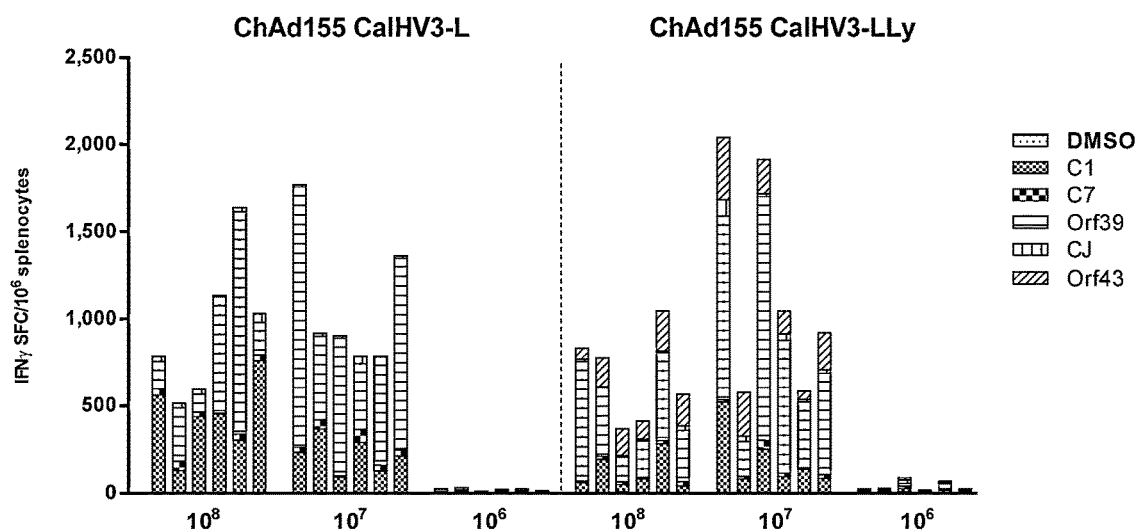

FIG. 5B: T-cell responses in mice immunized with adenoviral vectors encoding CalHV3 antigen constructs at doses of $10^6$, $10^7$ and $10^8$ vp. ChAd155-CalHV3-L and ChAd155-CalHV3-LLy elicited IFNγ secretion from splenocytes in a dose-dependent manner. T-cell responses to peptide pools covering CalHV3 latent antigens C1, C7 and ORF39 were detected in both CalHV3-L and CalHV3-LLy immunized mice. However, T-cell responses to the CalHV3 lytic protein, ORF43, were only detected in CalHV3-LLy immunized mice. No responses were detected to the CalHV3 junctional peptides (Cj) or the negative control, DMSO.

Figure 6A:
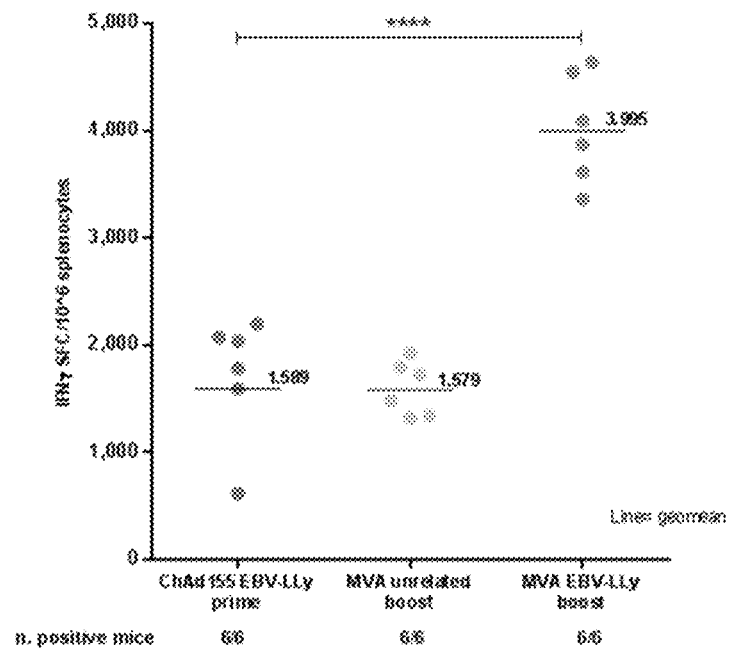
Figure 6B:
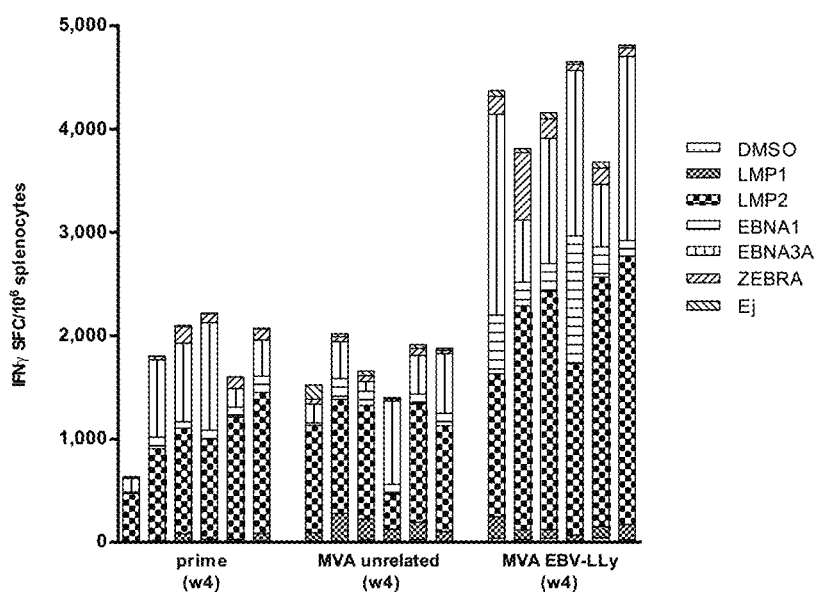

FIG. 6A-B: Effect of prime-boost dosing on EBV-LLy immunogenicity in mice. Immunization with ChAd155-EBV-LLy on day 0 followed by a boost immunization with MVA-EBV-LLy on day 21 (week 3) produced a significant increase in EBV-specific interferon gamma release, as compared to unboosted mice or mice receiving a "boost" injection of an MVA vector encoding an EBV-unrelated antigen. FIG. 6A presents the cumulative T-cell responses to all antigens (LMP1, LMP2, EBNA1, EBNA3A and ZEBRA), and FIG. 6B shows the responses to individual antigens and to the negative control, DMSO.

Figure 7:
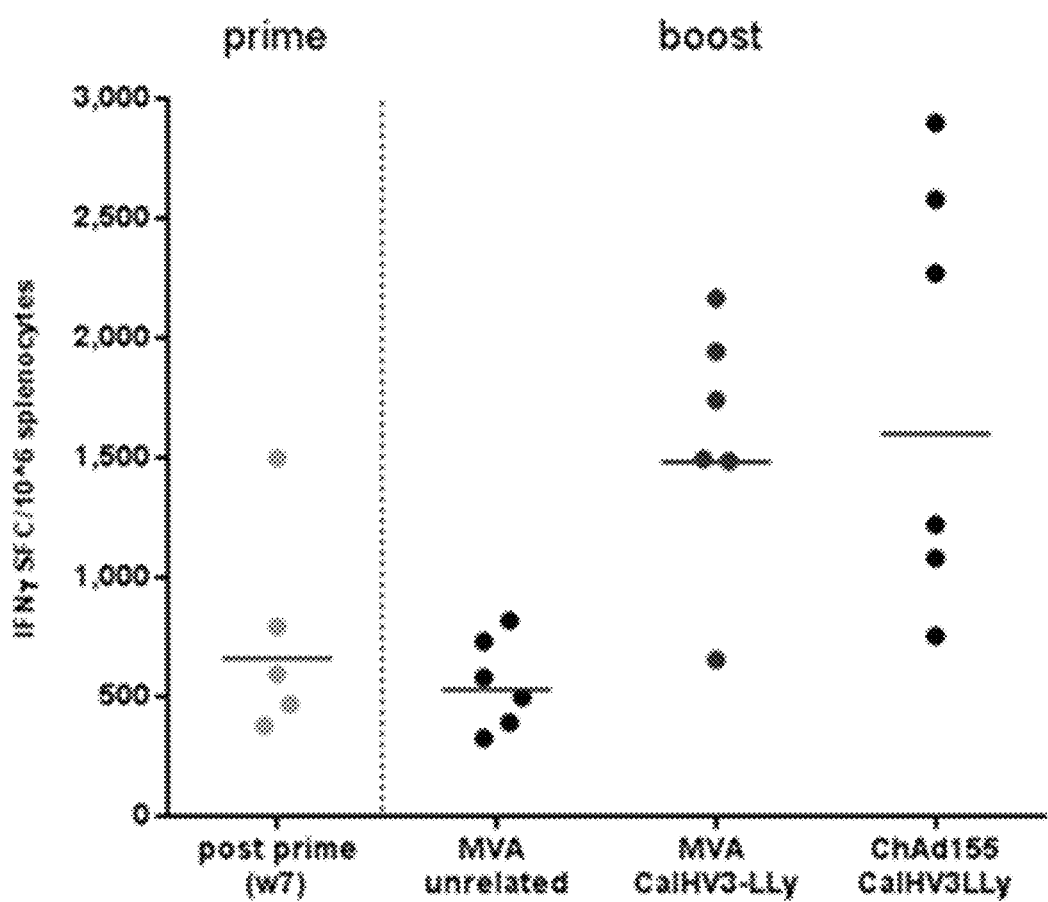

FIG. 7: Effect of prime-boost dosing on CalHV3-LLy immunogenicity in mice. Immunization with ChAd155-CalHV3-LLy ("prime") on day 0 followed by a boost immunization with either the same antigen construct (ChAd155-CalHV3-LLy) or MVA-CalHV3-LLy on day 42 (week 6) produced a significant increase in CalHV3-specific IFNγ release measured at week 7, as compared to unboosted mice or mice receiving a "boost" injection of an MVA vector encoding a CalHV3-unrelated antigen.

Figure 8:
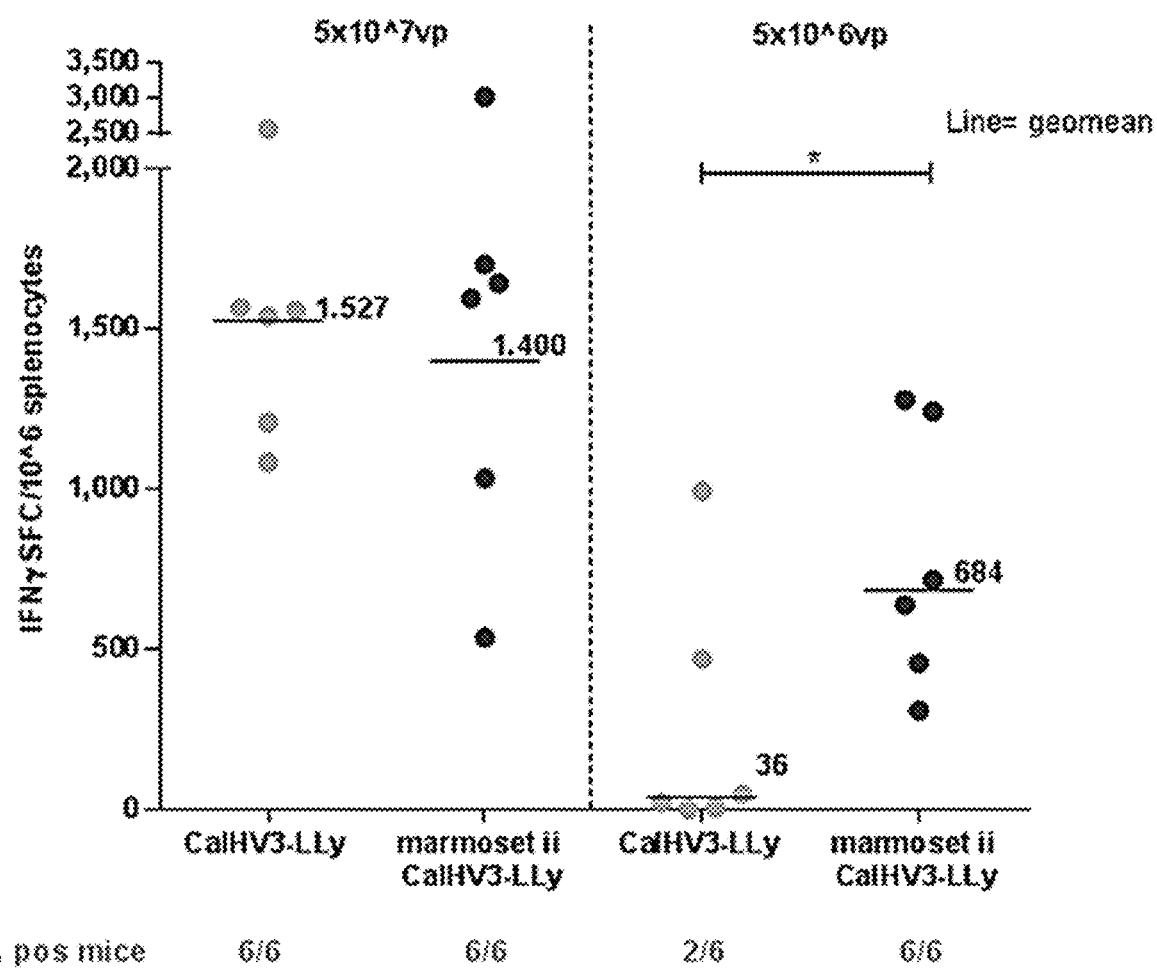

FIG. 8: Cumulative T-cell responses in mice two weeks after immunization with an invariant chain-CalHV3-LLy fusion protein (ChAd155-Ii-CalHV3-LLy). At the lower dose of antigen ($5\times10^6$ vp), ChAd155-Ii-CalHV3-LLy elicited significantly greater IFNγ release and a higher proportion (100%) of responding mice than ChAd155-CalHV3-LLy. No differences were observed at the higher antigen dose tested ($5\times10^7$ vp).

Figure 9:
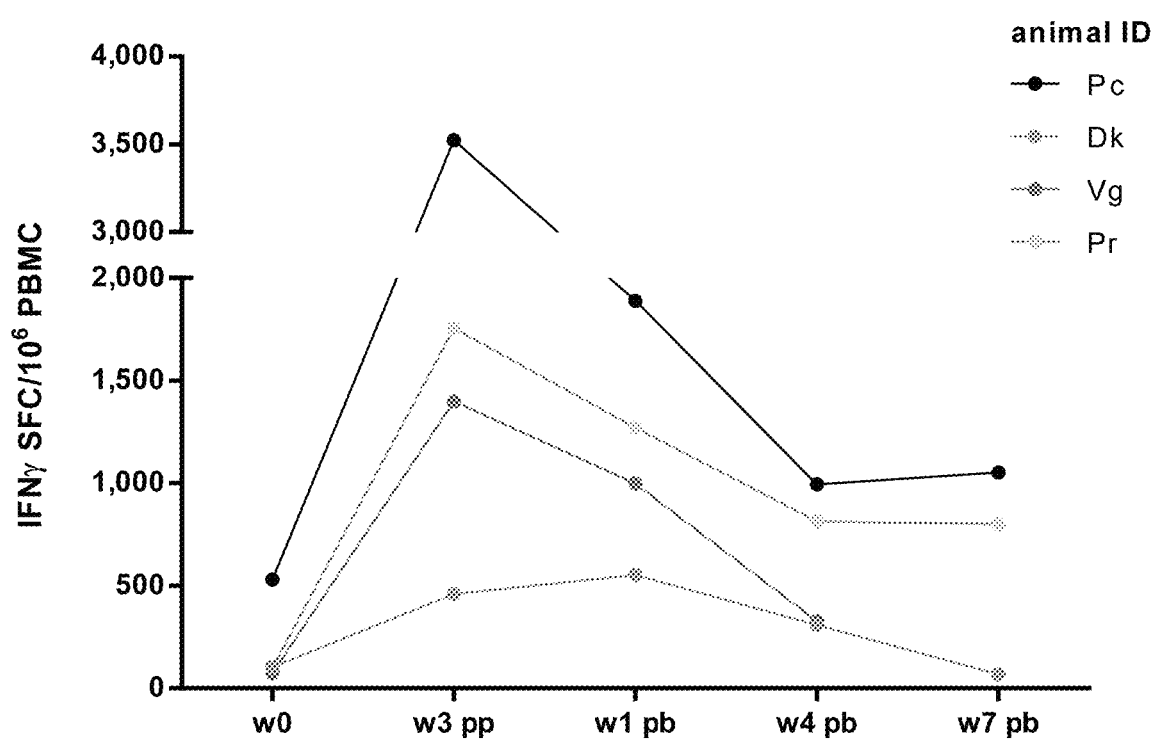

FIG. 9: Cumulative T-cell responses in CalHV3-infected marmosets. Prior to immunization (w0), animals exhibited baseline CalHV3-specific T-cell responses, consistent with the fact that the animals are virus carriers. Three weeks after ChAd155-CalHV3-LLy immunization (w3 pp), CalHV3-immunized animals exhibited significant expansion of pre-existing CalHV3-specific T cell responses. T-cell responses continued to be elevated above baseline 1 week post-boost (w1 pb) with MVA-CalHV3-LLy, and after contraction were still above baseline 7 weeks after boost.

Figure 10:
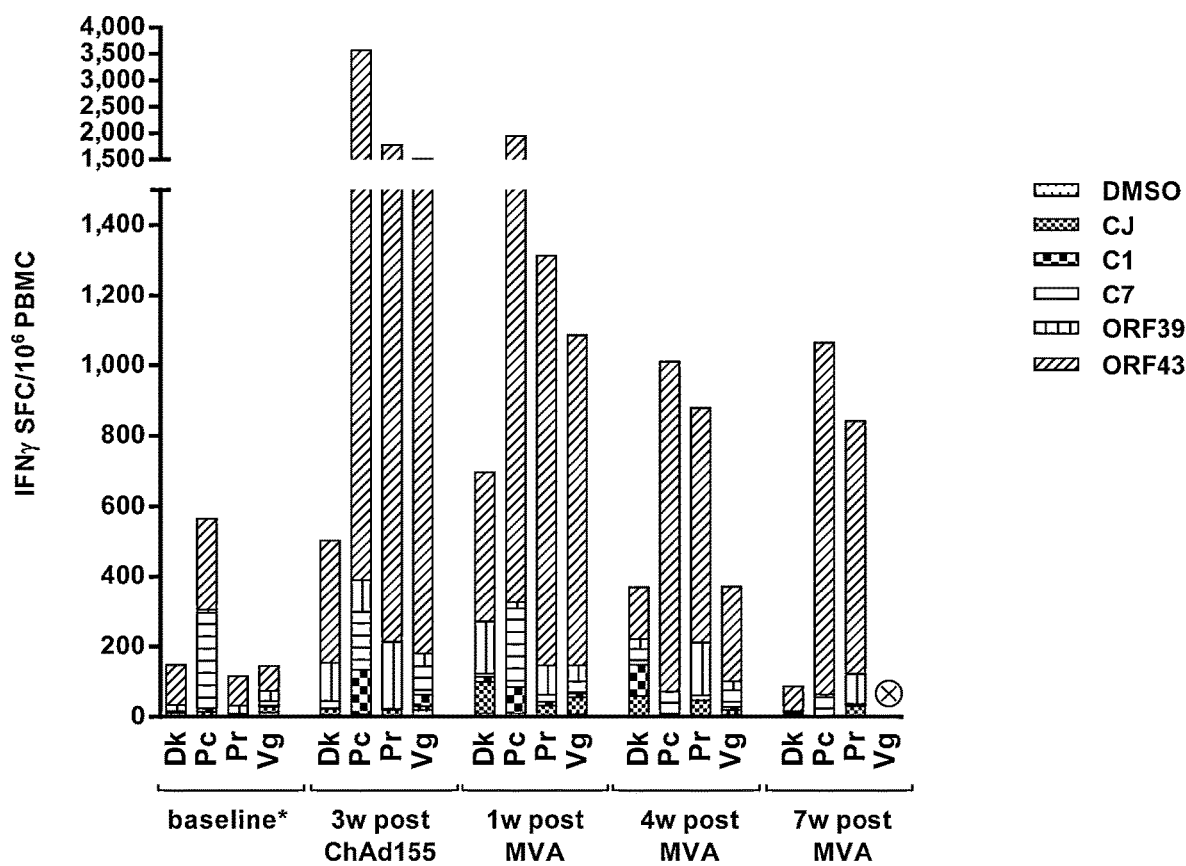

FIG. 10: The enhanced cumulative T-cell response to ChAd155-CalHV3-LLy shown in FIG. 9 was determined to be polyspecific, i.e., against CalHV3-LLy antigens C1, C7, ORF39 and ORF 43.

Figure 11:
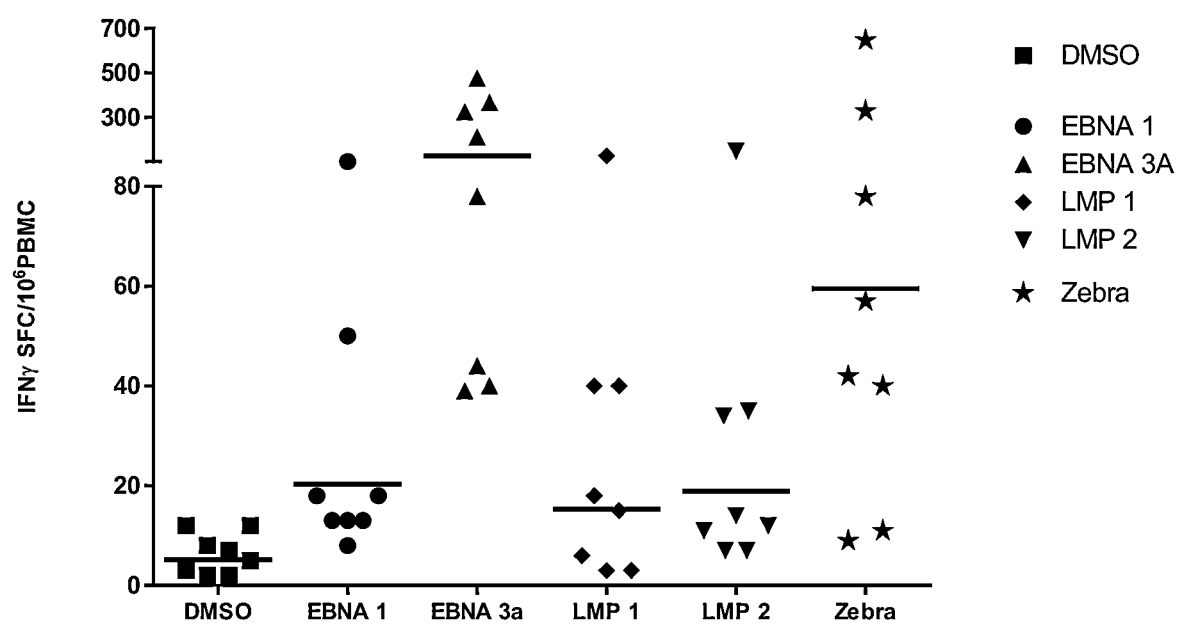

FIG. 11: EBV peptide pools corresponding to antigens encoded by ChAd155 and MVA latent+lytic EBV vaccines elicit IFNγ release in PBMCs from human healthy donors.

DESCRIPTION OF THE SEQUENCES

SEQ ID NO: 1 EBV LMP1 protein (Genbank No. P03230)
SEQ ID NO: 2 immunogenic fragment of EBV LMP1 protein
SEQ ID NO: 3 immunogenic fragment of EBV LMP1 protein
SEQ ID NO: 4 immunogenic fragment of EBV LMP1 protein
SEQ ID NO: 5 immunogenic fragment of EBV LMP1 protein
SEQ ID NO: 6 EBV LMP2 protein (Genbank No. P13285)
SEQ ID NO: 7 immunogenic fragment of EBV LMP2 protein
SEQ ID NO: 8 immunogenic fragment of EBV LMP2 protein
SEQ ID NO: 9 immunogenic fragment of EBV LMP2 protein
SEQ ID NO: 10 immunogenic fragment of EBV LMP2 protein
SEQ ID NO: 11 EBV EBNA1 protein (Genbank No. P03211)
SEQ ID NO: 12 immunogenic fragment of EBV EBNA1 protein
SEQ ID NO: 13 EBV EBNA3A protein (Genbank No. YP401669)
SEQ ID NO: 14 immunogenic fragment of EBV EBNA3A protein
SEQ ID NO: 15 immunogenic fragment of EBV EBNA3A protein
SEQ ID NO: 16 immunogenic fragment of EBV EBNA3A protein
SEQ ID NO: 17 immunogenic fragment of EBV EBNA3A protein
SEQ ID NO: 18 immunogenic fragment of EBV EBNA3A protein SEQ ID NO: 19 immunogenic fragment of EBV EBNA3A protein
SEQ ID NO: 20 immunogenic fragment of EBV EBNA3A protein
SEQ ID NO: 21 EBV ZEBRA protein (Genbank No. P03206)
SEQ ID NO: 22 immunogenic fragment of EBV ZEBRA protein
SEQ ID NO: 23 immunogenic fragment of EBV ZEBRA protein
SEQ ID NO: 24 EBV-L antigen polypeptide
SEQ ID NO: 25 DNA encoding EBV-L antigen polypeptide
SEQ ID NO: 26 EBV-LLy antigen polypeptide
SEQ ID NO: 27 DNA encoding EBV-LLy antigen polypeptide
SEQ ID NO: 28 CalHV3 C1 protein (Genbank No. NP_733852)
SEQ ID NO: 29 immunogenic fragment of CalHV3 C1 protein
SEQ ID NO: 30 immunogenic fragment of CalHV3 C1 protein
SEQ ID NO: 31 immunogenic fragment of CalHV3 C1 protein
SEQ ID NO: 32 CalHV3 C7 protein (Genbank No. NP_733851)
SEQ ID NO: 33 immunogenic fragment of CalHV3 C7 protein
SEQ ID NO: 34 immunogenic fragment of CalHV3 C7 protein
SEQ ID NO: 35 immunogenic fragment of CalHV3 C7 protein
SEQ ID NO: 36 CalHV3 ORF39 (Genbank No. NP_733892)
SEQ ID NO: 37 immunogenic fragment of CalHV3 ORF39
SEQ ID NO: 38 immunogenic fragment of CalHV3 ORF39
SEQ ID NO: 39 immunogenic fragment of CalHV3 ORF39
SEQ ID NO: 40 CalHv3 ORF43 protein (Genbank No. NP_733896)
SEQ ID NO: 41 immunogenic fragment of CalHv3 ORF43 protein
SEQ ID NO: 42 immunogenic fragment of CalHv3 ORF43 protein
SEQ ID NO: 43 marmoset invariant chain polypeptide
SEQ ID NO: 44 CalHv3_L antigen polypeptide
SEQ ID NO: 45 DNA encoding CalHV3_L antigen polypeptide
SEQ ID NO: 46 CalHV3_LLy antigen polypeptide
SEQ ID NO: 47 DNA encoding CalHV3_LLy antigen polypeptide
SEQ ID NO: 48 li_CalHV3_LLy antigen polypeptide
SEQ ID NO: 49 DNA encoding li_CalHV3_LLy antigen polypeptide
SEQ ID NO: 50 pChAd155 (ΔE1, ΔE4_Ad5E4 orf6) TetO hCMV-EBV-L expression vector
SEQ ID NO: 51 pChAd155 (ΔE1, ΔE3, ΔE4_Ad5E4 orf6) TetO hCMV-EBV-LLy expression vector
SEQ ID NO: 52 pChAd155 (ΔE1, ΔE4_Ad5E4 orf6) TetO hCMV-CalHV3-L expression vector
SEQ ID NO: 53 pChAd155 (ΔE1, ΔE3, ΔE4_Ad5E4 orf6) TetO hCMV-CalHV3-LLy expression vector
SEQ ID NO: 54 pChAd155 (ΔE1, ΔE3, ΔE4_Ad5E4 orf6) TetO hCMV-mli-CalHV3-LLy expression vector

DETAILED DESCRIPTION OF THE INVENTION

Epstein-Barr Virus Antigen Polypeptides

EBV antigen polypeptides of the invention include polypeptides comprising immunogenic fragments of one or more EBV latent and/or lytic proteins. EBV latent proteins include, for example, Latent Membrane Proteins (LMP1 and LMP2); and EBV Nuclear Antigens (EBNA1, EBNA2, EBNA3A, EBNA3B and EBNA3C). EBV lytic proteins include, for example, ZEBRA (encoded by the BZLF1 gene).

An "immunogenic fragment" of an EBV protein, as used herein, means a fragment smaller than a full-length EBV protein that is capable of inducing an immune response, for example a humoral (e.g., antibody) and/or cell-mediated (e.g., a cytotoxic T cell) response. Immunogenic fragments include fragments of at least 8, at least 9, at least 10, at least 11, at least 12, at least 13, at least 14, at least 15, at least 20, at least 30, at least 40, at least 50, at least 60, at least 70, at least 80, at least 90 and at least 100 amino acids of the full length protein. In some embodiments, immunogenic fragments consist of about 8, about 9, about 10, about 11, about 12, about 13, about 14, about 15, about 20, about 30, about 40, about 50, about 60, about 70, about 80, about 90 and about 100 amino acids of the full length protein. One aspect of the invention is to provide EBV antigen polypeptides capable of inducing T-cell responses against B-cells harboring latent EBV infection. Thus, in some embodiments, immunogenic fragments of EBV proteins comprise one or more T-cell epitopes capable of inducing an antigen-specific T-cell response.

Immunogenic fragments may have one or more substitutions, deletions or insertions relative to the full length protein from which the fragment is derived. Thus, immunogenic fragments include fragments at least 80%, at least 85%, at least 90%, at least 95% or at least 99% identical to the corresponding region of the full length protein.

In one embodiment, an EBV antigen polypeptide of the invention comprises a Latent Membrane Protein 1 (LMP1) antigen. LMP1 is a 386 amino acid protein expressed during the latent stage of the EBV viral life cycle. Immunogenic fragments of LMP1 suitable for use in the EBV antigen polypeptides of the invention include fragments of at least 8, at least 9, at least 10, at least 11, at least 12, at least 13, at least 14, at least 15, at least 20, at least 30, at least 40, at least 50, at least 60, at least 70, at least 80, at least 90 and at least 100 amino acids of SEQ ID NO: 1. In some embodiments, immunogenic fragments of LMP1 consist of about 8, about 9, about 10, about 11, about 12, about 13, about 14, about 15, about 20, about 30, about 40, about 50, about 60, about 70, about 80, about 90 and about 100 amino acids of SEQ ID NO: 1. In some embodiments, immunogenic fragments of LMP1 include fragments at least 80%, at least 85%, at least 90%, at least 95% or at least 99% identical to the corresponding region of SEQ ID NO: 1.

In some embodiments, an immunogenic fragment of LMP1 comprises one or more T-cell epitopes. In preferred embodiments, immunogenic epitopes of LMP1 include, but are not limited to, SEQ ID Nos: 2-5 and fragments at least 80%, at least 85%, at least 90%, at least 95% or at least 99% identical to SEQ ID Nos: 2-5.

In one embodiment, an EBV antigen polypeptide of the invention comprises a Latent Membrane Protein 2 (LMP2) antigen. LMP2 is a 497 amino acid protein expressed during the latent stage of the EBV viral life cycle. Immunogenic fragments of LMP2 suitable for use in the EBV antigen polypeptides of the invention include fragments of at least 8, at least 9, at least 10, at least 11, at least 12, at least 13, at least 14, at least 15, at least 20, at least 30, at least 40, at least 50, at least 60, at least 70, at least 80, at least 90 and at least 100 amino acids of SEQ ID NO: 6. In some embodiments, immunogenic fragments of LMP2 consist of about 8, about 9, about 10, about 11, about 12, about 13, about 14, about 15, about 20, about 30, about 40, about 50, about 60, about 70, about 80, about 90 and about 100 amino acids of SEQ ID NO: 6. In some embodiments, immunogenic fragments of LMP2 include fragments at least 80%, at least 85%, at least 90%, at least 95% or at least 99% identical to the corresponding region of SEQ ID NO: 6.

In some embodiments, an immunogenic fragment of LMP2 comprises one or more T-cell epitopes. In preferred embodiments, immunogenic epitopes of LMP2 include, but are not limited to, SEQ ID Nos: 7-10, and fragments at least 80%, at least 85%, at least 90%, at least 95% or at least 99% identical to SEQ ID Nos: 7-10.

In one embodiment, an EBV antigen polypeptide of the invention comprises an Epstein-Barr Nuclear Antigen 1 (EBNA1) antigen. EBNA1 is a 641 amino acid protein expressed during the latent stage of the EBV viral life cycle. Immunogenic fragments of EBNA1 suitable for use in the EBV antigen polypeptides of the invention include fragments of at least 8, at least 9, at least 10, at least 11, at least 12, at least 13, at least 14, at least 15, at least 20, at least 30, at least 40, at least 50, at least 60, at least 70, at least 80, at least 90 and at least 100 amino acids of SEQ ID NO: 11. In some embodiments, immunogenic fragments of EBNA1 consist of about 8, about 9, about 10, about 11, about 12, about 13, about 14, about 15, about 20, about 30, about 40, about 50, about 60, about 70, about 80, about 90 and about 100 amino acids of SEQ ID NO: 11. In some embodiments, immunogenic fragments of EBNA1 include fragments at least 80%, at least 85%, at least 90%, at least 95% or at least 99% identical to the corresponding region of SEQ ID NO: 11.

In some embodiments, an immunogenic fragment of EBNA1 comprises one or more T-cell epitopes. In preferred embodiments, immunogenic epitopes of EBNA1 include, but are not limited to, SEQ ID No: 12, and fragments at least 80%, at least 85%, at least 90%, at least 95% or at least 99% identical to SEQ ID No: 12.

In one embodiment, an EBV antigen polypeptide of the invention comprises an Epstein-Barr Nuclear Antigen 3A (EBNA3A) antigen. EBNA3A is a 944 amino acid protein expressed during the latent stage of the EBV viral life cycle. Immunogenic fragments of EBNA3A suitable for use in the EBV antigen polypeptides of the invention include fragments of at least 8, at least 9, at least 10, at least 11, at least 12, at least 13, at least 14, at least 15, at least 20, at least 30, at least 40, at least 50, at least 60, at least 70, at least 80, at least 90 and at least 100 amino acids of SEQ ID NO: 13. In some embodiments, immunogenic fragments of EBNA3A consist of about 8, about 9, about 10, about 11, about 12, about 13, about 14, about 15, about 20, about 30, about 40, about 50, about 60, about 70, about 80, about 90 and about 100 amino acids of SEQ ID NO: 13. In some embodiments, immunogenic fragments of EBNA3A include fragments at least 80%, at least 85%, at least 90%, at least 95% or at least 99% identical to the corresponding region of SEQ ID NO: 13.

In some embodiments, an immunogenic fragment of EBNA3A comprises one or more T-cell epitopes. In preferred embodiments, immunogenic epitopes of EBNA3A include, but are not limited to, SEQ ID Nos: 14-20, and fragments at least 80%, at least 85%, at least 90%, at least 95% or at least 99% identical to SEQ ID Nos: 14-20.

In one embodiment, an EBV antigen polypeptide of the invention comprises a ZEBRA antigen. ZEBRA is a 245 amino acid protein expressed during the lytic stage of the EBV viral life cycle. Immunogenic fragments of ZEBRA suitable for use in the EBV antigen polypeptides of the invention include fragments of at least 8, at least 9, at least 10, at least 11, at least 12, at least 13, at least 14, at least 15, at least 20, at least 30, at least 40, at least 50, at least 60, at least 70, at least 80, at least 90 and at least 100 amino acids of SEQ ID NO: 21. In some embodiments, immunogenic fragments of ZEBRA consist of about 8, about 9, about 10, about 11, about 12, about 13, about 14, about 15, about 20, about 30, about 40, about 50, about 60, about 70, about 80, about 90 and about 100 amino acids of SEQ ID NO: 21. In some embodiments, immunogenic fragments of ZEBRA include fragments at least 80%, at least 85%, at least 90%, at least 95% or at least 99% identical to the corresponding region of SEQ ID NO: 21.

In some embodiments, an immunogenic fragment of ZEBRA comprises one or more T-cell epitopes. In preferred embodiments, immunogenic epitopes of ZEBRA include, but are not limited to, SEQ ID Nos: 22-23, and fragments at least 80%, at least 85%, at least 90%, at least 95% or at least 99% identical to SEQ ID Nos: 22-23.

In some embodiments, an EBV antigen polypeptide is a polyvalent EBV antigen polypeptide. By "polyvalent" is intended a polypeptide comprising immunogenic fragments of two, three, four, five or more EBV proteins. By "fragment" is intended a fragment of at least 8, at least 9, at least 10, at least 11, at least 12, at least 13, at least 14, at least 15, at least 20, at least 30, at least 40, at least 50, at least 60, at least 70, at least 80, at least 90 or at least 100 amino acids of the full-length protein.

Thus, in one embodiment is provided a polypeptide comprising:
  (a) at least one fragment of least 8, at least 9, at least 10, at least 11, at least 12, at least 13, at least 14, at least 15, at least 20, at least 30, at least 40, at least 50, at least 60, at least 70, at least 80, at least 90 or at least 100 amino acids of SEQ ID NO: 1,
  (b) at least one fragment of least 8, at least 9, at least 10, at least 11, at least 12, at least 13, at least 14, at least 15, at least 20, at least 30, at least 40, at least 50, at least 60, at least 70, at least 80, at least 90 or at least 100 amino acids of SEQ ID NO: 6,
  (c) at least one fragment of least 8, at least 9, at least 10, at least 11, at least 12, at least 13, at least 14, at least 15, at least 20, at least 30, at least 40, at least 50, at least 60, at least 70, at least 80, at least 90 or at least 100 amino acids of SEQ ID NO: 11, and
  (d) at least one fragment of least 8, at least 9, at least 10, at least 11, at least 12, at least 13, at least 14, at least 15, at least 20, at least 30, at least 40, at least 50, at least 60, at least 70, at least 80, at least 90 or at least 100 amino acids of SEQ ID NO: 13.

Optionally, the polypeptide further comprises at least one fragment of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 21.

In some embodiments, a polyvalent EBV antigen polypeptide comprises at least two, at least three, at least four, at least five, at least six, at least seven, at least eight, at least nine, or at least ten fragments of one or more EBV proteins. Thus, in one embodiment, a polyvalent EBV antigen is a polypeptide comprising:
  (a) at least two fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 1,
  (b) at least two fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 6,
  (c) at least two fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 11,
  (d) at least two fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 13, or
  (e) at least two fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 21.

In one embodiment, a polyvalent EBV antigen is a polypeptide comprising:
  (a) at least three fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 1,
  (b) at least three fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 6,
  (c) at least three fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 11,
  (d) at least three fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 13, or
  (e) at least three fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 21.

In one embodiment, a polyvalent EBV antigen is a polypeptide comprising:
  (a) at least four fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 1,
  (b) at least four fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 6,
  (c) at least four fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 11,
  (d) at least four fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 13, or
  (e) at least four fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 21.

In one embodiment, a polyvalent EBV antigen is a polypeptide comprising:
  (a) at least five fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 1,
  (b) at least five fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 6,
  (c) at least five fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 11,
  (d) at least five fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 13, or
  (e) at least five fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 21.

In one embodiment, a polyvalent EBV antigen is a polypeptide comprising:
  (a) at least six fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 1,
  (b) at least six fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 6,
  (c) at least six fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 11,
  (d) at least six fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 13, or
(e) at least six fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 21.

In one embodiment, a polyvalent EBV antigen is a polypeptide comprising:
(a) at least seven fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 1,
(b) at least seven fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 6,
(c) at least seven fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 11,
(d) at least seven fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 13, or
(e) at least seven fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 21.

In one embodiment, a polyvalent EBV antigen is a polypeptide comprising:
(a) at least eight fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 1,
(b) at least eight fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 6,
(c) at least eight fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 11,
(d) at least eight fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 13, or
(e) at least eight fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 21.

In one embodiment, a polyvalent EBV antigen is a polypeptide comprising:
(a) at least nine fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 1,
(b) at least nine fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 6,
(c) at least nine fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 11,
(d) at least nine fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 13, or
(e) at least nine fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 21.

In one embodiment, a polyvalent EBV antigen is a polypeptide comprising:
(a) at least ten fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 1,
(b) at least ten fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 6,
(c) at least ten fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 11,
(d) at least ten fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 13, or
(e) at least ten fragments of at least 8, at least 9, at least 10, at least 11, at least 12, at least 13, at least 14, at least 15, at least 20, at least 30, at least 40, at least 50, at least 60, at least 70, at least 80 at least 90 or at least 100 amino acids of SEQ ID NO: 21.

In some embodiments, the polyvalent EBV antigen polypeptide comprises at least two immunogenic fragments derived from the same EBV protein, wherein the at least two immunogenic fragments are not adjacent to each other in the polyvalent EBV antigen polypeptide. By "not adjacent" is intended to mean that the at least two immunogenic fragments do not form a contiguous amino acid sequence in the EBV antigen polypeptide. Immunogenic fragments which are not adjacent are separated from each other by at least one, two, three, four, five, ten or more amino acids that are not from the same EBV protein as the immunogenic fragments.

For example, in one embodiment, the polyvalent EBV antigen polypeptide comprises at least two, at least three, at least four, at least five, at least six, at least seven, at least eight, at least nine, or at least ten fragments of LMP1 (SEQ ID NO: 1), wherein the fragments of LMP1 are not adjacent to each other.

In another embodiment, the polyvalent EBV antigen polypeptide comprises at least two, at least three, at least four, at least five, at least six, at least seven, at least eight, at least nine, or at least ten fragments of LMP2 (SEQ ID NO: 6), wherein the fragments of LMP2 are not adjacent to each other.

In another embodiment, the polyvalent EBV antigen polypeptide comprises at least two, at least three, at least four, at least five, at least six, at least seven, at least eight, at least nine, or at least ten fragments of EBNA1 (SEQ ID NO: 11), wherein the fragments of EBNA1 are not adjacent to each other.

In another embodiment, the polyvalent EBV antigen polypeptide comprises at least two, at least three, at least four, at least five, at least six, at least seven, at least eight, at least nine, or at least ten fragments of EBNA3A (SEQ ID NO: 13), wherein the fragments of EBNA3A are not adjacent to each other.

In another embodiment, the polyvalent EBV antigen polypeptide comprises at least two, at least three, at least four, at least five, at least six, at least seven, at least eight, at least nine, or at least ten fragments of ZEBRA (SEQ ID NO: 21), wherein the fragments of ZEBRA are not adjacent to each other.

In one embodiment, the polyvalent EBV antigen polypeptide comprises:
(a) a first and a second fragment of LMP1, wherein said first and second fragments of LMP1 are selected from the group consisting SEQ ID NOs: 2-5 and wherein said first and second fragments of LMP1 are not adjacent to each other in the polypeptide,
(b) a first and a second fragment of LMP2, wherein said first and second fragments of LMP1 are selected from the group consisting SEQ ID NOs: 7-10 and wherein said first and second fragments of LMP2 are not adjacent to each other in the polypeptide,
(c) a fragment of EBNA1 consisting of SEQ ID NO: 12, and
(d) a first and a second fragment of EBNA3A, wherein said first and second fragments of EBNA3A are selected from the group consisting SEQ ID NOs: 14-20 and wherein said first and second fragments of EBNA3A are not adjacent to each other in the polypeptide.

Optionally, the polyvalent EBV antigen further comprises:
(a) a first fragment of ZEBRA consisting of SEQ ID NO: 22, and
(b) a second fragment of ZEBRA consisting of SEQ ID NO: 23;
wherein the first and second ZEBRA fragments are not adjacent to each other.

In one embodiment, the polyvalent EBV antigen polypeptide comprises:
(a) a first fragment of LMP1 consisting of SEQ ID NO: 2,
(b) a second fragment of LMP1 consisting of SEQ ID NO: 3,
(c) a third fragment of LMP1 consisting of SEQ ID NO: 4,
(d) a fourth fragment of LMP1 consisting of SEQ ID NO: 5,
(e) a first fragment of LMP2 consisting of SEQ ID NO: 7,
(f) a second fragment of LMP2 consisting of SEQ ID NO: 8,
(g) a third fragment of LMP2 consisting of SEQ ID NO: 9,
(h) a fourth fragment of LMP2 consisting of SEQ ID NO: 10,
(i) a first fragment of EBNA1 consisting of SEQ ID NO: 12,
(j) a first fragment of EBNA3A consisting of SEQ ID NO: 14,
(k) a second fragment of EBNA3A consisting of SEQ ID NO: 15,
(l) a third fragment of EBNA3A consisting of SEQ ID NO: 16,
(m) a fourth fragment of EBNA3A consisting of SEQ ID NO: 17,
(n) a fifth fragment of EBNA3A consisting of SEQ ID NO: 18,
(o) a sixth fragment of EBNA3A consisting of SEQ ID NO: 19, and
(p) a seventh fragment of EBNA3A consisting of SEQ ID NO: 20;
wherein the first, second, third and fourth LMP1 fragments are not adjacent to each other; the first, second, third and fourth LMP2 fragments are not adjacent to each other; and the first, second, third, fourth, fifth, sixth, and seventh EBNA3A fragments are not adjacent to each other. Optionally, the polyvalent EBV antigen further comprises:
(a) a first fragment of ZEBRA consisting of SEQ ID NO: 22, and
(b) a second fragment of ZEBRA consisting of SEQ ID NO: 23;
wherein the first and second ZEBRA fragments are not adjacent to each other.

To facilitate a clear description of the polypeptides and polynucleotides described herein, particular sequence components are referred to as a "first" polypeptide or polynucleotide sequence, a "second" polypeptide or polynucleotide sequence, etc. It is to be understood that the first, second, etc. sequences can appear in any desired order or orientation, and that no particular order or orientation is intended by the words "first", "second" etc.

In some embodiments, the polyvalent EBV antigen does not contain junctional neo-epitopes that map to human (i.e. self) proteins. An immunogenic junctional neo-epitope is an epitope that elicits an immune response to the junction of two heterologous protein sequences, wherein the epitope is not present in either of the heterologous protein sequences themselves. T cell responses to junctional neo-epitopes can be identified using methods known in the art, for example immunological assays using peptide pools covering all junctions to be used, as described in Example 4.

Figure 2A:
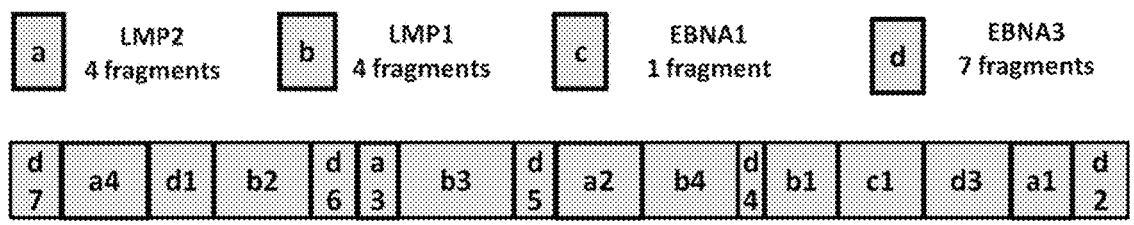
FIG. 2A-B: Schematic representation of polyvalent EBV antigen constructs.

In one embodiment, the polyvalent EBV antigen is the "EBV-L" construct illustrated in FIG. 2A. In another embodiment, the polyvalent EBV antigen polypeptide is a polypeptide at least 80%, at least 85%, at least 90%, at least 95% or at least 99% identical to SEQ ID NO: 24.

Figure 2B:
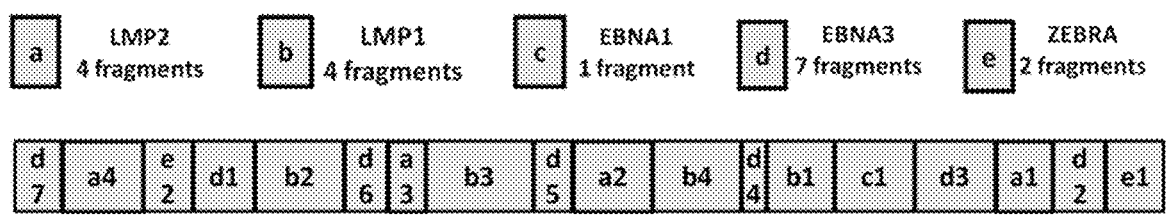

In another embodiment, the polyvalent EBV antigen is the "EBV-LLy" construct illustrated in FIG. 2B. In another embodiment, the polyvalent EBV antigen polypeptide is a polypeptide at least 80%, at least 85%, at least 90%, at least 95% or at least 99% identical to SEQ ID NO: 26.

In preferred embodiments, an EBV antigen polypeptide of the invention contains at least one amino acid insertion, deletion and/or substitution as compared to a wild type EBV protein.

In another embodiment, the EBV antigen polypeptide is a polypeptide encoded by a polynucleotide described herein.

Polynucleotides

Polynucleotides and expression cassettes encoding EBV antigen polypeptides described herein are also provided. By "expression cassette" is meant the combination of a selected heterologous gene (a "transgene" encoding an EBV antigen polypeptide) and the other regulatory elements necessary to drive translation, transcription and/or expression of the gene product in a host cell.

The invention provides a polynucleotide encoding an EBV antigen polypeptide of the invention.

In one embodiment is provided a polynucleotide encoding a polypeptide at least 80%, at least 85%, at least 90%, at least 95% or at least 99% identical to SEQ ID NO: 24. In one embodiment, the polynucleotide is at least 80%, at least 85%, at least 90%, at least 95% or at least 99% identical to SEQ ID NO: 25.

In one embodiment is provided a polynucleotide encoding a polypeptide at least 80%, at least 85%, at least 90%, at least 95% or at least 99% identical to SEQ ID NO: 26. In one embodiment, the polynucleotide is at least 80%, at least 85%, at least 90%, at least 95% or at least 99% identical to SEQ ID NO: 27.

Suitably the polynucleotides of the invention are recombinant. Recombinant means that the polynucleotide is the product of at least one of cloning, restriction, recombination or ligation steps, or other procedures that result in a polynucleotide that is distinct from a polynucleotide found in nature. A recombinant virus is a virus comprising a recombinant polynucleotide. A recombinant vector is a vector comprising a recombinant polynucleotide. A recombinant virus includes progeny of the original recombinant virus. A "recombinant vector" includes replicates of the original recombinant vector. A "recombinant polynucleotide" includes replicates of the original recombinant polynucleotide. Recombinant polynucleotides of the invention contain at least one nucleic acid substitution as compared to the wild-type EBV genome.

In some embodiments, EBV antigen-encoding polynucleotides of the invention are operatively linked to one or more control elements in a manner that permits its transcription, translation and/or expression in a cell transfected or infected with the polynucleotide. As used herein, "operably linked" sequences include both expression control sequences that are contiguous with the gene of interest and expression control sequences that act in trans or at a distance to control the gene of interest. Thus, in one embodiment a polynucleotide is operatively linked to one or more sequences which direct expression of said polypeptide in a host cell. In some embodiments the expression control sequence is heterologous to the EBV antigen-encoding polynucleotide Expression control sequences include appropriate transcription initiation, termination, promoter and enhancer sequences; efficient RNA processing signals such as splicing and polyadenylation (poly A) signals including rabbit beta-globin polyA; sequences that stabilize cytoplasmic mRNA; sequences that enhance translation efficiency (e.g., Kozak consensus sequence); sequences that enhance protein stability; and when desired, sequences that enhance secretion of the encoded product. Among other sequences, chimeric introns may be used.

A "promoter" is a nucleotide sequence that permits binding of RNA polymerase and directs the transcription of a gene. Typically, a promoter is located in the 5' non-coding region of a gene, proximal to the transcriptional start site of the gene. Sequence elements within promoters that function in the initiation of transcription are often characterized by consensus nucleotide sequences. Examples of promoters include, but are not limited to, promoters from bacteria, yeast, plants, viruses, and mammals (including humans). A great number of expression control sequences, including promoters which are internal, heterologous, native, constitutive, inducible and/or tissue-specific, are known in the art and may be utilized.

In one embodiment, the polynucleotide is operatively linked to a heterologous expression control sequence, such as a promoter. Typically, "heterologous" means derived from a genotypically distinct entity from that of the rest of the entity to which it is being compared. A heterologous nucleic acid sequence refers to any nucleic acid sequence that is not isolated from, derived from, or based upon a naturally occurring nucleic acid sequence of the adenoviral vector.

Examples of constitutive promoters include, without limitation, the TBG promoter, the retroviral Rous sarcoma virus LTR promoter (optionally with the enhancer), the cytomegalovirus (CMV) promoter (optionally with the CMV enhancer, see, e.g., Boshart et al, Cell, 41:521-530 (1985)), the CASI promoter (WO2012/115980), the SV40 promoter, the dihydrofolate reductase promoter, the β-actin promoter, the phosphoglycerol kinase (PGK) promoter, and the EF1a promoter (Invitrogen).

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. For example, inducible promoters include the zinc-inducible sheep metallothionine (MT) promoter and the dexamethasone (Dex)-inducible mouse mammary tumor virus (MMTV) promoter. Other inducible systems include the T7 polymerase promoter system; the ecdysone insect promoter, the tetracycline-repressible system and the tetracycline-inducible system. Other systems include the FK506 dimer, VP16 or p65 using castradiol, diphenol murislerone, the RU486-inducible system and the rapamycin-inducible system. The effectiveness of some inducible promoters increases over time. In such cases one can enhance the effectiveness of such systems by inserting multiple repressors in tandem, e.g., TetR linked to a TetR by an IRES.

In another embodiment, a native EBV promoter may be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

The transgene may be operably linked to a tissue-specific promoter. For instance, if expression in skeletal muscle is desired, a promoter active in muscle should be used. These include the promoters from genes encoding skeletal β-actin, myosin light chain 2A, dystrophin, muscle creatine kinase, as well as synthetic muscle promoters with activities higher than naturally occurring promoters. Examples of promoters that are tissue-specific are known for liver; hepatitis B virus core; alpha-fetoprotein, bone osteocalcin; bone sialoprotein, lymphocytes, immunoglobulin heavy chain; T cell receptor chain), neuronal such as neuron-specific enolase (NSE)

promoter, neurofilament light-chain gene, and the neuron-specific vgf gene, among others.

Vectors

Vectors containing polynucleotides encoding EBV antigen constructs as described herein are also provided. Such vectors will be suitable for delivery to and expression in a host cell. Vectors can be in the form of a replicating or replication defective vector, such as a viral vector. Numerous viral vectors suitable for introducing immunogenic nucleic acids into a subject are known in the art, and include both DNA and RNA viruses. Examples of vectors suitable for encoding EBV antigens described herein include: adenovirus vectors (replicating or replication deficient), pox virus vectors, including vaccinia virus vectors, such as modified vaccinia Ankara virus (MVA), NYVAC, avipox vectors, canarypox (ALVAC) and fowl pox virus (FPV), Alphavirus vectors (such as Sindbis virus, Semliki Forest virus (SFV), Ross River virus, and Venezuelan equine encephalitis (VEE) virus) and chimeras and replicons thereof, herpes virus vectors (e.g., cytomegalovirus (CMV)-derived vectors), arena virus vectors, such as lymphocytic choriomeningitis virus (LCMV) vectors, measles virus vectors, vesicular stomatitis virus vectors, pseudorabies virus, adeno-associated virus, retrovirus, lentivirus, viral like particles, and many others.

In one embodiment, the vector is an adenovirus. The production and use of adenovirus vectors are well known to those of ordinary skill in the art. In the context of the immunogenic combinations disclosed here, examples of disclosure of the design, production and use of adenovirus vectors expressing vaccine antigens can be found in, e.g., in US published application No. 2014/0141042 (WO 2012/089833); U.S. Pat. No. 8,216,834 (WO 2005/071093); US published application No. US 2012/0027788 (WO 2010/086189); and US published application No. US 2005/0214323.

Typically, an adenoviral vector is designed such that the expression cassette is located in a nucleic acid molecule which contains other adenoviral sequences in the region native to a selected adenoviral gene. The expression cassette may be inserted into an existing gene region to disrupt the function of that region, if desired. Alternatively, the expression cassette may be inserted into the site of a partially or fully deleted adenoviral gene. For example, the expression cassette may be located in the site of a mutation, insertion or deletion which renders non-functional at least one gene of a genomic region selected from the group consisting of E1A, E1B, E2A, E2B, E3 and E4. The term "renders non-functional" means that a sufficient amount of the gene region is removed or otherwise disrupted, so that the gene region is no longer capable of producing functional products of gene expression. If desired, the entire gene region may be removed (and suitably replaced with the expression cassette). Suitably, E1 genes of adenovirus are deleted and replaced with an expression cassette consisting of a promoter of choice, a cDNA sequence of the gene of interest and a poly A signal, resulting in a replication defective recombinant virus.

Adenoviral vectors of use in the present invention may be derived from a range of mammalian hosts. Over 100 distinct serotypes of adenovirus have been isolated which infect various mammalian species, 51 of which are of human origin. Thus one or more of the adenoviral vectors may be derived from a human adenovirus. Examples of such human-derived adenoviruses are Ad1, Ad2, Ad4, Ad5, Ad6, Ad11, Ad24, Ad26, Ad34, Ad35, Ad48, particularly Ad5, Ad11 and Ad35. The human and nonhuman adenoviral serotypes have been categorized into six subgenera (A-F) based on a number of biological, chemical, immunological and structural criteria.

Although Ad5-based vectors have been used extensively in a number of gene therapy trials, there may be limitations on the use of Ad5 and other human group C adenoviral vectors due to preexisting immunity in the general population due to natural infection. Ad5 and other human group C members tend to be among the most seroprevalent serotypes. Immunity to existing vectors may develop as a result of exposure to the vector during treatment. These types of preexisting or developed immunity to seroprevalent vectors may limit the effectiveness of gene therapy or vaccination efforts. Alternative adenovirus serotypes, thus constitute very important targets in the pursuit of gene delivery systems capable of evading the host immune response.

One such area of alternative serotypes are those derived from non-human primates, especially adenoviruses isolated from chimpanzee, bonobos and gorillas. See U.S. Pat. No. 6,083,716 which describes the genome of two chimpanzee adenoviruses.

It has been shown that non-human simian adenoviral vectors induce strong immune responses to transgene products as efficiently as human adenoviral vectors (Fitzgerald et al. (2003) J. Immunol. 170:1416; Colloca et al. (2012) Science Translational Medicine 4:1-9; Roy et al. (2004) Virology 324: 361-372; Roy et al. (2010) J. of Gene Medicine 13:17-25).

Non-human simian adenoviruses can be isolated from the mesenteric lymph nodes or feces of the animals and can replicate in vitro in HEK 293 cells. Despite these similarities, nonhuman simian adenoviruses are phylogenetically and immunologically distinct from the more common human serotypes (Ad2 and Ad5).

Thus, in one embodiment one or more of the adenoviral vectors may be derived from a non-human primate adenovirus eg a chimpanzee adenovirus such as one selected from serotypes ChAd3, ChAd63, ChAd83, ChAd155, Pan5, Pan6, Pan 7 (also referred to as C7) and Pan9. Specifically, the virus may be a non-human adenovirus, such as a simian adenovirus and in particular a chimpanzee adenovirus such as ChAd155, Pan 5, 6, 7 or 9. Examples of such strains are described in US 20040241181 (WO03/000283) and are available from the American Type Culture Collection, 10801 University Boulevard, Manassas, Va. 20110-2209, and other sources. Desirable chimpanzee adenovirus strains include Pan 5 [ATCC VR-591], Pan 6 [ATCC VR-592], and Pan 7 [ATCC VR-593]. Alternatively, adenoviral vectors may be derived from nonhuman simian adenoviruses derived from bonobos, such as PanAd1, PanAd2 or PanAd3. Examples of such vectors described herein can be found for example in US 20110217332 (WO2005/071093), US 2012/0027788 (WO2010/086189) and WO2016/198621.

Use of nonhuman simian adenoviruses is thought to be advantageous over use of human adenovirus serotypes because of low and infrequent pre-existing immunity, in particular the lack of cross-neutralising antibodies, to adenoviruses in the target population. Cross-reaction of the chimpanzee adenoviruses with pre-existing neutralizing antibody responses is only present in 2% of the target population compared with 35% in the case of certain candidate human adenovirus vectors. Pan 6 is less closely related to Pan 5, 7 and 9.

The adenovirus of the invention may be replication defective. This means that it has a reduced ability to replicate in non-complementing cells, compared to the wild type virus. This may be brought about by mutating the virus e.g. by deleting a gene involved in replication, for example deletion of the E1a, E1b, E3 or E4 gene.

The adenoviral vectors in accordance with the present invention may be derived from replication defective adenovirus comprising a functional E1 deletion. Thus the adenoviral vectors according to the invention may be replication defective due to the absence of the ability to express adenoviral E1a and E1b, i.e., are functionally deleted in E1a and E1b. The recombinant adenoviruses may also bear functional deletions in other genes [see, e.g., US 20040241181 (WO 03/000283)] for example, deletions in E3 or E4 genes. The adenovirus delayed early gene E3 may be eliminated from the adenovirus sequence which forms part of the recombinant virus. The function of E3 is not necessary to the production of the recombinant adenovirus particle. Thus, it is unnecessary to replace the function of this gene product in order to package a recombinant adenovirus useful in the invention. In one particular embodiment the recombinant adenoviruses have functionally deleted E1 and E3 genes. The construction of such vectors is described in Roy et al., (2004) Human Gene Therapy 15:519-530.

Recombinant adenoviruses may also be constructed having a functional deletion of the E4 gene, although it may be desirable to retain the E4 ORF6 function. Adenovirus vectors according to the invention may also contain a deletion in the delayed early gene E2a. Deletions may also be made in any of the late genes L1 through to L5 of the adenovirus genome. Similarly deletions in the intermediate genes IX and IVa may be useful.

Other deletions may be made in the other structural or non-structural adenovirus genes. The above deletions may be used individually, i.e. an adenovirus sequence for use in the present invention may contain deletions of E1 only. Alternatively, deletions of entire genes or portions thereof effective to destroy their biological activity may be used in any combination. For example in one exemplary vector, the adenovirus sequences may have deletions of the E1 genes and the E4 gene, or of the E1, E2a and E3 genes, or of the E1 and E3 genes (such as functional deletions in E1a and E1b, and a deletion of at least part of E3), or of the E1, E2a and E4 genes, with or without deletion of E3 and so on. Such deletions may be partial or full deletions of these genes and may be used in combination with other mutations, such as temperature sensitive mutations to achieve a desired result. Adenoviral vectors of use in the present invention include PanAd3 (WO 2010/086189) and ChAd155 (WO 2016/198621).

In another embodiment, the viral vector is a pox virus vector. In a specific embodiment, the poxvirus vector is a vaccinia virus vector, such as a modified vaccinia Ankara virus (MVA) vector. (MVA) vector is replication-deficient in humans and other mammals. It was initially developed to improve the safety of smallpox vaccination by passage of Vaccinia virus over 570 times in chicken embryo fibroblast (CEF) cells, resulting in multiple, fully characterised deletions after which the virus was highly attenuated and replication-deficient in humans and other mammals. The replication defect occurs at a late stage of virion assembly such that viral and recombinant gene expression is unimpaired, making MVA an efficient single round expression vector incapable of causing infection in mammals.

MVA has subsequently been extensively used as a viral vector to induce antigen-specific immunity against transgenes, both in animal models and in humans. A description of MVA can be found in Mayr A, et al. "The smallpox vaccination strain MVA: marker, genetic structure, experience gained with the parenteral vaccination and behavior in organisms with a debilitated defense mechanism. "Abstammung, Eigenschaften and Verwendung des attenuierten Vaccinia-Stammes MVA." Zentralbl Bakteriol B. 1978 December; 167(5-6):375-90 and in Mayr, A., Hochstein-Mintzel, V. & Stickl, H. (1975). Infection 3, 6-14.

In one embodiment, MVA is derived from the virus seed batch 460 MG obtained from the 571st passage of Vaccinia Virus on CEF cells. In a further embodiment, MVA is derived or produced prior to 31 December 1978 and is free of prion contamination.

MVA vectors and methods of production of such vectors are described, for example in U.S. Pat. No. 6,761,893 (WO02/042480); U.S. Pat. Nos. 7,964,395; 7,964,396; US published application no. US 2013/0183335 (WO2012/048817); and US Published Application No. 2015/0209421 (WO2014/019718). Each of the preceding is incorporated herein by reference for the teaching of suitable MVA vectors and methods.

In another embodiment, the viral vector is an Alphavirus vector, such as an alphavirus replicon or other self-replicating RNA vector. Exemplary alphavirus vectors and methods for producing and delivering them suitable for use in the context of the immunogenic combinations disclosed herein are described in, e.g., US20090104226 (WO2006078294); US20110300205 (WO2011005799); US20130195968 (WO 2012/006376); US20130177639 (WO2012006377); WO2013006838; and WO2013006842, each of which are incorporated herein for their disclosure of exemplary self-replicating RNA vectors suitable in the context of the disclosed immunogenic combinations.

Also provided is a method of producing a recombinant viral particle expressing an EBV antigen of the invention, comprising expressing a vector described herein in a host cell. Viral particles can be produced in any suitable cell line in which the viral vector is capable of replication.

Adenoviral vectors can be produced in any suitable cell line in which the virus is capable of replication. In particular, complementing cell lines which provide the factors missing from the viral vector that result in its impaired replication characteristics (such as E1 and/or E4) can be used. Without limitation, such a cell line may be HeLa [ATCC Accession No. CCL 2], A549 [ATCC Accession No. CCL 185], HEK 293, KB [CCL 17], Detroit [e.g., Detroit 510, CCL 72] and WI-38 [CCL 75] cells, among others. These cell lines are all available from the American Type Culture Collection, 10801 University Boulevard, Manassas, Va. 20110-2209. Other suitable parent cell lines may be obtained from other sources, such as PER.C6 cells, as represented by the cells deposited under ECACC no. 96022940 at the European Collection of Animal Cell Cultures (ECACC) at the Centre for Applied Microbiology and Research (CAMR, UK) or Her 96 cells (Crucell).

A particularly suitable complementation cell line is the Procell92 cell line. The Procell92 cell line is based on HEK 293 cells which express adenoviral E1 genes, transfected with the Tet repressor under control of the human phosphoglycerate kinase-1 (PGK) promoter, and the G418-resistance gene (Vitelli et al. PLOS One (2013) 8 (e55435): 1-9). Procell92.S is adapted for growth in suspension conditions and is also useful for producing adenoviral vectors expressing toxic proteins.

Vaccinia vectors can be produced according to methods described in the art. For example, preparation and use of MVA vectors is described in Ourmanov et al., J. Virol. (2009) 83:5388-5400; and Martinon et al. Vaccine (2008) 26:532-545.

Compositions

EBV antigen polypeptides, polynucleotides and vectors described herein may be administered in immunogenic compositions. An immunogenic composition as described herein is a composition comprising one or more recombinant polypeptides, polynucleotides and/or vectors capable of inducing an immune response, for example a humoral (e.g., antibody) and/or cell-mediated (e.g., a cytotoxic T cell) response. following delivery to a mammal, suitably a human.

The immunogenic compositions disclosed herein typically contain one or more pharmaceutically acceptable carriers and/or excipients. Pharmaceutically acceptable carriers and excipients are well known and can be selected by those of skill in the art. The adjective "pharmaceutically acceptable" indicates that the referent is suitable for administration to a subject (e.g., a human or animal subject). Remington's Pharmaceutical Sciences, by E. W. Martin, Mack Publishing Co., Easton, Pa., 15th Edition (1975), describes compositions and formulations (including diluents) suitable for pharmaceutical delivery of therapeutic and/or prophylactic compositions, including immunogenic compositions.

For example, the carrier or excipient can favorably include a buffer. Optionally, the carrier or excipient also contains at least one component that stabilizes solubility and/or stability. Examples of solubilizing/stabilizing agents include detergents, for example, laurel sarcosine and/or tween. Alternative solubilizing/stabilizing agents include arginine, and glass forming polyols (such as sucrose, trehalose and the like). Numerous pharmaceutically acceptable carriers and/or pharmaceutically acceptable excipients are known in the art and are described, e.g., in Remington's Pharmaceutical Sciences, by E. W. Martin, Mack Publishing Co., Easton, Pa., 5th Edition (1975).

Accordingly, suitable excipients and carriers can be selected by those of skill in the art to produce a formulation suitable for delivery to a subject by a selected route of administration.

Suitable excipients include, without limitation: glycerol, Polyethylene glycol (PEG), Sorbitol, Trehalose, N-lauroyl-sarcosine sodium salt, L-proline, Non detergent sulfobetaine, Guanidine hydrochloride, Urea, Trimethylamine oxide, KCl, Ca2+, Mg2+, Mn2+, Zn2+ and other divalent cation related salts, Dithiothreitol, Dithioerytrol, and 13-mercaptoethanol. Other excipients can be detergents (including: Tween80, Tween20, Triton X-00, NP-40, Empigen BB, Octylglucoside, Lauroyl maltoside, Zwittergent 3-08, Zwittergent 3-0, Zwittergent 3-2, Zwittergent 3-4, Zwittergent 3-6, CHAPS, Sodium deoxycholate, Sodium dodecyl sulphate, Cetyltrimethylammonium bromide).

Optionally, an immunogenic composition of the invention may be formulated to contain other components, including, e.g., adjuvants, stabilizers, pH adjusters, preservatives and the like. Examples of suitable adjuvants are provided below under "Adjuvants."

Methods of Use

EBV antigen polypeptides, polynucleotides, vectors described herein may be used in the prevention and/or treatment of EBV infection and EBV-associated diseases, e.g., as a vaccine for induction of an immune response. As used herein, induction of an immune response refers to the ability of a protein to induce a T cell and/or a humoral immune response to the protein.

As used herein, induction of an immune response refers to the ability of a protein, also known as an "antigen" or "immunogen," to induce a T cell and/or a humoral immune response to the protein. For example, an immunogenic composition may induce a memory T and/or B cell population relative to an untreated subject following immunization with the composition, particularly in those embodiments where the composition comprises a nucleic acid comprising a sequence which encodes an EBV antigen polypeptide. In some embodiments, the subject is a vertebrate, such as a mammal e.g. a human or a veterinary mammal.

Immune responses can be measured by methods known in the art, including assays of the induction of proliferation or effector function of the particular lymphocyte type of interest, e.g., B cells, T cells, T cell lines, and T cell clones.

Thus in one embodiment is provided a method of inducing an immune response in a subject comprising administering a polynucleotide, a polypeptide, a vector or an immunogenic composition of the invention to the subject. In one embodiment, the subject is Epstein-Barr virus seronegative. A subject is "seronegative" if the subject has no serological evidence of past or current EBV infection. In another embodiment the subject is Epstein-Barr virus seropositive. A subject is "seropositive" if the subject has serological evidence of past or current EBV infection.

Also provided is a method of treating or preventing an EBV-associated disease in a subject, comprising administering a polynucleotide, a polypeptide, a vector or an immunogenic composition of the invention to the subject. In one embodiment, the EBV-associated disease is an EBV-associated malignancy or an EBV-associated autoimmune disease. EBV-associated diseases, include, for example, multiple sclerosis, rheumatoid arthritis and systemic lupus erythematosus.

Also provided are dosing regimens designed to maximize the immunogenicity of polynucleotides, polypeptides, vectors and immunogenic compositions of the invention. Thus, in one embodiment is provided a method of inducing an immune response in a subject comprising administering two or more doses of a polynucleotide, a polypeptide, a vector and/or an immunogenic composition of the invention to the subject. In certain embodiments the doses are separated by one, two, three, four, five, six, seven, eight, nine, ten, eleven, twelve or more weeks. In another embodiment the doses are separated by one, two, three, four, five, six, seven, eight, nine, ten, eleven, twelve or more months. Alternatively, doses may be separated by one, two, three, four, five, six, seven, eight, nine, ten, eleven, twelve or more years.

In one embodiment is provided a method of inducing an immune response in a subject comprising:
  (a) administering an adenovirus vector comprising a polynucleotide of the invention; and
  (b) administering a vaccinia virus vector comprising a polynucleotide of the invention;
wherein steps (a) and (b) are conducted in either order. In one embodiment the adenovirus vector is ChAd155. In another embodiment the vaccinia virus vector is MVA. In one embodiment, step (b) is carried out one, two, three, four, five, six, seven, eight, nine, ten, eleven, twelve or more weeks after step (a). In one embodiment, step (b) is carried out one, two, three, four, five, six, seven, eight, nine, ten, eleven, twelve or more months after step (a).

In one embodiment is provided a method of treating or preventing an EBV-associated disease in a subject comprising:
(a) administering an adenovirus vector comprising a polynucleotide of the invention; and
(b) administering a vaccinia virus vector comprising a polynucleotide of the invention;

wherein steps (a) and (b) are conducted in either order. In one embodiment the adenovirus vector is ChAd155. In another embodiment the vaccinia virus vector is MVA. In one embodiment, step (b) is carried out one, two, three, four, five, six, seven, eight, nine, ten, eleven, twelve or more weeks after step (a). In one embodiment, step (b) is carried out one, two, three, four, five, six, seven, eight, nine, ten, eleven, twelve or more months after step (a).

Also provided is the use of a polynucleotide, vector, polypeptide, or immunogenic composition of the invention in the manufacture of a medicament for the treatment or prophylaxis of a disease caused by Epstein-Barr Virus infection.

Adjuvants

An "adjuvant" as used herein refers to a composition that enhances the immune response to an immunogen. A composition according to the invention that comprises an adjuvant can be used as a vaccine, e.g. for human subjects. The adjuvant accelerates, prolongs and/or enhances the quality and/or strength of an immune response to an antigen/immunogen in comparison to the administration of the antigen alone, thus, reduces the quantity of antigen/immunogen necessary in any given vaccine, and/or the frequency of injection necessary in order to generate an adequate immune response to the antigen/immunogen of interest.

Examples of adjuvants that may be used in the context of the compositions of the invention include inorganic adjuvants (e.g. inorganic metal salts such as aluminum phosphate or aluminum hydroxide), gel-like precipitates of aluminum hydroxide (alum); $AlPO_4^-$, alhydrogel; bacterial products from the outer membrane of Gram-negative bacteria, in particular monophosphoryl lipid A (MPLA), lipopolysaccharides (LPS), muramyl dipeptides and derivatives thereof; Freund's incomplete adjuvant; liposomes, in particular neutral liposomes, liposomes containing the composition and optionally cytokines; AS01B, AS01E, AS02, non-ionic block copolymers; ISCOMATRIX adjuvant; unmethylated DNA comprising CpG dinucleotides (CpG motif), in particular CpG ODN with a phosphorothioate (PTO) backbone (CpG PTO ODN) or phosphodiester (PO) backbone (CpG PO ODN); synthetic lipopeptide derivatives, in particular $Pam_3Cys$; lipoarabinomannan; peptidoglycan; zymosan; heat shock proteins (HSP), in particular HSP 70; dsRNA and synthetic derivatives thereof, in particular Poly I:poly C; polycationic peptides, in particular poly-L-arginine; taxol; fibronectin; flagellin; imidazoquinoline; cytokines with adjuvant activity, in particular GM-CSF, interleukin-(IL-2, IL-6, IL-7, IL-18, type I and II interferons, in particular interferon-gamma, TNF-alpha; 25-dihydroxyvitamin D3 (calcitriol); and synthetic oligopeptides, in particular MHCII-presented peptides. Non-ionic block polymers containing polyoxyethylene (POE) and polyoxypropylene (POP), such as POE-POP-POE block copolymers may be used as an adjuvant.

Additional examples of adjuvants include inorganic adjuvants (e.g. inorganic metal salts such as aluminium phosphate or aluminium hydroxide), organic adjuvants (e.g. saponins, such as QS21, or squalene), oil-based adjuvants (e.g. Freund's complete adjuvant and Freund's incomplete adjuvant), cytokines (e.g. IL-1β, IL-2, IL-7, IL-12, IL-18, GM-CFS, and INF-γ) particulate adjuvants (e.g. immunostimulatory complexes (ISCOMS), liposomes, biodegradable microspheres, virosomes, bacterial adjuvants (e.g. monophosphoryl lipid A, such as 3-de-O-acylated monophosphoryl lipid A (3D-MPL), or muramyl peptides), synthetic adjuvants (e.g. monophosphoryl lipid A (MPL), in particular 3-de-O-acylated monophosphoryl lipid A (3D-MPL and muramyl peptide analogues, or synthetic lipid A, and synthetic polynucleotides adjuvants, e.g., polyarginine or polylysine.

Saponins are also suitable adjuvants, for example, the saponin Quil A, derived from the bark of the South American tree Quillaja Saponaria Molina, and fractions thereof. Purified fractions of Quil A are also known as immunostimulants, such as squalene, QS21, QS17 and QS7, a non-haemolytic fraction of Quil-A. Combinations of QS21 and polysorbate or cyclodextrin are also suitable.

Another example of an adjuvant is an immunostimulatory oligonucleotide containing unmethylated cytosine-guanosine dinucleotide motifs present in DNA ("CpG"). CpG is known as an adjuvant when administered by both systemic and mucosal routes. When formulated into vaccines, it may be administered in free solution together with free antigen or covalently conjugated to an antigen or formulated with a carrier such as aluminium hydroxide.

Activation of specific receptors can stimulate an immune response. Such receptors are known to the skilled artisan and comprise, for example, cytokine receptors, in particular type I cytokine receptors, type II cytokine receptors, TNF receptors; and a vitamin D receptor acting as transcription factor; and the Toll-like receptors 1 (TLR1), TLR-2, TLR 3, TLR4, TLR5, TLR-6, TLR7, and TLR9. Agonists to such receptors have adjuvant activity, i.e., are immunostimulatory. Other suitable adjuvants include alkyl glucosaminide phosphates (AGPs) or pharmaceutically acceptable salts of AGPs. Some AGPs are TLR4 agonists, and some are TLR4 antagonists. An adjuvant of the composition of the present invention may be one or more Toll-like receptor agonists. In a more preferred embodiment, the adjuvant is a Toll-like receptor 4 agonist. In a particular preferred embodiment, the adjuvant is a Toll-like receptor 9 agonist.

Adjuvants such as those described above may be formulated together with carriers, such as liposomes, oil in water emulsions, and/or metallic salts (including aluminum salts such as aluminum hydroxide). For example, 3D-MPL may be formulated with aluminum hydroxide or oil in water emulsions; QS21 may be formulated with cholesterol containing liposomes, oil in water emulsions or alum; CpG may be formulated with alum or with other cationic carriers.

Combinations of adjuvants may be utilized in the present invention, in particular a combination of a monophosphoryl lipid A and a saponin derivative, more particularly the combination of QS21 and 3D-MPL or a composition where the QS21 is quenched in cholesterol-containing liposomes (DQ). Alternatively, a combination of CpG plus a saponin such as QS21 is an adjuvant suitable for use in the present invention, as is a potent adjuvant formulation involving QS21, 3D-MPL and tocopherol in an oil in water emulsion. Saponin adjuvants may be formulated in a liposome and combined with an immunostimulatory oligonucleotide. Thus, suitable adjuvant systems include, for example, a combination of monophosphoryl lipid A, preferably 3D-MPL, together with an aluminium salt. A further exemplary adjuvant comprises QS21 and/or MPL and/or CpG. QS21 may be quenched in cholesterol-containing liposomes.

The fusion of the MHC class II invariant chain (also known as CD74) to an antigen which is comprised by an expression system used for vaccination increases the immune response against said antigen, if it is administered with a viral vector, e.g. an adenovirus. Accordingly, in one embodiment of the invention, the immunogenic transgene may be co-expressed with invariant chain in a recombinant ChAd155 viral vector.

In another embodiment, the invention provides the use of the capsid of ChAd155 (optionally an intact or recombinant viral particle or an empty capsid is used) to induce an immunomodulatory response, or to enhance or adjuvant a cytotoxic T cell response to another active agent by delivering a ChAd155 capsid to a subject. The ChAd155 capsid can be delivered alone or in a combination regimen with an active agent to enhance the immune response thereto. Advantageously, the desired effect can be accomplished without infecting the host with an adenovirus.

Sequence Identity

Identity with respect to a sequence is defined herein as the percentage of amino acid residues in the candidate sequence that are identical with the reference amino acid sequence after aligning the sequences and introducing gaps, if necessary, to achieve the maximum percent sequence identity, and not considering any conservative substitutions as part of the sequence identity.

Sequence identity can be determined by standard methods that are commonly used to compare the similarity in position of the amino acids of two polypeptides. Using a computer program such as BLAST or FASTA, two polypeptides are aligned for optimal matching of their respective amino acids (either along the full length of one or both sequences or along a pre-determined portion of one or both sequences). The programs provide a default opening penalty and a default gap penalty, and a scoring matrix such as PAM 250 (a standard scoring matrix can be used in conjunction with the computer program. For example, the percent identity can then be calculated as the total number of identical matches multiplied by 100 and then divided by the sum of the length of the longer sequence within the matched span and the number of gaps introduced into the shorter sequences in order to align the two sequences.

Where the present disclosure refers to a sequence by reference to a UniProt or Genbank accession code, the sequence referred to is the current version as of the filing date of the present application.

The skilled person will recognise that individual substitutions, deletions or additions to a protein which alters, adds or deletes a single amino acid or a small percentage of amino acids is an "immunogenic derivative" where the alteration(s) results in the substitution of an amino acid with a functionally similar amino acid or the substitution/deletion/addition of residues which do not substantially impact the immunogenic function.

Conservative substitution tables providing functionally similar amino acids are well known in the art. In general, such conservative substitutions will fall within one of the amino-acid groupings specified below, though in some circumstances other substitutions may be possible without substantially affecting the immunogenic properties of the antigen. The following eight groups each contain amino acids that are typically conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M).

Suitably such substitutions do not occur in the region of an epitope, and do not therefore have a significant impact on the immunogenic properties of the antigen.

Immunogenic derivatives may also include those wherein additional amino acids are inserted compared to the reference sequence. Suitably such insertions do not occur in the region of an epitope, and do not therefore have a significant impact on the immunogenic properties of the antigen. One example of insertions includes a short stretch of histidine residues (e.g. 2-6 residues) to aid expression and/or purification of the antigen in question.

Immunogenic derivatives include those wherein amino acids have been deleted compared to the reference sequence. Suitably such deletions do not occur in the region of an epitope, and do not therefore have a significant impact on the immunogenic properties of the antigen.

The skilled person will recognise that a particular immunogenic derivative may comprise substitutions, deletions and additions (or any combination thereof).

General

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. The term "plurality" refers to two or more. Additionally, numerical limitations given with respect to concentrations or levels of a substance, such as solution component concentrations or ratios thereof, and reaction conditions such as temperatures, pressures and cycle times are intended to be approximate. The term "about" used herein is intended to mean the amount ±10%.

The term "comprises" means "includes." Thus, unless the context requires otherwise, the word "comprises," and variations such as "comprise" and "comprising" will be understood to imply the inclusion of a stated compound or composition (e.g., nucleic acid, polypeptide, antigen) or step, or group of compounds or steps, but not to the exclusion of any other compounds, composition, steps, or groups thereof. The abbreviation, "e.g." is derived from the Latin exempli gratia, and is used herein to indicate a non-limiting example. Thus, the abbreviation "e.g." is synonymous with the term "for example."

The invention will be further described by reference to the following, non-limiting, examples and figures.

EXAMPLES

Example 1: Antigen Design a. EBV Antigen Design

Polyvalent Epstein-Barr Virus antigen constructs were rationally designed with the following design goals in mind:
1) to broadly target EBV antigens that are expressed in EBV-associated multiple sclerosis (EBV-MS) by including multiple latent stage antigens in the design, and optionally including lytic stage antigens;

2) to reduce the risk of oncogenesis and immune interference by exclusion of known problematic regions, fragmenting and shuffling EBV protein antigens in the polyvalent antigen construct;

3) to focus the induced immune response on EBV-specific T-cell activation by including T-cell epitopes in the polyvalent antigen constructs; and 4) to exclude the presence of unwanted anti-self neo-epitopes in the final antigen sequence.

Two polyvalent EBV antigen constructs meeting these criteria were designed. The first polyvalent antigen construct (EBV-L; FIG. 2A) includes immunogenic fragments of latent stage EBV proteins LMP1, LMP2, EBNA1 and EBNA3A. A second construct (EBV-LLy; FIG. 2B) contains the same latent antigen fragments as EBV-L, and also includes an immunogenic fragment of the EBV lytic protein ZEBRA. The EBV latent proteins selected for inclusion in the antigen constructs have been reported to be expressed by B cells in post-mortem brain tissue of multiple sclerosis patients (Serafini et al., J. Exp. Medicine (2007) 204(12): 2899; Serafini et al., J. Neuropathol. Exp. Neurol. (2010) 69(7):677. Inclusion of the lytic antigen ZEBRA, a key regulator of the EBV switch from latency to lytic phase, is aimed at controlling the reactivation of the virus and limiting further amplification and spread of EBV.

Figure 1:
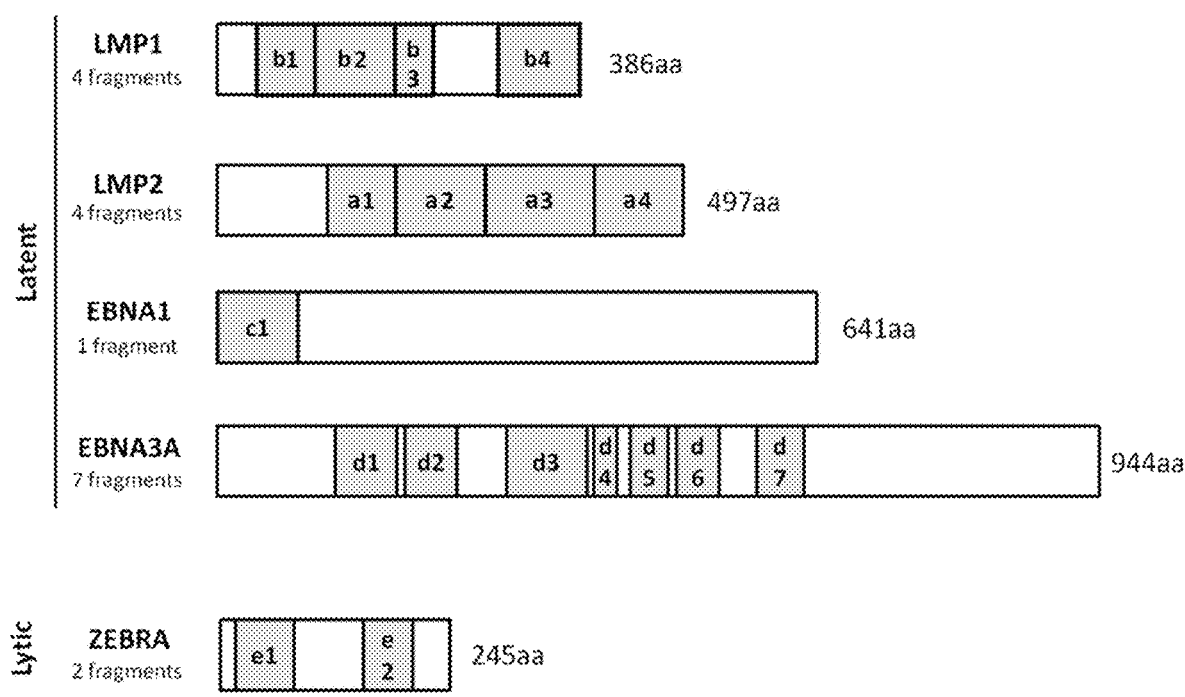
FIG. 1: Schematic representation of EBV latent (LMP1, LMP2, EBNA1 and EBNA3A) and lytic (ZEBRA) proteins. Numbered regions indicate immunogenic fragments used to construct polyvalent EBV antigen polypeptides. Alphanumeric identifiers (e.g., a1, a2, b1, b2) correspond to the fragments represented in polyvalent constructs shown in FIGS. 2A and 2B.

Full length EBV proteins have the potential to transform immune cells. Therefore, to improve the safety of the antigen constructs, problematic regions were excluded and only remaining fragments of the EBV proteins were selected for the construct designs. FIG. 1 illustrates the location of the selected immunogenic fragments in each of the EBV proteins. As illustrated in FIGS. 2A and 2B, the selected fragments were shuffled to produce a polyprotein comprising 16 (EBV-L) or 18 (EBV-LLy) immunogenic fragments, assembled so that fragments derived from the same EBV protein are not adjacent to each other.

Finally, to reduce the risk of unwanted junctional epitopes formed by joining two immunogenic fragments together, a bioinformatics screen was conducted to identify potential anti-self neoepitopes at the junctional areas of candidate antigen constructs. Briefly, sixteen amino acid-long peptides spanning the border (junction) region between each pair of two consecutive antigen fragments were extracted from the vaccine polypeptide sequence (8 amino acids from each antigen fragment). The length of 16 amino acids of the junction region guarantees that each 9mer sequence within the junction region contains amino acids from both antigens. For each 16mer junction peptide, all 9mer peptides were then compared with a collection of 9mer peptides representing the complete human proteome (generated from the NCBI RefSeq peptide database). In no case was a 9mer peptide from a junction region of the vaccine polypeptide sequence found to be present in a human protein.

b. CalHV3 Antigen Design

CalHV3 is a gamma herpesvirus isolated from common marmosets (*Callithrix jacchus*). Based on similarities in sequence and structure, viral reproduction cycle and pathogenesis, CalHV3 is considered to be the marmoset equivalent of human EBV. See, e.g., Cho et al., PNAS 98(3):1224-1229 (2001). CalHV3 is acquired early in life and is reported to be highly prevalent in natural as well as captive marmoset colonies.

To evaluate the capacity of a similar vaccine to re-expand functional T cell responses to latent and lytic viral antigens in gamma-herpesvirus latently infected individuals in the marmoset model, orthologous CalHV3 antigen constructs weresss developed. Briefly, a CalHV3 latent antigen construct (CalHV3-L, illustrated in FIG. 4A) was constructed from immunogenic fragments of proteins C1 (SEQ ID NO: 28), C7 (SEQ ID NO: 32) and ORF39 (SEQ ID NO: 36), which are the CalHV3 orthologs of EBV LMP1, LMP2 and EBNA1, respectively. As in the EBV-L antigen construct, antigenic regions included in CalHV3-L construct were fragmented and shuffled so that fragments from the same CalHV3 protein are not adjacent to each other. The amino acid sequence of the final CalHV3-L antigen construct is shown in SEQ ID NO: 44 (encoded by the polynucleotide shown in SEQ ID NO: 45).

A CalHV3 Latent/Lytic antigen construct (CalHV3-LLy, illustrated in FIG. 4B) was also constructed. In addition to containing fragments of the latent proteins C1, C7 and ORF39, CalHV3-LLy also contains fragments of ORF43, the CalHV3 ortholog of the EBV ZEBRA protein. The amino acid sequence of the final CalHV3-LLy antigen construct is shown in SEQ ID NO: 46 (encoded by the polynucleotide shown in SEQ ID NO: 47).

Finally, a genetically-adjuvanted version of CalHV3-LLy (Ii-CalHV3-LLy) was constructed by fusing a marmoset MHC class II-associated invariant chain polypeptide (SEQ ID NO: 43) to the N-terminus of CalHV3-LLy. The amino acid sequence of the final Ii-CalHV3-LLy antigen construct is shown in SEQ ID NO: 48 (encoded by the polynucleotide shown in SEQ ID NO: 49).

Example 2: Vector Construction

Polynucleotides encoding EBV-L (SEQ ID NO: 25) and EBV-LLy (SEQ ID NO: 27) were cloned into plasmid pvjTetOhCMV-bghpolyA, containing a tetOhCMV promoter and bovine growth hormone poly-adenylation signal (BGH pA), according to methods described in WO2016/198621. The EBV-L and EBV-LLy expression cassettes were then transferred into a ChAd155 vector backbone by homologous recombination in *E. coli* BJ5183 competent cells to produce the pChAd155 (ΔE1, ΔE4 Ad5E4 orf6) TetO hCMV-EBV-L (and EBV-LLy) vectors. The nucleic acid sequence of vector pChAd155 (ΔE1, ΔE4_Ad5E4 orf6) TetO hCMV-EBV-L is shown in SEQ ID NO: 50. The antigen-encoding region is at nucleotides 1348-4806 of SEQ ID NO: 50. The nucleic acid sequence of vector pChAd155 (ΔE1, ΔE3, ΔE4_Ad5E4 orf6) TetO hCMV-EBV-LLy expression vector is shown in SEQ ID NO: 51. The antigen-encoding region is at nucleotides 1348-5157 of SEQ ID NO: 51. ChAd155-EBV vector construction was confirmed by transgene sequencing and restriction analysis. The same methods can be used to prepare EBV adenoviral vectors based on alternative modified ChAd155 backbones as described, for example, in WO2016/198621.

The same methods were followed to prepare vectors ChAd155-CalHV3-L, ChAd155-CalHV3-LLy, and ChAd155-Ii-CalHV3-LLy (encoding CalHV3 antigens CalHV3-L, CalHV3-LLy, and Ii-CalHV3-LLy, respectively). The nucleic acid sequence of vector pChAd155 (ΔE1, ΔE4_Ad5E4 orf6) TetO hCMV-CalHV3-L is shown in SEQ ID NO: 52 (antigen-encoding region at nucleotides 1348-4482). The nucleic acid sequence of vector pChAd155 (ΔE1, ΔE3, ΔE4_Ad5E4 orf6) TetO hCMV-CalHV3-LLy is shown in SEQ ID NO: 53 (antigen-encoding region at nucleotides 1348-5238). The nucleic acid sequence of vector pChAd155 (AD, ΔE3, ΔE4_Ad5E4 orf6) TetO hCMV-Ii-CalHV3-LLy is shown in SEQ ID NO: 54 (antigen-encoding region at nucleotides 1348-5883).

MVA vectors encoding the EBV-LLy and CalHV3-LLy antigen constructs were also prepared, according to methods known in the art. See, e.g., Ourmanov et al., J. Virol. (2009) 83:5388-5400; and Martinon et al. Vaccine (2008) 26:532-545.

Example 3: Viral Particle Production

ChAd155 EBV-L and ChAD155 EBV-LLy vectors were linearized with the restriction endonuclease PmeI and transfected into a HEK293-derived cell line (Procell92.S), as described in Vitelli et al., PLOS One (2013) 8(e55435):1-9. These cells are genetically modified to constitutively express the TetO repressor in order to repress transgene expression during virus generation. Viral amplification was performed at small scale (shake flask) and ChAd155-EBV viral particles were purified on double CsCl gradient from 1 liter scale suspension culture. ChAd155-EBV viral particle titers were determined by QPCR targeting the tetOhCMV promoter. The same methods were followed to prepare viral particles from ChAd155-CalHV3-L, ChAd155-CalHV3-LLy, and ChAd155-II-CalHV3-LLy.

Recombinant MVA expressing the EBV-LLy and CalHV3-LLy antigen constructs were obtained using standard methods. Briefly, primary cell cultures of chicken embryo fibroblast (CEF) cells at a defined cell density were infected with MVA-EBV and MVA-CalHV3 viral seed at a defined multiplicity of infection. The MVA-EBV and MVA-CalHV3 virus harvest was purified by fractional gradient centrifugation.

Example 4: Immunogenicity of ChAd155-EBV and ChAd155-CalHV3 Antigens in Mice a. ChAd155-EBV The immunogenicity of ChAd155-EBV viral particles produced from vectors expressing latent or latent+lytic antigens was evaluated in mice using the experimental design shown in Table 1. Briefly, CB6F1 mice (6 per group) were administered a single dose ($10^6$, $10^7$ or $10^8$ viral particles, intramuscularly) of vectors ChAd155-EBV-L or ChAd155-EBV-LLy.

Three weeks after immunization, splenocytes were isolated and assayed for T-cell responses to EBV antigens according to a standard IFNγ ELISpot assay. Briefly, splenocytes from immunized animals were stimulated with overlapping 15mer peptides arranged in 5 pools, each covering the immunogenic fragments from each of the EBV proteins included in the vaccine (LMP1, LMP2, EBNA1, EBNA3A, ZEBRA; n=19 to 84 single peptides/pool). A sixth pool of 16mer peptides (EJ, n=18 peptides) covering each single junction between fragments, and DMSO (the peptide diluent) were also used as stimulants to monitor response to junctional epitopes and as negative control, respectively. T-cell activation was detected by enumerating IFNγ-secreting vaccine-elicited T cells by enzyme-linked immunoSpot (ELISPOT).

TABLE 1

| Group | Vector | n | dose (vp) |
|---|---|---|---|
| 1 | ChAd155 EBV-L | 6 | $10^8$ |
| 2 | ChAd155 EBV-L | 6 | $10^7$ |
| 3 | ChAd155 EBV-L | 6 | $10^6$ |
| 4 | ChAd155 EBV-LLy | 6 | $10^8$ |

TABLE 1-continued

| Group | Vector | n | dose (vp) |
|---|---|---|---|
| 5 | ChAd155 EBV-LLy | 6 | $10^7$ |
| 6 | ChAd155 EBV-LLy | 6 | $10^6$ |

The results are shown in FIG. 5A. Both ChAd155-EBV-L and ChAd155-EBV-LLy elicited T-cells secreting IFNγ in vaccinated mice in a dose-dependent manner. T-cell responses were detected to each of the EBV latent antigens (LMP1, LMP2, EBNA1 and EBNA3A) in both EBV-L and EBV-LLy immunized mice. However, T-cell responses to the EBV lytic protein, ZEBRA, were only detected in EBV-LLy immunized mice. No responses were detected to the EBV junctional peptides (Ej) or to DMSO negative control.

The results indicate that viral particles produced from ChAd155-EBV-L and ChAd155-EBV-LLy vectors are capable of eliciting antigen specific T-cell responses to the immunogenic fragments contained within the antigen constructs. Furthermore, the primary immune response to EBV-L and EBV-LLy antigen constructs is not directed to junctional epitopes.

b. ChAd155-CalHV3

The immunogenicity of ChAd155-CalHV3 viral particles was assessed following the same methods described above for ChAd155-EBV viral particles. Antigen stimulation of splenocytes 3 weeks post vaccination was carried out with overlapping 15mer peptides arranged in 4 pools, each covering the immunogenic fragments included in the vaccine (C1, C7, ORF39, ORF43, n=58 to 96 single peptides/pool). A fifth pool of 16mer peptides (CJ, n=12 peptides) covering each single junction between fragments, and DMSO (the peptide diluent) were also used as stimulants to monitor response to junctional epitopes and as negative control, respectively. The experimental design is summarized in Table 2.

TABLE 2

| Group | Vector | n | dose (vp) |
|---|---|---|---|
| 1 | ChAd155 CalHV3-L | 6 | $10^8$ |
| 2 | ChAd155 CalHV3-L | 6 | $10^7$ |
| 3 | ChAd155 CalHV3-L | 6 | $10^6$ |
| 4 | ChAd155 CalHV3-LLy | 6 | $10^8$ |
| 5 | ChAd155 CalHV3-LLy | 6 | $10^7$ |
| 6 | ChAd155 CalHV3-LLy | 6 | $10^6$ |

The results are shown in FIG. 5B. Both ChAd155-CalHV3-L and ChAd155-CalHV3-LLy elicited T cells secreting IFNγ in vaccinated mice in a dose-dependent manner. T-cell responses to peptide pools covering CalHV3 latent antigens C1, C7 and ORF39 were detected in both CalHV3-L and CalHV3-LLy immunized mice. However, T-cell responses to the CalHV3 lytic protein, ORF43, were only detected in CalHV3-LLy immunized mice. No responses were detected to the CalHV3 junctional peptides (Cj) or to the negative control, DMSO.

The results indicate that viral particles produced from ChAd155-EBV-L and ChAd155-EBV-LLy vectors are capable of eliciting antigen specific T-cell responses to the immunogenic fragments contained within the antigen constructs. Furthermore, the primary immune response to CalHV3-L and CalHV3-LLy antigen constructs is not directed to junctional epitopes.

Example 5: Effect of Prime-Boost in Mice a. EBV-LLy Prime-Boost

The ability of a second dose of EBV-LLy antigen to boost the immune response of a first dose of EBV-LLy antigen was evaluated using the experimental design summarized in Table 3. Briefly, groups of CB6F1 mice (n=5/group) were immunized intramuscularly on day 0 with $5 \times 10^7$ viral particles of Chad155-EBV-LLy. On day 21 (week 3), Group 2 received a second immunization with $10^7$ plaque forming units (PFU) of MVA-EBV-LLy. Control mice received either no additional immunizations (Group 3: "no boost") or a boost immunization with an MVA vector encoding an EBV unrelated antigen (Group 1: MVA-unrelated).

TABLE 3

| Group | Prime (w0) | Boost (w3) | n | dose (vp or pfu) |
|---|---|---|---|---|
| 1 | ChAd155 EBV-LLy | MVA-unrelated | 5 | $10^7$ vp/$10^7$ pfu |
| 2 | ChAd155 EBV-LLy | MVA EBV-LLy | 5 | $10^7$ vp/$10^7$ pfu |
| 3 | ChAd155 EBV-LLy | no boost | 5 | $10^7$ vp |

Four weeks after the first immunization, splenocytes were isolated from the mice and antigen-specific T-cell responses were assessed using the methods described in Example 4.

As shown in FIGS. 6A and 6B, immunization with ChAd155-EBV-LLy followed by a boost immunization with MVA-EBV-LLy produced a significant increase in EBV-specific interferon gamma release, as compared to unboosted mice or mice receiving a "boost" injection of an unrelated antigen. FIG. 6A presents the cumulative T-cell responses to all antigens (LMP1, LMP2, EBNA1, EBNA3A and ZEBRA), and FIG. 6B shows the responses to individual antigens.

b. CalHV3-LLy Prime-Boost

The ability to boost immune responses to CalHV3 antigens was assessed using the experimental design summarized in Table 4. Briefly, groups of CB6F1 mice (n=6/group) were immunized intramuscularly on day 0 with $5 \times 10^7$ viral particles of Chad155-CalHV3-LLy. On day 42 (week 6), Group 4 received a second immunization with same ChAd155-CalHV3-LLy antigen construct, while Group 3 received a boost immunization with MVA-CalHV3-LLy. Control mice received either no boost (Group 1) or a boost with an MVA encoding for a CalHV3-unrelated antigen (MVA-unrelated).

TABLE 4

| Group | Prime (w0) | Boost (w6) | n | dose (vp or pfu) |
|---|---|---|---|---|
| 1 | ChAd155 CalHV3-LLy | no boost | 6 | $5 \times 10^7$ vp |
| 2 | ChAd155 CalHV3-LLy | MVA-unrelated | 6 | $5 \times 10^7$ vp/$10^7$ pfu |
| 3 | ChAd155 CalHV3-LLy | MVA CalHV3-LLy | 6 | $5 \times 10^7$ vp/$10^7$ pfu |
| 4 | ChAd155 CalHV3-LLy | ChAd155 CalHV3-LLy | 6 | $5 \times 10^7$ vp/ $5 \times 10^7$ vp |

Seven weeks after the first immunization, splenocytes were isolated from the mice and antigen-specific T-cell responses were assessed using the methods described in Example 4.

As shown in FIG. 7, immunization with ChAd155-CalHV3-LLy followed by a boost immunization with either the same antigen construct (ChAd155-CalHV3) or MVA-CalHV3-LLy produced a significant increase in CalHV3-specific interferon gamma release at week 7, as compared to unboosted mice or mice receiving a "boost" injection of an unrelated antigen.

These results demonstrate the ability to enhance the immune response to EBV and CalHV3 antigen constructs using prime-boost regimens.

Example 6: Invariant Chain-CalHV3-LLy Fusion Proteins

Fusing antigens to the major histocompatibility complex (MHC) class II-associated invariant chain (Ii) has been reported to enhance antigen-specific T-cell responses. See, e.g., Capone et al., Mol Ther. 2014 May; 22(5): 1039-1047. Therefore, the immunogenicity of viral particles expressing the marmoset invariant chain (Ii) fused to the N-terminus of the CalHV3-LLy antigen polypeptide was assessed in CB6F1 mice according to the study design outlined in Table 5. Antigen-specific T-cell responses were assessed using the IFNγ assays described in Example 4.

TABLE 5

| Group | Prime (w0) | n | dose (vp) |
|---|---|---|---|
| 1 | ChAd155 CalHV3-LLy | 6 | $5 \times 10^7$ vp |
| 2 | ChAd155 CalHV3-LLy | 6 | $5 \times 10^6$ vp |
| 3 | ChAd155 marmoset Ii CalHV3-LLy | 6 | $5 \times 10^7$ vp |
| 4 | ChAd155 marmoset Ii CalHV3-LLy | 6 | $5 \times 10^6$ vp |

FIG. 8 summarizes cumulative T-cell responses to all CalHV3-LLy antigens (C1, C7, ORF39 and ORF43) observed two weeks after immunization. At the lower dose of antigen ($5 \times 10^6$ viral particles), ChAd155-II-CalHV3-LLy elicited significantly greater IFNγ release in immunized mice than ChAd155-CalHV3-LLy. No differences were observed at the higher antigen dose tested ($5 \times 10^7$ viral particles).

These results indicate that fusion of the CalHV3-LLy antigen polypeptide to an MHC class II-associated invariant chain polypeptide enhances the T-cell immune response to CalHV3 latent and lytic antigens.

Example 7: Immunogenicity of CalHV3 Antigens in Non-Human Primates

The immunogenicity of CalHV3 antigen constructs was evaluated in CalHV3 seropositive marmosets (*Callithrix jacchus*), a genus of New World primates. CalHV3 infection is known to be prevalent in marmosets. See, e.g., Cho et al., PNAS 98(3):1224-1229 (2001). Due to the structural and pathological similarities between CalHV3 and EBV, CalHV3-positive marmosets can serve as a valuable model of human EBV infection and pathology. Id.

Animals were immunized using a ChAd155 prime/MVA boost vaccination schedule. Briefly, a group composed of four adult animals (3 males and one female) received a prime immunization of ChAd155-CalHV3-LLy ($5 \times 10^{10}$ vp) on day 0 and a boost immunization of MVA-CalHV3-LLy ($2\times10^8$) on day 56 (week 8). Blood samples were drawn 2 weeks before prime injections, 3 weeks after prime injections, and 1, 4 and 7 weeks after boost injections. Antigen-specific T-cell responses in peripheral blood mononuclear cells (PBMCs) were assessed using the methods described in Example 4.

FIG. 9 shows cumulative T-cell responses in individual animals to all CalHV3-LLy antigens (01, C7, ORF39 and ORF43) observed at baseline (w0), at three weeks post-prime (w3 pp); and at one, four and seven weeks post-boost (w1, w4, w7 pb). Prior to immunizations, animals exhibited baseline CalHV3-specific T-cell responses, consistent with the fact that the animals are virus carriers. Three weeks after ChAd155-CalHV3-LLy immunization, animals exhibited significant expansion of pre-existing CalHV3-specific T cell responses. T cell responses continued to be elevated 1 week post-boost with MVA-CalHV3-LLy, and contracted in the following 2 months, still remaining above baseline levels in most animals. As shown in FIG. 10, the enhanced T-cell responses to CalHV3-LLy was sustained and was polyspecific (i.e., to C1, C7, ORF39 and ORF43).

These results indicate that ChAd155 and MVA vectors encoding CalHV3-LLy antigens can efficiently re-expand and sustain pre-existing antigen-specific T-cell responses in CalHV3-positive marmosets, and that circulating T cells elicited by gamma herpesviruses are not functionally impaired or exhausted.

Example 8: Recognition of EBV Fragments Encoded by ChAd155 and MVA Latent+Lytic EBV Vaccines by Human PBMC To validate the selection of EBV latent (EBNA1, EBNA3A, LMP1 and LMP2) and lytic (ZEBRA) antigenic fragments included in the vaccine, T cell responses to the corresponding peptide pools were measured in otherwise healthy human EBV carriers.

Briefly, frozen peripheral blood mononuclear cells (PBMC) from 8 healthy human donors were thawed and assayed for T-cell responses to EBV antigens according to a standard IFNγ ELISpot assay. PBMC were plated in triplicates at $2\times10^5$ cells/well and were stimulated overnight with overlapping 15-mer peptides arranged in 5 pools, each covering the immunogenic fragments from each of the EBV proteins included in the vaccine (LMP1, LMP2, EBNA1, EBNA3A, ZEBRA; n=19 to 84 single peptides/pool). Stimulation with DMSO (the peptide diluent) was used as negative control. T-cell activation was detected by enumerating IFNγ-secreting T cells by enzyme-linked immunoSpot (ELISPOT).

As shown in FIG. 11, the results indicate that antigen specific T-cell responses to the immunogenic fragments contained within the EBV Lly antigen constructs can be readily detected in healthy EBV carriers, with EBNA3A and ZEBRA being the most frequently recognized and eliciting the highest responses, consistent with previous reports (e.g., Taylor et al. Ann. Rev. Immunol. 33:787-821, 2015).

We claim:

1. A nucleic acid comprising:
   (A) a polynucleotide encoding a polypeptide, the polypeptide comprising:
      (a) an Epstein-Barr Virus (EBV) latent membrane protein 1 (LMP1) fragment, the EBV LMP1 fragment comprising one or more of SEQ ID NOs: 2-5;
      (b) an EBV latent membrane protein 2 (LMP2) fragment, the EBV LMP2 fragment comprising one or more of SEQ ID NOs: 7-10;
      (c) an EBV nuclear antigen 1 (EBNA1) fragment, the EBNA1 fragment comprising at least 8 amino acids of SEQ ID NO: 11;
      (d) an EBV nuclear antigen 3A (EBNA3A) fragment, the EBNA3A fragment comprising one or more of SEQ ID NOs: 14-20; or
      (e) an EBV ZEBRA fragment, the EBV ZEBRA fragment comprising one or both of SEQ ID NO: 22 or SEQ ID NO: 23;
      wherein the polypeptide is at least 80% identical to SEQ ID NO: 24 or SEQ ID NO: 26; and
   (B) a sequence that is capable of directing expression of the polypeptide in a host cell;
   wherein the polynucleotide is operatively linked to the sequence that is capable of directing expression of said polypeptide in the host cell.

2. The nucleic acid of claim 1, wherein the polypeptide comprises:
   (a) two or more of the EBV LMP1 fragments;
   (b) two or more of the EBV LMP2 fragments;
   (c) two or more of the EBNA1 fragments;
   (d) two or more of the EBNA3A fragments; or
   (e) SEQ ID NOs: 22 and 23.

3. The nucleic acid of claim 2, wherein the polypeptide comprises:
   (i) the two or more of the EBV LMP1 fragments, the two or more of the EBV LMP1 fragments being not adjacent to each other;
   (ii) the two or more of the EBV LMP2 fragments, the two or more of the EBV LMP1 fragments being not adjacent to each other;
   (iii) the two or more of EBNA3A fragments, the two or more EBNA3A fragments being not adjacent to each other; and
   (iv) SEQ ID NO: 22 and SEQ ID NO: 23, SEQ ID NO: 22 being not adjacent to SEQ ID NO: 23; and
   wherein the polypeptide is at least 80% identical to SEQ ID NO: 26.

4. The nucleic acid of claim 1, wherein the polypeptide comprises:
   (a) two or more of the EBV LMP1 fragments, the two or more of the EBV LMP1 fragments being not adjacent to each other;
   (b) two or more of the EBV LMP2 fragments, the two or more of the EBV LMP2 fragments being not adjacent to each other;
   (c) the EBNA1 fragment, the EBNA1 fragment consisting of SEQ ID NO: 12; and
   (d) two or more of the EBNA3A fragments, the two or more of the EBNA3A fragments being not adjacent to each other.

5. The nucleic acid of claim 1, wherein the polypeptide comprises:
   (a) a first EBV LMP1 fragment consisting of SEQ ID NO: 2;
   (b) a second EBV LMP1 fragment consisting of SEQ ID NO: 3;

(c) a third EBV LMP1 fragment consisting of SEQ ID NO: 4;
(d) a fourth EBV LMP1 fragment consisting of SEQ ID NO: 5;
(e) a first EBV LMP2 fragment consisting of SEQ ID NO: 7;
(f) a second EBV LMP2 fragment consisting of SEQ ID NO: 8;
(g) a third EBV LMP2 fragment consisting of SEQ ID NO: 9;
(h) a fourth EBV LMP2 fragment consisting of SEQ ID NO: 10;
(i) a first EBNA1 fragment consisting of SEQ ID NO: 12;
(j) a first EBNA3A fragment consisting of SEQ ID NO: 14;
(k) a second EBNA3A fragment consisting of SEQ ID NO: 15;
(l) a third EBNA3A fragment consisting of SEQ ID NO: 16;
(m) a fourth EBNA3A fragment consisting of SEQ ID NO: 17;
(n) a fifth EBNA3A fragment consisting of SEQ ID NO: 18;
(o) a sixth EBNA3A fragment consisting of SEQ ID NO: 19;
(p) a seventh EBNA3A fragment consisting of SEQ ID NO: 20;
(q) a first EBV ZEBRA fragment consisting of SEQ ID NO: 22; and
(r) a second EBV ZEBRA fragment consisting of SEQ ID NO: 23;
wherein:
  the polypeptide is at least 80% identical to SEQ ID NO: 26;
  the first, second, third, and fourth EBV LMP1 fragments are not adjacent to each other;
  the first, second, third, and fourth EBV LMP2 fragments are not adjacent to each other;
  the first, second, third, fourth, fifth, sixth, and seventh EBNA3A fragments are not adjacent to each other; and
  the first and second EBV ZEBRA fragments are not adjacent to each other.

6. The nucleic acid of claim 1, wherein the polypeptide is at least 85% identical to SEQ ID NO: 24 or SEQ ID NO: 26.

7. A vector comprising the nucleic acid of claim 1.

8. The nucleic acid of claim 1, wherein the polypeptide is at least 90% identical to SEQ ID NO: 24 or SEQ ID NO: 26.

9. The nucleic acid of claim 1, wherein the polypeptide comprises the EBNA1 fragment; and wherein the EBNA1 fragment comprises at least 50 amino acids of SEQ ID NO: 11.

10. The nucleic acid of claim 1, wherein the polypeptide comprises the EBNA1 fragment; and wherein the EBNA1 fragment comprises at least 80 amino acids of SEQ ID NO: 11.

11. A method of producing a recombinant viral particle, the recombinant viral particle comprising the vector of claim 7; the recombinant viral particle being capable of expressing the polypeptide in a cell that is infected with the recombinant viral particle; the method comprising expressing the vector in a host cell.

12. A method of inducing an immune response against EBV in a subject; the immune response against EBV in the subject being (a) a humoral response, (b) a cell-mediated response, or (c) the humoral response and the cell-mediated response; the method comprising administering a recombinant viral particle to the subject; the recombinant viral particle comprising the vector of claim 7; the recombinant viral particle being capable of expressing the polypeptide in the subject.

13. The method of claim 12, wherein the subject is EBV seronegative.

14. The method of claim 12, wherein the subject is EBV seropositive.

15. A method of treating or preventing an EBV-associated disease in a subject, the method comprising administering a recombinant viral particle to the subject; the recombinant viral particle comprising the polynucleotide of claim 1; and the recombinant viral particle being capable of expressing the polypeptide in the subject.

16. The method of claim 15, wherein the EBV-associated disease is an EBV-associated autoimmune disease or an EBV-associated malignancy.

17. The method of claim 15, wherein the EBV-associated disease is multiple sclerosis, rheumatoid arthritis, or systemic lupus erythematosus.

18. The nucleic acid of claim 1, wherein the polypeptide is at least 95% identical to SEQ ID NO: 24 or SEQ ID NO: 26.

19. The nucleic acid of claim 1, wherein the polypeptide is at least 99% identical to SEQ ID NO: 24 or SEQ ID NO: 26.

20. A nucleic acid comprising:
(A) a polynucleotide encoding a polypeptide, the polypeptide comprising SEQ ID NO: 24 or SEQ ID NO: 26; and
(B) a sequence that is capable of directing expression of the polypeptide in a host cell;
wherein the polynucleotide is operatively linked to the sequence that is capable of directing expression of said polypeptide in the host cell.

21. The nucleic acid of claim 1, wherein the polypeptide comprises:
(a) the EBV LMP1 fragment;
(b) the EBV LMP2 fragment;
(c) the EBNA1 fragment; and
(d) the EBNA3A fragment.

22. The nucleic acid of claim 1, wherein the polypeptide comprises:
(a) a first EBV LMP1 fragment consisting of SEQ ID NO: 2;
(b) a second EBV LMP1 fragment consisting of SEQ ID NO: 3;
(c) a third EBV LMP1 fragment consisting of SEQ ID NO: 4;
(d) a fourth EBV LMP1 fragment consisting of SEQ ID NO: 5;
(e) a first EBV LMP2 fragment consisting of SEQ ID NO: 7;
(f) a second EBV LMP2 fragment consisting of SEQ ID NO: 8;
(g) a third EBV LMP2 fragment consisting of SEQ ID NO: 9;
(h) a fourth EBV LMP2 fragment consisting of SEQ ID NO: 10;
(i) a first EBNA1 fragment consisting of SEQ ID NO: 12;
(j) a first EBNA3A fragment consisting of SEQ ID NO: 14;
(k) a second EBNA3A fragment consisting of SEQ ID NO: 15;
(l) a third EBNA3A fragment consisting of SEQ ID NO: 16;

(m) a fourth EBNA3A fragment consisting of SEQ ID NO: 17;
(n) a fifth EBNA3A fragment consisting of SEQ ID NO: 18;
(o) a sixth EBNA3A fragment consisting of SEQ ID NO: 19; and
(p) a seventh EBNA3A fragment consisting of SEQ ID NO: 20;
wherein:
the first, second, third, and fourth EBV LMP1 fragments are not adjacent to each other;
the first, second, third, and fourth EBV LMP2 fragments are not adjacent to each other; and
the first, second, third, fourth, fifth, sixth, and seventh EBNA3A fragments are not adjacent to each other.

23. The nucleic acid of claim 21, wherein the polypeptide is at least 85% identical to SEQ ID NO: 24 or SEQ ID NO: 26.

24. The nucleic acid of claim 21, wherein the polypeptide is at least 90% identical to SEQ ID NO: 24 or SEQ ID NO: 26.

25. The nucleic acid of claim 21, wherein the polypeptide is at least 95% identical to SEQ ID NO: 24 or SEQ ID NO: 26.

26. The nucleic acid of claim 21, wherein the polypeptide is at least 99% identical to SEQ ID NO: 24 or SEQ ID NO: 26.

27. The nucleic acid of claim 21, wherein the EBNA1 fragment comprises at least 50 amino acids of SEQ ID NO: 11.

28. The nucleic acid of claim 21, wherein the EBNA1 fragment comprises at least 80 amino acids of SEQ ID NO: 11.

29. The nucleic acid of claim 2, wherein the polypeptide is at least 85% identical to SEQ ID NO: 24 or SEQ ID NO: 26.

30. The nucleic acid of claim 2, wherein the polypeptide is at least 90% identical to SEQ ID NO: 24 or SEQ ID NO: 26.

31. The nucleic acid of claim 2, wherein the polypeptide is at least 95% identical to SEQ ID NO: 24 or SEQ ID NO: 26.

32. The nucleic acid of claim 2, wherein the polypeptide is at least 99% identical to SEQ ID NO: 24 or SEQ ID NO: 26.

33. The nucleic acid of claim 2, wherein the EBNA1 fragment comprises at least 50 amino acids of SEQ ID NO: 11.

34. The nucleic acid of claim 2, wherein the EBNA1 fragment comprises at least 80 amino acids of SEQ ID NO: 11.

35. The nucleic acid of claim 4, wherein the polypeptide is at least 85% identical to SEQ ID NO: 24 or SEQ ID NO: 26.

36. The nucleic acid of claim 4, wherein the polypeptide is at least 90% identical to SEQ ID NO: 24 or SEQ ID NO: 26.

37. The nucleic acid of claim 4, wherein the polypeptide is at least 95% identical to SEQ ID NO: 24 or SEQ ID NO: 26.

38. The nucleic acid of claim 4, wherein the polypeptide is at least 99% identical to SEQ ID NO: 24 or SEQ ID NO: 26.

39. The nucleic acid of claim 3, wherein the polypeptide is at least 85% identical to SEQ ID NO: 26.

40. The nucleic acid of claim 3, wherein the polypeptide is at least 90% identical to SEQ ID NO: 26.

41. The nucleic acid of claim 3, wherein the polypeptide is at least 95% identical to SEQ ID NO: 26.

42. The nucleic acid of claim 3, wherein the polypeptide is at least 99% identical to SEQ ID NO: 26.

43. The nucleic acid of claim 3, wherein the polypeptide comprises the EBNA1 fragment; and wherein the EBNA1 fragment comprises at least 50 amino acids of SEQ ID NO: 11.

44. The nucleic acid of claim 3, wherein the polypeptide comprises the EBNA1 fragment; and wherein the EBNA1 fragment comprises at least 50 amino acids of SEQ ID NO: 11.

* * * * *

SEQUENCE LISTING

```
Sequence total quantity: 54
SEQ ID NO: 1            moltype = AA  length = 386
FEATURE                 Location/Qualifiers
source                  1..386
                        mol_type = protein
                        organism = unidentified
                        note = Human herpesvirus 4
SEQUENCE: 1
MEHDLERGPP GPRRPPRGPP LSSSLGLALL LLLLALLFWL YIVMSDWTGG ALLVLYSFAL   60
MLIIILIIF  IFRRDLLCPL GALCILLLMI TLLLIALWNL HGQALFLGIV LFIFGCLLVL  120
GIWIYLLEML WRLGATIWQL LAFFLAFFLD LILLIIALYL QQNWWTLLVD LLWLLLFLAI  180
LIWMYYHGQR HSDEHHHDDS LPHPQQATDD SGHESDSNSN EGRHHLLVSG AGDGPPLCSQ  240
NLGAPGGGPD NGPQDPDNTD DNGPQDPDNT DDNGPHDPLP QDPDNTDDNG PQDPDNTDDN  300
GPHDPLPHSP SDSAGNDGGP PQLTEEVENK GGDQGPPLMT DGGGGHSHDS GHGGGDPHLP  360
TLLLGSSGSG GDDDDPHGPV QLSYYD                                      386

SEQ ID NO: 2            moltype = AA  length = 62
FEATURE                 Location/Qualifiers
source                  1..62
                        mol_type = protein
                        organism = unidentified
                        note = Human herpesvirus 4
SEQUENCE: 2
MSDWTGGALL VLYSFALMLI IIILIIFIFR RDLLCPLGAL CILLLMITLL LIALWNLHGQ   60
AL                                                                 62

SEQ ID NO: 3            moltype = AA  length = 85
FEATURE                 Location/Qualifiers
source                  1..85
                        mol_type = protein
                        organism = unidentified
                        note = Human herpesvirus 4
SEQUENCE: 3
FLGIVLFIFG CLLVLGIWIY LLEMLWRLGA TIWQLLAFFL AFFLDLILLI IALYLQQNWW   60
TLLVDLLWLL LFLAILIWMY YHGQR                                        85

SEQ ID NO: 4            moltype = AA  length = 40
FEATURE                 Location/Qualifiers
source                  1..40
                        mol_type = protein
                        organism = unidentified
                        note = Human herpesvirus 4
```

```
SEQUENCE: 4
HSDEHHHDDS LPHPQQATDD SGHESDSNSN EGRHHLLVSG                            40

SEQ ID NO: 5           moltype = AA  length = 114
FEATURE                Location/Qualifiers
source                 1..114
                       mol_type = protein
                       organism = unidentified
                       note = Human herpesvirus 4
SEQUENCE: 5
NGPHDPLPQD PDNTDDNGPQ DPDNTDDNGP HDPLPHSPSD SAGNDGGPPQ LTEEVENKGG      60
DQGPPLMTDG GGGHSHDSGH GGGDPHLPTL LLGSSGSGGD DDDPHGPVQL SYYD           114

SEQ ID NO: 6           moltype = AA  length = 497
FEATURE                Location/Qualifiers
source                 1..497
                       mol_type = protein
                       organism = unidentified
                       note = Human herpesvirus 4
SEQUENCE: 6
MGSLEMVPMG AGPPSPGGDP DGYDGGNNSQ YPSASGSSGN TPTPPNDEER ESNEEPPPPY      60
EDPYWGNGDR HSDYQPLGTQ DQSLYLGLQH DGNDGLPPPP YSPRDDSSQH IYEEAGRGSM     120
NPVCLPVIVA PYLFWLAAIA ASCFTASVST VVTATGLALS LLLLAAVASS YAAAQRKLLT    180
PVTVLTAVVT FFAICLTWRI EDPPFNSLLF ALLAAAGGLQ GIYVLVMLVL LILAYRRRWR    240
RLTVCGGIMF LACVLVLIVD AVLQLSPLLG AVTVVSMTLL LLAFVLWLSS PGGLGTLGAA    300
LLTLAAALAL LASLILGTLN LTTMFLLMLL WTLVVLLICS SCSSCPLSKI LLARLFLYAL    360
ALLLLASALI AGGSILQTNF KSLSSTEFIP NLFCMLLLIV AGILFILAIL TEWGSGNRTY    420
GPVFMCLGGL LTMVAGAVWL TVMSNTLLSA WILTAGFLIF LIGFALFGVI RCCRYCCYYC    480
LTLESEERPP TPYRNTV                                                  497

SEQ ID NO: 7           moltype = AA  length = 71
FEATURE                Location/Qualifiers
source                 1..71
                       mol_type = protein
                       organism = unidentified
                       note = Human herpesvirus 4
SEQUENCE: 7
MNPVCLPVIV APYLFWLAAI AASCFTASVS TVVTATGLAL SLLLLAAVAS SYAAAQRKLL      60
TPVTVLTAVV T                                                         71

SEQ ID NO: 8           moltype = AA  length = 94
FEATURE                Location/Qualifiers
source                 1..94
                       mol_type = protein
                       organism = unidentified
                       note = Human herpesvirus 4
SEQUENCE: 8
FFAICLTWRI EDPPFNSLLF ALLAAAGGLQ GIYVLVMLVL LILAYRRRWR RLTVCGGIMF      60
LACVLVLIVD AVLQLSPLLG AVTVVSMTLL LLAF                                94

SEQ ID NO: 9           moltype = AA  length = 115
FEATURE                Location/Qualifiers
source                 1..115
                       mol_type = protein
                       organism = unidentified
                       note = Human herpesvirus 4
SEQUENCE: 9
VLWLSSPGGL GTLGAALLTL AAALALLASL ILGTLNLTTM FLLMLLWTLV VLLICSSCSS      60
CPLSKILLAR LFLYALALLL LASALIAGGS ILQTNFKSLS STEFIPNLFC MLLLI          115

SEQ ID NO: 10          moltype = AA  length = 98
FEATURE                Location/Qualifiers
source                 1..98
                       mol_type = protein
                       organism = unidentified
                       note = Human herpesvirus 4
SEQUENCE: 10
VAGILFILAI LTEWGSGNRT YGPVFMCLGG LLTMVAGAVW LTVMSNTLLS AWILTAGFLI      60
FLIGFALFGV IRCCRYCCYY CLTLESEERP PTPYRNTV                             98

SEQ ID NO: 11          moltype = AA  length = 641
FEATURE                Location/Qualifiers
source                 1..641
                       mol_type = protein
                       organism = unidentified
                       note = Human herpesvirus 4
SEQUENCE: 11
MSDEGPGTGP GNGLGEKGDT SGPEGSGGSG PQRRGGDNHG RGRGRGRGRG GGRPGAPGGS      60
GSGPRHRDGV RRPQKRPSCI GCKGTHGGTG AGAGAGGAGA GGAGAGGGAG AGGGAGGAGG    120
```

```
AGGAGAGGGA GAGGGAGGAG GAGAGGGAGA GGGAGGAGAG GGAGGAGGAG AGGGAGAGGG    180
AGGAGAGGGA GGGAGGAGAG GAGAGGAGGA GGAGAGGAGA GGGAGGAGGA GAGGAGAGGA    240
GAGGAGAGGA GAGGAGAGGG AGAGGAGGAG GGGAGGAGAG GGGAGGAGAG GAGGAGAGGA    300
GGAGAGGAGG AGAGGGAGAG GAGAGGGGRG RGGSGGRGRG GSGGRGRGGS GGRRGRGRER    360
ARGGSRERAR GRGRGRGEKR PRSPSSQSSS SGSPPRRPPP GRRPFFHPVG EADYFEYHQE    420
GGPDGEPDVP PGAIEQGPAD DPGEPPSTGP RGQGDGGRRK KGGWFGKHRG QGGSNPKFEN    480
IAEGLRALLA RSHVERTTDE GTWVAGVFVY GGSKTSLYNL RRGTALAIPQ CRLTPLSRLP    540
FGMAPGPGPQ PGPLRESIVC YFMVFLQTHI FAEVLKDAIK DLVMTKPAPT CNIRVTVCSF    600
DDGVDLPPWF PPMVEGAAAE GDDGDDGDEG GDGDEGEEGQ E                       641

SEQ ID NO: 12           moltype = AA  length = 86
FEATURE                 Location/Qualifiers
source                  1..86
                        mol_type = protein
                        organism = unidentified
                        note = Human herpesvirus 4
SEQUENCE: 12
MSDEGPGTGP GNGLGEKGDT SGPEGSGGSG PQRRGGDNHG RGRGRGRGRG GGRPGAPGGS    60
GSGPRHRDGV RRPQKRPSCI GCKGTH                                        86

SEQ ID NO: 13           moltype = AA  length = 944
FEATURE                 Location/Qualifiers
source                  1..944
                        mol_type = protein
                        organism = unidentified
                        note = Human herpesvirus 4
SEQUENCE: 13
MDKDRPGPPA LDDNMEEEVP STSVVQEQVS AGDWENVLIE LSDSSSEKEA EDAHLEPAQK    60
GTKRKRVDHD AGGSAPARPM LPPQPDLPGR EAILRRFPLD LRTLLQAIGA AATRIDTRAI   120
DQFFGSQISN TEMYIMYAMA IRQAIRDRRR NPASRRDQAK WRLQTLAAGW PMGYQAYSSW   180
MYSYTDHQTT PTFVHLQATL GCTGGRRCHV TFSAGTFKLP RCTPGDRQWL YVQSSVGNIV   240
QSCNPRYSIF FDYMAIHRSL TKIWEEVLTP DQRVSFMEFL GFLQRTDLSY IKSFVSDALG   300
TTSIQTPWID DNPSTETAQA WNAGFLRGRA YGIDLLRTEG EHVEGATGET REESEDTESD   360
GDDEDLPCIV SRGGPKVKRP PIFIRRLHRL LLMRAGKRTE QGKEVLEKAR GSTYGTPRPP   420
VPKPRPEVPQ SDETATSHGS AQVPEPPTIH LAAQGMAYPL HEQHGMAPCP VAQAPPTPLP   480
PVSPGDQLPG VFSDGRVACA PVPAPAGPIV RPWEPSLTQA AGQAFAPVRP QHMPVEPVPV   540
PTVALERPVY PKPVRPAPPK IAMQGPGETS GIRRARERWR PAPWTPNPPR SPSQMSVRDR   600
LARLRAEAQV KQASVEVQPP QLTQVSPQQP MEGPLVPEQQ MFPGAPFSQV ADVVRAPGVP   660
AMQPQYFDLP LIQPISQGAP VAPLRASMGP VPPVPATQPQ YFDIPLTEPI NQGASAAHFL   720
PQQPMEGPLV PEQWMFPGAA LSQSVRPGVA QSQYFDLPLT QPINHGAPAA HFLHQPPMEG   780
PWVPEQWMFQ GAPPSQGTDV VQHQLDALGY TLHGLNHPGV PVSPAVNQYH LSQAAFGLPI   840
DEDESGEGSD TSEPCEALDL SIHGRPCPQA PEWPVQEEGG QDATEVLDLS IHGRPRPRTP   900
EWPVQGEGGQ NVTGPETRRV VVSAVVHMCQ DDEFPDLQDP PDEA                    944

SEQ ID NO: 14           moltype = AA  length = 66
FEATURE                 Location/Qualifiers
source                  1..66
                        mol_type = protein
                        organism = unidentified
                        note = Human herpesvirus 4
SEQUENCE: 14
IRDRRRNPAS RRDQAKWRLQ TLAAGWPMGY QAYSSWMYSY TDHQTTPTFV HLQATLGCTG    60
GRRCHV                                                               66

SEQ ID NO: 15           moltype = AA  length = 55
FEATURE                 Location/Qualifiers
source                  1..55
                        mol_type = protein
                        organism = unidentified
                        note = Human herpesvirus 4
SEQUENCE: 15
TFSAGTFKLP RCTPGDRQWL YVQSSVGNIV QSCNPRYSIF FDYMAIHRSL TKIWE         55

SEQ ID NO: 16           moltype = AA  length = 88
FEATURE                 Location/Qualifiers
source                  1..88
                        mol_type = protein
                        organism = unidentified
                        note = Human herpesvirus 4
SEQUENCE: 16
WIDDNPSTET AQAWNAGFLR GRAYGIDLLR TEGEHVEGAT GETREESEDT ESDGDDEDLP    60
CIVSRGGPKV KRPPIFIRRL HRLLLMRA                                       88

SEQ ID NO: 17           moltype = AA  length = 25
FEATURE                 Location/Qualifiers
source                  1..25
                        mol_type = protein
                        organism = unidentified
                        note = Human herpesvirus 4
```

```
                                    -continued

SEQUENCE: 17
GKRTEQGKEV LEKARGSTYG TPRPP                                             25

SEQ ID NO: 18           moltype = AA   length = 40
FEATURE                 Location/Qualifiers
source                  1..40
                        mol_type = protein
                        organism = unidentified
                        note = Human herpesvirus 4
SEQUENCE: 18
AQVPEPPTIH LAAQGMAYPL HEQHGMAPCP VAQAPPTPLP                              40

SEQ ID NO: 19           moltype = AA   length = 62
FEATURE                 Location/Qualifiers
source                  1..62
                        mol_type = protein
                        organism = unidentified
                        note = Human herpesvirus 4
SEQUENCE: 19
GRVACAPVPA PAGPIVRPWE PSLTQAAGQA FAPVRPQHMP VEPVPVPTVA LERPVYPKPV        60
RP                                                                      62

SEQ ID NO: 20           moltype = AA   length = 51
FEATURE                 Location/Qualifiers
source                  1..51
                        mol_type = protein
                        organism = unidentified
                        note = Human herpesvirus 4
SEQUENCE: 20
RPAPWTPNPP RSPSQMSVRD RLARLRAEAQ VKQASVEVQP PQLTQVSPQQ P                 51

SEQ ID NO: 21           moltype = AA   length = 245
FEATURE                 Location/Qualifiers
source                  1..245
                        mol_type = protein
                        organism = unidentified
                        note = Human herpesvirus 4
SEQUENCE: 21
MMDPNSTSED VKFTPDPYQV PFVQAFDQAT RVYQDLGGPS QAPLPCVLWP VLPEPLPQGQ        60
LTAYHVSTAP TGSWFSAPQP APENAYQAYA APQLFPVSDI TQNQQTNQAG GEAPQPGDNS       120
TVQTAAAVVF ACPGANQGQQ LADIGVPQPA PVAAPARRTR KPQQPESLEE CDSELEIKRY       180
KNRVASRKCR AKFKQLLQHY REVAAAKSSE NDRLRLLLKQ MCPSLDVDSI IPRTPDVLHE       240
DLLNF                                                                  245

SEQ ID NO: 22           moltype = AA   length = 66
FEATURE                 Location/Qualifiers
source                  1..66
                        mol_type = protein
                        organism = unidentified
                        note = Human herpesvirus 4
SEQUENCE: 22
DLGGPSQAPL PCVLWPVLPE PLPQGQLTAY HVSTAPTGSW FSAPQPAPEN AYQAYAAPQL        60
FPVSDI                                                                  66

SEQ ID NO: 23           moltype = AA   length = 51
FEATURE                 Location/Qualifiers
source                  1..51
                        mol_type = protein
                        organism = unidentified
                        note = Human herpesvirus 4
SEQUENCE: 23
RKPQQPESLE ECDSELEIKR YKNRVASRKC RAKFKQLLQH YREVAAAKSS E                 51

SEQ ID NO: 24           moltype = AA   length = 1153
FEATURE                 Location/Qualifiers
REGION                  1..1153
                        note = Description of Artificial Sequence: Synthetic
                         polypeptide
source                  1..1153
                        mol_type = protein
                        organism = synthetic construct
SEQUENCE: 24
MRPAPWTPNP PRSPSQMSVR DRLARLRAEA QVKQASVEVQ PPQLTQVSPQ QPVAGILFIL        60
AILTEWGSGN RTYGPVFMCL GGLLTMVAGA VWLTVMSNTL LSAWILTAGF LIFLIGFALF       120
GVIRCCRYCC YYCLTLESEE RPPTPYRNTV IRDRRRNPAS RRDQAKWRLQ TLAAGWPMGY       180
QAYSSWMYSY TDHQTTPTFV HLQATLGCTG GRRCHVFLGI VLFIFGCLLV LGIWIYLLEM       240
LWRLGATIWQ LLAFFLAFFL DLILLIIALY LQQNWWTLLV DLLWLLLFLA ILIWMYYHGQ       300
RGRVACAPVP APAGPIVRPW EPSLTQAAGQ AFAPVRPQHM PVEPVPVPTV ALERPVYPKP       360
VRPVLWLSSP GGLGTLGAAL LTLAAALALL ASLILGTLNL TTMFLLMLLW TLVVLLICSS       420
```

```
CSSCPLSKIL LARLFLYALA LLLLASALIA GGSILQTNFK SLSSTEFIPN LFCMLLLIHS   480
DEHHHDDSLP HPQQATDDSG HESDSNSNEG RHHLLVSGAQ VPEPPTIHLA AQGMAYPLHE   540
QHGMAPCPVA QAPPTPLPFF AICLTWRIED PPFNSLLFAL LAAAGGLQGI YVLVMLVLLI   600
LAYRRRWRRL TVCGGIMFLA CVLVLIVDAV LQLSPLLGAV TVVSMTLLLL AFNGPHDPLP   660
QDPDNTDDNG PQDPDNTDDN GPHDPLPHSP SDSAGNDGGP PQLTEEVENK GGDQGPPLMT   720
DGGGGHSHDS GHGGGDPHLP TLLLGSSGSG GDDDDPHGPV QLSYYDGKRT EQGKEVLEKA   780
RGSTYGTPRP PMSDWTGGAL LVLYSFALML IIIILIIFIF RRDLLCPLGA LCILLLMITL   840
LLIALWNLHG QALMSDEGPG TGPGNGLGEK GDTSGPEGSG GSGPQRRGGD NHGRGRGRGR   900
GRGGGRPGAP GGSGSGPRHR DGVRRPQKRP SCIGCKGTHW IDDNPSTETA QAWNAGFLRG   960
RAYGIDLLRT EGEHVEGATG ETREESEDTE SDGDDEDLPC IVSRGGPKVK RPPIFIRRLH  1020
RLLLMRAMNP VCLPVIVAPY LFWLAAIAAS CFTASVSTVV TATGLALSLL LLAAVASSYA  1080
AAQRKLLTPV TVLTAVVTTF SAGTFKLPRC TPGDRQWLYV QSSVGNIVQS CNPRYSIFFD  1140
YMAIHRSLTK IWE                                                    1153

SEQ ID NO: 25          moltype = DNA   length = 3459
FEATURE                Location/Qualifiers
misc_feature           1..3459
                       note = Description of Artificial Sequence: Synthetic
                       polynucleotide
source                 1..3459
                       mol_type = other DNA
                       organism = synthetic construct
SEQUENCE: 25
atgagacctg ctccctggac acctaatcct cccaggtccc ccagccagat gagcgtgaga    60
gacagactgc taggctgag agccgaggct caggtcaagc aggccagcgt cgaggtcaa    120
ccccctcagc tcacccaggt gtcccccag cagcctgtg ccggcattct gttcattctg    180
gccattctga ccgagtgggg aagcggcaac agaacctacg gccctgtctt catgtgcctc    240
ggaggactgc tgacaatggt ggctggcgcc gtgtggctca ccgtcatgtc caacaccctg    300
ctcagcgcct ggattctgac cgccggattc ctgatctttc tgatcggatt cgctctcttt    360
ggcgtcatca ggtgttgcag gtactgttgc tactactgcc tgaccctcga gagcgaggaa    420
agaccccca ccccctacag gaatacagtg attagggaca gaaggaggaa tcctgcctcc    480
aggagagacc aggccaaatg gagactccaa acactgccg ctggatggcc catgggctac    540
caggcctata gctcctggat gtacagctac accgaccatc agacaacacc caccttcgtg    600
catctgcagg ctacactggg ctgcaccgga gcagaaggt gtcacgtgtt tctgggaatc    660
gtgctgttca tctttggatg cctgctcgtg ctgggcatct gatttatct cctggagatg    720
ctctggagac tcggcgctac aatttggcag ctgctcgcct tttttctggc cttctttctg    780
gacctgatcc tcctgatcat cgcccgtac ctccaacaga actggtggac cctcctggtg    840
gatctgctgt ggctcctcct cttcctggcc atcctgatct ggatgtacta ccatggccag    900
agaggaaggg tcgcttgcgc tcctgtccct gctcctgcg gccccatcgt gaggccttga    960
gagccttccc tcacacaggc cgccggccag gcctttgctc ccgtgaggcc ccagcacatg   1020
cctgtggaac ccgtgcccgt ccccacagtg gctctgaaaa ggcctgtgta ccccaagccc   1080
gtgagacctg tcctctggct cagcagccct ggaggactcg gaacactcgg agccgctctc   1140
ctgacactgg ccgctgctct ggctctgctg gctagcctga cactgggaac cctcaacctc   1200
accaccatgt ttctcctcat gctcctgtgg accctcgtgg tgctgctcat ctgttccagc   1260
tgctccagct gcccctgag caagatcctg ctggccaggc tgttcctgta cgccctcgcc   1320
ctcctgctgc tggctagcgc cctgatcgct ggcggaagca tcctccagac caatttcaag   1380
agcctctcct ccaccgagtt catccccaac ctgttctgta tgttactgct gatccatagc   1440
gacgagcacc atcatgacga ctccctgccc catcctcagc aggccacaga cgactccggc   1500
cacgagagcg acagcaatag caatgagggc aggcaccatc tgctcgtgtc cggagctcaa   1560
gtccccgagc tcccaccat ccatctgcc gcccaggga tggcttaccc cctccacgag   1620
cagcacggca tggcccttg tccgctcgct caagccccc ctacacctct gccctttttc   1680
gccatttgtc tgacctggag aatcgaggac ccccccttca acagcctgct gttcgccctg   1740
ctcgccgccg ctgcggcct ccagggcatt tacgtcctcg tgatgctggt gctgctgatc   1800
ctcgcttaca ggagaagatg gaggagactg acagtgtgcg gcggcatcat gtttctcgcc   1860
tgcgtcctgg tcctgatcgt ggacgccgtc ctgcaactca gcccccctcg gggagctgtg   1920
acagtggtct ccatgaccct gctgctgctg gccttcaacg gacccccacg tcctctgccc   1980
caagatcctg acaataccga cgataacggc cccccaagacc ccgataacac cgacgacaat   2040
ggccctcacg accctctgcc ccatagccct tccgatagcg ctggcaacga tggcggcccc   2100
cctcagctga cagaggaggt ggaaaataag ggcggcgatc agggacccc cctgatgaca   2160
gatggcggag gaggacacag ccatgatagc ggacatggcg gaggcgatcc ccatctgcct   2220
acctcctcc tgggcagctc cggttctgga ggcgacgatg atgaccctca cggccctgtg   2280
cagctctcct actacgacgg caaaaggacc gaacaaggaa aagaggtcct ggagaaggcc   2340
aggggcagca catacggaac ccccaggcct ccatgtatcg attggaccgg aggagccctg   2400
ctggtcctct acagcttcgc cctgatgctg atcattatca tcctgatcat ctttatcttc   2460
agaagggacc tgctgtgccc tctcggcgcc ctgtgcatcc tgctgctcat gatcacactc   2520
ctcctgatcg ccctctggaa cctgcacgga caagccctga tgtccgatga gggacctgga   2580
acaggacccg gaacggact gggcgagaag ggagatacaa gcggcccga aggcagcggc   2640
ggaagcggac cccaaagag gggcggcgac aaccacggaa gaggaagagg caggggcaga   2700
ggcagaggag gaggaagacc tggagcccct ggcggttctg gaagcggaccaggcacagg   2760
gacggagtga ggaggcctca aaaaagaccc agctgcatcg gctgcaaggg aacccactgg   2820
attgatgata ccccctccac agagaccgct caggcctgga acgccggctt cctgagggga   2880
agagcctatg gcatcgatct gctgaggacc gagggcgaac acgtggaggg agccaccgga   2940
gagacaaggg aggaaagcga agacacagaa agcgatggcg acgacgaaga cctgccctgc   3000
attgtgtcca gggcggcccta caaggtgaag aggcctatct cttttatcag aaggctccat   3060
agactgctcc tgatgagggc catgaaccct gtgtgcctgc ccgtgatcgt ggccccctac   3120
ctcttttggc tggccgccat tgccgctagc tgcttcaccg cctccgtgtc cacagtggtg   3180
acagccaccg gcctcgccct gagcctgctg ctcctcgctg ccgtggcctc cagctacgcc   3240
gctgctcaaa gaaagctcct gacccctgtc accgtcctga cagccgtcgt gaccaccttt   3300
tccgctggca ccttcaagct gcctaggtgc acacctggca caggcagtg gctctacgtg   3360
```

```
cagagctccg tgggcaatat tgtgcagagc tgcaatccca ggtacagcat ttttttcgac   3420
tacatggcca tccataggtc cctcaccaag atctgggag                          3459

SEQ ID NO: 26           moltype = AA  length = 1270
FEATURE                 Location/Qualifiers
REGION                  1..1270
                        note = Description of Artificial Sequence: Synthetic
                        polypeptide
source                  1..1270
                        mol_type = protein
                        organism = synthetic construct
SEQUENCE: 26
MRPAPWTPNP PRSPSQMSVR DRLARLRAEA QVKQASVEVQ PPQLTQVSPQ QPVAGILFIL     60
AILTEWGSGN RTYGPVFMCL GGLLTMVAGA VWLTVMSNTL LSAWILTAGF LIFLIGFALF    120
GVIRCCRYCC YYCLTLESEE RPPTPYRNTV RKPQQPESLE ECDSELEIKR YKNRVASRKC    180
RAKFKQLLQH YREVAAAKSS EIRDRRRNPA SRRDQAKWRL QTLAAGWPMG YQAYSSWMYS    240
YTDHQTTPTF VHLQATLGCT GGRRCHVFLG IVLFIFGCLL VLGIWIYLLE MLWRLGATIW    300
QLLAFFLAFF LDLILLIIAL YLQQNWWTLL VDLLWLLLFL AILIWMYYHG QRGRVACAPV    360
PAPAGPIVRP WEPSLTQAAG QAFAPVRPQH MPVEPVPVPT VALERPVYPK PVRPVLWLSS    420
PGGLGTLGAA LLTLAAALAL LASLILGTLN LTTMFLLMLL WTLVVLLICS SCSSCPLSKI    480
LLARLFLYAL ALLLLASALI AGGSILQTNF KSLSSTEFIP NLFCMLLLIH SDEHHHDDSL    540
PHPQQATDDS GHESDSNSNE GRHHLLVSGA QVPEPPTIHL AAQGMAYPLH EQHGMAPCPV    600
AQAPPPTPLPF FAICLTWRIE DPPFNSLLFA LLAAAGGLQG IYVLVMLVLL ILAYRRRWRR    660
LTVCGGIMFL ACVLVLIVDA VLQLSPLLGA VTVVSMTLLL LAFNGPHDPL PQDPDNTDDN    720
GPQDPDNTDD NGPHDPLPHS PSDSAGNDGG PPQLTEEVEN KGGDQGPPLM TDGGGHSHD    780
SGHGGGDPHL PTLLLGSSGS GGDDDDPHGP VQLSYYDGKR TEQGKEVLEK ARGSTYGTPR    840
PPMSDWTGGA LLVLYSFALM LIIIILIIFI FRRDLLCPLG ALCILLLMIT LLLIALWNLH    900
GQALMSDEGP GTGPGNGLGE KGDTSGPEGS GGSGPQRRGG DNHGRGRGRG RGRGGGRPGA    960
PGGGSGSGPRH RDGVRRPQKR PSCIGCKGTH WIDDNPSTET AQAWNAGFLR GRAYGIDLLR   1020
TEGEHVEGAT GETREESEDT ESDGDDEDLP CIVSRGGPKV KRPPIFIRRL HRLLLMRAMN   1080
PVCLPVIVAP YLFWLAAIAA SCFTASVSTV VTATGLALSL LLLAAVASSY AAAQRKLLTP   1140
VTVLTAVVTT FSAGTFKLPR CTPGDRQWLY VQSSVGNIVQ SCNPRYSIFF DYMAIHRSLT   1200
KIWEDLGGPS QAPLPCVLWP VLPEPLPQGQ LTAYHVSTAP TGSWFSAPQP APENAYQAYA   1260
APQLFPVSDI                                                          1270

SEQ ID NO: 27           moltype = DNA  length = 3810
FEATURE                 Location/Qualifiers
misc_feature            1..3810
                        note = Description of Artificial Sequence: Synthetic
                        polynucleotide
source                  1..3810
                        mol_type = other DNA
                        organism = synthetic construct
SEQUENCE: 27
atgagacctg ctccctggac acctaatcct cccaggtccc ccagccagat gagcgtgaga     60
gacagactgg ctaggctgag agccgaggct caggtcaagc aggccagcgt cgaggtgcaa    120
ccccctcagc tcacccaggt gtcccccca cagcctgtgg ccggcattct gttcattctg    180
gccattctga ccgagtgggg aagcggcaac agaacctacg gccctgtctt catgtgcctc    240
ggaggactgc tgacaatggt ggctggcgcc gtgtggctca ccgtcatgtc caacaccctg    300
ctcagcgcct ggattctgac cgccggattc ctgatctttc tgatcggatt cgctctcttt    360
ggcgtcatca ggtgttgcag gtactgttgc tactactgcc tgaccctcga gagcgaggaa    420
agaccccca ccccctacag gaatacagtg aggaaacctc agcagcccga gagcctcgag     480
gagtgcgata cgagctgga gattaaaagg tataagaata gggtggcctc caggaagtgt    540
agggctaaat tcaaacagct cctgcaacac tataggaag tggccgccgc caagtccagc    600
gagattaggg acagaaggag aatcctgcc tccaggagg accaggcaa atggagactc    660
caaacactcg ccgctggatg gcccatgggc taccaggcct atagctcctg gatgtacagc    720
tacaccgacc atcagacaac acccaccttc gtgcatctgc aggctacact gggctgcacc    780
ggaggcagaa ggtgtcacgt gtttctggga atcgtgctgt tcatctttgg atgcctgctc    840
gtgctgggca tctggattta tctcctggag atgctctgga gactcggcgc tacaatttgg    900
cagctgctcg ccttttttct ggccttcttt ctggacctga tcctcctgat catcgccctg    960
tacctccaac agaactggtg gaccctcctg gtggatctgc tgtggctcct cctcttcctg   1020
gccatcctga tctggatgta ctaccatggc cagagaggaa gggtcgcttg cgctcctgtc   1080
cctgctcctg ctggccccat cgtgaggcct gggagcctt ccctcacaca ggccgccggc    1140
caggcctttg ctcccgtgag gccccagcac atgcctgtgg aacccgtgcc cgtcccaca    1200
gtggctctgg aaaggcctgt gtaccccaag cccgtgagac ctgtcctctg gctcagcagc   1260
cctggaggac tcggaacact cggagccgct ctcctgacac tggccgctgc tctggctctg   1320
ctggctagcc tgatcctggg aaccctcaac ctcaccacca tgtttctcct catgctcctg   1380
tggaccctcg tggtgctgct catctgttcc agctgctcca gctgccccc gagcaagatc   1440
ctgctggcca ggctgttcct gtacgccctc gccctcctgc tggctgtag cgccctgatc   1500
gctggcggaa gcatcctcca gaccaatttc aagagcctcc tccaccga gttcatcccc    1560
aacctgttct gtatgttact gctgatccat agcgacgagc accatcatga cgactccctg   1620
ccccatcctg agcaggccac agacgactcc ggccacgaga gcgacagcaa tagcaatgag   1680
ggcaggcacc atctgctcgt gtccgagct caagtccccg agcctccac catccatctc    1740
gccgccagg aatccgctta ccccctccac gagcacgca gcatggccca ttgtcccgtc   1800
gctcaagccc ccctacacc tctgcccttt ttcgccattt gtctgacctg gagaatcgag   1860
gacccccct tcaacagcct gctgttcgcc ctgctcgccg ccgctggcgg cctccagggc   1920
atttacgtcc tcgtgatgct ggtgctgctg atcctcgctt acaggagaag atggaggaga   1980
ctgacagtgt gcggcggcat catgtttctc gcctgcgtcc tggtcctgat cgtggacgcc   2040
gtcctgcaac tcagcccct cctggagct gtgacagtgg tctccatgac cctgctgctg   2100
```

```
ctggccttca acggacccca cgatcctctg ccccaagatc ctgacaatac cgacgataac    2160
ggccccccaag accccgataa caccgacgac aatggccctc acgaccctct gccccatagc    2220
ccttccgata gcgctggcaa cgatggcggc cctcctcagc tgacagagga ggtggaaaat    2280
aagggcggcg atcagggacc ccccctgatg acagatggcg gaggaggaca cagccatgat    2340
agcggacatg gcggaggcga tccccatctg cctaccctcc tcctgggcag ctccggttct    2400
ggaggcgacg atgatgaccc tcacggcccc gtgcagctct cctactacga cggcaaaagg    2460
accgaacaag gaaaagaggt cctggagaag gccaggggca gcacatacgg aaccccccagg   2520
cctcccatgt ccgattggac cggaggagcc ctgctggtcc tctacagctt cgccctgatg    2580
ctgatcatta tcatcctgat catctttatc ttcagaaggg acctgctgtg ccctctcggc    2640
gccctgtgca tcctgctgct catgatcaca ctcctcctga tcgccctctg gaacctgcac    2700
ggacaagccc tgatgtccga tgagggacct ggaacaggac ccggaaacgg actgggcgag    2760
aagggagata caagcggccc gaaggcagc ggcggaagcg acccccaaag aagggcggc      2820
gacaaccacg aagaggaag aggcaggggc agaggcagag gaggaggaag acctggagcc    2880
cctggcggtt ctgaaagcgg aaccaggcac agggacggag tgaggaggcc tcaaaaaaga    2940
cccagctgca tcggctgcaa gggaacccac tggattgatg ataaccctc cacagagacc     3000
gctcaggcct ggaacgccgg cttcctgagg ggaaagagcct atggcatcga tctgctgagg    3060
accgagggcg aacacgtgga gggagccacc ggagagacaa gggaggaaag cgaagacaca    3120
gaaagcgatg gcgacgacga agacctgccc tgcattgtgt ccaggggcag acccaaggtg    3180
aagaggcccc ctatctttat cagaaggctc catagactgc tcctgatgag ggccatgaac    3240
cctgtgtgcc tgcccgtgat cgtggccccc tacctctttt ggctggccgc cattgccgct    3300
agctgcttca ccgcctccgt gtccacagtg gtgacagcca ccggcctcgc cctgagcctg    3360
ctgctcctcg ctgccgtggc tccagctac gccgctgctc aaagaaagct cctgacccct    3420
gtcaccgtcc tgacagccgt cgtgaccacc ttttccgctg gcaccttcaa gctgcctagg    3480
tgcacacctg cgacaggca gtggctctac gtgcagagct ccgtgggcaa tattgtgcag    3540
agctgcaatc caggtacag catttttttc gactacatgg ccatccatag gtccctcacc    3600
aagatctggg aggatctggg aggccttcc caggctcctc tgccctgcgt gctgtggcct    3660
gtgctgcctg agcctctgcc caaggccag ctgacagcct atcacgtgtc caccgctcct    3720
acaggttctt ggttcagcgc tccccagccc gctcccgaaa acgcttacca ggcttacgcc    3780
gccccccagc tgttccccgt ctccgacatc                                    3810

SEQ ID NO: 28           moltype = AA   length = 355
FEATURE                 Location/Qualifiers
source                  1..355
                        mol_type = protein
                        organism = unidentified
                        note = Callitrichine gammaherpesvirus 3
SEQUENCE: 28
MAPRRRLSGP PWLTVLLLLS TLSVAALLIL FLIFSAGATI STEASLLVLL LLFVTLLLPL     60
LSSNGLQLPA ALILIQCFLL AADYLAYLIL PTISEDFLIL IAILVIVILV GTITTLVGAI   120
GGIRARRSFL FICIFFLFLS LFLTILALLL GFSWLLLVAI LFWVLWLVIL ILLLLVYPIP   180
HHHPLPTSLRF RMKQRVSSDP TGSDRSPQGS HNSLNSPDEE DPKDDTKQPL CNMTQGGPPV  240
NGQLLGQHAQ CPPHYPCCHI QHPDGEDSDG DDGKSWGDAG EEDNGPNDPN TNNGNEGGEG   300
DDYKSWRKPE EEDNGPNDPN TNNRIEDGDG DDGKSWRNPE EEDNRKQDRL GTKPF         355

SEQ ID NO: 29           moltype = AA   length = 93
FEATURE                 Location/Qualifiers
source                  1..93
                        mol_type = protein
                        organism = unidentified
                        note = Callitrichine gammaherpesvirus 3
SEQUENCE: 29
MAPRRRLSGP PWLTVLLLLS TLSVAALLIL FLIFSAGATI STEASLLVLL LLFVTLLLPL     60
LSSNGLQLPA ALILIQCFLL AADYLAYLIL PTI                                  93

SEQ ID NO: 30           moltype = AA   length = 198
FEATURE                 Location/Qualifiers
source                  1..198
                        mol_type = protein
                        organism = unidentified
                        note = Callitrichine gammaherpesvirus 3
SEQUENCE: 30
SEDFLILIAI LVIVILVGTI TTLVGAIGGI RARRSFLFIC IFFLFLSLFL TILALLLGFS     60
WLLLVAILFW VLWLVILILL LLVYPIPHHP LPTSLRFRMK QRVSSDPTGS DRSPQGSHNS   120
LNSPDEEDPK DDTKQPLCNM TQGGPPVNGQ LLGQHAQCPP HYPCCHIQHP DGEDSDGDDG   180
KSWGDAGEED NGPNDPNT                                                  198

SEQ ID NO: 31           moltype = AA   length = 64
FEATURE                 Location/Qualifiers
source                  1..64
                        mol_type = protein
                        organism = unidentified
                        note = Callitrichine gammaherpesvirus 3
SEQUENCE: 31
NNGNEGGEGD DYKSWRKPEE EDNGPNDPNT NNRIEDGDGD DGKSWRNPEE EDNRKQDRLG     60
TKPF                                                                  64

SEQ ID NO: 32           moltype = AA   length = 413
FEATURE                 Location/Qualifiers
source                  1..413
```

```
                        mol_type = protein
                        organism = unidentified
                        note = Callitrichine gammaherpesvirus 3
SEQUENCE: 32
MAGHWYESVI PGLFLCPLIL PSLFWICSLL TFLVGHGANI VSAVLFLVLA WCLLIANWNV      60
TREDFVSGRR SSMSSLSVAA STATAMFASF LTLSFDGLGL LLFGTALVIQ TIYVLYLVVM     120
EITVWIMMFR YLHFWITLLF LLSPIILSVA CLIIQSSALL IEAVVVTTIT VLAIFLWLPP     180
QGAEADLGTA LLILNTALCL VVLILTAIPT DAQILTVFCL FCQWTLFICL GIRMICNWRG     240
KLTRIICLKF CLYGLISASL SFGWYAFLKE VTLPTTATVD PRQLPLFLFI LSSVLVILAI     300
MMEFQTSSSL FAALFVIIAG MLCVTVGVIF LLAGVKPLLS GMICASGITM LVLGVVLLVV     360
CTRASTRESI YEDLRYPTRD ANGEYENVGY PPRDGDAPHR LGEPVYDDVE QAT            413

SEQ ID NO: 33           moltype = AA   length = 210
FEATURE                 Location/Qualifiers
source                  1..210
                        mol_type = protein
                        organism = unidentified
                        note = Callitrichine gammaherpesvirus 3
SEQUENCE: 33
MAGHWYESVI PGLFLCPLIL PSLFWICSLL TFLVGHGANI VSAVLFLVLA WCLLIANWNV      60
TREDFVSGRR SSMSSLSVAA STATAMFASF LTLSFDGLGL LLFGTALVIQ TIYVLYLVVM     120
EITVWIMMFR YLHFWITLLF LLSPIILSVA CLIIQSSALL IEAVVVTTIT VLAIFLWLPP     180
QGAEADLGTA LLILNTALCL VVLILTAIPT                                     210

SEQ ID NO: 34           moltype = AA   length = 153
FEATURE                 Location/Qualifiers
source                  1..153
                        mol_type = protein
                        organism = unidentified
                        note = Callitrichine gammaherpesvirus 3
SEQUENCE: 34
DAQILTVFCL FCQWTLFICL GIRMICNWRG KLTRIICLKF CLYGLISASL SFGWYAFLKE      60
VTLPTTATVD PRQLPLFLFI LSSVLVILAI MMEFQTSSSL FAALFVIIAG MLCVTVGVIF     120
LLAGVKPLLS GMICASGITM LVLGVVLLVV CTR                                  153

SEQ ID NO: 35           moltype = AA   length = 50
FEATURE                 Location/Qualifiers
source                  1..50
                        mol_type = protein
                        organism = unidentified
                        note = Callitrichine gammaherpesvirus 3
SEQUENCE: 35
ASTRESIYED LRYPTRDANG EYENVGYPPR DGDAPHRLGE PVYDDVEQAT                 50

SEQ ID NO: 36           moltype = AA   length = 327
FEATURE                 Location/Qualifiers
source                  1..327
                        mol_type = protein
                        organism = unidentified
                        note = Callitrichine gammaherpesvirus 3
SEQUENCE: 36
MPRGRSTGRK GRDTEKERSR SPLRAPGGSD GPSTRAGCGA GPCQLSSPIA GGSRGGRGGR      60
GGRGGSRGRG ASRGRGGRGG RGGRGGRGGR GGRGGRGSPG DDSPSPCHHR DEPPSRSPSP     120
QPTVSEQSQQ SPRQQSPQGT SQGSTRPQVP GGATTRKRGG VRGQPAKCHG KYTTTAEGLT     180
ALLNRRHSPR TSNEGRWMNG VMAVNLSKWP LYSLRRALAL AANEVRISPL FRLPYGSAFG     240
PGPQPGPILE SSTWGFLVFT QTSLFADDIA DAIRDYCTTH PGPTRNTQVV LMNFEGSGVP     300
LPMFFPPGEE TEEQREGDRA SDSDESE                                         327

SEQ ID NO: 37           moltype = AA   length = 51
FEATURE                 Location/Qualifiers
source                  1..51
                        mol_type = protein
                        organism = unidentified
                        note = Callitrichine gammaherpesvirus 3
SEQUENCE: 37
MPRGRSTGRK GRDTEKERSR SPLRAPGGSD GPSTRAGCGA GPCQLSSPIA G               51

SEQ ID NO: 38           moltype = AA   length = 119
FEATURE                 Location/Qualifiers
source                  1..119
                        mol_type = protein
                        organism = unidentified
                        note = Callitrichine gammaherpesvirus 3
SEQUENCE: 38
SPSPCHHRDE PPSRSPSPQP TVSEQSQQSP RQQSPQGTSQ GSTRPQVPGG ATTRKRGGVR      60
GQPAKCHGKY TTTAEGLTAL LNRRHSPRTS NEGRWMNGVM AVNLSKWPLY SLRRALALA     119

SEQ ID NO: 39           moltype = AA   length = 106
FEATURE                 Location/Qualifiers
```

```
source                  1..106
                        mol_type = protein
                        organism = unidentified
                        note = Callitrichine gammaherpesvirus 3
SEQUENCE: 39
ANEVRISPLF RLPYGSAFGP GPQPGPILES STWGFLVFTQ TSLFADDIAD AIRDYCTTHP    60
GPTRNTQVVL MNFEGSGVPL PMFFPPGEET EEQREGDRAS DSDESE                  106

SEQ ID NO: 40           moltype = AA  length = 252
FEATURE                 Location/Qualifiers
source                  1..252
                        mol_type = protein
                        organism = unidentified
                        note = Callitrichine gammaherpesvirus 3
SEQUENCE: 40
MDLDGTGGGE GYSQMVPIAT APGSHAATY QDLQAAPYII WPLQTDCQPV ATTFASPGQI     60
QWYTSAVPQP TEHCSQFTNA PTVNQQQPIS QPQPENPPAF TFTQPASIIP GVISASNLNV   120
SASPIIPSDH VLPIITSVTS LAQPNNDEHA ISASHHASDG SVNQQKENQP QTLEECKTDQ   180
ERKRYRNRLA SRRCRAKFRN QLEHFRTVAA AKTEENNRLR VLIRQMCPTL DVESIVPSTS   240
AGYHEPLNHL TH                                                      252

SEQ ID NO: 41           moltype = AA  length = 146
FEATURE                 Location/Qualifiers
source                  1..146
                        mol_type = protein
                        organism = unidentified
                        note = Callitrichine gammaherpesvirus 3
SEQUENCE: 41
MDLDGTGGGE GYSQMVPIAT APGSHAATY QDLQAAPYII WPLQTDCQPV ATTFASPGQI     60
QWYTSAVPQP TEHCSQFTNA PTVNQQQPIS QPQPENPPAF TFTQPASIIP GVISASNLNV   120
SASPIIPSDH VLPIITSVTS LAQPNN                                       146

SEQ ID NO: 42           moltype = AA  length = 106
FEATURE                 Location/Qualifiers
source                  1..106
                        mol_type = protein
                        organism = unidentified
                        note = Callitrichine gammaherpesvirus 3
SEQUENCE: 42
DEHAISASHH ASDGSVNQQK ENQPQTLEEC KTDQERKRYR NRLASRRCRA KFRNQLEHFR    60
TVAAAKTEEN NRLRVLIRQM CPTLDVESIV PSTSAGYHEP LNHLTH                  106

SEQ ID NO: 43           moltype = AA  length = 216
FEATURE                 Location/Qualifiers
source                  1..216
                        mol_type = protein
                        organism = Callithrix jacchus
SEQUENCE: 43
MDDQRDLISN NEQLPMLGQR PGAPESKCSR GAVYTVFSIL VALLLAGQAT TAYFLYQQQG    60
RLDKLTVTSQ NLQLENLRMK LPKPAKPLSQ MRMATPLLMQ ALPMAGLPQK PMQNATKHGN   120
MTEDHVMHLL LNADPLKVYP PLKGSLSENL KHLKNTMETM DWKVFESWLH HWLLFEMSKH   180
SLEQKPTEAP PKESLELEDP SSGLGVTKQD LGPVAM                            216

SEQ ID NO: 44           moltype = AA  length = 1045
FEATURE                 Location/Qualifiers
REGION                  1..1045
                        note = Description of Artificial Sequence: Synthetic
                         polypeptide
source                  1..1045
                        mol_type = protein
                        organism = synthetic construct
SEQUENCE: 44
MSEDFLILIA ILVIVILVGT ITTLVGAIGG IRARRSFLFI CIFFLFLSLF LTILALLLGF    60
SWLLLVAILF WVLWLVILIL LLLVYPIPHH PLPTSLRFRM KQRVSSDPTG SDRSPQGSHN   120
SLNSPDEEDP KDDTKQPLCN MTQGGPPVNG QLLGQHAQCP PHYPCCHIQH PDGEDSDGDD   180
GKSWGDAGEE DNGPNDPNTA STRESIYEDL RYPTRDANGE YENVGYPPRD GDAPHRLGEP   240
VYDDVEQATA NEVRISPLFR LPYGSAFGPG PQPGPILESS TWGFLVFTQT SLFADDIADA   300
IRDYCTTHPG PTRNTQVVLM NFEGSGVPLP MFFPPGEETE EQREGDRASD SDESEDAQIL   360
TVFCLFCQWT LFICLGIRMI CNWRGKLTRI ICLKFCLYGL ISASLSFGWY AFLKEVTLPT   420
TATVDPRQLP LFLFILSSVL VILAIMMEFQ TSSSLFAALF VIIAGMLCVT VGVIFLLAGV   480
KPLLSGMICA SGITMLVLGV VLLVVCTRSP SPCHHRDEPP SRSPSPQPTV SEQSQQSPRQ   540
QSPQGTSQGS TRPQVPGGAT TRKRGGVRGQ PAKCHGKYTT TAEGLTALLN RRHSPRTSNE   600
GRWMNGVMAV NLSKWPLYSL RRALALAMAP RRRLSGPPWL TVLLLLSTLS VAALLILFLI   660
FSAGATISTE ASLLVLLLLF VTLLLPLLSS NGLQLPAALI LIQCFLLAAD YLAYLILPTI   720
MPRGRSTGRK GRDTEKERSR SPLRAPGGSD GPSTRAGCGA GPCQLSSPIA GNNGNEGGEG   780
DDYKSWRKPE EEDNGPNDPN TNNRIEDGDG DDGKSWRNPE EEDNRKQDRL GTKPFMAGHW   840
YESVIPGLFL CPLILPSLFW ICSLLTFLVG HGANIVSAVL FLVLAWCLLI ANWNVTREDF   900
```

| | | | | | | |
|---|---|---|---|---|---|---|
| VSGRRSSMSS | LSVAASTATA | MFASFLTLSF | DGLGLLLFGT | ALVIQTIYVL | YLVVMEITVW | 960 |
| IMMFRYLHFW | ITLLFLLSPI | ILSVACLIIQ | SSALLIEAVV | VTTITVLAIF | LWLPPQGAEA | 1020 |
| DLGTALLILN | TALCLVVLIL | TAIPT | | | | 1045 |

```
SEQ ID NO: 45          moltype = DNA   length = 3135
FEATURE                Location/Qualifiers
misc_feature           1..3135
                       note = Description of Artificial Sequence: Synthetic
                       polynucleotide
source                 1..3135
                       mol_type = other DNA
                       organism = synthetic construct
SEQUENCE: 45
atgtccgagg actttctgat tctgatcgcc atcctggtga tcgtgattct cgtgggcaca   60
atcacaaccc tggtgggcgc catcggcggc attagggcca ggaggagctt cctcttcatt  120
tgcatcttct tcctgttcct ctccctcttc ctgacaatcc tcgccctgct gctgggcttc  180
agctggctcc tgctggtggc catcctgttc tgggtgctct ggctggtcat cctcattctg  240
ctgctgctgg tgtaccctat tcctcaccac ccctgccca cctccctcag gtttagaatg  300
aagcagaggg tgagcagcga ccccacaggt tctgacagaa gccctcaggg cagccataat  360
agcctgaact cccccgatga ggaggacccc aaggatgaca ccaagcaacc tctgtgcaac  420
atgacccagg gcggacctcc cgtcaatgga cagctcctcg acaacatgc tcaatgcccc  480
cctcactatc cctgctgcca tattcagcat cccgacgagg aggattccga tggagacgat  540
ggcaagtcct ggggcgatgc cggagaggaa gacaatggcc ctaacgaccc taacaccgat  600
agcaccagag agtccattta cgaggacctc agataccccca aagggacgc caatggcgag  660
tatgagaacg tgggataccc ccctaggggac ggagatgccc tcataggct cggagagcct  720
gtgtatgacg atgtggagca agccaccgct aacgaggtga gaatctcccc tctgttcaga  780
ctgcccctacg gaagcgcttt cggacctggc cccccagcctg gacccattcc ggagagctcc  840
acatggggct ttctggtctt cacacagacc tccctgttcg ccgacgacat tgccgacgct  900
attagggact actgcacaac ccaccctggc ccacaagga acaccaggt ggtcctcatg  960
aacttcgagg gcagcggagt gccccctgcc tgttttttc ccctggaga ggagacagaa 1020
gagcagagag agggcgatag agctagcgac tccgacgagt ccgaagacgc tcagatcctg 1080
accgtgttct gcctgttttg ccagtggaca ctctttatct gcctggggaat caggatgatc 1140
tgtaactgga ggggcaaact caccaggatc atctgcctga agttctgcct ctacggactg 1200
atttccgcct ccctgtcctt cggctggtac gcttttcta aggaagtgac cctccccacc 1260
acagccaccg ttgatcctag gcaactcccc ctgttcctct tcatcctgag ctccgtgctg 1320
gtgattctcg ccatcatgat ggagtttcaa acatcctcca gcctcttcgc tgctctgttc 1380
gtgattatcg ccggaatgct gtgcgtcaca gtgggcgtga tttttctgct ggctggcgtc 1440
aagcctctcc tgacgcggcat gatctgcgcc tccggcatca caatgctcgt gctcggcgtc 1500
gtgctgctgg tggtgtgcac cagaagcccc agcccttgtc atcacaggga tgaacccccc 1560
tccagaagcc ccagccctca acccaccgtc tccgagcagt cccagcagtc ccccaggcag 1620
cagagccctc aaggcacatc ccagggttct acaagaccctc aggtgcctgg aggcgccacc 1680
accagaaaaa gaggcggcgt gagaggccaa cctgccaagt gtcacggcaa gtacaccaca 1740
accgccggga gactgaccgc tctcctgaat aggaggcaga gccccaggac atccaacgag 1800
ggcaggtgga tgaatggagt catggctgtg aacctctcca aatggcccct gtacagcctg 1860
aggagagccc tggccctcgc catggctcct agaaggaggc tctccggccc tccctggctg 1920
acagtgctgc tgctgctgtc cacactgagc gtggccgccc tgctgattct cttcctgatt 1980
ttcagcgccg gcgccaccat tagcacagaa gccagcctgc tggtcctgct gctgctgttt 2040
gtgaccctgc tgctgcctct cctgtcctcc aacggactcc agctccctgc cgccctgatt 2100
ctgatccagt gtttcctcct ggccgctgat tatctcgcct acctgattct gcctaccatt 2160
atgcccaggg gcagaagcac aggaaggaag gcagggaca cagagaaaga gaggagcaga 2220
tccccctctca gagctcctgg cggttctgat ggacccagca caagggctgg ctgtgggaca 2280
ggacccctgtc agctgagcag ccccatcgcc ggaaacaacg gcaatgaagg cggcgagggc 2340
gacgactaca agagctggag gaagcccgag aagaggaca acggcccaa tgaccccaat 2400
accaacaaca ggattgagga tggagacggc gacgacgaa atcctggag aatcctgag 2460
gaggagagaa acagaaagca ggacaggcta ggcaccagca ctttcatggc cggccactgg 2520
tatgagagcg tgattcccgg cctgttcctc tgccccctga tcctcccttc cctgttctgg 2580
atttgctccc tgctgacctt cctggtgggc acggagcca atattgtgag cgccgtcctg 2640
ttcctcgtgc tggcttggtg tctcctcatt gccaactgga acgtgacaag agaggacttc 2700
gtgtccggca ggagaagctc catgagcagc ctgtccgtgg ccgcttccac cgccacagcc 2760
atgttcgcca gcttcctcac cctgagcttt gatggcctgg gcctgctgct gtttggcacc 2820
gccctggtga tccagacaat ttacgtgctg tatctggtgg tcatggagat caccgtgtgg 2880
atcatgatgt ttaggtatct ccactttttg atcaccctgc tgttcctgct gagccccatt 2940
attctctccg tcgcctgtct catcatccaa tcctccgccc tgctgatcga ggctgtggtc 3000
gtcaccacca tcacagtcct ggccattttt ctgtggctcc ctcctcaagg cgctgaggcc 3060
gatctcggca ccgccctgct gattctgaat accgccctgt gcctggtcgt gctgatcctg 3120
accgctatcc ctaca                                                    3135

SEQ ID NO: 46          moltype = AA   length = 1270
FEATURE                Location/Qualifiers
REGION                 1..1270
                       note = Description of Artificial Sequence: Synthetic
                       polypeptide
source                 1..1270
                       mol_type = protein
                       organism = synthetic construct
SEQUENCE: 46
```

| | | | | | | |
|---|---|---|---|---|---|---|
| MRPAPWTPNP | PRSPSQMSVR | DRLARLRAEA | QVKQASVEVQ | PPQLTQVSPQ | QPVAGILFIL | 60 |
| AILTEWGSGN | RTYGPVFMCL | GGLLTMVAGA | VWLTVMSNTL | LSAWILTAGF | LIFLIGFALF | 120 |
| GVIRCCRYCC | YYCLTLESEE | RPPTPYRNTV | RKPQQPESLE | ECDSELEIKR | YKNRVASRKC | 180 |

```
RAKFKQLLQH YREVAAAKSS EIRDRRRNPA SRRDQAKWRL QTLAAGWPMG YQAYSSWMYS   240
YTDHQTTPTF VHLQATLGCT GGRRCHVFLG IVLFIFGCLL VLGIWIYLLE MLWRLGATIW   300
QLLAFFLAFF LDLILLIIAL YLQQNWWTLL VDLLWLLLFL AILIWMYYHG QRGRVACAPV   360
PAPAGPIVRP WEPSLTQAAG QAFAPVRPQH MPVEPVPVPT VALERPVYPK PVRPVLWLSS   420
PGGLGTLGAA LLTLAAALAL LASLILGTLN LTTMFLLMLL WTLVVLLICS SCSSCPLSKI   480
LLARLFLYAL ALLLLASALI AGGSILQTNF KSLSSTEFIP NLFCMLLLIH SDEHHHDDSL   540
PHPQQATDDS GHESDSNSNE GRHHLLVSGA QVPEPPTIHL AAQGMAYPLH EQHGMAPCPV   600
AQAPPTPLPF FAICLTWRIE DPPFNSLLFA LLAAAGGLQG IYVLVMLVLL ILAYRRRWRR   660
LTVCGGIMFL ACVLVLIVDA VLQLSPLLGA VTVVSMTLLL LAFNGPHDPL PQDPDNTDDN   720
GPQDPDNTDD NGPHDPLPHS PSDSAGNDGG PPQLTEEVEN KGGDQGPPLM TDGGGGHSHD   780
SGHGGGDPHL PTLLLGSSGS GGDDDDPHGP VQLSYYDGKR TEQGKEVLEK ARGSTYGTPR   840
PPMSDWTGGA LLVLYSFALM LIIIILIIFI FRRDLLCPLG ALCILLLMIT LLLIALWNLH   900
GQALMSDEGP GTGPGNGLGE KGDTSGPEGS GGSGPQRRGG DNHGRGRGRG RGRGGGRPGA   960
PGGSGSGPRH RDGVRRPQKR PSCIGCKGTH WIDDNPSTET AQAWNAGFLR GRAYGIDLLR  1020
TEGEHVEGAT GETREESEDT ESDGDDEDLP CIVSRGGPKV KRPPIFIRRL HRLLLMRAMN  1080
PVCLPVIVAP YLFWLAAIAA SCFTASVSTV VTATGLALSL LLLAAVASSY AAAQRKLLTP  1140
VTVLTAVVTT FSAGTFKLPR CTPGDRQWLY VQSSVGNIVQ SCNPRYSIFF DYMAIHRSLT  1200
KIWEDLGGPS QAPLPCVLWP VLPEPLPQGQ LTAYHVSTAP TGSWFSAPQP APENAYQAYA  1260
APQLFPVSDI                                                        1270

SEQ ID NO: 47            moltype = DNA  length = 3810
FEATURE                  Location/Qualifiers
misc_feature             1..3810
                         note = Description of Artificial Sequence: Synthetic
                         polynucleotide
source                   1..3810
                         mol_type = other DNA
                         organism = synthetic construct
SEQUENCE: 47
atgagacctg ctccctggac acctaatcct cccaggtccc ccagccagat gagcgtgaga     60
gacagactgg ctaggctgag agccgaggct caggtcaagc aggccagcgt cgaggtgcaa    120
ccccctcagc tcacccaggt gtcccccag cagcctgtgg ccggcattct gttcattctg    180
gccattctga ccgagtgggg aagcggcaac agaacctacg ccctgtctt catgtgcctc    240
ggaggactgc tgcaaatggt ggctggcgcc gtgtggctca ccgtcatgtc caacaccctg    300
ctcagcgcct ggattctgac cgccggattc ctgatcgttc gctctcttt                360
ggcgtcatca ggtgttgcag gtactgttgc tactactgcc tgaccctcga gagcgaggaa    420
agaccccca cccctacag gaatacgtg aggaaacctc agcagcccga gagcctcgag      480
gagtgcgata gcgagctgga gattaaaagg tataagaata gggtggcctc caggaagtgt    540
agggctaaat tcaaacagct cctgcaacac tataggaag tggccgccgc caagtccagc    600
gagattaggg acagaaggag gaatcctgcc tccaggagag accaggccaa atggagactc    660
caaacactcg ccgctggatg gcccatgggc taccaggcct atagctcctg gatgtacagc    720
tacaccgacc atcagacaac acccaccttc gtgcatctgc aggctacact gggctgcacc    780
ggaggcagaa ggtgtcacgt gtttctggga atcgtgctgt tcatcttgg actgctgctc    840
gtgctgggca tctggattta ctcctggag atgctcggag actcggcgc tacaatttgg    900
cagctgctcg cctttttct ggccttcttt ctggacctga tcctcctgat catcgccctg     960
tacctccaac agaactggtg gaccctcctg gtggatctgc tgtggctcct cctcttcctg   1020
gccatcctga tctggatgta ctaccatggc cagagagga gggtcgcttg cgctcctgtc    1080
cctgctcctg ctggccccat cgtgaggcct gggagccttc ccctcacaca ggcgccggc    1140
caggcctttg ctcccgtgag gccccagcac atgcctgtgg aacccgtgcc cgtccccaca    1200
gtggctctg aaaggcctgt gtaccccaag cccgtgagac ctgtcctctg gctcagcagc   1260
cctggaggac tcggaaacact cggagccgct cctcctgcca tggccgctgc tctggctctg   1320
ctggctagcc tgatcctggg aaccctcaac ctcaccacca tgtttctcct catgctcctg   1380
tggaccctcg tggtgctgct catctgttcc agctgctcca gctgccccct gagcaagatc   1440
ctgctggcca ggctgttcct gtacgccctc gccctcctgc tgctggctag cgccctgatc   1500
gctgcggaa gcatcctcca gaccaatttc aagagcctct cctccaccga gttcatcccc   1560
aacctgttct gtatgttact gctgatccat agcgacgagc accatcatga cgactccctg   1620
ccccatcctc agcaggccac agacgactcc ggccacgaga gcgacagcaa tagcaatgag   1680
ggcaggcacc atctgctcgt gtccggagct caagtcccgg agcctccac catccatctc   1740
gccgcccagg gaatggctta cccctccac gagcagcacg gcatgccccc ttgtcccgtc   1800
gctcaagccc ccccctacc tctgcccttt ttcgccattt gtctgacctg gagaatcgag   1860
gacccccct tcaacagcct gctgttcgcc ctgctcgccg ccgctggcgg cctcagggc   1920
atttacgtcc tcgtgatgct ggtgctgctg atcctcgctt acaggagaag atggaggaga   1980
ctgacagtgt gcgcggcat catgtttctc gcctgcgtct tggtcctgat cgtggacgcc   2040
gtcctgcaac tcagcccct cctgggagct gtgacagtgg tctccatgac cctgctgctg   2100
ctggccttca acggacccca cgatcctctg ccccaagatc ctgacaatac cgacgataac   2160
ggccccccaa gaccccgataa caccgacgac aatggccctc acgaccctct gccccatagc   2220
ccttccgata gcgctggcaa cgatggcggc cctcctcagc tgacagagga ggtggaaaat   2280
aagggcggcg atcagggacc cccctgatg acagatggcg gaggaggaca cagccatgat   2340
agcggacatg gcggaggcga tcccatctg ctacccctcc tcctgggcag ctccggttct   2400
ggaggcgacg atgatgaccc tcacggccct gtgcagctct cctactacga cggcaaaagg   2460
accgaacaag gaaaagaggt cctggagaag gccaggggca gcacatacgg aaccccagg   2520
cctcccatgt ccgattggac cggaggagcc ctgctggtcc tctacagctt cgccctgatg   2580
ctgatcatta tcatcctgat catctttatc ttcagaaggg acctgctgtg ccctctcggc   2640
gccctgtgca tcctgctgct catgatcaca ctcctcctga gaacctgcac   2700
ggacaagccc tgatgtccga tgagggacct ggaacaggac ccggaaacgg actgggcgag   2760
aagggagata caagcggccc cgaaggcagc ggcggaagcg accccaaag aagggccggc   2820
gacaaccacg gaagaggaag aggcaggggc agaggcagag aggaggaag acctggagcc   2880
cctggcggtt ctggaagcgg acccaggcac agggacggag tgaggaggcc tcaaaaaga   2940
cccagctgca tcggctgcaa gggaacccac tggattgatg ataaccctc cacagagacc   3000
```

-continued

```
gctcaggcct ggaacgccgg cttcctgagg ggaagagcct atggcatcga tctgctgagg    3060
accgagggcg aacacgtgga gggagccacc ggagagacaa gggaggaaag cgaagacaca    3120
gaaagcgatg gcgacgacga agacctgccc tgcattgtgt ccaggggcgg acccaaggtg    3180
aagaggcccc ctatctttat cagaaggctc catagactgc tcctgatgag ggccatgaac    3240
cctgtgtgcc tgcccgtgat cgtggccccc tacctctttt ggctggccgc cattgccgct    3300
agctgcttca ccgcctccgt gtccacagtg gtgacagcca ccggcctcgc cctgagcctg    3360
ctgctcctcg ctgccgtggc ctccagctac gccgctgctc aaagaaagct cctgaccccT    3420
gtcaccgtcc tgacagccgt cgtgaccacc ttttccgctg caccttcaa gctgcctagg    3480
tgcacacctg gcgacaggca gtggctctac gtgcagagct ccgtgggcac tatttgtgca    3540
agctgcaatc ccaggtacag cattttttc gactacatgg ccatccatag gtccctcacc    3600
aagatctggg aggatctggg aggccttcc caggctcctc tgccctgcgt gctgtggcct    3660
gtgctgcctg agcctctgcc ccaaggccag ctgacagcct atcacgtgtc caccgctcct    3720
acaggttctt ggttcagcgc tccccagccc gctcccgaaa acgcttacca ggcttacgcc    3780
gccccccagc tgttccccgt ctccgacatc                                     3810

SEQ ID NO: 48          moltype = AA  length = 1512
FEATURE                Location/Qualifiers
REGION                 1..1512
                       note = Description of Artificial Sequence: Synthetic
                       polypeptide
source                 1..1512
                       mol_type = protein
                       organism = synthetic construct
SEQUENCE: 48
MDDQRDLISN NEQLPMLGQR PGAPESKCSR GAVYTVFSIL VALLLAGQAT TAYFLYQQQG     60
RLDKLTVTSQ NLQLENLRMK LPKPAKPLSQ MRMATPLLMQ ALPMAGLPQK PMQNATKHGN    120
MTEDHVMHLL LNADPLKVYP PLKGSLSENL KHLKNTMETM DWKVFESWLH HWLLFEMSKH    180
SLEQKPTEAP PKESLELEDP SSGLGVTKQD LGPVAMSEDF LILIAILVIV ILVGTITTLV    240
GAIGGIRARR SFLFICIFFL FLSLFLTILA LLLGFSWLLL VAILFWVLWL VILILLLLVY    300
PIPHHPLPTS LRFRMKQRVS SDPTGSDRSP QGSHNSLNSP DEEDPKDDTK QPLCNMTQGG    360
PPVNGQLLGQ HAQCPPHYPC CHIQHPDGED SDGDDGKSWG DAGEEDNGPN DPNTASTRES    420
IYEDLRYPTR DANGEYENVG YPPRDGDAPH RLGEPVYDDV EQATANEVRI SPLFRLPYGS    480
AFGPGPQPGP ILESSTWGFL VFTQTSLFAD DIADAIRDYC TTHPGPTRNT QVVLMNFEGS    540
GVPLPMFFPP GEETEEQREG DRASDSDESE DAQILTVFCL FCQWTLFICL GIRMICNWRG    600
KLTRIICLKF CLYGLISASL SFGWYAFLKE VTLPTTATVD PRQLPLFLFI LSSVLVILAI    660
MMEFQTSSSL FAALFVIIAG MLCVTVGVIF LLAGVKPLLS GMICASGITM LVLGVVLLVV    720
CTRDEHAISA SHHASDGSVN QQKENQPQTL EECKTDQERK RYRNRLASRR CRAKFRNQLE    780
HFRTVAAAKT EENNRLRVLI RQMCPTLDVE SIVPSTSAGY HEPLNHLTHS PSPCHHRDEP    840
PSRSPSPQPT VSEQSQQSPR QQSPQGTSQQ STRPQVPGGA TTRKGGVRG QPAKCHGKYT    900
TTAEGLTALL NRRHSPRTSN EGRWMNGVMA VNLSKWPLYS LRRALALAMA PRRRLSGPPW    960
LTVLLLLSTL SVAALLILFL IFSAGATIST EASLLVLLLL FVTLLLPLLS SNGLQLPAAL   1020
ILIQCFLLAA DYLAYLILPT IMPRGRSTGR KGRDTEKERS RSPLRAPGGS DGPSTRAGCG   1080
AGPCQLSSPI AGNNGNEGGE GDDYKSWRKP EEEDNGPNDP NTNNRIEDGD GDDGKSWRNP   1140
EEEEDNRKQDR LGTKPFMDLD GTGGGEGYSQ MVPIATAPGS GHAATYQDLQ AAPYIIWPLQ   1200
TDCQPVATTF ASPGQIQWYT SAVPQPTEHC SQFTNAPTVN QQQPISQPQP ENPPAFTFTQ   1260
PASIIPGVIS ASNLNVSASP IIPSDHVLPI ITSVTSLAQP NNMAGHWYES VIPGLFLCPL   1320
ILPSLFWICS LLTFLVGHGA NIVSAVLFLV LAWCLLIANW NVTREDFVSG RRSSMSSLSV   1380
AASTATAMFA SFLTLSFDGL GLLLFGTALV IQTIYVLYLV VMEITVWIMM FRYLHFWITL   1440
LFLLSPIILS VACLIIQSSA LLIEAVVVTT ITVLAIFLWL PPQGAEADLG TALLILNTAL   1500
CLVVLILTAI PT                                                       1512

SEQ ID NO: 49          moltype = DNA  length = 4536
FEATURE                Location/Qualifiers
misc_feature           1..4536
                       note = Description of Artificial Sequence: Synthetic
                       polynucleotide
source                 1..4536
                       mol_type = other DNA
                       organism = synthetic construct
SEQUENCE: 49
atggacgacc agcgggacct gatcagcaac aacgagcagc tgcccatgct gggccagagg     60
cctggcgccc tgagagcaa gtgtagcaga ggcgccgtgt acaccgtgtt cagcatcctg    120
gtggccctgc tgctggccgg acaggccacc accgcctact tctgtatca gcagcaggga    180
cggctggaca agctgaccgt gaccagccag aacctgcagc tggaaaacct gcggatgaag    240
ctgcccaagc ccgccaagcc cctgagccag atgagaatgg ccacccccct gctgatgcag    300
gccctgccta tggccggcct gccccagaaa cccatgcaga acgccaccaa gcacggcaac    360
atgaccgagg accacgtgat gcatctgctg ctgaacgccg acccccctgaa ggtgtacccc    420
ccactgaagg gcagcctgag cgagaacctg aagcacctga gaaacaccat ggaaaccatg    480
gactggaaag tgttcgagag ctggctgcac cactggctgc tgttcgagat gagcaagcac    540
agcctggaac agaagcccac cgaggcccct cccaaagaga gcctggaact ggaagatccc    600
agcagcggcc tgggcgtgac caagcaggat ctgggcccg tggctatgtc cgaggacttt    660
ctgattctga tcgccatcct ggtgatcgtg attctcgtgg gcacaatcac aaccctggtg    720
ggcgccatcg gcggcattag ggccaggagg agcttcctct tcatttgcat cttcttcctg    780
ttcctctccc tcttcctgac aatcctcgcc ctgctgctgg gcttcagctg gctcctgctg    840
gtggccatcc tgttctgggt gctctggctg gtcatcctgc ttctgctgct ctggtgtac    900
cctattcctc accaccccct gcccacctcc tcaggtttta aatgaagca gaggtgagc    960
agcgacccca caggttctga cagaagccct caggcagcc ataatagcct gaactccccc   1020
gatgaggagg accccaagga tgacaccaag caacctctgt gcaacatgac ccagggcgga   1080
cctcccgtca atggacagct cctcggacaa catgctcaat gccccctca ctatccctgc   1140
```

```
tgccatattc agcatcccga cggagaggat tccgatggag acgatggcaa gtcctgggc      1200
gatgccggag aggaagacaa tggccctaac gaccctaaca ccgccagcac cagagagtcc      1260
atttacgagg acctcagata ccccacaagg gacgccaatg gcgagtatga gaacgtggga      1320
tacccccta gggacggaga tgcccctcat aggctcggag agcctgtgta tgacgatgtg      1380
gagcaagcca ccgctaacga ggtgagaatc tcccctctgt tcagactgcc ctacggaagc      1440
gctttcggac ctggcccca gcctggaccc attctggaga gctccacatg gggctttctg      1500
gtcttcacac agacctccct gttcgccgac gacattgccg acgctattag ggactactgc      1560
acaacccacc ctggccccac aaggaacacc caggtggtcc tcatgaactt cgagggcagc      1620
ggagtgcccc tgcctatgtt ttttcccct ggagaggaga cagaagagca gagagaggc      1680
gatagagcta gcgactccga cgagtccgaa gacgctcaga tcctgaccgt gttctgcctg      1740
ttttgccagt ggacactctt tatctgcctg ggaatcagga tgatctgtaa ctggaggggc      1800
aaactcacca ggatcatctg cctgaagttc tgcctctacg gactgatttc cgcctccctg      1860
tccttcggct ggtacgcttt tctgaaggaa gtgaccctcc ccaccacagc caccgttgat      1920
cctaggcaac tcccccctgtt cctcttcatc ctgagctccg tgctggtgat tctcgccatc      1980
atgatggagt ttcaaacatc ctccagcctc ttcgctgctc tgttcgtgat tatcgccgga      2040
atgctgtgcg tcacagtggg cgtgattttt ctgctggctg gcgtcaagcc tctcctgagc      2100
ggcatgatct gcgcctccgg catcacaatg tctcgtgctcg gcgtcgtgct gctggtggtg      2160
tgcaccagag atgagcacgc tatttccgcc agccaccatg ctagcgatgg ctccgtgaat      2220
cagcagaagg aaaatcagcc ccagaccctg gaggaatgca agacagatca ggagaggaag      2280
aggtacagga acaggctggc ctccaggagg tgtagagcta agttcaggaa ccagctggaa      2340
catttttagga cagtcgccgc tgctaagaca gaggagaaca acaggctcag ggtgctcatc      2400
aggcagatgt gtcctacact ggacgtgaa tccatcgtcc cctccacctc cgccggctac      2460
cacgagcctc tgaatcacct gacccacagc cccagcccctt gtcatacag ggatgaaccc      2520
ccctccagaa gccccagccc tcaacccacc gtctccgagc agtcccagca gtcccccagg      2580
cagcagagcc ctcaaggcac atcccagggt tctacaagac ctcaggtgcc tggaggcgcc      2640
accaccagaa aaagaggcgg cgtgagaggc caacctgcca agtgtcacgg caagtacaacc      2700
acaaccgccg agggactgac cgctctcctg aataggaggc acagcccag gacatccaac      2760
gagggcaggt ggatgaatgg agtcatggct gtgaacctct ccaaatggcc cctgtacagc      2820
ctgacagtgc cctggccct cgccatggct cctagaagga ggctctccgg ccctccctgg      2880
ctgacagtgc tgctgctgcc gtccacactg agcgtgccgc ccctgctgat tctcttcctg      2940
attttcagcg ccggcgccac cattagcaca gaagccagcc tgctggtcct gctcctgctg      3000
tttgtgaccc tgctgctgcc tctcctgtcc tccaacggac tccagctccc tgccgccctg      3060
attctgatcg agtgtttcct cctggccgct gattatctcg cctacctgat tctgcctacc      3120
attatgccca ggggcagaag cacaggaagg aagggcaggg acacagagaa agaggagag      3180
agatcccctc tcagagctcc tggcggttct gatggaccca gcacaagggc tggctgtgga      3240
gccggacccct gtcagctgag cagccccatc gccggaaaca acggcaatga aggcggcgag      3300
ggcgacgact acaagagctg gaggaagccc gaggaagagg acaacggccc caatgacccc      3360
aataccaaca acaggattga ggatggagac ggcgacgacg gaaaatcctg gaggaatcct      3420
gaggaggaga ataacagaaa gcaggacagg ctgggcacaa agcctttcat ggacctcgaa      3480
ggaaccggcg gaggcgaggg ctacagccag atggtcccta tcgccaccgc ccccggaagc      3540
ggccacgccg ctacctatca ggatctccag gccgccctt acatcatctg gcctctccag      3600
accgattgcc agcctgtggc taccaccttc gcctcccccg gacagatcca gtggtataca      3660
agcgccgtgc cccagcccac agagcattgc tcccagttta caaacgctcc caccgtcaac      3720
cagcagcagc ctattagcca accccagccc gaaatcccc ctgctttcac ctttacccag      3780
cccgcttcca tcattcccgg cgtcattagc gcctccaacc tgaacgtgag cgcttcccct      3840
atcatcccta gcgaccatgt cctccccatc attacctccg tgaccagcct cgcccaacct      3900
aataacatgg ccggccactg gtatgagagc gtgattccgg cgtgttcct ctgccccctg      3960
atcctccctt ccctgttctg gatttgctcc ctgctgacct tcctggtggg ccacggagcc      4020
aatattgtga gcgccgtcct gttcctcgtg ctggcttggt gtctcctcat gccaactgg      4080
aacgtgacaa gagaggactt cgtgtccggc aggagaagct ccatgagcag cctgtccgtg      4140
gccgcttcca ccgccacagc catgttcgcc agcttcctca ccctgagctt tgatggcctg      4200
ggcctgctgc tgtttggcac cgccctggtg atccagacaa tttacgtgct gtatctggtg      4260
gtcatggaga tcaccgtgtg gatcatgatg tttaggtatc tccactttg gatcaccctg      4320
ctgttcctgc tgagccccat tattctctcc gtcgcctgtc tcatcatcca atcctccgcc      4380
ctgctgatcg aggctgtggt cgtcaccacc atcacagtgc tggccatttt tctgtggctc      4440
cctcctcaag gcgctgaggc cgatctcggc accgccctgc tgattctgaa taccgccctg      4500
tgcctggtcg tgctgatcct gaccgctatc cctaca                                4536
```

| SEQ ID NO: 50 | moltype = DNA   length = 44035 |
|---|---|
| FEATURE | Location/Qualifiers |
| misc_difference | 15712 |
| | note = modified_base - a, c, t, g, unknown or other |
| misc_feature | 1..44035 |
| | note = Description of Artificial Sequence: Synthetic polynucleotide |
| source | 1..44035 |
| | mol_type = other DNA |
| | organism = synthetic construct |

SEQUENCE: 50

```
catcatcaat aatataccctt atttggatt gaagccaata tgataatgag atgggcggcg       60
cggggcgggg cgcggggcgg gaggcggggtt tgggggcggg ccggcggggcg gggcggttgtg      120
gcggaagtgg actttgtaag tgtggcggat gtgacttgct agtgccgggc gcggtaaaag      180
tgacgttttc cgtgcgcgac aacgccccg ggaagtgaca ttttttcccgc ggtttttacc      240
ggatgttgta gtgaatttgg gcgtaaccaa gtaagatttg gccattttcg cgggaaaact      300
gaaacgggga agtgaaatct gattaatttt gcgttagtca taccgcgtaa tatttgtcta      360
gggccgaggg actttggccg attacgtgga ggactcgccc aggtgttttt tgaggtgaat      420
ttccgcgttc cgggtcaaag tctgcgtttt attattatag gatatcccat tgcatacgtt      480
gtatccatat cataatatgt acatttatat tggctcatgt ccaacattac cgccatgttg      540
acattgatta ttgactagtt attaatagta atcaattacg gggtcattag ttcatagccc      600
```

```
atatatggag ttccgcgtta cataacttac ggtaaatggc ccgcctggct gaccgcccaa    660
cgacccccgc ccattgacgt caataatgac gtatgttccc atagtaacgc caatagggac    720
tttccattga cgtcaatggg tggagtattt acggtaaact gcccacttgg cagtacatca    780
agtgtatcat atgccaagta cgccccctat tgacgtcaat gacggtaaat ggcccgcctg    840
gcattatgcc cagtacatga ccttatggga cttcctact tggcagtaca tctacgtatt    900
agtcatcgct attaccatgg tgatgcggtt ttggcagtac atcaatgggc gtggatagcg    960
gtttgactca cggggatttc caagtctcca ccccattgac gtcaatggga gtttgttttg   1020
gcaccaaaat caacgggact ttccaaaatg tcgtaacaac tccgcccat tgacgcaaat   1080
gggcggtagg cgtgtacggt gggaggtcta tataagcaga gctctcccta tcagtgatag   1140
agatctccct atcagtgata gagatttcg acgagctcgt ttagtgaacc gtcagatcgc   1200
ctggagacgc catccacgct gttttgacct ccatagaaga caccgggacc gatccagcct   1260
ccgcggccgg aacggtgca ttggaacgcg gattcccgt gccaagagtg agatcttccg   1320
tttatctagg taccagatat cgccaccatg agacctgctc cctggacacc taatcctccc   1380
aggtccccca gccagatgag cgtgagagac agactggtca ggctgagagc cgaggctcag   1440
gtcaagcagg ccagcgtcga ggtgcaaccc cctcagctca cccaggtgtc ccccagcag   1500
cctgtgccg gcattctgtt cattctggcc attctgaccg agtggggaag cggcaacaga   1560
acctacggcc ctgtcttcat gtgcctcgga ggactgctga caatggtggc tggcgccgtg   1620
tggctcaccg tcatgtccaa caccctgctc agcgcctgga ttctgaccgc cggattcctg   1680
atctttctga tcggattcgc tctctttggc gtcatcaggt gttgcaggta ctgttgctac   1740
tactgctga ccctcgagag cgaggaaaga ccccccaccc cctacaggaa tacagtgatt   1800
agggacagaa ggaggaatcc tgcctccagg agagaccagg ccaaatggag actccaaaca   1860
ctcgccgctg gatgcccat gggctaccag gcctatagct ggctgatta cagctacacc   1920
gaccatcaga caacacccac cttcgtgcat ctgcaggcta cactgggctg caccggaggc   1980
agaaggtgtc acgtgtttct gggaatcgtg ctgttcatct ttggatgcct gctcgtgctg   2040
ggcatctgga tttatctcct ggagatgctc tggagactcg cgctacaat ttggcagctg   2100
ctcgccttt ttctggcctt cttttctgga ctgatcctcc tgatcatcgc cctgtacctc   2160
caacagaact ggtggaccct cctggtggat ctgctgtggc tcctcctctt cctggccatc   2220
ctgatctgga tgtactacca tggccagaga ggaaggtcg cttgcgctcc tgtccctgct   2280
cctgctggcc ccatcgtgag gccttgggag ccttccctca cacaggccgc cggccaggcc   2340
tttgctcccg tgaggcccca gcacatgcct gtggaaccg tgccccgtcc cacagtggt   2400
ctggaaaggc ctgtgtaccc caagcccgtg agacctgtcc tctggctcag cagccctgga   2460
ggactcggaa cactcggagc cgctctcctg acactggccg ctgctctggc tctgctggct   2520
agcctgatcc tgggaaccct caacctcacc accatgtttc tcctcatgct cctgtgggacc   2580
ctcgtggtgc tgctcatctg ttccagctgc tccagctgcc ccctgagcaa gatcctgctg   2640
gccaggctgt tcctgtacgc cctcgccctc ctgctgctgg ctagcgccct gatcgctgc   2700
ggaagcatcc tccagaccaa tttcaagagc ctctcctcca ccgagttcat ccccaacctg   2760
ttctgtatgt tactgctgat ccatagcgac gagcaccatc atgacgactc cctgccccat   2820
cctcagcagg ccacagacga ctccggccac gagagcgaca gcaatagcaa tgagggcagg   2880
caccatctgc tcgtgtccgg agctcaagtc ccgagccctc ccaccatcca tctcgccgcc   2940
cagggaatgg cttaccccct ccacgagcag cacggcatgg cccccttgtcc cgtcgctcaa   3000
gcccccccta cacctctgcc cttttcgcc atttgtctga cctggagaat cgaggacccc   3060
cccttcaaca gcctgctgtt cgccctgctc gccgccgctg cggcctcca gggcatttac   3120
gtcctcgtga tgctggtgct gctgatcctc gcttacagga gaatgggag ggaactgaca   3180
gtgtgcggcg catcatgtt tctcgcctgc gtcctggtcc tgatcgtgga cgccgtcctg   3240
caactcagcc ccctcctggg agctgtgaca gtggtctcca tgaccctgct gctgctggcc   3300
ttcaacggac cccacgatcc tctgcccaaa gatcctgaca ataccgacga taacggcccc   3360
caagacccg ataacaccga cgacaatgga cctcacgacc tctgcccca tagccttcc   3420
gatgcgctg gcaacgatgg cggccctcct cagctgacag aggaggtgga aaataaggc   3480
ggcgatcagg gacccccct gatgacagat ggcggaggag gacacagcca tgatagcgga   3540
catggcggag gcgatcccca tctgcctacc ctcctcctgg gcagctccgg ttctggaggc   3600
gacgatgatg accctcacgg cccctgtgcag ctctcctact acgacggcaa aaggaccgaa   3660
caaggaaaag aggtcctgga gaaggccagg ggcagcacat acggaacccc caggcctccc   3720
atgtccgatt ggaccggagg agccctgctg tgcctctaca gcttcgccct gatgctgatc   3780
attatcatcc tgatcatctt tatcttcaga agggacctgc tgtgccctct cggcgccctg   3840
tgcatcctgc tgctcatgat cacactcctc ctgatcgccc tctgcaacct gcacggacaa   3900
gccctgatgt ccgatgaggg acctggaaca ggaccggaa acggactggg cgagaaggga   3960
gatacaagcg ggcccgaagg cagcggcgga agcggacccc aaagaaggg cggcgacaac   4020
cacgggaagag gaagaggcag gggcagaggc agaggaggag gaagacctgg agccctggc   4080
ggttctggaa gcggaccag gcacagggac ggagtgagga ggcctcaaaa aagacccgag   4140
tgcatcggct gcaagggaac ccactgagatt gatgataacc cctccacaga gaccgctcag   4200
gcctggaacg ccggcttcct gagggaaga gcctatggca tcgatctgct gaggaccgag   4260
ggcgaacacg tggagggagc caccggagag acaagggagg aaagcgaaga cacagaaagc   4320
gatggcgacg acgaagacct gccctgcatt gtgtccaggg gcggacccaa ggtgaagagg   4380
ccccctatct ttatcagaag gctccataga ctgctccaga tgaaccctgg gaaccctgga   4440
tgcctgccg tgatcgtggc ccctacctc ttttggctgg ccgccattgc cgctagctgc   4500
ttcaccgcct ccgtgtccac agtggtgaca gccaccggcc tcgccctgag cctgctgctc   4560
ctcgctgccg tggcctccag ctacgccgct gctcaaagaa agctcctgac ccctgtcacc   4620
gtcctgcagg ccgtcgtgac cacctttcc gctggcacct tcaagctgcc taggtgcaca   4680
cctggcgcaca ggcagtggct ctacgtgcag agctccgtg gcaatattgc gcagagctgc   4740
aatcccaggt acagcatttt tttcgactac atggccatcc ataggtccct caccaagatc   4800
tgggagtgat gatgagcggc cgcgatctgc tgtgccttct agttgccagc catctgttgt   4860
ttgcccctcc ccgtgccttt ccttgaccct ggaaggtgcc actcccactg tccttttccta   4920
ataaaatgag gaaattgcat cgcattgtct gagtaggtgt cattctattc tggggggtgg   4980
ggtggggcag gacagcaagg gggaggattg ggaagacaat agcaggcatg ctggggatgc   5040
ggtgggctct atggccgatc agcgatcgct gaggtgggtg agtgggcgtg gctggggtg   5100
gtcatgaaaa tatataagtt gggggtctta ggtctctttt atttgtgttg cagagaccgc   5160
cggagccatg agcgggagca gcagcagcag cagtagcagc agcgccttgg atggcagcat   5220
cgtgagccct tatttgacga cgcggatgcc ccactgggac ggggtgcgtc agaatgtgat   5280
gggctccagc atcgacggcc gacccgtcct gcccgcaaat tccgccacgc tgacctatgc   5340
```

```
gaccgtcgcg gggacgccgt tggacgccac cgccgccgcc gccgccaccg cagccgcctc  5400
ggccgtgcgc agcctggcca cggactttgc attcctggga ccactggcga caggggctac  5460
ttctcgggcc gctgctgccg ccgttcgcga tgacaagctg accgccctgc tggcgcagtt  5520
ggatgcgctt actcgggaac tgggtgacct ttctcagcag gtcatggccc tgcgccagca  5580
ggtctcctcc ctgcaagctg gcgggaatgc ttctcccaca aatgccgttt aagataaata  5640
aaccagact  ctgtttggat taaagaaaag tagcaagtgc attgctctct ttatttcata  5700
attttccgcg cgcgataggc cctagaccag cgttctcggt cgttgagggt gcggtgtatc  5760
ttctccagga cgtggtagag gtggctctgg acgttgagat acatgggcat gagcccgtcc  5820
cggggtgga  ggtagcacca ctgcagagct tcatgctccg gggtggtgtt gtagatgatc  5880
cagtcgtagc aggagcgctg ggcatggtgc ctaaaaatgt ccttcagcag caggccgatg  5940
gccagggga  ggcccttggt gtaagtgttt acaaaacggt taagttggga agggtgcatt  6000
cggggagaga tgatgtgcat cttgactgt  attttagat tggcgatgtt tccgcccaga  6060
tcccttctgg gattcatgtt gtgcaggacc accagtacag tgtatccggt gcacttgggg  6120
aatttgtcat gcagcttaga gggaaaagcg tggaagaact tggagacgcc tttgtggcct  6180
cccagatttt ccatgcattc gtccatgatg atgcaatgag gcccgcggga ggcagcttgg  6240
gcaaagatat ttctggggtc gctgacgtcg tagttgtgtt ccagggtgag gtcgtcatag  6300
gccattttta caaagcgcgg gcggagggtg cccgactggg ggatgatggt cccctctggc  6360
cctgggtcg  agttgccctc gcagatctgc atttcccagg ccttaatctc ggaggggga   6420
atcatatcca cctgcggggc gatgaagaaa acgtttccg  gagccgggga gattaactgg  6480
gatgagagca ggtttctaag cagctgtgat tttccacaac cggtgggccc ataaataaca  6540
cctataaccg gttcagctg  gtagtttaga gagctgcagc tgccgtcgtc ccggaggagg  6600
ggggccacct cgttgagcat gtccctgacg cgcatgttct ccccgaccag atccgccaga  6660
aggcgctcgc cgcccaggga cagcagctct tgcaaggaag caaagttttt cagcggcttg  6720
aggccgtccg ccgtgggcat gttttcagg  gtctggctca gcagctccag gcggtcccag  6780
agctcggtga cgtgctctac ggcatctcta tccagcatat ctcctcgttt cgcgggttgg  6840
ggcgactttc gctgtagggc accaagcggt ggtcgtccag cggggccaga gtcatgtcct  6900
tccatgggcg caggtcctc  gtcagggtgg tctgggtcac ggtgaagggg tgcgctccgg  6960
gctgagcgct tgccaaggtg cgcttgaggc tggttctgct ggtgctgaag cgctgccggt  7020
cttcgccctg cgcgtcggcc aggtagcatt tgaccatggt gtcatagtcc agcccctccg  7080
cggcgtgtcc cttggcgcgc agcttgccct tggaggtggc gccgcacgag gggcagagca  7140
ggctcttgag cgcgtagagc ttgggggcga ggaagaccga ttcggggga  taggcgtccg  7200
cgccgcagac cccgcacacg gtctcgcact ccaccagcca ggtgagctcg gggcgcgccg  7260
ggtcaaaaac caggtttccc ccatgctttt tgatgcgttt cttacctcgg gtctccatga  7320
ggtggtgtcc ccgctcggtg acgaagaggc tgtccgtgtc tccgtagacc gacttgaggg  7380
gtcttttctc caggggggtc cctcggtctt cctcgtagag gaactcggac cactctgaga  7440
cgaaggcccg cgtccaggcc aggacgaagg aggctatgtg ggagggtag  cggtcgttgt  7500
ccactagggg gtccaccttc tccaaggtgt gaagacacat gtcgccttcc tcggcgtcca  7560
ggaaggtgat tggcttgtag gtgtaggcca cgtgaccggg ggttcctgac ggggggtat   7620
aaaagggt  ggggggcgc  tcgtcgtcac tctcttccga atcgctgtct gcgagggcca  7680
gctgctgggg tgagtattcc ctctcgaagg cgggcatgac ctccgcgctg aggttgtcag  7740
tttccaaaaa cgaggaggat ttgatgttca cctgtcccga ggtgatacct ttgagggtac  7800
ccgcgtccat ctggtcagaa aacacgatct ttttattgtc cagcttggtg gcgaacgacc  7860
cgtagaggc  gttggagagc agcttggcga tggagcgcag ggtctggttc ttgtccctgt  7920
cggcgcgctc cttggccgcg atgttgagct gcacgtactc gcgcgcgacg cagcgccact  7980
cggggaagac ggtggtgcgc tcgtcgggca ccaggcgcac gcgccagccg cggttgtgca  8040
gggtgaccag gtccacgctg gtggcgacct cgccgcgcag gcgctcgttg gtccagcaga  8100
gacggccgcc cttgcgcgag cagaagggg  gcaggggtcg gagctggttc tcgtccgggg  8160
ggtccgcgtc cacggtgaaa accccggggc gcaggcgcgc gtcgaagtag tctatcttgc  8220
aaccttgcat gtccagcgcc tgctgccagt cgcgggcgcg gagcgcgcgc tcgtagggt   8280
tgagcggcgg gccccagggc atgggtgggt gagtgcgga  ggcgtacatg ccgcagatgt  8340
catagacgta gagggctcc  cgcaggaccc cgatgtaggt gggtagcagg cggccgccga  8400
ggatgctggc gcgcacgtag tcatacagct cgtgcgaggg ggcgaggagg tcggggccca  8460
ggttggtgcg ggcggggcgc tccgcgcgga agacgatctg cctgaagatg gcatgcgagt  8520
tggaagagat ggtggggcgc tggaagacgt tgaagctggc gtcctgcagg ccgacggcgt  8580
cgcgcacgaa ggaggcgtag gagtcgcgca gcttgtgtac cagctcggcg gtgacctgca  8640
cgtcgagcgc gcagtagtcg agggtctcgc ggatgatgtc atatttagcc tgccccttct  8700
ttttccacag ctcgcggttg aggacaaact cttcgcggtc tttccagtac tcttggatcg  8760
ggaaccgtc  cggttccgaa cggtaagagc ctagcatgta gaactggttg acggcctggt  8820
aggcgcagca gcccttctcc acggggaggg cgtaggcctg cgccggcctt cggagcgagg  8880
tgtgggtcag ggcgaaggtg tccctgacca tgactttgag gtactggttg ttgaagtcgg  8940
agtcgtcgca gccgccccgc tcccagagcg agaagtcggt gcgcttcttg gagcggggt   9000
tgggcagagc gaaggtgaca tcgttgaaga ggattttgcc cgcgcgggc  atgaagttgc  9060
gggtgatgcg gaagggcccc ggcacttcag agcggttgtt gatgacctgg gcggcgagca  9120
cgatctcgtc gaagccgttg atgttgtggc ccacgatgta gagttccagg aagccgggcc  9180
ggcccttac  ggtgggcagc ttctttagct cttcgtaggt gagctcctcg ggcgaggcga  9240
ggccgtgctc ggccagggcc cagtccgcga ggtgcgggtt gtctctgagg aaggacttcc  9300
agaggtcgcg ggcaggagg  gtctgcaggc ggtctctgaa ggtcctgaac tggcggccca  9360
cggccatttt tcggggggtg atgcagtaga aggtgagggg gtcttgctgc cagcggtccc  9420
agtcgagctg caggggcagg tcgcgcgcgg cggtgaccag cgctcgtcg  ccccgaatt   9480
tcatgaccag catgaagggc acgagctgct ttccgaaggc ccccatccaa gtgtaggtct  9540
ctacatcgta ggtgacaaag aggcgctccg tgcgaggatg cgagccgatc gggaagaact  9600
ggatctcccg ccaccagttg gaggagtggc tgttgatgtg gtggaagtag aagtcccgtc  9660
gccgggccga acactcgtgc tggcttttgt aaaagcgagc gcagtactgg cagcgctgca  9720
cgtctgtac  ctcatgcacg agatgcacct ttcgcccgcg cacgaggaag ccgaggggaa  9780
atctgagccc cccgcctggc tcgcggcatg gctggttctc ttctactttg gatgcgtgtc  9840
cgtctccgtc tggctcctcg aggggtgtta cggtggagcg gaccaccacg ccgcgcgagc  9900
cgcaggtcca gatatcggcg cgcggcggtc ggagtttgat gacgacatcg cgcagctggg  9960
agctgtccat ggtctggagc tcccgcgcg  gcggcaggtc agcgggagt  tcttgcaggt  10020
tcacctcgca gagtcgggcc agggcgcggg gcaggtctag gtggtacctg atctctaggg  10080
```

```
gcgtgttggt ggcggcgtcg atggcttgca ggagcccgca gccccggggg gcgacgacgg  10140
tgccccgcgg ggtggtggtg gtggtggcgg tgcagctcag aaggcggtgcc gcgggcgggc  10200
ccccggaggt aggggggggct ccggtcccgc gggcaggggc ggcagcggca cgtcggcgtg  10260
gagcgcgggc aggagttggt gctgtgcccg gaggttgctg gcgaaggcga cgacgcggcg  10320
gttgatctcc tggatctggc gcctctgcgt gaagacgacg ggcccggtga gcttgaacct  10380
gaaagagagt tcgacagaat caatctcggg gtcattgacc gcggcctggc gcaggatctc  10440
ctgcacgtct cccgagttgt cttggtaggc gatctcggcc atgaactgct cgatctcttc  10500
ctcctggagg tctccgcgtc cggcgcgttc cacggtggcc gccaggtcgt tggagatgcg  10560
ccccatgagc tgcgagaagg cgttgagtcc gccctcgttc cagactcggc tgtagaccac  10620
gccccctgg tcatcgcggg cgcgcatgac cacctgcgcg aggttgagct ccacgtgccg  10680
cgcgaagacg gcgtagttgc gcagacgctg gaagaggtag ttgagggtgg tggcggtgtg  10740
ctcggccacg aagaagttca tgacccagcg gcgcaacgtg gattcgttga tgtcccccaa  10800
ggcctccagc cgttccatgg cctcgtagaa gtccacggcc aagttgaaaa actgggagtt  10860
gcgcgccgac acggtcaact cctcctccag aagacggatg agctcggcga cggtgtccgg  10920
cacctcgcgc tcgaaggcta tgggatctc ttcctccgct agcatcacca cctcctcctc  10980
ttcctcctct tctggcactt ccatgatggc ttcctcctct tcgggggggtg gcggcggcgg  11040
cggtgggga ggggcgctc tgcgccggcg gcggcgcacc gggaggcggt ccacgaagcg  11100
cgcgatcatc tccccggcgg ggcggcgcat ggtctcggtg acggcgcggc cgttctcccg  11160
ggggcgcagt tggaagacgc cgccggacat ctggtgctgg ggcgggtggc cgtgaggcag  11220
cgagacggcg ctgacgatgc atctcaacaa ttgctgcgta ggtacgccgc cgagggacct  11280
gagggagtcc atatccaccg gatccgaaaa cctttcgagg aaggcgtcta accagtcgca  11340
gtcgcaaggt aggctgagca ccgtggcggg cggcgggggg tgggggagt gtctggcgga  11400
ggtgctgctg atgatgtaat tgaagtaggc ggacttgaca cggcggatgg tcgacaggag  11460
caccatgtcc ttgggtccgg cctgctggat gcggaggcgg tcggctatgc cccaggcttc  11520
gttctggcat cggcgcaggt ccttgtagta gtcttgcatg agcctttcca ccggcacctc  11580
ttctccttcc tcttctgctt cttccatgtc tgcttcgcc ctggggcggc gccgcgcccc  11640
cctgcccccc atgcgcgtga ccccgaaccc cctgagcggt tggagcaggg ccaggtcggc  11700
gacgacgcgc tcgccagga tggcctgctg cacctgcgtg agggtggttt ggaagtcatc  11760
caagtccacg aagcggtggt aggcgcccgt gttgatggtg taggtgcagt tggccatgac  11820
ggaccagttg acggtctggt ggcccggttg cgacatctcg gtgtacctga gtcgcgagta  11880
ggcgcgggag tcgaagacgt agtcgttgca agtccgcacc aggtactggt agcccaccag  11940
gaagtgcggc ggcggctggc ggtagagggg ccagcgcagg gtggcggggg ctccgggggc  12000
caggtcttcc agcatgaggc ggtggtaggc gtagatgtac ctggacatcc aggtgatacc  12060
cgcggcggtg gtggaggcgc gcgggaagtc gcgcaccgg ttcagatgt tgcgcagggg  12120
cagaaagtgc tccatggtag gcgtgctctg tccagtcaga cgcgcgcagt cgttgatact  12180
ctagaccagg gaaaacgaaa gccggtcagc gggcactctt ccgtggtctg gtgaatagat  12240
cgcaagggta tcatggcgga gggcctcggt tcgagcccccg gtccgggcc ggacggtccg  12300
ccatgatcca cgcggttacc gcccgcgtgt cgaacccagg tgtgcgacgt cagacaacgg  12360
tggagtgttc ctttggcgt ttttctggcc gggcgccggg gccgcgtaag agactaagcc  12420
gcgaaagcga aagcagtaag tggctcgctc cccgtagccg gagggatcct tgctaagggt  12480
tgcgttgcg cgaaccccgg ttcgaatccc gtactcgggc cggccggacc cgcggctaag  12540
gtgttggatt ggcctccccc tcgtataaag accccgcttg cggattgact ccggacacgg  12600
ggacgagccc cttttatttt tgctttcccc agatgcatcc ggtgctgcgg cagatgcgcc  12660
ccccgcccca gcagcagcaa caacaccagc aagagcggca gcaacagcag cgggagtcat  12720
gcaggggccc ctcacccacc ctcggcgggc cggccacctc ggcgtccgcg gccgtgtctg  12780
gcgcctgcgg cggcggcggg gggccggctg acgaccccga ggagccccg cggcgcaggg  12840
ccagacacta cctggacctg gagggagcg aggccctggc gcgctgggg gccgcgtctc  12900
ccgagcgcca cccgcgggtg cagctgaagc gcgactcgcg cgaggcgtac gtgcctcggc  12960
agaacctgtt cagggaccgc gcgggcgagg agcccgagga gatgcgggac aggaggttca  13020
gcgcagggc ggagctgcgg caggggctga accgcgagcg gctgctgcgc gaggaggact  13080
ttgagcccga cgcgcgacg gggatcagcc ccgcgcgcac gcacgtggcg gccgccgta  13140
tggtgacggc gtacgagcag acggtgaacc aggagatcaa cttccaaaag agtttcaaca  13200
accacgtgcg cacgctggtg gcgcgcgagg aggtgaccat cgggctgatg cacctgtggg  13260
actttgtaag cgcgctggtg cagaaccccca acagcaagcc tctgacgcg cagctgttcc  13320
tgatagtgca gcacagcagg gacaacgagg cgtttaggga cgcgctgctg aacatcaccg  13380
agcccgaggg tcgtggcctg ctggacctga ttaacatcct gcagagcata gtggtgcagg  13440
agcgcagcct gagcctggcc gacaaggtgg cggccatcaa ctactcgatg ctgagcctgg  13500
gcaagttttta cgcgcgcaag atctaccaga cgccgtacgt gcccatagac aaggaggtga  13560
agatcgacgg ttttttacatg cgcatggcgc tgaaggtgct caccctgagc gacgacctgg  13620
gcgttgtaccg caacgagcgc atccacaagg ccgtgagcgt gagccggccg cgcgagctga  13680
gcgaccgcga gctgatgcac agcctgcagc gggcgctggc gggcgccggc agcggcgaca  13740
gggaggcgga gtcctacttc gatgcggggg cggacctgcg ctgggcgccc agccggcggg  13800
ccctggaggc cgcggggtc cgcgaggact atgacgagga cggcgaggag gatgaggagt  13860
acgagctaga ggagggcgag tacctggact aaacccggg tggtgtttcc ggtagatgca  13920
agacccgaac gtggtggacc cggcgctgcg ggcggctctg cagagccagc cgtccggcct  13980
taactcctca gacgactggc gacaggtcat ggaccgcatc atgtcgctga cggcgcgtaa  14040
cccggacgcg ttccggcagc agccgcaggc caacaggctc tccgccatcc tggaggcggt  14100
ggtgcctgcg cgctcgaacc ccacgcacga gaaggtgctg gccatagtga acgcgctggc  14160
cgagaacagg gccatccgcc gcgacgaggc cgggcggtg tacgacgcc tgctgcacgg  14220
cgtggcccgc tacaacagcg gcaacgtgca gaccaacctg gaccggctgg tgggggacgt  14280
gcgcgaggcg gtggcgcagc gcgagcgcgc ggatcggcag ggcaacctgg gctccatggt  14340
ggcgctgaat gccttcctga gcacgcagcc ggccaacgtg ccgcgggggc aggaagacta  14400
caccaacttt gtgagcgcgc tgcggctgat ggtgaccgag accccccaga gcgaggtgta  14460
ccagtcgggc cggactact tcttccagac cagcagacgg gcggtgaactc  14520
gagccaggct ttcaagaacc tgcgggggct gtggggcgtg aaggcgccca ccggcgaccg  14580
ggcgacggtg tccagcctgc tgacgcccaa ctcgcgcctg ctgctgctgc tgatcgcgcc  14640
gttcacggac agcggcagcg tgtcccggga cacctacctg gggcacctgc tgaccctgta  14700
ccgcgaggcc atcgggcagg cgcaggtgga cgagcacacc ttccaggaga tcaccagcgt  14760
gagccgcgcg ctggggcagg aggacacgag cagcctggag gcgactctga actacctgct  14820
```

```
gaccaaccgg cggcagaaga ttccctcgct gcacagcctg acctccgagg aggagcgcat   14880
cttgcgctac gtgcagcaga gcgtgagcct gaacctgatg cgcgacgggg tgacgcccag   14940
cgtggcgctg gacatgaccg cgcgcaacat ggaaccgggc atgtacgccg cgcaccggcc   15000
ttacatcaac cgcctgatgg actacctgca tcgcgcggcg gccgtgaacc ccgagtactt   15060
taccaacgcc atcctgaacc cgcactgctc cccgccgccc gggttctaca gcgggggctt   15120
cgaggtcccg gagaccaacg atggcttcct gtgggacgac atggacgaca cgtgttctc    15180
cccgcggccc caggcgctgg cggaagcgtc cctgctgcgt cccaagaagg aggaggagga   15240
ggaggcgagt cgccgccgcg gcagcagcgg cgtggcttct ctgtccgagc tggggcggc    15300
agccgccgcg cgccccgggt ccctgggcgg cagcccctt  ccgagcctgg tggggtctct   15360
gcacagcgag cgcaccaccc gccctcggct gctgggcgag gacgagtacc tgaataactc   15420
cctgctgcag ccggtgcggg agaaaaacct gcctcccgcc ttcccaaaca acggatagaa   15480
gagcctggtg gacaagatga gcagatggaa gacctatgcg caggagcaca gggacgcgcc   15540
tgcgctccgg ccgcccacgc ggcgccagcg ccacgaccgg cagcggggc  tggtgtggga   15600
tgacgaggac tccgcggacg atagcagcgt gctggacctg gggaggagcg gcaacccgtt   15660
cgcgcacctg cgccccccgcc tggggaggat gttttaaaaa aaaaaaaaaa angcaagaag   15720
catgatgcaa aaattaaata aaactcacca aggccatggc gaccgagcgt tggtttcttg   15780
tgttcccttc agtatgcggc gcgcggcgat gtaccaggag ggacctcctc cctcttacga   15840
gagcgtggtg ggcgcggcgg cggcgcgcc  ctcttctccc tttgcgtcgc agctgctgga   15900
gccgccgtac gtgcctccgc gctacctgcg gcctacgggg gggagaaaca gcatccgtta   15960
ctcggagctg cgcgccctgt tcgacaccac ccgggtgtac ctggtggaca caagtcggc    16020
ggacgtggcc tccctgaact accagaacga ccacagcaat tttttgacca cggtcatcca   16080
gaacaatgac tacagcccga gcgaggccag cacccagacc atcaatctgg atgaccggtc   16140
gcactgggcg ggcgacctga aaaccatcct gcacaccaac atgcccaacg tgaacgagtt   16200
catgttcacc aataagttca aggcgcgggt gatggtgtcg cgctcgcaca ccaaggaaga   16260
ccgggtggag ctgaagtacg agtgggtgga gttcgagctg ccagagggca actactccga   16320
gaccatgacc attgacctga tgaacaacgc gatcgtggag cactatctga aagtgggcag   16380
gcagaacggg gtcctggaga gcgacatcgg ggtcaagttc gacaccagga acttccgcct   16440
ggggctggac cccgtgaccg ggctggttat gcccggggtg tacaccaacg aggccttcca   16500
tcccgacatc atcctgctgc ccggctgcgg ggtggacttc acttacagcc gcctgagcaa   16560
cctcctggga atccgcaagc ggcagcccct tccaggagggc ttcaggatca cctacgagga   16620
cctggagggg ggcaacatcc ccgcgctcct cgatgtggag gcctaccagg atagcttgaa   16680
ggaaaatgag gcgggacagg aggataccgc ccccgccgcc tccgcgcgcc ccagcagggg   16740
cgaggatgct gctgacaccg cggccgcgga cggggcagag gccgaccccg ctatggtggt   16800
ggaggctccc gagcaggagg aggacatgaa tgacagtgcg gtgcgcggag acaccttcgt   16860
cacccggggg gaggaaaagc aagcggaggc cgaggccgcg gccgaggaaa agcaactggc   16920
ggcagcagcg gcgcggcggg cgttggccgc ggcggaggct gagtctgagg ggaccaagcc   16980
cgccaaggag cccgtgatta gcccctgac  cgaagatagc aagaagcgca gttacaacct   17040
gctcaaggac agcaccaaca ccgcgtaccg cagctggtac ctggcctaca actacggcga   17100
cccgtcgacg ggggtgcgct cctggaccct gctgtgcacg ccggacgtga cctgcggtc    17160
ggagcaggtg tactggtcgc tgcccgacat gatgcaagac cccgtgacct tccgctccac   17220
gcggcaggtc agcaacttcc cggtggtggg cgccgagctg ctgcccgtgc actccaagag   17280
cttctacaac gaccaggccg tctactccca gctcatccgc cagttcacct ctctgaccca   17340
cgtgttcaat cgctttcctg agaaccagat tctggcgcgc gcgcccccc  ccaccatcac   17400
caccgtcagt gaaaacgttc ctgctctcac agatcacggg acgtaccgc  tgcgcaacag   17460
catcggagga gtccagcgag tgaccgttac tgacgccaga cgccacctg  ccctacgt     17520
ttacaaggcc ttgggcatag tctcgccgcg cgtcctttcc agccgcactt tttgagcaac   17580
accaccatca tgtccatcct gatctcaccc agcaataact tgtccaggt  actgctgcgc   17640
gcgcccagca agatgttcgg aggggcgagg aagcgttccg agcagcaccc cgtgcgcgtg   17700
cgcgggcact tccgcgcccc ctggggagcg cacaaacgcg gccgcgcggg gcgcaccacc   17760
gtggacgacg ccatcgactc ggtggtggag caggcgcgca actacaggcc cgcggtctct   17820
accgtggagc cggccatcca gaccgtggtg cgggccgcgg ggcggtacgc caagctgaag   17880
agccgccgga agcgcgtggc ccgccgccac cgccgccgac ccggggccgc cgccaaacgc   17940
gccgccgcgg ccctgcttcg ccgggccaag cgcacgggcc gccgcgccgc catgagggcc   18000
gcgcgccgct tggccgccgg catcaccgcc gccaccatgg ccccccgtac ccgaagacgc   18060
gcggccgccg ccgccgccgc cgccatcagt gacatggcca gcaggcgccg gggcaacgtg   18120
tactgggtgc gcgactcggt gaccggcacg cgcgtgcccg tgcgcttccg ccccccgcgg   18180
acttgagatg atgtgaaaaa acaacactga gtctcctgct gttgtgtgta tcccagcggc   18240
ggcggcgcgc gcagcgtcat gtccaagcgc aaaatcaaag aagagatgct ccaggtcgtc   18300
gcgccggaga tctatgggcc cccgaagaag gaagagcagg attcgaagcc ccgcaagata   18360
aagcgggtca aaaagaaaaa gaaagatgat gacgatgccg atggggaggt ggagttcctg   18420
cgcgccacgc cgcccaggcg ccccggtcag tggaagggcc ggcgcgtaaa gcgcgtcctg   18480
cgccccggca ccgcggtggt cttcacgccc ggcgagcgct ccaccggga  tttcaagcgc   18540
gtctatgacg aggtgtacgg cgacgaagac ctgctggagc aggccaacga gcgcttcgga   18600
gagtttgctt acgggaagcg tcagcgggcg ctgggggagg aggaacctgc gggcgctccg   18660
ctggaccagg gcaaccccac ccccagtctg aagcccgtga ccctgcagca ggtgctgccg   18720
agcagcgcac cctccgaggc gaagcggggt ctgaagcgcg agggcggcga cctggcccc    18780
accgtgcagc tcatggtgcc caagcggcag aggctggagg atgtgctgga aaaatgaaa    18840
gtagacccg  gtctgcagc  ggacatcagg gtccgcccca tcaagcaggt ggcgccgggc   18900
ctcggcgtgc agaccgtgga cgtggtcatc cccaccgaca actccgccag ccgccacc    18960
actaccgctg cctccacgga catggagaca cagaccgatc ccgccgcagc cgcagcgca    19020
gccgccgccg cgacctcctc ggcggaggtg cagacgacc  cctggctgcc gccggcgatg   19080
tcagctcccc gcgcgcgtcg cgggcgcagg aagtacggcg ccgccaacgc gctcctgccc   19140
gagtacgcct tgcatccttc catcgcgccc accccggct  accgaggcta tacctaccgc   19200
ccgcgaagag ccaagggttc caccccgcgt ccccgccgc  ccacccgcac cagcacccgc   19260
cgccgccgcc gcagacgcca gcccgcactg ctccagtct ccgtgaggaa agtggcgcgc    19320
gacggacaca cctgtggtgct gcccaggcg  cgctaccacc ccagcatcgt ttaaaagcct   19380
gttgtggttc ttgcagatat ggccctcact tgccgcctcc gtttcccggt gccgggtac    19440
cgaggaggaa gatcgcgccg caggagggt  ctggccggcc gcggcctgag cggaggcagc   19500
cgccgcgcgc accggcggcg acgcgccacc agccgacgca tgcgcggcgg ggtgctgccc   19560
```

```
ctgttaatcc ccctgatcgc cgcggcgatc ggcgccgtgc ccgggatcgc ctccgtggcc    19620
ttgcaagcgt cccagaggca ttgacagact tgcaaacttg caaatatgga aaaaaaaacc    19680
ccaataaaaa agtctagact ctcacgctcg cttggtcctg tgactatttt gtagaatgga    19740
agacatcaac tttgcgtcgc tggccccgcg tcacggctcg cgcccgttcc tgggacactg    19800
gaacgatatc ggcaccagca acatgagcgg tggcgcctca agttgggggct tctctgtggag   19860
cggcattaaa agtatcgggt ctgccgttaa aaattacggc tcccgggcct ggaacagcag    19920
cacgggccag atgttgagag acaagttgaa agagcagaac ttccagcaga aggtggtgga    19980
gggcctggcc tccggcatca acggggtggt ggacctggcc aaccaggccg tgcagaataa    20040
gatcaacagc agactggacc cccggccgcc ggtggaggag gtgccgccgg cgctggagac    20100
ggtgtccccc gatgggcgtg gcgagaagcg cccgcggccc gataggggaag agaccactct    20160
ggtcacgcag accgatgagc cgccccgta tgaggaggcc ctgaagcaag gtctgcccac    20220
cacgcggccc atcgcgccca tggccaccgg ggtggtgggc cgccacaccc ccgccacgct    20280
ggacttgcct ccgcccgccg atgtgccgca gcagcagaag gcggcacagc cgggcccgcc    20340
cgcgaccgcc tcccgttcct ccgccggtcc tctgcgccag gcggccagcg gcccccgcgg    20400
gggggtcgcg aggcacggca actggcagag cacgctgaac agcatcgtgg gtctgggggt    20460
gcggtccgtg aagcgccgcc gatgctactg aatagcttag ctaacgtgtt gtatgtgtgt    20520
atgcgcccta tgtcgccgcc agaggagctg ctgagtcgcc gccgttcgcg cgcccaccac    20580
caccgccact ccgccccctca agatggcgac cccatcgatg atgccgcagt ggtcgtacat    20640
gcacatctcg ggccaggacg cctcggagta cctgagcccc gggctggtgc agttcgcccg    20700
cgccaccgag agctacttca gcctgagtaa caagtttagg aaccccacgg tggcgcccac    20760
gcacgatgtg accaccgacc ggtctcagcg cctgacgctg cggttcattc ccgtggaccg    20820
cgaggacacc gcgtactcgt acaaggcgcg gttcacccgtg gccgtgggcg acaaccgcgg    20880
gctggacatg gcctccacct actttgacat ccgcgggtg ctggaccggg gtcccacttt    20940
caagccctac tctggcaccg cctacaactc cctggccccc aagggcgctc ccaactcctg    21000
cgagtgggag caagaggaaa ctcaggcagt tgaagaagca gcagaagagg aagaagaaga    21060
tgctgacggt caagctgagg aagagcaagc agctaccaaa aagactcatg tatatgctca    21120
ggctcccctt tctggcgaaa aaattagtaa agatgtctg caaataggaa cggacgctac    21180
agctacagaa caaaaaccta tttatgcaga ccctacattc cagcccgaac cccaaatcgg    21240
ggagtccag tggaatgagg cagatgctac agtcgccggc ggtagagtgc taaagaaatc    21300
tactcccatg aaaccatgct atggttccta tgcaagaccc acaaatgcta atggaggtca    21360
gggtgtacta acggcaaatg cccagggaca gctagaatct caggttgaaa tgcaattctt    21420
ttcaacttct gaaaacgccc gtaacgaggc taacaacatt cagcccaaat tggtgctgta    21480
tagtgaggat gtgcacatgg agaccccgga tacgcacctt tcttacaagc ccgcaaaaag    21540
cgatgcaaat tcaaaaatca tgctgggtca gcagtccatg cccaacagac ctaattacat    21600
cggcttcaga gacaacttta ttcggcctcat gtattacaat agcactggca acatgggagt    21660
gcttgcaggt caggcctctc agttgaatgc agtggtggac ttgcaagaca gaaacacaga    21720
actgtcctac cagctcttgc ttgattccat gggtgacaga accagatact tttccatgtg    21780
gaatcaggca gtggacagtt atgacccaga tgttagaatt attgaaaatc atggaactga    21840
agcagactc cccaactatt gttccctct gggtggcata ggggtaactg acacttacca    21900
ggctgttaaa accaacaatg gcaataacgg gggccaggtg acttggacaa aagatgaaac    21960
ttttgcagat cgcaatgaaa tagggtgtggg aaacaatttc gctatggaga tcaacctcag    22020
tgccaacctg tggagaaact tcctgtactc caacgtggcg ctgtacctac cagacaagct    22080
taagtacaac ccctccaatg tggacatctc tgacaacccc aacacctacg attacatgaa    22140
caagcgagtg gtggccccgg ggctggtgga ctgctacatc aacctgggcg cgcgctggtc    22200
gctggactac atggacaacg tcaacccctt caaccaccac cgcaatgcgg gcctgcgcta    22260
ccgctccatg ctcctgggca cgggcgctaa cgtgccttc cacatccagg tgccccagaa    22320
gttctttgcc atcaagaacc tcctcctcct gccgggctcc tacacctacg agtggaactt    22380
caggaaggat gtcaacatgg tcctccagag ctctctgggt aacgatctca gggtggacgg    22440
ggccagcatc aagttcgaga gcatctgcct ctacgccacc ttcttcccca tggcccacaa    22500
cacggcctcc acgctcgagg ccatgctcag gaacgacacc aacgaccagt ccttcaatga    22560
ctacctctcc gccgccaaca tgctctaccc catacccgcc aacgccacca acgtcccccat    22620
ctccatcccc tcgcgcaact gggcggcctt ccgcggctgg gccttcaccc gcctcaagac    22680
caaggagacc ccctcctgg gctcgggatt cgacccctac tacacctact cgggctccat    22740
tccctacctg gacggcacct tctacctcaa ccacactttc aagaaggtct cggtcacctt    22800
cgactcctcg tcagctggc cgggcaacga ccgtctgctc accccccaacg agttcgagat    22860
caagcgctcg gtcgacgggg agggctacaa cgtggcccag tgcaacatga ccaaggactg    22920
gttcctggtc cagatgctgg ccaactacaa catcggctac caggggcttct acatcccaga    22980
gagctacaag gacaggatgt actccttctt caggaacttc cagcccatga gccggcaggt    23040
ggtggaccag accaagtaca aggactacca ggaggtgggc atcatccac agcacaacaa    23100
ctcggggcttc gtgggctacc tcgccccac catgcgcgag ggacaggcct acccccgcaa    23160
cttcccctat ccgctcatag gcaagaccgc ggtcgacagc atcacccaga aaaagttcct    23220
ctgcgaccgc accctctggc gcatcccctt ctccagcaac ttcatgtcca tgggtgcgct    23280
ctcggacctg ggccagaact tgctctacgc caactccgcc cacgccctcg acatgacctt    23340
cgaggtcgac cccatgacg agcccaccct tctctatgtt ctgttcgaag tcttgacgt    23400
ggtccgggtc caccagccgc accgcggcgt catcgagacc gtgtacctgc gtacgccctt    23460
ctcggccggc aacgccacca cctaaagaag caagccgcag tcatcgccgc ctgcatgccg    23520
tcgggttcca ccgagcaaga gctcagggcc atcgtcagag acctgggatg cgggccctat    23580
ttttgggca ccttcgacaa gcgcttccct ggctttgtct cccacacaa gctggcctgc    23640
gccatcgtca acacggccgg ccgcgagacc gggggcgtgc actgctgcc cttcgctgga    23700
aaccgcgct ccaaaacatg cttcctcttt gaccccttcg gcttttcgga ccagcggctc    23760
aagcaaatct acgagttcga gtacgagggc ttgctgcgtc gcagcgccat cgcctcctcg    23820
cccgaccgct gcgtcaccct cgaaaagtcc acccagaccg tgcaggggcc cgactcggcc    23880
gcctgcggtc tcttctgctg catgtttctg cacgcctttg tgcactggcc tcagagtccc    23940
atggacacag acccccacat gaacttgctg acggggggtgc ccaactcat gctccagacc    24000
ccccaggtcg agcccaccct gcgccgcaac caggagcagc tctacagctt cctggagcgc    24060
cactcgcctt acttccgccg ccacagcgca cagatcagga ggccacctc cttctgccac    24120
ttgcaagaga tgcaagaagg gtaataacga tgtacacact tttttttctca ataaatggca    24180
tcttttatt tatacaagct ctctgggta ttcatttccc accaccaccc gccgttgtcg    24240
ccatctggct ctatttagaa atcgaaaggg ttctgccggg agtcgccgtg cgccacgggc    24300
```

```
agggacacgt tgcgatactg gtagcgggtg ccccacttga actcgggcac caccaggcga   24360
ggcagctcgg ggaagttttc gctccacagg ctgcgggtca gcaccagcgc gttcatcagg   24420
tcgggcgccg agatcttgaa gtcgcagttg gggccgccgc cctgcgcgcg cgagttgcgg   24480
tacaccgggt tgcagcactg gaacaccaac agcgccgggt gcttcacgct ggccagcacg   24540
ctgcggtcgg agatcagctc ggcgtccagg tcctccgacg tgctcagcgc gaacggggtc   24600
atcttgggca cttgccgccc caggaagggc gcgtgccccg gtttcgagtt gcagtcgcag   24660
cgcagcggga tcagcaggtg cccgtgcccg gactcggcgt tggggtacag cgcgcgcatg   24720
aaggcctgca tctggcggaa ggccatctgg gccttggcgc cctccgagaa gaacatgccg   24780
caggacttgc ccgagaactg gtttgcgggg cagctgcgt cgtgcaggca gcagcgcgcg   24840
tcggtgttgg cgatctgcac cacgttgcgc ccccaccggt tcttcacgat cttggccttg   24900
gacgattgct ccttcagcgc gcgctgcccg ttctcgctgg tcacatccat ctcgatcaca   24960
tgttccttgt tcaccatgct gctgccgtgc agacacttca gctcgccctc cgtctcggtg   25020
cagcggtgct gccacagcgc gcagcccgtg ggctcgaaag acttgtaggt cacctccgcg   25080
aaggactgca gtaccccctg caaaaagcgg cccatcatga tcacgaaggt cttgttgctg   25140
ctgaaggtca gctgcagccc gcggtgctcc tcgttcagcc aggtcttgca cacggccgcc   25200
agcgcctcca cctggtcggg cagcatcttg aagttcacct tcagctcatt ctccacgtgg   25260
tacttgtcca tcagcgtgcg cgccgcctcc atgcccttct cccaggccga caccagcggc   25320
aggctcacgg ggttcttcac catcaccgtg gccgccgcc gccgcgcgt ttcgctttcc   25380
gccccgctgt tctcttcctc ttcctcctct tcctcgccgc cgcccactcg cagccccgc   25440
accacgggg cgtcttcctg caggcgctgc accttgcgct tgccgttgcg cccctgcttg   25500
atgcgcacgg gcgggttgct gaagcccacc atcaccagcg cggcctcttc ttgctcgtcc   25560
tcgctgtcca gaatgacctc cgggggaggg gggttggtca tcctcagtac cgaggcacgc   25620
ttcttttcct tcctgggggc gttcgccagc tccgcggctg cggccgctgc cgaggtcgaa   25680
ggccgagggc tgggcgtgcg cggcaccagc gcgtcctgcg agccgtcctc gtcctcctcg   25740
gactcgagac ggaggcgggc ccgcttcttc ggggcgcgc ggggcggcgg aggcggcggc   25800
ggcgacggag acggggacga gacatcgtcc agggtgggag gcggggagcg cgcgcgcgt   25860
ccgcgctcgg gggtggtctc gcgctggtcc tcttccgac tggccatctc ccactgctcc   25920
ttctcctata ggcagaaaga gatcatggag tctctcatgc gagtcgagaa ggaggaggac   25980
agcctaaccg cccctctga gccctccacc accgccgcca ccaccgccaa tgccgccgcg   26040
gacgacgcgc ccaccgagac caccgccagt accaccctcc cagccgacgc accccgctc   26100
gagaatgaag tgctgatcga gcaggacccg ggttttgtga gcggagagga ggatgaggtg   26160
gatgagaagg agaaggagga ggtcgccgcc tcagtgccaa aagaggataa aaagcaagac   26220
caggacgacg cagataagga tgagacagca gtcgggcggg ggaacggaag ccatgatgct   26280
gatgcaggct acctagacgt gggagagcgc gtgctgctta agcacctgca ccgccagtgc   26340
gtcatcgtct gcgacgcgct gcaggagcgc tgcgaagtgc ccctggacgt ggcggaggtc   26400
agccgcgcct acgagcggca cctcttcgcg ccgcacgtgc ccccaagcg ccgggagaac   26460
ggcacctgcg agcccaaccc gcgtctcaac ttctacccgg tcttcgcggt acccgaggtg   26520
ctggccacct accacatctt tttccaaaac tgcaagatcc cctctcctg ccgcgccaac   26580
cgcacgcgcc ccgacaaaac cctgaccctg cggcagggcg cccacatacc tgatatcgcc   26640
tctctggagg aagtgcccaa gatcttcgag ggtctcggtc gcgacgagaa acgggcggcg   26700
aacgctctgc acggagacag cgaaaacgag agtcactcgg gggtgctggt ggagctcgag   26760
ggcgacaacg cgcgcctggc cgtactcaag cgcagcatag aggtcaccca ctttgcctac   26820
ccggcgctca acctgccccc caaggtcatg agtgtggtca tcatgatcgc   26880
cgcgcccagc ccctggccgc ggatgcaaac ttgcaagagt cctccgagga aggcctgccc   26940
gcggtcagcg acgagcagct ggcgcgctgg ctggagaccc gcgaccccgc gcagctggag   27000
gagcggcgca agctcatgat ggccgcggtg ctggtcaccg tggagctcga gtgtctgcag   27060
cgcttcttcg cggaccccga gatgcagcgc aagctcgagg agaccctgca ctacaccttc   27120
cgccagggct acgtgcgcca ggcctgcaag atctccaacg tggagctctg caacctggtc   27180
tcctacctgg gcatcctgca cgagaaccgc ctcgggcaga acgtcctgca ctccaccctc   27240
aaaggggagg cgcgccgcga ctacatccgc gactgcgcct acctcttcct ctgctacacc   27300
tggcagacgg ccatggggt ctggcagcag tgcctggagg agcgcaacct caaggagctg   27360
gaaaagctcc tcaagcgcac cctcaggac ctctggacgg gcttcaacga gcgctcggtg   27420
gccgccgcgc tggcggacat catctttccc gagcgcctgc tcaagaccct gcagcagggc   27480
ctgcccgact tcaccagcca gagcatgctg cagaacttca ggactttcat cctggagcgc   27540
tcgggcatcc tgccggccat ttgctgcgcg ctgcccagcg acttcgtgc catcaagtac   27600
agggagtgcc cgccgccgct ctggggccac tgctacctct tccagctggc caactacctc   27660
gcctaccact cggacctcat ggaagacgtg agcggcgagg gctgctcga gtgccactgc   27720
cgctgcaacc tctgcacgcc ccaccgctct ctagtctgca acccgcagct gctcagcgag   27780
agtcagatta tcggtacctt cgagctgcag ggtccctcgc ctgacgagaa gtccgcgct   27840
ccagggctga aactcactcc ggggctgtgg acttccgcct acctacgcaa atttgtacct   27900
gaggactacc acgcccacga gatcaggttc tacgaagacc aatcccgccc gcccaaggcg   27960
gagctcaccg cctgcgtcat cacccagggg cacatcctgg gccaattgca agccatcaac   28020
aaagcccgcc gagagttctt gctgaaaaag ggtcgggggg tgtacctgga cccccagtcc   28080
ggcagagggc taaacccgct acccccgccg ccgcccage gcggggacct tgcttcccag   28140
gatggcaccc agaaagaagc agcagccgcc gccgccgccg cagccataca tgcttctgga   28200
ggaagaggag gaggactggg acagtcaggc agaggaggtt tcgacgagg agcaggagga   28260
gatgatggaa gactgggagg aggacagcag cctagacgag gaagcttcag aggccgaaga   28320
ggtggcagac gcaacaccat cgccctcggt cgcagccccc tcgcggggc ccctgaaatc   28380
ctccgaaccc agcacccccg ctataacctc cgctcctccg gcgccgggc caccgcccg   28440
cagacccaac cgtagatggg acaccacagg aacggggtc ggtaagtcca agtgcccgcc   28500
gccgccaccg cagcagcagc agcagcagcg ccagggctac cgtcgtggc gcgggcacaa   28560
gaacgccata gtcgcctgct tgcaagactg cgggggcaac atctctttcg cccgccgctt   28620
cctgctattc caccacgggg tcgcctttcc ccgcaatgtc ctgcattact accgtcatct   28680
ctacagccct tactgcagcg gccacccaga ggctgccacag cggcgaccac   28740
cacctaggaa gatatcctcc gcgggcaaga cagcggcagc agcggccagg agacccgcg   28800
cagcagcggc gggagcggtg ggcgcactgc gcctctcgcc caacgaaccc ctctcgaccc   28860
gggagctcag acacaggatc ttccccactt tgtatgccat cttccaacag agcagaggcc   28920
aggagcagga gctgaaaata aaaaacagat ctctgcgctc cctcacccgc agctgtctgt   28980
atcacaaaag cgaagatcag cttcggcgca cgctggagga cgcggaggca ctcttcagca   29040
```

```
aatactgcgc gctcactctt aaagactagc tccgcgccct tctcgaattt aggcggaga  29100
aaactacgtc atcgccggcc gccgcccagc ccgcccagcc gagatgagca aagagattcc  29160
cacgccatac atgtggagct accagccgca gatgggactc gcggcgggag cggcccagga  29220
ctactccacc cgcatgaact acatgagcgc gggaccccac atgatctcac aggtcaacgg  29280
gatccgcgcc cagcgaaacc aaatactgct ggaacaggcg gccatcaccg ccacgcccg  29340
ccataatctc aaccccgaa attggcccgc cgccctcgtg taccaggaaa ccccctccgc  29400
caccaccgta ctacttccgc gtgacgccca ggccgaagtc cagatgacta actcaggggc  29460
gcagctcgcg ggcggctttc gtcacggggc gcggccgctc cgaccaggta taagacacct  29520
gatgatcaga ggccgaggta tccagctcaa cgacgagtcg gtgagctctt cgctcggtct  29580
ccgtccggac ggaactttcc agctcgccgg atccggccgc tcttcgttca cgcccgcca  29640
ggcgtacctg actctgcaga cctcgtcctc ggagccccgc tccggcggca tcggaaccct  29700
ccagttcgtg gaggagttcg tgccctcggt ctacttcaac cccttctcgg gacctccggg  29760
acgctacccc gaccagttca ttccgaactt tgacgcggtg aaggactcgg cggacggcta  29820
cgactgaatg tcaggtgtcg aggcagagca gcttcgcctg agacacctcg agcactgccg  29880
ccgcacaag tgcttcgccc gcggttctgg tgagttctgc tactttcagc tacccgagga  29940
gcataccgag gggccggcgc acggcgtccg cctgaccacc cagggcgagg ttacctgttc  30000
cctcatccgg gagtttaccc tccgtcccct gctagtggag cgggagcggg gtccctgtgt  30060
cctaactatc gcctgcaact gccctaaccc tggattacat caagatcttt gctgtcatct  30120
ctgtgctgag tttaataaac gctgagatca gaatctactg gggctcctgt cgccatcctg  30180
tgaacgccac cgtcttcacc caccccgacc aggcccaggc gaacctcacc tgcggtctgc  30240
atcggagggc caagaagtac ctcacctggt acttcaacgg cacccctt gtggtttaca  30300
acagcttcga cggggacgga gtctccctga aagaccagct ccggtctc agctactcca  30360
tccacaagaa caccaccctc caactcttcc ctccctacct gccgggaacc tacgagtgcc  30420
tcaccggccg ctgcacccac ctcccgcc tgatcgtaaa ccagagcttt ccgggaacag  30480
ataactccct cttccccaga acaggaggtg agctcaggaa actccccggg gaccagggcg  30540
gagacgtacc ttcgaccctt gtgggttag gattttttat taccggttg ctggctcttt  30600
taatcaaagt ttccttgaga tttgttcttt ccttctacgt gtatgaacac ctcaacctcc  30660
aataactcta ccctttcttc ggaatcaggt gacttctctg aaatcgggct tggtgtgctg  30720
cttactctgt tgatttttt ccttatcata ctcagccttc tgtgcctcag gctcgccgcc  30780
tgctgcgcac acatctatat ctactgctgg ttgctcaagt gcaggggtcg caccccaaga  30840
tgaacaggta catggtccta tcgatcctag gcctgctggc cctggcgcc tgcagccgcg  30900
ccaaaaaga gattaccttt gaggagcccg cttgcaatgt aactttcaag cccgagggtg  30960
accaatgcac caccctcgtc aaatgcgtta ccaatcatga gaggctgcgc atcgactaca  31020
aaacaaaac tggccagttt gcggtctata gtgtgtttac gcccggagac ccctctaact  31080
actctgtcac cgtcttccag ggcggacagt ctaagatatt caattacact ttccctttt  31140
atgagttatg cgatgcggtc atgtacatgt caaaacagta caacctgtgg cctccctctc  31200
cccaggcgtg tgtggaaaat actgggtctt actgctgtat ggctttcgca atcactacgc  31260
tcgctctaat ctgcacggtg ctatacataa aattcaggca gaggcgaatc tttatcgatg  31320
aaaagaaat gccttgatcg ctaacaccgg cttctatct gcagaatgaa tgcaatcacc  31380
tccctactaa tcaccaccac cctccttgcg attgcccatg ggttgacacg aatcgaagtg  31440
ccagtggggt ccaatgtcac catggtgggc cccgccggca attccaccct catgtgggaa  31500
aaatttgtcc gcaatcaatg ggttcatttc tgctctaacc gaatcagtat caagcccaga  31560
gccatctgcg atgggcaaaa tctaactctg atcaatgtgc aaatgatgga tgctgggtac  31620
tattacgggc agcggggaga aatcattaat tactggcgac cccacaagga ctacatgctg  31680
catgtagtcg aggcacttcc cactaccacc cccactacca cctctcccac caccaccacc  31740
actactacta ctactactac tactactact actaccacta ccgctgcccg ccatacccgc  31800
aaaagcacca tgattagcac aaagcccct cgtgctcact cccacgccgg cgggcccatc  31860
ggtgcgacct cagaaaccac cgagctttgc ttctgccaat gcactaacgc cagcgctcat  31920
gaactgttcg acctggagaa tgaggatgtc cagcagagct ccgcttgcct gacccaggag  31980
gctgtggagc ccgttgccct gaagcagatc ggtgattcaa taattgactc ttcttctttt  32040
gccactcccg aataccctcc cgattctact tccacatca cgggtaccaa agaccctaac  32100
ctctctttct acctgatgct gctgctctgt atctctgtgg tctcttccgc gctgatgtta  32160
ctggggatgt tctgctgcct gatctgccgc agaaagagaa aagctcgctc tcagggccaa  32220
ccactgatgc ccttccccta ccccccggat tttgcagata caagatatg agctcgctgc  32280
tgacactaac cgctttacta gcctgcgctc taacccttgt cgcttgcgac tcgagattcc  32340
acaatgtcac agctgtggca ggagaaaatg ttactttcaa ctccacggcc gatacccagt  32400
ggtcgtggag tggctcaggt agctacttaa ctatctgcaa tagctccact tccccggca  32460
tatccccaac caagtaccaa tgcaatgcca gcctgttcac cctcatcaac gcttccaccc  32520
tggacaatgg actctatgta ggctatgtac cctttggtgg gcaaggaaag acccacgctt  32580
acaacctgga agttcgccag cccagaacca ctaccaggc ttctcccacc accaccacca  32640
ccaccaccat caccagcagc agcagcagca gcagcacag cagcagcagc agattattga  32700
ctttggtttt ggccagctca tctgccgcta cccaggccat ctacagctct gtgcccgaaa  32760
ccactcagat ccaccgccca gaaacgacca ccgccaccac cctacacacc tccagcgatc  32820
agatgccgac caacatcacc ccttggctc ttcaaatggg acttacaagc ccactccaa  32880
aaccagtgga tgcggccgag gtctccgccc tcgtcaatga ctgggcgggg ctggaatgt  32940
ggtggttcgc ataggcatg atggcgctct gcctgcttct gctctggctc atctgctgcc  33000
tccaccgcag gcgagccaga ccccccatct atagacccat cattgtcctg aaccccgata  33060
atgatgggat ccatagattg gatggcctga aaaacctact tttttctttt acagtatgat  33120
aaattgagac atgcctcgca ttttcttgta catgttcctt ctcccacctt ttctgggtg  33180
ttctacgctg gccgctgtgt ctcacctgga ggtagactgc ctctcaccct tcactgtcta  33240
cctgctttac ggattggtca ccctcactct catctgcagc ctaatcacag taatcatcgc  33300
cttcatccag tgcattgatt acatctgtgt gcgcctcgca tacttcagac caccccgca  33360
gtaccgagac aggaacattg cccaacttct aagactgctc taatcatgca taagactgtg  33420
atctgccttc tgatcctctg tagcctgccc accctcacct cctgccagta caccacaaaa  33480
tctccgcgca aaagacatgc ctcctgccgc ttcacccaac tgtggaatat acccaaatgc  33540
tacaacgaaa agagcgagct ctccgaagct tggctgtatg gggtcatctg tgtcttagtt  33600
ttctgcagca ctgtctttgc cctcataatc taccccact ttgatttggg atggaacgcg  33660
atcgatgcca tgaattaccc cacctttccc gcacccgaga taattccact gcgacaagtt  33720
gtaccgcgttg tcgttaatca acgcccccca tcccctacgc ccactgaaat cagctacttt  33780
```

```
aacctaacag gcggagatga ctgacgccct agatctagaa atggacggca tcagtaccga   33840
gcagcgtctc ctagagaggc gcaggcaggc ggctgagcaa gagcgcctca atcaggagct   33900
ccgagatctc gttaacctgc accagtgcaa aagaggcatc ttttgtctgg taaagcaggc   33960
caaagtcacc tacgagaaga ccggcaacag ccaccgcctc agttacaaat tgcccaccca   34020
gcgccagaag ctggtgctca tggtgggtga gaatcccatc accgtcaccc agcactcggt   34080
agagaccgag gggtgtctgc actcccctg tcggggtcca gaagacctct gcaccctggt    34140
aaagaccctg tgcggtctca gagatttagt ccccttaaac taatcaaaca ctggaatcaa   34200
taaaaagaat cacttactta aaatcagaca gcaggtctct gtccagttta ttcagcagca   34260
cctccttccc ctcctcccaa ctctggtact ccaaacgcct tctggcggca aacttcctcc   34320
acaccctgaa gggaatgtca gattcttgct cctgtccctc cgcacccact atcttcatgt   34380
tgttgcagat gaagcgcacc aaaacgtctg acgagagctt caaccccgtg taccccatg    34440
acacggaaag cggccctccc tccgtccctt cctcacccc tcccttcgtg tctcccgatg    34500
gattccaaga aagtccccc ggggtcctgt ctctgaacct ggccgagccc ctggtcactt    34560
cccacggcat gctcgccctg aaaatgggaa gtggcctctc cctggacgac gctggcaacc   34620
tcacctctca agatatcacc accgctagcc ctcccctcaa aaaaaccaag accaacctca   34680
gcctagaaac ctcatccccc ctaactgtga gcacctcagg cgccctcacc gtagcagccg   34740
ccgctcccct ggcggtggcc ggcacctccc tcaccatgca atcagaggcc ccctgacag    34800
tacaggatgc aaaactcacc ctggccacca aaggccccct gaccgtgtct gaaggcaaac   34860
tggccttgca aacatcggcc ccgctgacgg ccgctgacag cagcaccctc acagtcagtg   34920
ccacaccacc ccttagcaca agcaatggca gcttgggtat tgacatgcaa gcccccattt   34980
acaccaccaa tggaaaacta ggacttaact ttggcgctcc cctgcatgtg gtagacagcc   35040
taaatgcact gactgtagtt actggccaag gtcttacgat aaacggaaca gccctacaaa   35100
ctagagtctc aggtgccctc aactatgaca catcaggaaa cctagaattg agagctgcag   35160
ggggtatgcg agttgatgca aatggtcaac ttatccttga tgtagcttac ccatttgatg   35220
cacaaaacaa tctcagcctt aggcttggac agggacccct gtttgttaac tctgcccaca   35280
acttggatgt taactacaac agaggcctct acctgttcac atctggaaat accaaaaagc   35340
tagaagttaa tatcaaaaca gccaagggtc tcatttatga tgacactgct atagcaatca   35400
atgcgggtga tgggctacag tttgactcag gctcagatac aaatccatta aaaactaaac   35460
ttggattagg actggattat gactccagca gagccataat tgctaaactg ggaactggcc   35520
taagctttga caacacaggt gccatcacag taggcaacaa aaatgatgac aagcttacct   35580
tgtggaccac accagaccca tcccctaact gtagaatcta ttcagagaaa gatgctaaat   35640
tcacacttgt tttgactaaa tgcggcagtc aggtgttggc cagcgtttct gttttatctg   35700
taaaaggtag ccttgcgccc atcagtggca cagtaactag tgctcagatt gtcctcagat   35760
ttgatgaaaa tggagttcta ctaagcaatt ctttcccttga ccctcaatac tggaactaca   35820
gaaaaggtga cctttacgag ggcactgcat ataccaacga agtgggattt atgcccaacc   35880
tcacagcata cccaaaaaca cagagccaaa ctgctaaaag caacattgta agtcaggttt   35940
acttgaatgg ggacaaatcc aaacccatga ccctcaccat taccctcaat ggaactaatg   36000
aaacaggaga tgccacagta agcacttact ccatgtcatt ctcatggaac tggaatggaa   36060
gtaattacat taatgaaacg ttccaaacca actccttcac ctttctcctac atcgcccaag   36120
aataaaaagc atgacgctgt tgatttgatt caatgtgttt ctgtttttatt ttcaagcaca   36180
acaaaatcat tcaagtcatt cttccatctt agcttaatag acacagtagc ttaatagacc   36240
cagtagtgca aagcccccatt ctagcttata actagtggag aagtactcgc ctacatgggg   36300
gtagagtcat aatcgtgcat caggataggg cggtggtgct gcagcagcgc gcgaataaac   36360
tgctgccgcc gccgctccgt cctgcaggaa tacaacatgg cagtggtctc ctcagcgatg   36420
attcgcaccg cccgcagcat aaggcgcctt gtcctccggg cacagcagcg caccctgatc   36480
tcacttaaat cagcacagta actgcagcac agcaccacaa tattgttcaa aatcccacag   36540
tgcaaggcgc tgtatccaaa gctcatgcg gggaccacag aacccacgtg gccatcatac   36600
cacaagcgca ggtagattaa gtggcgaccc ctcataaaca cgctggacat aaacattacc   36660
tcttttggca tgttgtaatt caccacctcc cggtaccata taaacctctg attaaacatg   36720
gcgccatcca ccaccatcct aaaccagctg gccaaaacct gcccgccggc tatacactgc   36780
agggaaccgg gactggaaca atgacagtgg agagcccagt actcgtaacc atggatcatc   36840
atgctcgtca tgatatcaat gttggcacaa cacaggcaca cgtgcataca cttcctcagg   36900
attacaagct cctcccgcgt tagaaccata tcccagggaa caaccccattc ctgaatcagc   36960
gtaaatccca cactgcaggg aagacctcgc acgtaactca cgttgtgcat tgtcaaagtg   37020
ttacattcgg gcagcagcgg atgatcctcc agtatggtga cgcggggttt c tgtctcaaaa   37080
ggaggtagac gatccctact gtacggagtg cgccgagaca accgagatcg tgttggtcgt   37140
agtgtcatgc caaatggaac gccggacgta gtcatatttc ctgaagtctt agatctctca   37200
acgcagcacc agcaccaaca cttcgcagtg taaaaggcca agtgccgaga gagtatatat   37260
aggaataaaa agtgacgtaa acgggcaaag tccaaaaaac gcccagaaaa accgcacgcg   37320
aacctacgcc ccgaaacgaa agccaaaaaa cactagacac tcccttccgg cgtcaacttc   37380
cgctttccca cgctacgtca cttgcccccag tcaaacaaac tacatatccc gaacttccaa   37440
gtcgccacgc ccaaaacacc gcctacacct ccccgcccgc cggcccgccc caaacccgc    37500
ctcccgcccc gcgccccgcc ccgcgccgcc catctcatta tcatattggc ttcaatccaa   37560
aataaggtat attattgatg atggtttaaa cggatcctct agagtcgacc tgcaggcatg   37620
caagcttgag tataaccccc ttgcggccgc ccggccgtc gaccaattct catgtttgac    37680
agcttatcat cgaatttctg ccattcatcc gcttattatc acttattcag gcgtagcaac   37740
caggcgttta agggcaccaa taactgcctt aaaaaaatta cgccccgccc tgccactcat   37800
cgcagtactg ttgtaattca ttaagcattc tgccgacatg gaagccatca caacgggcat   37860
gatgaacctg aatcgccagc ggcatcagca ccctgtcgcc ttgcgtataa tatttgccag   37920
tggtgaaaac gggggcgaag aagttgtcca tattggccac gtttaaatca aaactggtga   37980
aactcaccca gggattggct gagacgaaaa acatattctc aataaacct taggggaaat    38040
aggccaggtt ttcaccgtaa cacgccacat cttgcgaata tatgtgtaga aactgccgga   38100
aatcgtcgtg gtattcactc cagagcgatg aaaacgtttc agtttgctca tggaaaacgg   38160
tgtaacaagg gtgaacacta tcccatatca ccagctcacc gtctttcatt gccatacgga   38220
attccggatg agcattcatc aggcgggcaa gaatgtgaat aaaggccgga taaaacttgt   38280
gcttattttt ctttacggtc tttaaaaagg ccgtaatatc cagctgaacg gtctggttat   38340
aggtacattg agcaactgac tgaaatgcct caaaatgttc tttacgatgc cattgggata   38400
tatcaacggt ggtatatcca gtgattttt tctccatttt agcttcctta gctcctgaaa   38460
atctcgataa ctcaaaaaat acgcccggta gtgatcttat ttcattatgg tgaaagttgg   38520
```

```
aacctcttac gtgccgatca acgtctcatt ttcgccaaaa gttggcccag ggcttcccgg  38580
tatcaacagg gacaccagga tttatttatt ctgcgaagtg atcttccgtc acaggtattt  38640
attcgcgata agctcatgga gcggcgtaac cgtcgcacag gaaggacaga gaaagcgcgg  38700
atctgggaag tgacggacag aacggtcagg acctggattg gggaggcggt tgccgccgct  38760
gctgctgacg gtgtgacgtt ctctgttccg gtcacaccac atacgttccg ccattcctat  38820
gcgatgcaca tgctgtatgc cggtataccg ctgaaagttc tgcaaagcct gatgggacat  38880
aagtccatca gttcaacgga agtctacacg aaggtttttg cgctggatgt ggctgcccgg  38940
caccgggtgc agtttgcgat gccggagtct gatgcggttg cgatgctgaa acaattatcc  39000
tgagaataaa tgccttggcc tttatatgga aatgtggaac tgagtggata tgctgttttt  39060
gtctgttaaa cagagaagct ggctgttatc cactgagaag cgaacgaaac agtcgggaaa  39120
atctcccatt atcgtagaga tccgcattat taatctcagg agcctgtgta gcgtttatag  39180
gaagtagtgt tctgtcatga tgcctgcaag cggtaacgaa aacgatttga atatgccttc  39240
aggaacaata gaaatcttcg tgcggtgtta cgttgaagtg gagcggatta tgtcagcaat  39300
ggacagaaca acctaatgaa cacagaacca tgatgtgctc tgtcctttta cagccagtag  39360
tgctcgccgc agtcgagcga cagggcgaag ccctcgagtg agcgaggaag caccagggaa  39420
cagcacttat atattctgct tacacacgat gcctgaaaaa acttcccttg ggttatcca   39480
cttatccacg gggatatttt tataattatt tttttttag ttttttagatc ttctttttta  39540
gagcgccttg taggcccttta tccatgctgg ttctagagaa ggtgttgtga caaattgccc  39600
tttcagtgtg acaaatcacc ctcaaatgac agtcctgtct gtgacaaatt gcccttaacc  39660
ctgtgacaaa ttgccctcag aagaagctgt ttttcacaa agttatccct gcttattgac   39720
tcttttttat ttagtgtgac aatctaaaaa cttgtcacac ttcacatgga tctgtcatgg  39780
cggaaacagc ggttatcaat cacaagaaac gtaaaaatag cccgcgaatc gtccagtcaa  39840
acgacctcac tgaggcggca tatagtctct cccgggatca aaaacgtatg ctgtatctgt  39900
tcgttgacca gatcagaaaa tctgatggca ccctacagga acatgacggt atctgcgaga  39960
tccatgttgc taaatatgct gaaatattcg gattgacctc tgcggaagcc agtaaggata  40020
tacggcggc attgaagagt ttcgcgggga aggaagtggt tttttatcgc cctgaagagg  40080
atgccggcga tgaaaaggc tatgaatctt ttccttggtt tatcaaacgt gcgcacagtc  40140
catccagagg gctttacagt gtacatatca acccatatct cattcccttc tttatcgggt  40200
tacagaaccg gtttacgcag tttcggctta gtgaaacaaa agaaatcacc aatccgtatg  40260
ccatgcgttt atacgaatcc ctgtgtcagt atcgtaagcc ggatggctca ggcatcgtct  40320
ctctgaaaat cgactggatc atagagcgtt accagctgcc tcaaagttac cagcgtatgc  40380
ctgacttccg ccgccgcttc ctgcaggtct gtgttaatga gatcaacagc agaactccaa  40440
tgcgcctctc atacattgag aaaaagaaag gccgccagac gactcatatc gtatttttcct  40500
tccgcgatat cacttccatg acgacaggat agtctgaggg ttatctgtca cagatttgag  40560
ggtggttcgt cacatttgtt ctgacctact gagggtaatt tgtcacagtt ttgctgtttc  40620
cttcagcctg catggatttt ctcatacttt ttgaactgta atttttaagg aagccaaatt  40680
tgagggcagt ttgtcacagt tgatttcctt ctctttccct tcgtcatgtg acctgatatc  40740
gggggttagt tcgtcatcat tgatgagggt tgattataca agtttattac tctgaattgg  40800
ctatccgcgt gtgtacctct acctggagtt tttcccacgg tggatatttc ttcttgcgct  40860
gagcgtaaga gctatctgac agaacagttc ttctttgctt cctcgccagt tcgctcgcta  40920
tgctcggtta cacggctgcg gcgagcgcta gtgataataa gtgactgagg tatgtgctct  40980
tcttatctcc ttttgtagtg ttgctcttat ttttaacaac tttgcggttt tttgatgact  41040
ttgcgatttt gttgttgctt tgcagtaaat tgcaagattt aataaaaaaa cgcaaagcaa  41100
tgattaaagg atgttcagaa tgaaactcat ggaaacactt aaccagtgca taaacgctgg  41160
tcatgaaatg acgaaggcta tcgccattgc acagtttaat gatgacagcc cggaagcgag  41220
gaaaataacc cggcgctgga gaataggtga agcagcggat ttagttgggg ttcttctcta  41280
ggctatcaga gatgccgaga aagcagggcg actaccgcac ccggatatgg aaattcgagg  41340
acggggttgag caacgtgttg gttatacaat tgaacaaatt aatcatatgc gtgatgtgtt  41400
tggtacgcga ttgcgacgtg ctgaagacgt atttccaccg gtgatcgggg ttgctgccca  41460
taaaggtggc gtttacaaaa cctcagtttc tgttcatctt gctcaggatc tggctctgaa  41520
ggggtcagcgt gttttgctcg tggaaggtaa cgacccccag ggaacagcct caatgtatca  41580
cggatgggta ccagatcttc atattcatgc agaagcacat ctcctgcctt tctatcttgg  41640
ggaaaaggac gatgtcactt atgcaataaa gcccacttgc tggccggggc ttgacattat  41700
tccttcctgt ctggctctgc accgtattga aactgagtta atgggcaaat tgatgaaggg  41760
taaactgccc accgatccac acctgatgct ccgactgcgc attgaaactg ttgctcatga  41820
ctatgatgtc atagttattg acagcgcgcc taacctgggt atcggcacga ttaatgtcgt  41880
atgtgctgct gatgtgctga ttgttccac gcctgctgag ttgtttgact acacctccgc  41940
actgcagttt ttcgatatgc ttcgtgatct gctcaagaac gttgatctta aagggttcga  42000
gcctgatgta cgtatttgc ttaccaaata cagcaatagt aatggctctc agtcccgtg    42060
gatggaggag caaattcggg atgcctgggg aagcatggtt ctaaaaaatg ttgtacggca  42120
aacggatgaa gttggtaaag gtcagatccg gatgagaact gttttgaac aggccattga  42180
tcaacgctct tcaactggtg cctggagaaa tgctctttct atttgggaac tgtctgcaa   42240
tgaaattttc gatcgtctga ttaaaccacg ctgggagatt agataatgaa gcgtgcgcct  42300
gttattccaa aacatacgct caatactcaa ccggttgaag atacttcgtt atcgacacca  42360
gctgccccga tggtggattc gttaattgcg cgcgtaggta taatggctcg cggtaatgcc  42420
attactttgc ctgtatgtgg tcggatgtg aagtttactc ttgaagtgct ccggggtgat   42480
agtgttgaga agacctctcg ggtatggtca ggtaatgaac gtgaccagga gctgcttact  42540
gaggacgcac tggatgatct catcccttct ttttctactga ctggtcaaca gacaccggcg  42600
ttcggtcgaa gagtatctgg tgtcatagaa attgccgatg ggagtcgccg tcgtaaagct  42660
gctgcactta ccgaaagtga ttatcgtgtt ctggttggcg agctggatga tgagcagatg  42720
gctgcattat ccagattggg taacgattat cgcccaacaa gtgcttatga acgtggtcag  42780
cgttatgcaa gccgattgca gaatgaattt gctggaaata tttctgcgct ggctgatgcg  42840
gaaaatattt cacgtaagat tattacccgc tgtatcaaca ccgccaaatt gcctaaatca  42900
gttgttgctc tttttttctca ccccggtgaa ctatctgccg tcaggtga tgcacttcaa  42960
aaagccttta cagataaaga ggaattactt aagcagcagg catctaacct tcatgagcag  43020
aaaaaagctg gggtgatatt tgaagctgaa gaagttatca ctctttttaac ttctgtgctt  43080
aaaacgtcat ctgcatcaag aactagttta agctcacgac atcagtttgc tcctggagcg  43140
acagtattgt ataagggcga taaaatggtg cttaacctgg acaggtctcg tgttccaact  43200
gagtgtatag agaaaattga ggccattctt aaggaacttg aaaagccagc accctgatgc  43260
```

```
gaccacgttt tagtctacgt ttatctgtct ttacttaatg tcctttgtta caggccagaa  43320
agcataactg gcctgaatat tctctctggg cccactgttc cacttgtatc gtcggtctga  43380
taatcagact gggaccacgg tcccactcgt atcgtcggtc tgattattag tctgggacca  43440
cggtcccact cgtatcgtcg gtctgattat tagtctggga ccacggtccc actcgtatcg  43500
tcggtctgat aatcagactg gaccacggt  cccactcgtc gtcggtct gattattagt  43560
ctgggaccat ggtcccactc gtatcgtcgg tctgattatt agtctgggac cacggtccca  43620
ctcgtatcgt cggtctgatt attagtctgg aaccacggtc ccactcgtat cgtcggtctg  43680
attattagtc tgggaccacg gtcccactcg tatcgtcggt ctgattatta gtctgggacc  43740
acgatcccac tcgtgttgtc ggtctgatta tcggtctggg accacggtcc cacttgtatt  43800
gtcgatcaga ctatcagcgt gagactacga ttccatcaat gcctgtcaag ggcaagtatt  43860
gacatgtcgt cgtaacctgt agaacggagt aactcggtg tgcggttgta tgcctgctgt  43920
ggattgctgc tgtgtcctgc ttatccacaa cattttgcgc acggttatgt ggacaaaata  43980
cctggttacc caggccgtgc cggcacgctc ggtacccggg gatcctcgtt taaac       44035

SEQ ID NO: 51           moltype = DNA    length = 41464
FEATURE                 Location/Qualifiers
misc_difference         16063
                        note = modified_base - a, c, t, g, unknown or other
misc_feature            1..41464
                        note = Description of Artificial Sequence: Synthetic
                        polynucleotide
source                  1..41464
                        mol_type = other DNA
                        organism = synthetic construct
SEQUENCE: 51
catcatcaat aatataccct attttggatt gaagccaata tgataatgag atgggcggcg  60
cggggcgggg cgcggggcgg gaggcgggtt tggggggcgg ccggcgggcg gggcggtgtg  120
gcggaagtgg actttgtaag tgtggcggat gtgacttgct agtgccgggc gcggtaaaag  180
tgacgttttc cgtgcgcgac aacgccccg ggaagtgaca ttttttcccgc ggttttacc   240
ggatgttgta gtgaatttgg gcgtaaccaa gtaagatttg gccattttcg cgggaaaact  300
gaaacgggga agtgaaatct gattaatttt gcgttagtca taccgcgtaa tatttgtcta  360
gggccgaggg actttggccg attacgtgga ggactcgccc aggtgttttt tgaggtgaat  420
ttccgcgttc cgggtcaaag tctgcgtttt attattatag gatatcccat tgcatacgtt  480
gtatccatat cataaatgt  acatttatat tggctcatta ccaacattac cgccatgttg  540
acattgatta ttgactagtt attaatagta atcaattacg gggtcattag ttcatagccc  600
atatatggag ttccgcgtta cataacttac ggtaaatggc ccgcctggct gaccgcccaa  660
cgaccccgc ccattgacgt caataatgac gtatgttccc atagtaacgc caatagggac  720
tttccattga cgtcaatggg tggagtattt acggtaaact gcccacttgg cagtacatca  780
agtgtatcat atgccaagta cgccccctat tgacgtcaat gacggtaaat ggcccgcctg  840
gcattatgcc cagtacatga ccttatggga ctttcctact tggcagtaca tctacgtatt  900
agtcatcgct attaccatgg tgatgcggtt ttggcagtac atcaatgggc gtggatagcg  960
gtttgactca cggggatttc caagtctcca ccccattgac gtcaatggga gtttgttttg  1020
gcaccaaaat caacgggact ttccaaaatg tcgtaacaac tccgccccat tgacgcaaat  1080
gggcggtagg cgtgtacggt gggaggtcta tataagcaga gctctcccta tcagtgatag  1140
agatctccct atcagtgata gagatcgtcg acgagctcgt ttagtgaacc gtcagatcgc  1200
ctggagacgc catccacgct gttttgacct ccatagaaga caccgggacc gatccagcct  1260
ccgcgttggg gaacggtgca ttggaacgcg gattcccgt  gccaagagtg agatcttccg  1320
tttatctagg taccagatat cgccaccatg agacctgctc cctggacacc taatcctccc  1380
aggtccccca gccagatgag cgtgagagac agactggcta ggctgagagc cgaggctcag  1440
gtcaagcagg ccagcgtcga ggtgcaaccc cctcagctca cccaggtgtc cccccagcag  1500
cctgtggccg gcattctgtt cattctggcc attctgaccg agtggggaag cggcaacaga  1560
acctacggcc ctgtcttcat gtgcctcgga ggactgctga caatggtggc tggcgccgtg  1620
tggctcaccg tcatgtccaa caccctgctc agcgcctgga ttctgaccgc cggattcctg  1680
atctttctga tcgattcgc tctctttggc gtcatcaggt gttgcaggta ctgttgctac  1740
tactgcctga ccctcgagag cgaggaaaga cccccccaaa cctacaggaa tacagtgagg  1800
aaacctcagc agcccgagag cctcgaggag tgcgatagcg agctggatgat taaaaggtat  1860
aagaataggg tggcctccag gaagtgtagg gctaaattca aacagctcct gcaacactat  1920
agggaagtgg ccgccgccaa gtccagcgag attagggaca gaaggaggaa tcctgcctcc  1980
aggagagacc aggccaaatg gagactccaa acactcgccg ctggatggcc catgggctac  2040
caggcctata gctcctggat gtacagctac accgaccatc agacaacacc caccttcgtg  2100
catctgcagg ctacactggg ctgcaccgga ggcagaaggt gtcacgtgtt tctgggaatc  2160
gtgctgttca tctttggatg cctgctctgt ctgggcatct ggatttatct cctggagatg  2220
ctctggagac tcggcgctac aatttggcag ctgctcgcct ttttctggc cttctttctg  2280
gacctgatcc tcctgatcat cgccctgtac ctccaacaga actgtgacc tcctcatgc   2340
gatctgctgt ggctcctcct cttcctggcc atcctgatct ggatgtacta ccatggccag  2400
agaggaaggg tcgcttgcgc tcctgtccct gctcctgctg gccccatcgt gaggccttgg  2460
gagccttccc tcacacaggc cgccggccag gcctttgctc ccgtgaggcc cagcacatg   2520
cctgtggaac ccgtgcccgt ccccacagtg gctctggaaa ggctcgtgta ccccaagccc  2580
gtgagacctg tcctctggct cagcagccct ggaggactcg gaacactcgg agccgctctc  2640
ctgacactgg ccgctgctct ggctctgctg gctagcctga tcctgggaac cctcaacctc  2700
accaccatgt ttctcctcat gctcctgtgg acccttcgtgg tgctgctcat ctgttccagc  2760
tgctccagct gcccctgag caagatcctg ctggccagg tgttcctgta cgccctcgcc  2820
ctcctgctgc tggctagcgc cctgatcgct ggcggagca tcctccagac caattttcaag  2880
agcctctcct ccaccgagtt catccccaac ctgttctgt tgttactgct gatccataagc  2940
gacgagcacc atcatgacga ctccctgccc catcctcagc aggccacaga cgactccggc  3000
cacgagagcg acagcaatag caatgagggc aggcaccatc tgctcgtgtc ggagctcaa   3060
gtccccgagc ctcccaccat ccatctgccc gcccagggaa tggcttaccc cctcacgag   3120
cagcacggca tggcccctttg tccggcgct caagccccc ctaacctct gccttttt     3180
gccatttgtc tgacctggag aatcgaggac ccccccttca acagcctgct gttcgccctg  3240
```

-continued

```
ctcgccgccg ctggcggcct ccagggcatt tacgtcctcg tgatgctggt gctgctgatc 3300
ctcgcttaca ggagaagatg gaggagactg acagtgtgcg gcggcatcat gtttctcgcc 3360
tgcgtcctgg tcctgatcgt ggacgccgtc ctgcaactca gcccctcct gggagctgtg 3420
acagtggtct ccatgaccct gctgctgctg gccttcaacg accccacga tcctctgccc 3480
caagatcctg acaataccga cgataacggc ccccaagacc ccgataacac cgacgacaat 3540
ggccctcacg accctctgcc ccatagccct tccgatagcc ctggcaacga tggcggccct 3600
cctcagctga cagaggaggt ggaaaataag ggcggcgatc agggacccc cctgatgaca 3660
gatggcggag gaggacacag ccatgatagc ggacatggcg gaggcgatcc ccatctgcct 3720
accctcctcc tgggcagctc cggttctgga ggcgacgatg atgaccctca cggccctgtg 3780
cagctctcct actacgacgg caaaaggacc gaacaaggaa aagaggtcct ggagaaggcc 3840
aggggcagca catacggaac ccccaggcct cccatgtccg attggaccgg aggagccctg 3900
ctggtcctct acagcttcgc cctgatgctg atcattatca tcctgatcat ctttatcttc 3960
agaagggacc tgctgtgccc tctcggcgcc ctgtgcatcc tgctgctcat gatcacactc 4020
ctcctgatcg ccctctggaa cctgcacgga caagccctga tgtccgatga gggacctgga 4080
acaggacccg gaaacggact gggcgagaag ggagatacaa gcggccccga aggcagcggc 4140
ggaagcggac cccaaagaag gggcggcgac aaccacggaa gaggaagagg caggggcaga 4200
ggcagaggag gaggaagacc tggagcccct ggcggttctg gaagcggacc caggcacagg 4260
gacggagtga ggaggcctca aaaaagacc agctgcatcg gctgcaaggg aaccactgga 4320
attgatgata accctccac agagaccgct caggcctgga acgccggctt cctgagggga 4380
agacctatg gcatcgatct gctgaggacc gagggcgaac acgtggaggg agccaccgga 4440
gagacaaggg aggaaagcga agacacagaa agcgatggcg acgacgaaga cctgccctgc 4500
attgtgtcca ggggcggacc caaggtgaag aggcccccta tctttatcag aaggctccat 4560
agactgctcc tgatgagggc catgaaccct gtgtgcctgc ccgtgatcgt ggccccctac 4620
ctcttttggc tggccgccat tgccgctagc tgcttcaccg cctccgtgtc cacagtggtg 4680
acagccaccg gcctcgccct gagcctgctg ctcctcgctg ccgtggcctc cagctacgcc 4740
gctgctcaaa gaaagtcct gaccctgtc accgtcctga cagccgtcgt gaccaccttt 4800
tccgctggca ccttcaagct gcctaggtgc acacctggcg acaggcagtg gctctacgtg 4860
cagagctccg tgggcaatat tgtgcagagc tgcaatccca ggtacagcat ttttttcgac 4920
tacatggcca tccataggtc cctcaccaag atctgggagg atctgggagg cccttcccag 4980
gctcctctgc cctgcgtgct gtggcctgtg ctgcctgagc ctccccca aggccagctg 5040
acagcctatc acgtgtccac cgctcctaca ggttcttggt tcagcgctcc ccagcccgct 5100
cccgaaaacg cttaccaggc ttacgccgcc cccagctgt tccccgtctc cgacatctga 5160
tgatgagcgg ccgcgatctg ctgtgccttc tagttgccag ccatctgttg tttgcccctc 5220
cccgtgcct tccttgaccc tggaaggtgc cactcccact gtcctttcct aataaaatga 5280
ggaaattgca tcgcattgtc tgagtaggtg tcattctatt ctggggggtg gggtggggca 5340
ggacagcaag ggggaggatt gggaagacaa tagcaggcat gctggggatg cggtgggctc 5400
tatgccgat cagcgatcgc tgaggtgggg gagtgggcgt ggcctgggt ggtcatgaaa 5460
atatataagt tgggggtctt agggtctctt tatttgtgtt gcagagaccg ccggagccat 5520
gagcgggagc agcagcagca gcagtagcag cggcccttg gatgcagca tcgtgagccc 5580
ttatttgacg acgcggatgc cccactgggc cggggtgcgt cagaatgtga tgggctccag 5640
catcgacggc cgaccgtcc tgcccgcaaa ttccgccacg ctgacctatg cgaccgtcgc 5700
ggggacgccg ttgacgcca ccgccgccgc cgccgccacc gcagccgcct cggccgtgcg 5760
cagcctgcc acggactttg cattcctggg accactggca acagggcta cttctcggtc 5820
cgctgctgcc gccgttcgcg atgacaagct gaccgccctg ctggcgcagt ggatgcgct 5880
tactcgggaa ctgggtgacc tttctcagca ggtcatggcc ctgcgccagc aggtctcctc 5940
cctgcaagct ggcgggaatg cttctcccac aaatgccgtt taagataaat aaaaccagac 6000
tctgtttga ttaaagaaaa atagcaagtg cattgctctc tttatttcat aattttccgc 6060
gcgcgatagg ccctagacca gcgttctcgg tcgttgaggg tgcggtgtat cttctccagg 6120
acgtggtaga ggtggctctg gacgttgaga tacatgggca tgagcccgtc ccggggggtgg 6180
aggtagcacc actgcagagc ttcatgctcc ggggtggtgt tgtagatgat ccagtcgtag 6240
caggagcgct gggcatggtg cctaaaaatg tccttcagca gcaggccgat ggccagggga 6300
aggcccttgg tgtaagtgtt tacaaaacgg ttaagttggg aagggtgcat tcggggagag 6360
atgatgtgca tcttgactg tattttaga ttggcgatgt ttccgcccag atcccttctg 6420
ggattcatgt tgtgcaggac caccagtaca gtgtatccgg tgcacttggg gaatttgtca 6480
tgcagcttag agggaaaagc gtggaagaac ttggagacgc ctttgtgcc tcccagattt 6540
tccatgcatt cgtccatgat gatggcaatg ggcccgcggg aggcagcttg ggcaaagata 6600
tttctggggt cgctgacgtc gtagttgtgt tccaggtga ggtcgtcata ggccattttt 6660
acaaagcgcg gcggagggt gcccgactgg gggatgatgg tccctctgg ccctggggcg 6720
tagttgccct cgcagatctg catttcccag gccttaatct cggaggggg aatcatatcc 6780
acctgcgggg cgatgaagaa aacgttttcc ggagccgggg agattaactg ggatgagagc 6840
aggtttctaa gcagctgtga ttttccacaa ccggtgggcc cataaataac acctataacc 6900
ggttgcagct ggtagtttag agagctgcag ctgccgtcgt cccggaggag gggggccacc 6960
tcgttgagca tgtccctgac gcgcatgttc tccccgacca gatccgccag aaggcgctcg 7020
ccgccagggg acaagctc ttgcaaggaa gcaaagtttt tcagcggctt gaggccgtcc 7080
gccgtgggca tgttttcag ggtctggctc agcagctcca ggcggtccca gagctcggtg 7140
acgtgctcta cggcatctct atccagcata tctcctcgtt tcgcgggttg gggcgacttt 7200
cgctgtaggc accaagcgg tggtcgtcca gcggggccag agtcatgtcc ttccatgggc 7260
gcagggtcct cgtcagggtg gtctgggtca cggtgaaggg gtgcgctccg ggctgagcgc 7320
ttgccaaggt gcgcttgagg ctggttctgc tggtgctgaa gcgctgccgg tcttcgcgc 7380
gcgcgtcggc caggtagcat ttgaccatgc tgtcatagtc cagcccctcc gcggcgtgtc 7440
ccttggcgcg cagcttgccc ttggaggtgg cgccacacga gggcagagc aggctcttga 7500
gcgcgtgagg cttgggggcg aggaagaccg attcggggga gtaggcgtcc gcgccgcaga 7560
ccccgcacac ggtctcgcac tccaccagcc aggtgagctc gggcgcgcc gggtcaaaaa 7620
ccaggttcc catgctttt ttgatgcgtt tcttacctcg gagtggtctc 7680
cccgctcggt gacgaagagg ctgtccgtgt ctccgtagac cgacttgagg ggtcttttct 7740
ccaggggggt ccctcggtct tcctcgtaga ggaactcgga ccactctgag acgaaggccc 7800
gcgtccaggc caggacgaag gaggctatgt gggagggta gcggtcgttg tccactaggg 7860
ggtccacctt ctccaaggtg tgaagacaca tgtcgccttc tcggcgtcc aggaaggtga 7920
ttggcttgta ggtgtaggcc acgtgaccgg gggttcctga cgggggggta taaaagggg 7980
```

```
tgggggcgcg ctcgtcgtca ctctcttccg catcgctgtc tgcgaggggcc agctgctggg   8040
gtgagtattc cctctcgaag gcgggcatga cctccgcgct gaggttgtca gtttccaaaa   8100
acgaggagga tttgatgttc acctgtcccg aggtgatacc tttgagggta cccgcgtcca   8160
tctggtcaga aaacacgatc tttttattgt ccagcttggt ggcgaacgac ccgtagaggg   8220
cgttggagag cagcttggcg atggagcgca gggtctggtt cttgtccctg tcggccgcgct  8280
ccttggccgc gatgttgagc tgcacgtact cgcgcgcgca gcagcgccac tcggggaaga   8340
cggtggtgcg ctcgtcgggc accaggcgca cgcgccagcc gcggttgtgc agggtgacca   8400
ggtccacgct ggtggcgacc tcgccgcgca ggcgctcgtt ggtccagcag agacggccgc   8460
ccttgcgcga gcagaagggg ggcaggggt cgagctgggt ctcgtccggg gggtccgcgt    8520
ccacggtgaa aaccccgggg cgcaggcgcg cgtcgaagta gtctatcttg caaccttgca   8580
tgtccagcgc ctgctgccag tcgcgggcgg cgagcgcgcg ctcgtagggg ttgagcggcg   8640
ggccccaggg catgggtgg gtgagtgcgg aggcgtacat gccgcagatg tcatagacgt    8700
agaggggctc ccgcaggacc ccgatgtagg tggggtagca gcggccgccg cggatgctgg    8760
cgcgcacgta gtcatacagc tcgtgcgagg gggcgaggag gtcggggcca aggttggtgc   8820
gggcggggcg ctccgcgcgg aagacgatct gcctgaagat ggcatgcgag ttggaagaga   8880
tggtgggggcg ctggaagacg ttgaagctgg cgtcctgcag gccgacggcg tcgcgcacga  8940
aggaggcgta ggagtcgcgc agcttgtgta ccagctcggc ggtgacctgc acgtcgagcg   9000
cgcagtagtc gagggtctcg gatgatgt catatttagc ctgcccttc tttttccaca     9060
gctcgcggtt gaggacaaac tcttcgcggt cttttccagta ctcttggatc gggaaaccgt   9120
ccggttccga acgtaagag cctagcatgt agaactggtt gacggcctgg taggcgcagc    9180
agcccttctc cacggggagg gcgtaggcct gcgcggcctt gcggagcgag gtgtgggtca   9240
gggcgaaggt gtccctgacc atgactttga ggtactggtg cttgaagtcg gagtcgtcgc   9300
agccgccccg ctcccagagc gagaagtcgg tgcgcttctt ggagcggggg ttgggcagag   9360
cgaaggtgac atcgttgaag aggattttgc ccgcgcgggg catgaagttg cgggtgatgc   9420
ggaagggccc cggcacttca gagcggttgt tgatgacctg ggcggcgagc acgatctcgt   9480
cgaagccgtt gatgttgtgg cccacgatgt agagttccag gaagcggggc cggcccttta   9540
cggtgggcag cttctttagc tcttcgtagg tgagctcctc gggcgaggcg aggccggtgct  9600
cggcagggc ccagtccgcg aggtgcgggt tgtctctgag gaaggacttc cagaggtcgc    9660
gggccaggag ggtctgcagg cggtctctga aggtcctgaa ctggcggccc acggccattt   9720
tttcggggggt gatgcagtag aaggtgaggg ggtcttgctg ccagcggtcc cagtcgagct   9780
gcagggcgag gtcgcgcgcg gcggtgacca ggcgctcgtc gcccccgaat tcatgacca    9840
gcatgaaggg cacgagctgc tttccgaagg cccccatcca agtgtaggtc tctacatcgt   9900
aggtgacaaa gaggcgctcc gtgcgaggat gcgagccgat cgggaagaac tggatctccc   9960
gccaccagtt ggaggagtgg ctgttgatgt ggtggaagta gaagtcccgt cgccgggccg   10020
aacactcgtg ctggcttttg taaaagcgag cgcagtactg gcagcgctgc acggctgta   10080
cctcatgcac gagatgcacc tttcgcccgc gcacgaggaa gccgagggga aatctgagcc   10140
ccccgcctgg ctcgcggcat ggctggttct cttctacttt ggatgcgtgt ccgtctccgt   10200
ctggctcctc gagggggtgtt acggtggagc ggaccaccac gccgcgcgag ccgcaggtcc   10260
agatatcggc gcgcggcggt cggagtttga tgacgacatc gcgcagctgg gagctgtcca   10320
tggtctggag ctcccgcggc ggcggcaggt cagccgggag ttcttgcagg ttcacctcgc   10380
agagtcgggc cagggcgcgg ggcaggtcta ggtggtacct gatctctagg ggcgtgttgg   10440
tggcggcgtc gatggcttgc aggagcccgc agccccgggg ggcgacgacg gtgccccgcg   10500
gggtggtggt ggtggtggcg gtgcagctca gaagcggtgc cgcgggcggg ccccccggagg   10560
taggggggc tccggtcccg cgggcagggg cggcagcggc acgtcggcgt ggagcgcggg   10620
caggagttgg tgctgtgccc ggaggttgct ggcgaaggcg acgacgcggc ggttgatctc   10680
ctggatctgc cgcctctgcg tgaagacgac gggcccggtc agcttgaacc tgaaagagag   10740
ttcgacagaa tcaatctcgg tgtcattgac cgcggcctgg cgcaggatct cctgcacgtc   10800
tcccgagttg tcttggtagg cgatctcggc catgaactgc tcgatctctt cctcctggag   10860
gtctccgcgt ccggcgcgtt ccacggtggc cgccaggtc ttggagatgc gccccatgag   10920
ctgcgagaag gcgttgagtc cgccctcgtt ccagactcgg ctgtagacca cgcccccctg   10980
gtcatcgcgg gcgcgcatga ccacctcgcg gaggttgagc tccacgtgcc tccacgtgcc   11040
ggcgtagttg cgcagacgct ggaagaggta gttgaggggtg gtggcggtgt gctcggccac   11100
gaagaagttc atgacccagc ggcgcaacgt ggattcgttg atgtccccca aggcctccag   11160
ccgttccatg gcctcgtaga agtccacggc gaagttgaaa aactgggagt tgcgcgccga   11220
cacggtcaac tcctcctcca gaagacggat gagctcgggg agcacctcgcg acctcgcg    11280
ctcgaaggct atgggggatct cttcctccgc tagcatcacc acctcctcct cttcctcctc   11340
ttctggcact tccatgatgg cttcctcctc ttcgggggggt ggcggcggcg gcggtgggg   11400
agggggcgct ctgcgccggc ggcggcgcac cgggaggcgg tccacgaagc gcgcgatcat   11460
ctccccgcgg cggcggcgca tggtctcggt gacggcgcgg ccgttctccc gggggcgcag   11520
ttggaagacg ccgccggaca tctggtgctg gggcgggtgg ccgtgaggca gcgagacggc   11580
gctgacgatg catctcaaca attgctgcgt aggtacgccg ccgagggacc tgagggagtc   11640
catatccacc ggatccgaaa acctttcgag gaaggcgtct aaccagtcgc agtcgcaagg   11700
taggctgagc accgtggcgg gcggcgggg gtggggggag tgtctggcgg aggtgctgct   11760
gatgatgtaa ttgaagtagg cggacttgac acggcagga gcaccatgtc 11820
cttgggtccg gcctgctgga tgcggaggcg gtcggctatg ccccaggctt cgttctggca   11880
tcggcgcagg tccttgtagt agtccttgcat gagcctttcc accggcacct cttctccttc   11940
ctcttctgct tcttccatgt ctgcttcggc cctgggggcgg cgccgcgccc ccctgccccc   12000
catgcgcgtg accccgaacc ccctgagcgg ttggagcagg gccaggtcgg cgacgacgcg   12060
ctcggccagg atggcctgct gcacctgcgt gagggtgctt tggaagtcat ccaagtccac   12120
gaagcggtgg taggcgcccg tgttgatggt gtaggtgcag ttggccatga cggaccagtt   12180
gacggtctgt tggcccggtt gcgacatctc ggtgtacctg agtcgcgagt aggcgcggga   12240
gtcgaagacg tagtcgttgc aagtccgcac caggtactgg tagcccacca ggaagtgcgg   12300
cggcggctgc cggtagaggg gccagcgcag ggtggcgggg gctccggggg ccaggtcttc   12360
cagcatgagg cggttggtagg cgtagatgta cctggacatc caggtgatac gccgggcgt   12420
ggtgggaggcc gcgggggaagt cgcgcacccg gttccagatg ttgcgcaggg gcagaaagtg  12480
ctccatggta ggcgtgctct gtccagtcag acgcgcgcag tcgttgatac tctagaccag   12540
ggaaaacgaa agcggtcag cgggcactct tccgtggtct ggtgaataga tcgcaagggt    12600
atcatgcgcg agggcctcgg ttcgagcccc gggtccgggc cggacggtcc gccatgatcc   12660
acgcggttac cgcccgcgtg tcgaacccag gtgtgcgacg tcagacaacg gtggagtgtt   12720
```

```
cctttggcg   tttttctggc  cgggcgccgg  cgccgcgtaa  gagactaagc  cgcgaaagcg  12780
aaagcagtaa  gtggctcgct  ccccgtagcc  ggagggatcc  ttgctaaggg  ttgcgttgcg  12840
gcgaaccccg  gttcgaatcc  cgtactcggg  ccggccggac  ccgcggctaa  ggtgttggat  12900
tggcctcccc  ctcgtataaa  gaccccgctt  gcggattgac  tccggacacg  gggacgagcc  12960
ccttttattt  ttgctttccc  cagatgcatc  cggtgctgcg  cagatgcgcc  ccccgcccc   13020
agcagcagca  acaacaccag  caagagcgg   agcaacagca  gcgggagtca  tgcagggccc  13080
cctcacccac  cctcggcggg  ccggccacct  cggcgtccgc  ggccgtgtct  ggcgcctgcg  13140
gcggcggcgg  ggggccggct  gacgaccccg  aggagccccc  gcggcgcagg  gccagacact  13200
acctggacct  ggaggagggc  gagggcctgg  cgcggctggg  ggcgccgtct  cccgagcgcc  13260
acccgcgggt  gcagctgaag  cgcgactcgc  gcgaggcgta  cgtgcctcgg  cagaacctgt  13320
tcagggaccg  cgcggggcgag gagcccgagg  agatgcggga  caggaggttc  agcgcagggc  13380
gggagctgcg  gcaggggctg  aaccgcgagc  ggctgctgcg  cgaggaggac  tttgagcccg  13440
acgcgcggac  ggggatcagc  cccgcgcgcg  cgcacgtggc  ggccgccgac  ctggtgacgg  13500
cgtacgagca  gacggtgaac  caggagatca  acttccaaaa  gagtttcaac  aaccacgtgc  13560
gcacgctggt  ggcgcgcgag  gaggtgacca  tcgggctgat  gcacctgtgg  gactttgtaa  13620
gcgcgctggt  gcagaacccc  aacagcaagc  ctctgacggc  gcagctgttc  ctgatagtgc  13680
agcacagcag  ggacaacgag  gcgtttaggg  acgcgctgct  gaacatcacc  gagcccgagg  13740
gtcggtggct  gctggacctg  attaacatcc  tgcagagcat  agtggtgcag  gagcgcagcc  13800
tgagcctggc  cgacaaggtg  gcggccatca  actactcgat  gctgagcctg  ggcaagtttt  13860
acgcgcgcaa  gatctaccag  acgcgtacg   tgcccataga  caaggaggtg  aagatcgacg  13920
gttttttacat cgcgcatggcg ctgaaggtgc  tcaccctgag  cgacgacctg  ggcgtgtacc  13980
gcaacgagcg  catccacaag  gccgtgagcg  tgagccgcg   gcgcagcgtg  agcgaccgcg  14040
agctgatgca  cagcctgcag  ggggcgctgg  cgggcgccgg  cagcggcgac  agggaggcgg  14100
agtcctactt  cgatgcgggg  gcggacctgc  gctgggcgcc  cagccggcgg  gccctggagg  14160
ccgcggggt   ccgcgaggac  tatgacgagg  acggcgagga  ggatgaggag  tacgagctag  14220
aggaggcga   gtacctggac  taaaccgcgg  gtggtgtttc  cggtagatgc  aagacccgaa  14280
cgtggtggac  ccggcgctgc  gggcggctct  gcagagccag  ccgtccgcc   ttaactcctc  14340
agacgactgg  cgacaggtca  tggaccgcat  catgtcgctg  acggcgcgta  acccggacgc  14400
gttccgcag   cagccgcagg  ccaacaggct  ctccgccatc  ctggaggcgg  tggtcctgc   14460
gcgctcgaac  cccacgtacg  agaaggtgct  ggccatagtg  aacgcgctgg  ccgagaacag  14520
ggccatccgc  ccggacgagg  ccgggctggt  gtacgacgcg  ctgctgcagc  gcgtggcccg  14580
ctacaacagc  ggcaacgtgc  agaccaacct  ggaccggctg  gtgggggacg  tgcgcgaggc  14640
ggtggcgcag  cgcgagcgcg  cggatcggca  gggcaacctg  ggctccatgg  tggcgctgaa  14700
tgccttcctg  agcacgcagc  cggccaacgt  gccgcggggg  caggaagact  acaccaactt  14760
tgtgagcgcg  ctgcggctga  tggtgaccga  gacccccag   agcgaggtgt  accagtcgcg  14820
cccgactac   ttcttccaga  ccagcagaca  gggcctgcag  acggtgaacc  tgagccaggc  14880
tttcaagaac  ctgcgggggc  tgtggggcgt  gaaggcgccc  accggcgacc  gggcgacggt  14940
gtccagcctg  ctgacgccca  actcgcgcct  gctgctgctg  ctgatcgcgc  cgttcacgga  15000
cagccgcagc  gtgtcccggg  acacctacct  gggcgcacctg ctgaccctgt  accgcgaggc  15060
catcgggcag  gcgcaggtgg  acgagcacac  cttccaggag  atcaccagcg  tgagccgcgc  15120
gctgggcag   gaggacacga  gcagcctgga  ggcgactctg  aactacctgc  tgaccaaccg  15180
gcggcagaag  attccctcgc  tgcacagcct  gacctccgag  gaggagcgca  tcttgcgcta  15240
cgtgcagcag  agcgtgagcc  tgaacctgat  gcgcgacggg  gtgacgccca  gcgtggcgct  15300
ggacatgacc  gcgcgcaaca  tggaaccggg  catgtacgcc  gcgcaccggc  cttacatcaa  15360
ccgcctgatg  gactacctgc  atcgcgcggc  ggccgtgaac  cccgagtact  ttaccaacgc  15420
catcctgaac  ccgcactggc  tcccgccgcc  cgggttctac  agcgggggct  cgaggtccc   15480
ggagaccaac  atggcttcc   tgtgggacga  catggacgac  gcgtgttct   ccccgccgcc  15540
gcaggcgctg  gcggaagcgt  ccctgctgcg  tcccaagaag  gaggaggagg  aggaggcgag  15600
tcgccgccgc  ggcagcagcg  gcgtggcttc  tctgtccgag  ctgggggcgg  cagccgccgc  15660
gcgccccggg  tccctgggcg  gcagcccctt  tccgagcctg  gtggggtctc  tgcacagcga  15720
gcgcaccacc  cgcctcggc   tgctgggcga  ggacgagtac  ctgaataact  ccctgctgca  15780
gccggtgcgg  gagaaaaacc  tgcctcccgc  cttccccaac  aacgggatag  agagcctggt  15840
ggacaagatg  agcagatgga  agaccctatgc gcaggagcac agggacgcgc  ctgcgctccg  15900
gccgcccacg  cggcgccagc  gccacgaccg  gcagcggggg  ctggtgtggg  atgacgagga  15960
ctccgcggac  gatagcagcg  tgctggacct  gggagggagg  ggcaacccgt  tcgccgcacct 16020
gcgccccgc   ctgggagga   tgttttaaaa  aaaaaaaaa   aangcaagaa  gcatgatgca  16080
aaaattaaat  aaaactcacc  aaggccatgg  cgaccgagcg  ttggtttctt  gtgttccctt  16140
cagtatgcgc  cgcgcggcga  tgtaccagga  gggacctcct  ccctcttacg  agagcgtggt  16200
gggcgcggcg  gcggccggcg  cctcttctcc  ctttgcgtcg  cagctgctgg  agccgccgta  16260
cgtgcctccg  cgctacctgc  ggcctacggg  ggagaaac    agcatccgtt  actcggagct  16320
ggcgcccctg  ttcgacacca  cccgggtgta  cctggtggac  aacaagtcgg  cggacgtggc  16380
ctccctgaac  taccagaacg  accacagcaa  ttttttgacc  acgtcatcc   agaacaatga  16440
ctacagcccg  agcgaggcca  gcacccgac   catcaatctg  gatgaccggt  cgcactgggg  16500
cggcgacctg  aaaaccatcc  tgcaccaa    catgccaac   gtgaacgagt  tcatgttcac  16560
caataagttc  aaggcgcggg  tgatggtgtc  gcgctcgcac  accaaggaag  accgggtgga  16620
gctgaagtac  gagtgggtgg  agttcgagct  ccagagggc   aactactccg  agaccatgac  16680
cattgacctg  atgaacaacg  cgatcgtgga  gcactatctg  aaagtgggca  ggcagaacgg  16740
ggtcctggag  agcgacatcg  gggtcaagtt  cgacaccagg  aacttccgcc  tggggctgga  16800
cccccgtgacc gggcggtta   tgcccgggt   gtacaccaac  gaggccttcc  atcccgacat  16860
catcctgctg  cccggctgcg  gggtggactt  cacttacagc  cgcctgagca  acctcctgg   16920
catccgcaag  cggcagccct  tccaggaggg  cttcaggatc  acctacgagg  acctggaggg  16980
gggcaacatc  cccgcgctcc  tcgatgtgga  ggcctaccag  gatagcttga  aggaaaatga  17040
ggcgggacag  gaggataccg  cccccgccgc  ctccgccgcc  gccgagcagg  gcgaggatgc  17100
tgctgacaac  ccggcgaccc  acggggcaga  gccgctggtgg tggaggctcc           17160
cgagcaggag  gaggacatga  atgacagtgc  ggtgcgcgga  gacaccttcg  tcacccgggg  17220
ggaggaaaag  caagcggagg  ccgaggccgc  ggccgaggaa  aagcaactgg  cggcagcagc  17280
ggcggcggcg  gcgttggccg  cggcggaggc  tgagtctgag  gggaccaagc  cgccaagga   17340
gcccgtgatt  aagcccctga  ccgaagatag  caagaagcgc  agttacaacc  tgctcaagga  17400
cagcaccaac  ccgcgtacc   gcagctggta  cctggcctac  aactacggcg  acccgtcgac  17460
```

-continued

```
gggggtgcgc tcctggaccc tgctgtgcac gccggacgtg acctgcggct cggagcaggt   17520
gtactggtcg ctgcccgaca tgatgcaaga ccccgtgacc ttccgctcca cgcggcaggt   17580
cagcaacttc ccggtggtgg gcgccgagct gctgcccgtg cactccaaga gcttctacaa   17640
cgaccaggcc gtctactccc agctcatccg ccagttcacc tctctgaccc acgtgttcaa   17700
tcgcttttcct gagaaccaga ttctggcgcg cccgcccgcc cccaccatca ccaccgtcag   17760
tgaaaacgtt cctgctctca cagatcacgg gacgctaccg ctgcgcaaca gcatcggagg   17820
agtccagcga gtgaccgtta ctgacgccag acgccgcacc tgcccctacg tttacaaggc   17880
cttgggcata gtctcgccgc gcgtcctttc cagccgcact ttttgagcaa caccaccatc   17940
atgtccatcc tgatctcacc cagcaataac tcccggctggg gactgctgcg cgcgcccagc   18000
aagatgttcg gaggggcgag gaagcgttcc gagcagcacc ccgtgcgcgt gcgcgggcac   18060
ttccgcgccc cctggggagc gcacaaacgc ggccgcgcgg ggcgcaccac cgtgacgac   18120
gccatcgact cggtggtgga gcaggcgcgc aactacaggc ccgcggtctc taccgtggac   18180
gcggccatcc agaccgtggt gcggggcgcg cggcggtacg ccaagctgaa gagccgccgg   18240
aagcgcgtgg cccgccgcca ccgccgccga cccgggggcc gccgccaaacg cgccgcccgg   18300
gccctgcttc gccgggccaa gcgcacgggc cgccgcgccg ccatgagggc gcgcgcgccg   18360
ttggccgccg gcatcaccgc cgccaccatg gccccccgta cccgaagacg cgcggccgcc   18420
gccgccgccg ccgccatcag tgacatggcc agcaggcgcc ggggcaacgt gtactgggtg   18480
cgcgactcgg tgaccggcac gcgcgtgccc gtgcgcttcc gccccccgcg gacttgagat   18540
gatgtgaaaa acaacactg agtcctcctgc tgttgtgtgt atcccagcgg cggcggcgcg   18600
cgcagccgtca tgtccaagcg caaaatcaaa gaagagatgc tccaggtcgt cgcgcccgag   18660
atctatgggc ccccgaagaa ggaagagcag gattcgaagc cccgcaagat aaagcgggtc   18720
aaaaagaaaa agaaagatga tgacgatgcc gatggggagg tggagttcct gcgcgccacg   18780
gcgcccaggc gcccggtgca gtggaagggc cggcgcgtaa agccgcgtcct cgcgccccggc   18840
accgcggtgg tcttcacgcc cggcgagcgc tccaccccga ctttcaagcg cgtctatgac   18900
gaggtgtacg cgacgaaga cctgctggag caggccaacg agcgcttcgg agagtttgct   18960
tacggggaagc gtcagcgggc gctgggggaag gaggacctgc tggcgctcgc gctggaccag   19020
ggcaaccccca ccccccagtct gaagcccgtg accctgcagc aggtgctgcc gagcagcgca   19080
ccctccgagg cgaagcgggg tctgaagcgc gagggcggcg acctggcgcc caccgtgcag   19140
ctcatggtgc ccaagcggca gaggctggag gatgtgctgg agaaaatgaa agtagacccc   19200
ggtctgcagc cggacatcag ggtccgcccc atcaagcagg tggcgccggg cctcggcgtg   19260
cagaccgtgg acgtggtcat ccccaccggc aactccccg ccgccgccac cactaccgct   19320
gcctccacgg acatgagac acagaccgat cccgccgcag ccgcagccgc agccgccgcc   19380
gcgacctcct cggcggaggt gcagacggac ccctggctgc cgccggcgat gtcagctccc   19440
cgcgcgcgtc gcgggcgcag gaagtacggc gccgccaacg cgctcctgcc cgagtacgg   19500
ttgcatcctt ccatcgcgcc cacccccggc taccgaggct ataccctaccg cccgcgaaga   19560
gccaagggtt ccacccgccg tcccccgcga cgcgccgccg ccaccacccg ccgccgccgc   19620
cgcagacgcc agcccgcact ggctccagtc tccgtgagga aagtggcgcg cgacggacac   19680
accctggtgc tgcccagggc gcgctaccac cccagcatcg tttaaaagcc tgttgtggtt   19740
cttgcagata tggccctcac ttgccgcctc cgtttccggt tgccgggata ccgaggagga   19800
agatcgcgcc gcaggagggg tctgccggcc cgcggcctga gcggaggcag cgccgcgcg   19860
caccggcggc gacgcgccac cagccgacgc atgcgcggcg gggtgctgcc cctgttaatc   19920
ccctgatcg ccgcggcgat cggcgccgtg cccgggatcc cctccgtggc cttgcaagcg   19980
tcccagagac attgacagac ttgcaaactt gcaaatatgg aaaaaaaaac tccaataaaa   20040
aagtctagac tctcacgctc gcttggtcct gtgactattt tgtagaatgg aagacatcaa   20100
ctttgcgtcg ctggcccccg cgtcacggctc gcgcccgtttc ctgggacact ggaacgatat   20160
cggcaccagc aacatgagcg gtggcgcctt cagttggggc tctctgtgga gcggcattaa   20220
aagtatcggg tctgccgtta aaaattacgg ctcccgggcc tggaacagca gcacgggcca   20280
gatgttgaga gacaagttga aagagcagaa cttccagcag aaggtggtgg agggcctggc   20340
ctccggcatc aacggggtgg tggacctggc caaccaggcc gtgcagaata agatcaacag   20400
cagactggac ccccggccgc cggtggagga ggtgccgccg gcgctggaga cggtgtcccc   20460
cgatgggcgt ggcgagaagc gcccgcggcc cgatagggaa gagaccactc tggtcacgca   20520
gaccgatgag ccgcccccgt atgaggaggc cctgaagcaa ggtctgccca ccacgcgggg   20580
catcgcgccc atgccaccg gggtggtggg ccgccacacc cccgccacgc tggacttgcc   20640
tccgcccgcc gatgtgccgc agcagcagaa ggcggcacag ccgggccgcc ccgcgaccgc   20700
ctcccgttcc tccgccggtc ctctgcccg cgccgccagg ggggcctgcc ggggggtcgc   20760
gaggcacggc aactggcaga gcacgctgaa cagcatcgtg ggtctggggg tgcggtccgt   20820
gaagcgccgc cgatgctact gaatagctta gctaacgtgt tgtatgtgtg tatgcgccct   20880
atgtcgccgc cagaggagct gctgagtcgc gccgttcgc gcgcccacca ccaccgccac   20940
tccgccccte aagatggcga ccccatcgat gatgccgcag tggtcgtaca tgcacatctc   21000
gggccaggac gcctcggagt acctgagccc cgggctggtg cagttcgccc gcgccaccga   21060
gagctacttc agcctgagta acaagtttag gaacccacg gtggcgccca cgcacgatgt   21120
gaccaccgac cggtctcagc gcctgacgct gcggttcatt cccgtggacc gcgaggacac   21180
cgcgtactcg tacaaggcgc ggttcacccct ggccgtgggc gacaaccgcg tgctggacat   21240
ggcctccacc tacttttgaca tccgcggggt gctggaccgg ggtccccactt tcaagcccta   21300
ctctggcacc gcctacaact ccctggcccc caagggcgct cccaactcct gcgagtggga   21360
gcaagaggaa actcaggcag ttgaagaagc agcagaagag gaagaagaag atgctgacgg   21420
tcaagctgag gaagagcaag cagctaccaa aaagactcat gtatatgctc aggctccct   21480
ttctggcgaa aaaattagta aagatggtct gcaaatagga acgacgctca cagctacaga   21540
acaaaaaacct atttatgcag accctacatt ccagcccgaa cccaaaatcg gggagtccca   21600
gtggaatgag gcagatgcta cagtcgccgg cggtagagtg ctaaagaaat ctactcccat   21660
gaaaccatgc tatggttcct atgcaagacc cacaaatgct aatggagtc agggtgtact   21720
aacggcaaat gcccagggac agctagaatc tcaggttgaa atgcaattct tcaacttc   21780
tgaaaacgcc cgtaacgagg ctaacaacat tcagcccaaa ttggtgctgt atagtgagga   21840
atcatgcatg gagaccccgg atacgcacct ttcttacaag cccgcaaaaa gcgatgacaa   21900
ttcaaaaatc atgctgggtc agcagtccat gccaacagaa cctaattaca tcggcttcag   21960
agacaacttt atcggcctca tgtattacaa tagcactggc aacatgggag tgcttcagg   22020
tcaggcctct cagttgaatg cagtggtgga cttgcaagac agaaacacag aactgtccta   22080
ccagctcttg cttgattcca tgggtgacag aaccagatac ttttcatgt ggaatcaggc   22140
agtggacagt tatgacccag atgttagaat tattgaaaat catggaactg aagacgagct   22200
```

```
ccccaactat tgtttccctc tgggtggcat aggggtaact gacacttacc aggctgttaa   22260
aaccaacaat ggcaataacg ggggccaggt gacttggaca aaagatgaaa cttttgcaga   22320
tcgcaatgaa ataggggtgg gaaacaattt cgctatggag atcaacctca gtgccaacct   22380
gtggagaaac ttcctgtact ccaacgtggc gctgtaccta ccagacaagc ttaagtacaa   22440
ccctccaat gtggacatct ctgacaaccc caacacctac gattacatga acaagcgagt    22500
ggtggcccg gggctggtgg actgctacat caacctgggc gcgcgctggt cgctggacta    22560
catggacaac gtcaacccct tcaaccacca ccgcaatgcg ggcctgcgct accgctccat   22620
gctcctgggc aacgggcgct acgtgccctt ccacatccag gtgccccaga agttctttgc   22680
catcaagaac ctcctcctcc tgccgggctc ctacacctac gagtggaact tcaggaagga   22740
tgtcaacatg gtcctccaga gctctctggg taacgatctc agggtggacg gggccagcat   22800
caagttcgag agcatctgcc tctacgccac cttcttcccc atggcccaca acacggcctc   22860
cacgctcgag gccatgctca ggaacgacac caacgaccag tccttcaatg actacctctc   22920
cgccgccaac atgctctacc ccataccgc caacgccacc aacgtcccca tctccatccc    22980
ctcgcgcaac tgggcggcct tccgcggctg ggccttcacc cgcctcaaga ccaaggagac   23040
cccctccctg ggctcgggat tcgaccccta ctacacctac tcgggctcca ttccctacct   23100
ggacggcacc ttctacctca accacacttt caagaaggtc tcggtcacct tcgactcctc   23160
ggtcagctgg ccgggcaacg accgtctgct caccccaac gagttcgaga tcaagcgctc    23220
ggtcgacggg gagggctaca acgtggccca gtgcaacatg accaaggact ggttcctggt   23280
ccagatgctg gccaactaca acatcggcta ccagggcttc tacatcccag agagctacaa   23340
ggacaggatg tactccttct tcaggaactt ccagcccatg agccggcagg tggtggacca   23400
gaccaagtac aaggactacc aggaggtggg catcatccac cagcacaaca actcgggctt   23460
cgtgggctac ctcgccccca ccatgcgcga gggacaggcc taccccgcca acttcccta    23520
tccgctcata ggcaagaccg cggtcgacag catcacccag aaaaagttcc tctgcgaccg   23580
caccctctgg cgcatcccct tctccagcaa cttcatgtcc atgggtgcgc tctcggacct   23640
gggccagaac ttgctctacg ccaactccgc ccacgccctc gacatgacct tcgaggtcga   23700
ccccatggac gagcccaccc ttctctatgt tctgttcgaa gtctttgacg tggtccggat   23760
ccaccagccg caccgcgcg tcatcgagac cgtgtacctg cgtacgccct tctcggccga    23820
caacgccacc acctaaagaa gcaagccgca gtcatcgccg cctgcatgcc gtcgggttcc   23880
accgagcaag agctcaggc catcgtcaga gacctgggat gcgggcccta ttttttgggc    23940
accttcgaca agcgcttccc tggctttgtc tccccacaca agctgccgtc cgccatcgtc   24000
aacacggccg gccgcgagac cgggggcgtg cactggctgg ccttcgcctg gaacccgcgc   24060
tccaaaacat gcttcctctt tgacccctc ggcttttcgg accagcggct caagcaaatc    24120
tacgagttcg agtacgaggg cttgctgcgt cgcagcgcca tcgcctcctc gcccgaccgc   24180
tgcgtcaccc tcgaaaagtc cacccagacc gtgcagggc ccgactcggc cgcctgcggt    24240
ctcttctgct gcatgtttct gcacgccttt gtgcactggc ctcagagtcc catggaccgc   24300
aaccccacca tgaacttgct gacggggtg cccaactcca tgctccagag cccccaggtc    24360
gagcccaccc tgcgccgcaa ccaggagcag ctctacagct tcctggagcg ccactcgcct   24420
tacttccgcc gccacagcgc acagatcagg agggccacct ccttctgcca cttgcaagag   24480
atgcaagaag ggtaataacg atgtacacac ttttttttc aataaatgac atctttttat    24540
ttatacaagc tctctggggt attcatttcc caccaccacc cgccgttgtc gccatctggc   24600
tctatttaga aatcgaaagg gttctgccgg gagtcgccgt gcgccacggg cagggacacg   24660
ttgcgatact ggtagcgggt gccccacttg aactcgggca ccaccaggcg aggcagctcg   24720
gggaagtttt cgctccacag gctgcgggtc agcaccaggc cgttcatcag gtcgggcgcc   24780
gagatcttga agtcgcagtt ggggccgccg ccctgcgcgc gcgagttgcg gtacaccggg   24840
ttgcagcact ggaacaccaa cagcgccggg tgcttcacgc tggccagcac gctgcggtcg   24900
gagatcagct cggcgtccag gtcctccgcg ttgctcagcg cgaacggggt catcttgggc   24960
acttgccgcc ccaggaaggg cgcgtgcccc ggtttcgagt tgcagtcgca gcgcagcggg   25020
atcagcaggt gcccgtgccc ggactcggcg ttggggtaca gcgcgcgcat gaaggcctgc   25080
atctggcgga aggccatctg ggccttggcg ccctccgaga gaacatgcc gcaggacttg    25140
cccgagaact ggtttgcggg gcagctggcg tcgtgcaggc agcagcgcgc gtcggtgttg   25200
gcgatccgca ccacgttgcg ccccaccgg ttcttcacga tcttggcctt ggacgattgc    25260
tccttcagcg cgcgctgccc gttctcgctg gtcacatcca tctcgatcac atgttccttg   25320
ttcaccatgc tgctgccgtg cagacacttc agctcgccct ccgtctcggt gcagcggtgc   25380
tgccacagcg cgcagcccgt gggctcgaaa gacttgtagg tcacctccgc gaaggactgc   25440
aggtaccct gcaaaaagcg gcccatcatg gtcacgaagg tcttgttgct gctgaaggtc    25500
agctgcagcc cgcggtgctc ctcgttcagc caggtcttgc acacggccgc cagcgcctcc   25560
acctggtcgg gcagcatctt gaagttcacc ttcagctcat tctccacgtg gtacttgtcc   25620
atcagcgtgc gcgccgcctc catgcccttc tcccaggccg acaccagcgg caggctcacg   25680
gggttcttca ccatcaccgt ggccgccgcc tccgccgcgc tttcgctttc cgccccgctg   25740
ttctcttcct cttcctcctc ttcctccgcg ccgcccactc gcagccccg caccacgggg    25800
tcgtcttcct gcaggcgctg caccttgcgc ttgccgttgc gcccctgctt gatgcgcacg   25860
ggcggggttgc tgaagcccac catcaccagc gcggcctctt cttgctcgtc ctcgctgtcc   25920
agaatgacct ccggggaggg ggggttggtc atcctcagta ccgaggcacg cttcttttc    25980
ttcctgggga cgttcgccaa ctccgcggct gcggcccg ccgaggtcga aggccgaggg     26040
ctggcgtgc gcggcaccag cgcgtcctgc gagccgtcct cgtcctcctc ggactcgaga    26100
cggaggcggg cccgcttctt cggggcgcg cggggcggcg gagcggcgg cggcgacgga     26160
gacgggacg agacatcgtc cagggtgggt ggacggcggg ccgcgccgcg tccgcgctcg    26220
ggggtggtct cgcgctggtc ctcgttcccga ctggctcaga ccccactgctc ctttctccat   26280
aggcagaaag agatcatgga gtctctcatg cgagtcgaga aggaggagga cagcctaacc   26340
gccccctctg agccctccac caccgccgcc accaccgcca atgccgccgc ggacgacccg   26400
cccaccgaga ccaccgccag taccaccctc ccagcgacg caccccccgct cgagaatgaa    26460
gtgctgatcg agcaggaccc ggggttttgtg agcgagagg aggatgaggt ggatgagaag    26520
gagaaggagg aggtcgccgc ctcagtgcca aaagaggata aaaagcaaga ccaggacgac   26580
gcaggtaagg atgagacagc agtcgggcgg gggaacggaa gcgatgatgc tgatgacgac   26640
tacctagacg tgggagacga cgtgctgctt aagcacctgc accgcagtg cgtcatcgtc     26700
tgcgacgcgc tgcaggagcg ctgcgaagtg ccctggacg tggcggaggt cagccgcgcc     26760
tacgagcggc acctcttcgc gccgcacgtg ccccccaagc gccgggagaa cggcacctgc   26820
gagcccaacc cgcgtctcaa cttctacccg gtcttcgcgg tacccgaggt gctggccacc   26880
taccacatct ttttccaaaa ctgcaagatc cccctctcct gccgcgccaa ccgcacccgc   26940
```

```
gccgacaaaa ccctgaccct gcggcagggc gcccacatac ctgatatcgc ctctctggag   27000
gaagtgccca agatcttcga gggtctcggt cgcgacgaga aacgggcggc gaacgctctg   27060
cacggagaca gcgaaaacga gagtcactcg ggggtgctgg tggagctcga gggcgacaac   27120
gcgcgcctgg ccgtactcaa gcgcagcata gaggtcaccc actttgccta cccggcgctc   27180
aacctgcccc ccaaggtcat gagtgtggtc atgggcggac tcatcatgcg acgcgcccag   27240
cccctggccg cggatgcaaa cttgcaagag tcctccgagg aaggcctgcc cgcggtcagc   27300
gacgagcagc tggcgcgctg gctggagacc cgcgaccccg cgcagctgga ggagcggcgc   27360
aagctcatga tggccgcggt gctggtcacc gtggagctcg agtgtctgca gcgcttcttc   27420
gcggacccg agatgcagcg caagctcgag gagaccctgc actacacctt ccgcagggc   27480
tacgtgcgcc aggcctgcaa gatctccaac gtggagctct gcaacctggt ctcctacctg   27540
ggcatcctgc acgagaaccg cctcgggcag aacgtcctgc actccaccct caaaggggag   27600
gcgcgccgcg actacatccg cgactgcgcc tacctcttcc tctgctacac ctggcagacg   27660
gccatggggg tctggcagca gtgcctggag gagcgcaacc tcaaggagct ggaaaagctc   27720
ctcaagcgca ccctcaggga cctctggacg ggcttcaacg agcgctcggt ggccgccgcg   27780
ctggcggaca tcatctttcc cgagcgcctc ctcaagaccc tgcagcaggg cctgcccgac   27840
ttcaccagcc agagcatgct gcagaacttc aggactttca tcctggagcg ctcgggcatc   27900
ctgccggcca cttgctgcgc gctgcccagc gacttcgtgc ccatcaagta cagggagtgc   27960
ccgccgccc tctggggcca tctctacctc ttccagctgg ccaactacct cgcctaccac   28020
tcggacctca tggaagacgt gagcggcgag ggcctgctcg agtgccactg ccgctgcaac   28080
ctctgcacgc cccaccgctc tctagtctgc aacccgcagc tgctcagcga gagtcagatt   28140
atcggtacct tcgagctgca gggtccctcg cctgacgaga agtccgcggc tccagggctg   28200
aaactcactc cggggctgtg gacttccgcc tacctacgca aatttgtacc tgaggactac   28260
cacgcccacg agatcaggtt ctacgaagac caatcccgcc cgcccaaggc ggagctcacc   28320
gcctgcgtca tcacccaggg gcacatcctg ggccaattgc aagccatcaa caaagcccgc   28380
cgagagttct tgctgaaaaa gggtcggggg gtgtacctgg acccccagtc cggcgaggag   28440
ctaaaccgc taccccgcc gccgcccag cagcgggacc ttgcttccca ggatggcacc   28500
cagaaagaag cagcagccgc cgccgccgcc gcagcatac atgcttctgg aggaagagga   28560
ggaggactgg gacagtcagg cagaggaggt ttcggacgag gagcaggagg agatgatgga   28620
agactgggag gaggacagca gcctagacga ggaagcttca gaggccgaag aggtggcaga   28680
cgcaacacca tcgccctcgg tcgcaacccc ctcgccgggg ccctgaaat cctccgaacc   28740
cagcaccagc gctataacct ccgctcctcc ggcgccgagc ccaccgccc gcagacccaa   28800
ccgtagatgg gacaccacag gaaccggggt cggtaagtcc aagtgcccgc cgccgccacc   28860
gcagcagcag cagcagcagc gccagggcta ccgctcgtgg cgcgggcaca gaacgccat   28920
agtcgcctgc ttgcaagact gcgggggcaa catctctttc gcccgccgct tcctgctatt   28980
ccaccacggg gtcgccttc cccgcaatgt cctgcattac taccgtcatc tctacagccc   29040
ctactgcagc ggcgacccag aggcggcagc ggcagccaca gcggcgacca ccacctagga   29100
agatatcctc cgcggcaag acagcggcag cagcggccag gagacccgcg gcagcagcgg   29160
cgggagcggt gggcgcactg cgcctctcgc ccaacgaacc cctctcgacc cgggagctca   29220
gacacaggat cttccccact ttgtatgcca tcttccaaca gagcagaggc caggagcagg   29280
agctgaaaat aaaaaacaga tctctgcgct ccctcacccg cagctgtctg tatcacaaaa   29340
gcgaagatca gcttcggcgc acgctggagg acgcggaggc actcttcagc aaatactgcg   29400
cgctcactct taaagactag ctccgcgccc ttctcgaatt taggcgggag aaaactacgt   29460
catcgccgc cgccgcccag cccgcccagc cgagatgcaa aaagagattc ccacgccata   29520
catgtggagc taccagccgc agatgggact cgcggcggga gcggcccagg actactccac   29580
ccgcatgaac tacatgagcg cggaccccca catgatctca caggtcaacg ggatccgcgc   29640
ccagcgaaac caaatactgc tggaacaggc ggccatcacc gccacgcccc gccataatct   29700
caaccccga aattggcccg ccgccctcgt gtaccaggaa accccctccg ccaccaccgt   29760
actacttccg cgtgacgccc aggccgaagt ccagatgact aactcagggg cgcagctcgc   29820
gggcggcttt cgtcacgggg cgcggccgct ccgaccaggt ataagacacc tgatgatcag   29880
aggccgaggt atccagctca acgacgagtc ggtgagctct tcgctcggtc tccgtccgga   29940
cggaactttc cagctgccg gatccggccg ctcttcgttc acgcccgcc aggcggtact   30000
gactctgcag acctcgtcct cggagccccg ctccggcggc atcggaaccc tccagttcgt   30060
ggaggagttc gtgccctcgg tctacttcaa ccccttctcg ggacctcccg gacgctaccc   30120
cgaccagttc attccgaact ttgacgcggt gaaggactcg gcggacgct acgactgaat   30180
gtcaggtgtc gaggcagagc agcttcgcct gagcacctcc gagcactgcc gccgccacaa   30240
gtgcttcgcc cgcggttctg gtgagttctg ctactttcag ctacccgagg agcataccga   30300
ggggccggcg cacggcgtcc gcctgaccac ccagggcgag gttacctgtt ccctcatccg   30360
ggagtttacc ctccgtcccc tgctagtgga gcggagcgg ggtccctgtg tcctaactat   30420
cgcctgcaac tgccctaacc ctgattaca tcaagatctt tgctgtcatc tctgtgctga   30480
gtttaataaa cgctgagatc agaatctact gggatttagt ccccttttaac taatcaaaca   30540
ctggaatcaa taaaaagaat cacttactta aaatcagaca gcaggtctct gtccagttta   30600
ttcagcagca cctccttccc ctcctcccaa ctctggtact ccaaacgcct tctggcggca   30660
aacttcctcc acaccctgaa gggaatgtca gattcttgct cctgtccctc cgcacccact   30720
atcttcatgt tgttgcagat gaagcgcacc aaaacgtcga acgagagctt caaccccgtg   30780
taccccctatg acacggaaag cggccctccc tccgtccctt tcctcacccc tcccttcgtg   30840
tctcccgatg gattccaaga aagtccccc gggtcctgt ctctgaacct ggccgagccc   30900
ctggtcactt cccacggcat gctcgccctg aaaatgggaa gtggcctctc cctgacgac   30960
gctggcaacc tcacctctca agatatccac accgctagcc ctccccctca aaaaaccaag   31020
accaacctca gcctagaaac ctcatccccc ctaactgtga gcacctcagg cgccctcacc   31080
gtagcagccg ccgctcccct ggcggtggcc ggcacctccc tcaccatgca atcagaggcc   31140
cccctgacag tacaggatgc aaaaactcacc ctggccacca aaggcccct gaccgtgtct   31200
gaaggcaaac tggccttgca aacatcgcc ccgctgacgg ccgctgacag cagcaccctc   31260
acagtcagtg ccacaccacc ccttagcaca agcaatggca gcttgggtat tgacatgcaa   31320
gccccccattt acaccaccaa tggaaaacta ggacttaact ttgcgctcc cctgcatgtg   31380
gtagacagcc taaatgcact gactgtagtt actggccaag gtcttacgat aaacggaaca   31440
gccctacaaa ctagagtctc aggtcccctc aactatgaca catcaggaaa cctagaattg   31500
agagctgcag ggggtatgcg agttgatgca aatggtcaac ttatccttga tgtagcttac   31560
ccatttgatg cacaaaacaa tctcagcctt aggcttggac agggacccct gtttgttaac   31620
tctgcccaca acttggatgt taactacaac agaggcctct acctgttcac atctggaaat   31680
```

```
accaaaaagc tagaagttaa tatcaaaaca gccaagggtc tcatttatga tgacactgct   31740
atagcaatca atgcgggtga tgggctacag tttgactcag gctcagatac aaatccatta   31800
aaaactaaac ttggattagg actggattat gactccagca gagccataat tgctaaactg   31860
ggaactggcc taagctttga caacacaggt gccatcacag taggcaacaa aaatgatgac   31920
aagcttacct tgtggaccac accagaccca tcccctaact gtagaatcta ttcagagaaa   31980
gatgctaaat tcacacttgt tttgactaaa tgcggcagtc aggtgttggc cagcgtttct   32040
gttttatctg taaaaggtag ccttgcgccc atcagtggca cagtaactag tgctcagatt   32100
gtcctcagat ttgatgaaaa tggagttcta ctaagcaatt cttcccttga ccctcaaatac  32160
tggaactaca gaaaaggtga ccttacagag ggcactgcat ataccaacgc agtgggattt   32220
atgcccaacc tcacagcata cccaaaaaca cagagccaaa ctgctaaaag caacattgta   32280
agtcaggttt acttgaatgg ggacaaatcc aaacccatga ccctcaccat taccctcaat   32340
ggaactaatg aaacaggaga tgccacagta agcacttact ccatgtcatt ctcatggaac   32400
tggaatggaa gtaattacat taatgaaacg ttccaaacca actccttcac cttctcctac   32460
atcgcccaag aataaaaagc atgacgctgt tgatttgatt caatgtgttt ctgttttatt   32520
ttcaagcaca acaaaatcat tcaagtcatt cttccatctt agcttaatag acacagtagc   32580
ttaatagacc cagtagtgca aagcccatt ctagcttata actagtggag aagtactcgc    32640
ctacatgggg gtagagtcat aatcgtgcat caggataggg cggtggtgct gcagcagcgc   32700
gcgaataaac tgctgccgcc gccgctccgt cctgcaggaa tacaacatgg cagtggtctc   32760
ctcagcgatg attcgcaccg cccgcagcat aaggcgcctt gtcctccggg cacagcagcg   32820
caccctgatc tcacttaaat cagcacagta actgcagcac agcaccacaa tattgttcaa   32880
aatcccacag tgcaaggcgc tgtatccaaa gctcatggcg gggaccacag aacccacgtg   32940
gccatcatac cacaagcgca ggtagattaa gtggcgaccc ctcataaaca cgctggacat   33000
aaacattacc tcttttggca tgttgtaatt caccacctcc cggtaccata taaacctctg   33060
attaaacatg gcgccatcca ccaccatcct aaaccagctg gccaaaacct gcccgccggc   33120
tatacactgc agggaaccgg gactggaaca atgacagtgg agagcccagg actcgtaacc   33180
atggatcatc atgctcgtca tgatatcaat gttggcacaa cacaggcaca cgtgcataca   33240
cttcctcagg attacaagct cctcccgcgt tagaaccata tcccagggaa caacccattc   33300
ctgaatcagc gtaaatccca cactgcaggg aagacctcgc acgtaactca cgttgtgcat   33360
tgtcaaagtg ttacattcgg gcagcagcgg atgatcctcc agtatggtag cgcgggtttc   33420
tgtctcaaaa ggaggtagac gatccctact gtacggagtg cgccgagaca accgagatcg   33480
tgttggtcgt agtgtcatgc caaatggaac gccggacgta gtcatatttc ctgaagtctt   33540
agatctctca acgcagcacc agcaccaaca cttcgcagtg taaaaggcca agtgccgaga   33600
gagtatatat aggaataaaa agtgacgtaa acgggcaaag tccaaaaaac gcccagaaaa   33660
accgcacgcg aacctacgcc ccgaaacgaa agccaaaaaa cactagacac tcccttccgg   33720
cgtcaacttc cgcttttccca cgctacgtca cttgccccag tcaaacaaac tacatatccc   33780
gaacttccaa gtcgccacgc ccaaaacacc gcctacacct ccccgcccgc cggcccgccc   33840
ccaaacccgc ctcccgcccc gcgccccgcc ccgcgccgcc catctcatta tcatattggc   33900
ttcaatccaa aataaggtat attattgatg atggtttaaa cggatcctct agagtcgacc   33960
tgcaggcatg caagcttgag tattctatag tgtcacctaa atagcttggc gtaatcatgg   34020
tcatagctgt ttcctgtgtg aaattgttat ccgctcacaa ttccacacaa catacgagcc   34080
ggaagcataa agtgtaaagc ctgggggtgcc taatgagtga gctaactcac attaattgcg   34140
ttgcgctcac tgcccgcttt ccagtcggga aacctgtcgt gccagctgca ttaatgaatc   34200
ggccaacgcg aacccttgc ggcgccccgg gccgtcgacc aattctcatg tttgacagct    34260
tatcatcgaa tttctgccat tcatccgctt attatcactt attcaggcgt agcaaccagg   34320
cgtttaaggg caccaataac tgccttaaaa aaattacgcc ccgccctgcc actcatcgca   34380
gtactgttgt aattcattaa gcattctgcc gacatggaag ccatcacaaa cggcatgatg   34440
aacctgaatc gccagcggca tcagcacctt gtcgccttgc gtataatatt tgcccatggt   34500
gaaaacgggg gcgaagaagt tgtccatatt ggccacgttt aaatcaaaac tggtgaaact   34560
cacccaggga ttggctgaga cgaaaaacat attctcaata aacccttag ggaaataggc    34620
caggttttca ccgtaacacg ccacatcttg cgaatatatg tgtagaaact gccggaaatc   34680
gtcgtggtat tcactccaga gcgatgaaaa cgtttcagtt tgctcatgga aaacggtgta   34740
acaagggtga acactatccc atatcaccag ctcaccgtct ttcattgcca tacgaaattc   34800
cggatgagca ttcatcaggc gggcaagaat gtgaataaag gccggataaa acttgtgctt   34860
attttttcttt acggtcttta aaaaggccgt aatatccagc tgaacggtct ggttataggt   34920
acattgagca atgtgcttta catttgatta aatattgcg catggt
```
acattgagca atgtgactgaa atgcctcaaa atgttcttta cgatgccatt gggatatatc   34980
aacggtggta tatccagtga ttttttttctc cattttagct tccttagctc ctgaaaatct   35040
cgataactca aaaaatacgc ccggtagtga tcttatttca ttatggtgaa agttggaacc   35100
tcttacgtgc cgatcaacgt ctcatttttcg ccaaaagttg gcccagggct tcccggtatc   35160
aacagggaca ccaggattta tttattctgc gaagtgttc tccgtcacag gtatttattc    35220
gcgataagct catggagcgg cgtaaccgtc gcacaggaag gacagagaaa gcgcggatct   35280
gggaagtgac ggacagaacg gtcaggacct ggattgggga ggcggttgcc gccgctgctg   35340
ctgacggtgt gacgttctct gttccggtca caccacatac gttccgccat tcctatgcga   35400
tgcacatgct gtatgccggt ataccgctga agttctgca aagcctgatg ggacataagt    35460
ccatcagttc aacggaagtc tacacgaagg tttttgcgct ggatgtgcct gccgggacc    35520
gggtgcagtt tgcgatgccg gagtctgatg cggttgcgat gctgaaacaa ttatcctgag   35580
aataaatgcc ttggccttta tggaaatg tggaactgag tggatatgct gttttttgtct    35640
gttaaacaga gaagctggct gttatccact gagaagcgaa cgaaacagtc gggaaaatct   35700
cccattatcg tagagatccg cattattaat ctcaggaacc tgtgtagcgt ttataggaag   35760
tagtgttctg tcatgatgcc tgcaagcggt aacgaaaacg atttgaatat gccttcagga   35820
acaatagaaa tcttcgtgcg gtgttacgtt gaagtggagc ggattatgtc agcaatggac   35880
agaacaacct aatgaacaca gaaccatgat gtggtctgtc cttttacagc cagtagtgct   35940
cgccgcagtc gagcgacagg gcgaagccct cgagtgagcg aggaagcacc agggaacagc   36000
acttatatat tctgcttaca cacgatgcct gaaaaaactt cccttggggt tatccactta   36060
tccacgggga tatttttata attattttt ttatagtttt tagatcttct tttttagagc    36120
gccttgtagg cctttatcca tgctggttct agagaaggtg ttgtgacaaa ttgccctttc   36180
agtgtgacaa atcaccctca aatgacagtc ctgtctgtga caaattgccc ttaaccctgt   36240
gacaaattgc cctcagaaga agctgttttt tcacaaagtt atccctgctt attgactctt   36300
tttttatttag tgtgacaatc taaaaacttg tcacacttca catggatctg tcatggcgga   36360
aacagcggtt atcaatcaca agaaacgtaa aaatagcccg cgaatcgtcc agtcaaacga   36420

```
cctcactgag gcggcatata gtctctcccg ggatcaaaaa cgtatgctgt atctgttcgt   36480
tgaccagatc agaaaatctg atggcaccct acaggaacat gacgtatct gcgagatcca    36540
tgttgctaaa tatgctgaaa tattcggatt gacctctgcg gaagccagta aggatatacg   36600
gcaggcattg aagagtttcg cggggaagga agtggttttt tatcgccctg aagaggatgc   36660
cggcgatgaa aaaggctatg aatcttttcc ttggtttatc aaacgtgcgc acagtccatc   36720
cagagggctt tacagtgtac atatcaaccc atatctcatt cccttcttta tcggttaca   36780
gaaccggttt acgcagtttc ggcttagtga aacaaaagaa atcaccaatc cgtatgccat   36840
gcgtttatac gaatccctgt gtcagtatcg taagccggat ggctcaggca tcgtctctct   36900
gaaaatcgac tggatcatag agcgttacca gctgcctcaa agttaccagc gtatgcctga   36960
cttccgccgc cgcttcctgc aggtctgtgt taatgagatc aacagcagaa ctccaatgcg   37020
cctctcatac attgagaaaa agaaaggccg ccagacgact catatcgtat tttccttccg   37080
cgatatcact tccatgacga caggatagtc tgagggttat ctgtcacaga tttgagggtg   37140
gttcgtcaca tttgttctga cctactgagg gtaatttgtc acagttttgc tgtttccttc   37200
agcctgcatg gattttctca tacttttttga actgtaattt ttaaggaagc caaatttgag   37260
ggcagtttgt cacagttgat ttccttctct ttcccttcgt catgtgacct gatatcgggg   37320
gttagttcgt catcattgat gagggttgat tatcacagtt tattactctg aattggctat   37380
ccgcgtgtgt acctctacct ggagttttttc ccacggtgga tatttcttct tgcgctgagc   37440
gtaagagcta tctgacagaa cagttcttct ttgcttcctc gccagttcgc tcgctatgct   37500
cggttacacg gctgcggcga cgctagtga taataagtga ctgaggtatg tgctcttctt   37560
atctcctttt gtagtgttgc tcttattta aacaactttg cggttttttg atgactttgc   37620
gattttgttg ttgctttgca gtaaattgca agatttaata aaaaaacgca aagcaatgat   37680
taaaggatgt tcagaatgaa actcatggaa acacttaaac agtgcataaa cgctggtcat   37740
gaaatgacga aggctatcgc cattgcacag tttaatgatg acagcccgga agcgaggaaa   37800
ataacccggc gctggagaat aggtgaagca gcggatttag ttggggtttc ttctcaggct   37860
atcagagatg ccgagaaagc agggcgacta ccgcacccgg atatgaaat tcgaggacgg   37920
gttgagcaac gtgttggtta tacaattgaa caaattaatc atatgcgtga tgtgtttggt   37980
acgcgattgc gacgtgctga agacgtattt ccaccggtga tcggggttgc tgcccataaa   38040
ggtggcgttt acaaaacctc agtttctgtt catcttgctc aggatctggc tctgaagggg   38100
ctacgtgttt tgctcgtgga aggtaacgac ccccagggaa cagcctcaat gtatcacgga   38160
tgggtaccag atcttcatat tcatgcagaa gacactctcc tgcctttcta tcttggggaa   38220
aaggacgatg tcacttatgc aataaagccc acttgctggc cggggcttga cattattcct   38280
tcctgtctgg ctctgcaccg tattgaaact gagttaatgg gcaaatttga tgaaggtaaa   38340
ctgcccaccg atccacacct gatgctccga ctggccattg aaactgttgc tcatgactat   38400
gatgtcatag ttattgacag cgcgcctaac ctggggtatg gcacgattaa tgtcgtatgt   38460
gctgctgatg tgctgattgt tcccacgcct gctgagttgt ttgactacac ctccgcactg   38520
cagtttttcg atatgcttcg tgatctgctc aagaacgttg atcttaaagg gttcgagcct   38580
gatgtacgta ttttgcttac caaatacagc aatagtaatg gctctcagtc cccgtggatg   38640
gaggagcaaa ttcgggatgc ctggggaagc atggttctaa aaatgttgt acgtgaaacg   38700
gatgaagttg gtaaaggtca gatccggatg agaactgttt ttgaacaggc cattgatcaa   38760
cgctcttcaa ctggtgcctg gagaaatgct cttttctattt gggaacctgt ctgcaatgaa   38820
attttcgatc gtctgattaa accacgctgg gagattagat aatgaagcgt gcgcctgtta   38880
ttccaaaaca tacgctcaat actcaaccgg ttgaagatac ttcgttatcg acaccagctg   38940
ccccgatggt ggattcgtta attgcgcgcg taggagtaat ggctcgcggt aatgccatta   39000
ctttgcctgt atgtggtcgg gatgtgaagt ttactcttga agtgctccgg ggtgatagtg   39060
ttgagaagac ctctcgggta tggtcaggta atgaacgtga ccaggagctg cttactgagg   39120
acgcactgga tgatctcatc ccttctttttc tactgactgg tcaacagaca ccggcgttcg   39180
gtcgaaagat atctggtgtc atagaaattg ccgatgggaa tcgccgtcgt aaagctgctg   39240
cacttaccga aagtgattat cgtgttctgg ttggcgagct ggatgatgag cagatgcctg   39300
cattatccag attgggtaac gattatcgcc caacaagtgc ttatgaacgt ggtcagcgtt   39360
atgcaagccg attgcagaat gaatttgctg gaaatatttc tgcgctggct gatgcggaaa   39420
atatttcacg taagattatt acccgctgta tcaacaccgc caaattgcct aaatcagttg   39480
ttgctcttttt ttctcacccc ggtgaactat ctgcccggtc aggtgatgca cttcaaaaag   39540
cctttacaga taaagaggaa ttacttaagc agcaggcatc taaccttcat gagcagaaaa   39600
aagctggggt gatatttgaa gctgaagaag ttatcactct tttaacttct gtgcttaaaa   39660
cgtcatctgc atcaagaact agtttaagct cacgacatca gtttgctcct ggagcgacag   39720
tattgtataa gggcgataaa atggtgctta acctggacag gtctcgtgtt ccaactgagt   39780
gtatagagaa aattgaggcc attcttaagg aacttgaaaa gccagcaccc tgatgcgacc   39840
acgttttagt ctacgtttat ctgtctttac ttaatgtcct tgttacagg ccagaaagca    39900
taactggcct gaatattctc tctgggccca ctgttccact tgtatcgtcg gtctgataat   39960
cagactggga ccacggtccc actcgtatcg tcggtctgat tattagtctg ggaccacgtg   40020
cccactcgta tcgtcggtct gattattagt ctgggaccac ggtcccactc gtatcgtcgg   40080
tctgataatc agactgggac cacggtccca ctcgtatcgt cggtctgatt attagtctgg   40140
gaccatggtc ccactcgtat cgtcggtctg attattagtc tgggaccacg gtcccactcg   40200
tatcgtcggt ctgattatta gtctggaacc acggtcccact gatctgatta   40260
ttagtctggg accacggtcc cactcgtatc gtcggtctga ttattagtct gggaccacga   40320
tcccactcgt gttgtcggtc tgattatcgg tctgggacca cggtcccact tgtattgtcg   40380
atcagactat cagcgtgaga ctacgattcc atcaatgcct gtcaagggca agtattgaca   40440
tgtcgtcgta acctgtagaa cggagtaacc tcggtgtgcg gttgtatgcc tgctgtggat   40500
tgtctgtgtg tcctgcttat ccacaacatt ttgcgcacgg ttatgtggac aaaatacctg   40560
gttacccagg ccgtgccggc acgttaaccg ggctgcatcc gatgcaagtg tgtcgctgtc   40620
gacgagctcg cgagctcgga catgaggttg ccccgtattc agtgtcgctg atttgtattg   40680
tctgaagttg ttttttacgtt aagttgatgc agatcaatta atacgatacc tgcgtcataa   40740
ttgattattt gacgtggttt gatggcctcc acgcacgttg tgatatgtag atgataatca   40800
ttatcacttt acggtgcctt tccggtgatc cggggacggg acctcgggta   40860
ttttcgctat ttatgaaaat tttccggttt aaggcgtttc cgttcttctt cgtcataact   40920
taatgttttt atttaaaata ccctctgaaa agaaaggaaa cgacaggtgc tgaaagcgag   40980
cttttttggcc tctgtcgttt cctttctctg tttttgtccg tggaatgaac aatggaagtc   41040
cgagctcatc gctaataact tcgtatagca tacattatac gaagttatat tcgatgcggc   41100
cgcaaggggt tcgcgtcagc gggtgttggc gggtgtcggg gctggcttaa ctatgcggca   41160
```

```
tcagagcaga ttgtactgag agtgcaccat atgcggtgtg aaataccgca cagatgcgta    41220
aggagaaaat accgcatcag gcgccattcg ccattcaggc tgcgcaactg ttgggaaggg    41280
cgatcggtgc gggcctcttc gctattacgc cagctggcga aagggggatg tgctgcaagg    41340
cgattaagtt gggtaacgcc agggttttcc cagtcacgac gttgtaaaac gacggccagt    41400
gaattgtaat acgactcact atagggcgaa ttcgagctcg gtacccgggg atcctcgttt    41460
aaac                                                                 41464
```

| | |
|---|---|
| SEQ ID NO: 52 | moltype = DNA  length = 43711 |
| FEATURE | Location/Qualifiers |
| misc_difference | 15388 |
| | note = modified_base - a, c, t, g, unknown or other |
| misc_feature | 1..43711 |
| | note = Description of Artificial Sequence: Synthetic polynucleotide |
| source | 1..43711 |
| | mol_type = other DNA |
| | organism = synthetic construct |

```
SEQUENCE: 52
catcatcaat aatatacctt attttggatt gaagccaata tgataatgag atgggcggcg      60
cggggcgggg cgcggggcgg gaggcgggtt tggggcggg ccggcgggcg gggcggtgtg     120
gcggaagtga actttgtaag tgtggcggat gtgacttgct agtgccgggc gcggtaaaag    180
tgacgttttc cgtgcgcgac aacgcccccg ggaagtgaca tggttttacc                240
ggatgttgta gtgaatttgg gcgtaaccaa gtaagatttg gccattttcg cgggaaaact    300
gaaacgggga agtgaaatct gattaatttt gcgttagtca taccgcgtaa tatttgtcta    360
gggccgaggg actttggccg attacgtgga ggactcgccc aggtgttttt tgaggtgaat    420
ttccgcgttc cgggtcaaag tctgcgtttt attattatag gatatcccat tgcatacgtt    480
gtatccatat cataatatgt acatttatat tggctcatgt ccaacattac cgccatgttg    540
acattgatta ttgactagtt attaatagta atcaattacg gggtcattag ttcatagccc    600
atatatggag ttccgcgtta cataacttac ggtaaatggc ccgcctggct gaccgcccaa    660
cgaccccgc ccattgacgt caataatgac gtatgttccc atagtaacgc caatagggac    720
tttccattga cgtcaatggg tggagtattt acggtaaact gcccacttgg cagtacatca    780
agtgtatcat atgccaagta cgccccctat tgacgtcaat gacggtaaat ggcccgcctg    840
gcattatgcc cagtacatga ccttatggga ctttcctact tggcagtaca tctacgtatt    900
agtcatcgct attaccatgg tgatgcggtt ttggcagtac atcaatgggc gtggatagcg    960
gtttgactca cggggatttc caagtctcca ccccattgac gtcaatgggg gtttgttttg   1020
gcaccaaaat caacgggact ttccaaaatg tcgtaacaac tccgccccat tgacgcaaat   1080
gggcggtagg cgtgtacggt gggaggtcta tataagcaga gctctcccta tcagtgatag   1140
agatctccct atcagtgata gagatcgtcg acgagctcgt ttagtgaacc gtcagatcgc   1200
ctggagacgc catccacgct gttttgacct ccatagaaga caccgggacc gatccagcct   1260
ccgcggccgg gaacggtgca ttggaacgcg gattccccgt gccaagagtg atcttccg    1320
tttatctagg taccagatat cgccaccatg tccgaggact ttctgattct gatcgccatc   1380
ctggtgatcg tgattctcgt gggcacaatc acaaccctgg tgggcgccat cggcggcatt   1440
agggccagga ggagcttcct cttcatttgc atcttctct tgttcctctc ttcttcctg    1500
acaatcctcg ccctgctgct gggcttcagc tggctcctgc tggtggccat cctgttctgg   1560
gtgctctggc tggtcatcct cattctgctg ctgctggtgt accctattcc tcaccacccc   1620
ctgcccacct ccctcaggtt tagaatgaag cagagggtga gcagcgaccc cacaggttct   1680
gacagaagcc ctcagggcag ccataatagc ctgaactccc ccgatgagga ggaccccaag   1740
gatgacacca agcaacctct gtgcaacatg acccagggcg acctccgt caatggacag   1800
ctcctcggac aacatgctca atgccccct cactatccct gctgcatat tcagcatccc   1860
gacggagagg attccgatgg agacgatggc aagtcctggg cgatgccgg agaggaagac   1920
aatggcccta acgaccctaa caccgccagc accagagagt ccatttacga ggacctgca   1980
taccccacaa gggacgccaa tggcgagtat gagaacgtgg gatacccccc tagggacgga   2040
gatgcccctc ataggctcgg agagcctgtg tatgacgatg tggagcaagc caccgctaac   2100
gaggtgagaa tctcccctct gttcagactg ccctacggaa gcgctttcgg acctggcccc   2160
cagctggac ccattctgga gagctccaca tgggctttc tggtcttcac acagacctcc   2220
ctgttcgccg acgacattgc cgacgctatt ggggactact gcacaaccca ccctggcccc   2280
acaaggaaca cccaggtggt cctcatgaac ttcgagggca gcggagtgcc cctgcctatg   2340
ttttttcccc ctgagagga cacagaagag cagagagg gcgatagagc tagcgactcc   2400
gacgagtccg aagacgctca gatcctgacc gtgttctgcc tgttttgcca gtggacactg   2460
tttatctgcc tgggaatcag gatgatctgt aactggaggg gcaaactcac caggatcatc   2520
tgcctgaagt tctgcctcta cggactgatt tccgcctccc tgtccttcgg ctggtacgct   2580
tttctgaagg aagtgaccct ccccaccaca gccaccgttg atcctaggca actcccctg    2640
ttcctcttca tcctgagctc cgtgctggtg attctcgcca tcatgatgga gtttcaaaca   2700
tcctccagcc tcttcgctgc tctgttcgtg attatcgcg gaatgctgtc cgtcacagtg   2760
ggcgtgattt ttctgctggc tggcgtcaag cctctcctga gcggcatgat ctgcgctcc    2820
ggcatcacaa tgctcgtgct cggcgtcgtg ctgctggtgg tgtgcaccag aagcccagc    2880
ccttgtcatc acagggatga accccctcc agaagcccca gccctcaacc caccgtctcc   2940
gagcagtccc agcagtcccc caggcagcag agccctcaag gcacatccca gggttctaca   3000
agacctcagg tgcctggagg cgccaccacc agaaaaggag cggcgtgag aggccaacct    3060
gccaagtgtc acgcaagta caccacaacc gccgagggac tgaccgctct cctgaatagg   3120
aggcacagcc caggacatc caacgagggc aggtggatga atggagtcat ggctgtgaac    3180
ctctccaaat ggccctgta cagcctgagg agagcctgg ccctgccat ggctcctaga   3240
aggaggctct ccggccctcc ctggctgaca gtgctgctgc tgctgtccac actgagcgtg   3300
gccgctgtg tgattctctt cctgatttt agcgccgcg ccaccattag cacagaagcc   3360
agcctgctgg tcctgctcct gctgtttgtg accctgctgc tgcctctcct gtcctccaac   3420
ggactccagc tccctgccgc cctgattctg atccagtgtt tcctcctggc cgctgattat   3480
ctcgcctacc tgattctgcc taccattatg cccagggggca gaagcacagg aagaaggggc   3540
aggggacacag agaaagagag gagcagatcc cctctcagag ctcctggcgg ttctgatgga   3600
cccagcacaa gggctggctg tggagccgga ccctgtcagc tgacagccc catcgccgga   3660
```

```
aacaacggca atgaaggcgg cgagggcgac gactacaaga gctgaggaa gcccgaggaa  3720
gaggacaacg gccccaatga ccccaatacc aacaacagga ttgaggatgg agacggcgac  3780
gacggaaaat cctggaggaa tcctgaggag gaggataaca gaaagcagga caggctgggc  3840
accaagcctt tcatggccgg ccactggtat gagagcgtga ttcccggcct gttcctctgc  3900
ccctgatcc tcccttccct gttctggatt tgctccctgc tgaccttcct ggtgggccac  3960
ggagccaata ttgtgagcgc cgtcctgttc ctcgtgctgg cttggtgtct cctcattgcc  4020
aactggaacg tgacaagaga ggacttcgtg tccggcagga gaagctccat gagcagcctg  4080
tccgtggccg cttccaccgc cacagccatg ttcgccagct tcctcaccct gagctttgat  4140
ggcctgggcc tgctgctgtt tggcaccgcc ctggtgatcc agacaattta cgtgctgtat  4200
ctggtggtca tggagatcac cgtgtggatc atgatgttta ggtatctcca cttttggatc  4260
accctgctgt tcctgctgag ccccattatt ctctccgtcg cctgtctcat catccaatcc  4320
tccgccctgc tgatcgaggc tgtggtcgtc accaccatca cagtcctggc cattttttctg  4380
tggctcccctc ctcaaggcgc tgaggccgat ctcggcaccg ccctgctgat tctgaatacc  4440
gccctgtgcc tggtcgtgct gatcctgacc gctatcccta catgatgatg agcggccgcg  4500
atctgctgtg cctctagtt gccagccatc tgttgtttgc ccctccccg tgccttcctt  4560
gaccctggaa ggtgccactc ccactgtcct ttcctaataa aatgaggaaa ttgcatcgca  4620
ttgtctgagt aggtgtcatt ctattctggg gggtggggtg gggcaggaca gcaagggga  4680
ggattgggaa gacaatagca ggcatgctgg ggatgcggtg ggctctatgg ccgatcagg  4740
atcgctgagg tgggtgagtg ggcgtggcct ggggtggtca tgaaaatata aagttggg  4800
gtcttagggt ctctttattt gtgttgcaga gaccgccgga gccatgagcg ggagcagcag  4860
cagcagcagt agcagcagcg ccttggatgg cagcatcgtg agcccttat tgacgacgcg  4920
gatgccccac tgggcggg tgcgtcagaa tgtgatgggc ggctcatcg acggccgacc  4980
cgtcctgccc gcaaattccg ccacgctgac ctatgcgacc gtcgcgggga cgccgttgga  5040
cgccaccgcc gccgccgccg ccaccgcagc cgcctcggcc gtgcgcagcc tggccacgga  5100
ctttgcattc ctgggaccac tggcgacagg ggctacttct cgggccgctg ctgccgccgt  5160
tcgcgatgac aagctgaccg ccctgctggc gcagttgcat ggcgcttactc gggaactggg  5220
tgacctttct cagcaggtca tggccctgcg ccagcaggtc tcctccctgc aagctggcgg  5280
gaatgcttct cccacaaatg ccgtttaaga taaataaaac cagactctgt ttggattaaa  5340
gaaaagtagc aagtgcattg ctctctttat ttcataattt tccgcgcgcg ataggccta  5400
gaccagcgtt ctcggtcgtt gagggtgcgg tgtatcttct ccaggacgtg gtagaggtgg  5460
ctctggacgt tgagatacat gggcatgagc ccgtccgggg ggtggaggta gcaccactgc  5520
agagcttcat gctccggggt ggtgttgtag atgatccagt cgtagcagga gcgctgggca  5580
tggtgcctaa aaatgtcctt cagcagcagg ccgatggcca gggggaggcc cttggtgtaa  5640
gtgtttacaa aacggttaag ttgggaaggg tgcattcggg gagagatgat gtgcatcttg  5700
gactgtatt ttagattggc gatgtttccg cccagatccc ttctgggatt catgttgtgc  5760
aggaccacca gtacagtgta tccggtgcac ttggggaatt tgtcatgcag cttagaggga  5820
aaaagcgtgga agaacttgga gacgcctttg tggcctccca gattttccat gcattcgtcc  5880
atgatgatgg caatgggccc gcgggaggca gcttgggcaa agatatttct ggggtcgctg  5940
acgtcgtagt tgtgttccag ggtgaggtcg tcataggcca ttttttacaaa gcgcgggcgg  6000
agggtgcccg actgggggat gatggtcccc tctggccctg gggcgtagtt gccctcgcag  6060
atctgcattt cccaggcctt aatctcggag ggggaatca tatccacctg cggggcgatg  6120
aagaaaacg tttccggagc cggggagatt aactgggatg agagcaggtt tctaagcagc  6180
tgtgattttc cacaaccggt gggccataaa ataacaccta taaccggttg cagctggtag  6240
tttagagagc tgcagctgcc gtcgtcccgg aggaggggg ccacctcgtt gagcatgtcc  6300
ctgacgcgca tgttctcccc gaccagatcc gccagaaggc gctcgccgcc cagggacagc  6360
agctcttgca aggaagcaaa gtttttcagc ggcttgaggc cgtccgccgt gggcatgttt  6420
ttcaggtct ggctcagcag ctccagggcgg tcccagagct cggtgacgtg ctctacggca  6480
tctctatcca gcatatctcc tcgtttcgcg ggttgggcg actttcgctg tagggcacca  6540
agcggtggtc gtccagcggg gccagagtca tgtccttcca tgggcgcagg gtcctcgtca  6600
gggtggtctg ggtcacggtg aagggtgcg ctccgggctg agcgcttgcc aaggtgcgct  6660
tgaggctggt tctgctggtg ctgaagcgct gccggtcttc gccctgccg tcggccaggt  6720
agcatttgac catggtgtca tagtccagcc cctccgcggc gtgtcccttg gcgcgcagct  6780
tgcccttgga ggtggcgccg cacgaggggc agagcaggct cttgagcgcg tagagcttgg  6840
gggcgaggaa gaccgattcg ggggagtagg cgtccgcgcc gcagaccccg cacacggtct  6900
cgcactccac cagccaggtg agctcgggc gcgccggtcc aaaaaccagg tttccccccat  6960
gcttttttgat gcgtttctta cctcgggtct ccatgaggtg gtgtcccgc tcggtgacga  7020
agaggctgtc cgtgtctccg tagaccgact tgaggggtct ttctccagg ggggtccctc  7080
ggtcttcctc gtagaggaac tcggaccact ctgagacgaa ggcccgcgtc caggccagga  7140
cgaaggagc tatgtgggag gggtagcggt cgttgtccac tagggggtcc accttctcca  7200
aggtgtgaag acacatgtcg ccttcctcgg cgtccaggaa ggtgattggc ttgtaggtgg  7260
aggccacgtg accgggggtt cctgacgggg gggtataaaa ggggggtggg gcgcgctcgt  7320
cgtcactctc ttccgcatcg ctgtctgcga gggccagctg ctggggtgag tattccctct  7380
cgaaggcggg catgacctcc gcgctgaggt tgtcagtttc caaaaacgag gaggatttga  7440
tgttcacctg tcccgaggtg ataccctttga gggtacccgg cccatctgg tcagaaaaca  7500
cgatctttt attgtccagc ttggtggcga acgacccgta gagggcgttg gagagcagct  7560
tggcgatgga gcgcagggtc tggttcttgt ccctgtcggc gcgctccttg gccgcgatgt  7620
tgagctgcac gtactcgcgc gcgacgcagc gccactcggg gaagacgtg gtgcgctcgt  7680
cgggcaccag gcgcacgcgc cagccgcggt tgtgcagggt gaccaggtcc acgctggtgg  7740
cgacctcgcc ggcggtcgcc tcgttggtcc agcagagacg gccgcccttg ccgcgagcga  7800
agggggggcag gggtcgagc tgggtctcgt ccggggggtc cgcgtccacg gtgaaaaccc  7860
cggggcgcag gcgcgcgtcg aagtagtcta tcttgcaacc ttgcatgtcc agcgcctgct  7920
gccagtcgcg ggcggcgagc gcgcgctcgt aggggttgag cggcggggccc cagggcatgg  7980
ggtgggtgag tgcggaggcg tacatgccgc agatgtcata gacgtagagg ggctcccgca  8040
ggaccccgat gtaggtgggg tagcacggc cgcgcggat gctggcgtgc acgtagtcat  8100
acagctcgtg cgagggggcg aggaggtcgg ggcccaggtt ggtgcgggcg ggcgctccg  8160
cgcggaaagac gatctgcctg aagatggcat gcgagttgga agagatgtg gggcgctgga  8220
agacgttgaa gctggcgtcc tgcaggccga cggcgtcgcg cacgaaggag gcgtaggagt  8280
cgcgcagctt gtgtaccagc tcggcggtga cctgacgtc gagcgcgcag tagtcgaggg  8340
tctcgcggat gatgtcatat ttagcctgcc ccttcttttt ccacagctcg cggttgagga  8400
```

```
caaactcttc gcggtctttc cagtactctt ggatcgggaa accgtccggt tccgaacggt    8460
aagagcctag catgtagaac tggttgacgg cctggtaggc gcagcagccc ttctccacgg    8520
ggagggcgta ggcctgcgcg gccttgcgga gcgaggtgtg ggtcaggncg aaggtgtccc    8580
tgaccatgac tttgaggtac tggtgcttga agtcggagtc gtcgcagccg ccccgctccc    8640
agagcgagaa gtcggtgcgc ttcttggagc gggggttcga cagagcgaag gtgacatcgt    8700
tgaagaggat tttgcccgcg cggggcatga agttgcgggt gatgcggaag ggccccggca    8760
cttcagagcg gttgttgatg acctgggcgg cgagcacgat ctcgtcgaag ccgttgatgt    8820
tgtgcccac gatgtagagt tccaggaagc ggggccggcc ctttacggtg gcagcttct    8880
ttagctcttc gtaggtgagc tcctcgggcg aggcgaggcc gtgctcggcc agggcccagt    8940
ccgcgaggtg cgggttgtct ctgaggaagg acttccagag gtcgcgggcc aggagggtct    9000
gcaggcggtc tctgaaggtc ctgaactggc ggcccacggc catttttcg ggggtgatgc    9060
agtagaaggt gaggggtct tgctgccagc ggtcccagtc gagctgcagg gcgaggtcgc    9120
gcgcggcggt gaccaggcgc tcgtcgcccc cgaatttcat gaccagcatg aagggcacga    9180
gctgctttcc gaaggccccc atccaagtgt aggtctctac atcgtaggtg acaaagaggc    9240
gctccgtgcg aggatgcgag ccgatcggga agaactggat ctccgccac cagttggagg    9300
agtggctgtt gatgtggtgg aagtagaagt cccgtcgccg ggcgaacac tcgtgctggc    9360
ttttgtaaaa gcgagcgcag tactggcagc gctgcacggg ctgtacctca tgcacgagat    9420
gcacctttcg cccgcgcacg aggaagccga ggggaaatct gagccccccg cctggctcgc    9480
ggcatggctg gttctcttct actttggatg cgtgtccgtc tccgtctggc tcctcgaggg    9540
gtgttacggt ggagcggacc accaccgcg gcgagccgca ggtccagata tcggcgcgcg    9600
gcggtcgag tttgatgacg acatcgcgca gctgggagct gtccatggtc tggagctccc    9660
ggggcggcgg caggtcagcc gggagttctt gcaggttcac ctcgcagagt cggccaggg    9720
cgcggggcag gtctaggtgg tacctgatct ctagggggcgt gttggtgcg gcgtcgatgc    9780
cttgcaggag cccgcagccc cggggggcga cgacggtgcc ccgcggggtg gtggtggtgg    9840
tggcggtgca gctcagaagc ggtgccgcgg gcgggccccc ggaggtaggg ggggctccgg    9900
tcccgcgggc aggggcggca gcgcacgtc ggcgtgagc gcggcagga gttggtgctg    9960
tgcccggagg ttgctggcga aggcgacgac gcggcggttg atctcctgga tctggccgct   10020
ctgcgtgaag acgacgggcc cggtgagctt gaacctgaaa gagagttcga cagaatcaat   10080
ctcggtgtca ttgaccgcgg cctggcgcag gatctcctgc acgtctcccg agttgtcttg   10140
gtaggcgatc tcggccatga actgctcgat ctcttcctcc tggaggtctc cgcgtccggc   10200
gcgttccacg gtggccgcca ggtcgttgga gatgcgcccc atgagctgcg agaaggcgtt   10260
gagtccgccc tcgttccaga ctcggctgta gaccacgccc cctggtcat cgcgggcgcg   10320
catgaccacc tgcgcgaggt tgagctccac gtgccgcgcg aagacggcgt agttgcgcag   10380
acgctggaag aggtagttga gggtggtggc ggtgtgctcg gccacgaaga agttcatgac   10440
ccagcggcgc aacgtggatt cgttgatgtc ccccaaggcc tccagccgtt ccatggcctc   10500
gtagaagtcc acggcgaagt tgaaaaactg ggagttgcgc gccgacacgg tcaactcctc   10560
ctccagaaga cggatgagct cggcgacggt gtcgcgcacc tcgcgctcga aggctatggg   10620
gatctcttcc tccgctagca tcaccacctc ctcctcttcc tcctcttctg gcacttccat   10680
gatggcttcc tcctcttcgg ggggtggcgg cggcggcggt gggggagggg gcgctctgcg   10740
ccggcggcgg cgcaccggga ggcggtccac gaagcgcgcg atcatctccc cggcggcgg   10800
gcgcatggtc tcggtgacgg cgcggccgtt ctccgggggg gcagttgga agacgccgcc   10860
ggacatctgt gctggggcg ggtggccgtg aggcagcgag acgcgctga cgatgcatct   10920
caacaattgc tgcgtaggta cgccgccgag ggacctgagg agtccatat ccaccggatc   10980
cgaaaacctt tcgaggaagg cgtctaacca gtcgcagtcg caaggtaggc tgagcaccgt   11040
ggcggggcggc ggggggtggg gggagtgtct ggcggaggtg ctgctgatga tgtaattgaa   11100
gtaggcggac ttgacacggc ggatggtcga caggagcacc atgtccttgg gtccggcctg   11160
ctggatgcga aggcggttcgg ctatgcccca ggcttcgttc tggcatcggc gcaggtcctt   11220
gtagtagtct tgcatgagcc tttccaccgg cacctcttct ccttcctctt ctgcttcttc   11280
catgtctgct tcggccctgg ggcggcgccg cgcccccctg cccccatgc gcgtgacccc   11340
gaaccccctg agcggttgga gcagggccag gtcgcgacg acgcgctcgg ccaggatggc   11400
ctgctgcacc tgcgtgaggg tggtttggaa gtcatccaag tccacgaagc ggtaggtaggc   11460
gcccgtgttg atggtgtagg tgcagttggc catgacggac cagttgacgg tctggtggcc   11520
cggttgcgac atctcggtgt acctgagtcg cgagtaggcg cgggagtcga agacgtagtc   11580
gttcaagtc cgcaccaggt actggtagcc caccaggaag tgcggcggcg gctggcggta   11640
gaggggcgag cgcagggtgg cgggggctcc ggggggccagg tcttccagca tgaggcgggg   11700
gtaggcgtag atgtacctgg acatccaggt gataccgcg gcggtggtgg aggcgccgcgg   11760
gaagtcgcgc acccggttcc agatgttgcg caggggcaga aagtgctcca tggtaggcgt   11820
gctctgtcca gtcagacgcg cgcagtcgtt gatactctag accagggaaa acgaaagccg   11880
gtcagcgggc actcttccgt ggtctggtga atagatcgca agggtatcat ggcggagggc   11940
ctcggttcga gccccgggtc cgggccggac ggtccgccat gatccacgcg gttaccgccg   12000
gcgtgtcgaa cccaggtgtg cgacgtcaga caacggtgga gtgttccttt tggcgttttt   12060
ctggccgggc gccggcgccg cgtaagagac taagccgcga aagcgaaagc agtaagtggc   12120
tcgctccccg tagccggagg gatccttgct aagggttgcg ttgcggcgaa ccccggttcg   12180
aatcccgtac tcggggcggc cggacccgcg gctaaggtgt tggattggcc tcccccctcg   12240
ataaagaccc cgcttgcgga ttgactccgg acacgggac gagccccttt tattttttgct   12300
ttccccagat gcatccggtg ctgcggcaga tgcgcccccc gcccagcag cagcaacaac   12360
accagcaaga gcggcagcaa cagcagcggg agtcatgcag ggccccctca cccacccctg   12420
gcgggccggc cacctcggcg tccgcggccg tgtctgcgc ctgcggcggc ggcggggggc   12480
cggctgacga ccccgaggag ccccccgggc gcagggcgac acactacctg gacctggagg   12540
agggcgaggg cctggcgcgg ctgggggcgc cgtctcccga gcgccacccg cgggtgcagc   12600
tgaagcgcga ctcgcgcgag gcgtacgtgc ctcggcagaa cctgttcagg gaccgcgcgg   12660
gcgaggagcc cgaggagatg cgggacagga ggttcagcgc agggcgggag ctgcggcagg   12720
ggctgaaccg cgagcggctg ctgcgcgagg aggactttga gcccgacgcg cggacgggga   12780
tcagcgccgc cgtgcgcgcc gtgggccgg ccgacctggc gacggcgtac gacgagcaga   12840
tgaaccagga gatcaacttc caaaagagtt tcaacaacca cgtgcgcacg ctggtggcgc   12900
gcgaggaggt gaccatcggg ctgatgcacc tgtgggactt tgtaagcgcg ctggtgcaga   12960
ccccaacag caagcctctg acggcgcagc tgttcctgat agtgcagcac agcagggaca   13020
acgaggcgtt tagggacgcg ctgctgaaca tcaccgagcc cgagggtcgg tggctgctgg   13080
acctgattaa catcctgcag agcatagtgg tgcaggagcc cagcctgagc ctggccgaca   13140
```

```
aggtggcggc catcaactac tcgatgctga gcctgggcaa gttttacgcg cgcaagatct   13200
accagacgcc gtacgtgccc atagacaagg aggtgaagat cgacggtttt tacatgcgca   13260
tggcgctgaa ggtgctcacc ctgagcgacg acctgggcgt gtaccgcaac gagcgcatcc   13320
acaaggccgt gagcgtgagc cggcggcgcg agctgagcga ccgcgagctg atgcacagcc   13380
tgcagcgggc gctggcgggc gccggcagcg gcgacaggga ggcggagtcc tacttcgatg   13440
cggggcggga cctgcgctgg gcgcccagcc ggcgggccct ggaggccgcg ggggtccggc   13500
aggactatga cgaggacggc gaggaggatg aggagtacga gctagaggag ggcgagtacc   13560
tggactaaac cgcgggtggt gtttccggta gatgcaagac ccgaacgtgg tggacccggc   13620
gctgcgggcg gctctgcaga gccagccgtc cggccttaac tcctcagacg actggcgaca   13680
ggtcatggac cgcatcatgt cgctgacggc gcgtaaccgg gacgcgttcc ggcagcagc   13740
gcaggccaac aggctctccg ccatcctgga ggcggtggtg cctgcgcgct cgaaccccac   13800
gcacgagaag gtgctggcca tagtgaacgc gctggccgag aacagggcca tccgcccgga   13860
cgaggccggg ctggtgtacg acgcgctgct gcagcgcgtg gcccgctaca acagcggcaa   13920
cgtgcagacc aacctggacc ggctggtggg ggacgtgcga gaggcggtgg cgcagcgcga   13980
gcgcgcggat cggcagggca acctgggctc catggtggcg ctgaatgcct tcctgagcac   14040
gcagccggcc aacgtgccgc gggggcagga agactacacc aactttgtga gcgcgctgcg   14100
gctgatggtg accgagaccc cccagagcga ggtgtaccag tcgggcccgg actacttctt   14160
ccagaccagc agacagggcc tgcagacggt gaacctggac caggctttca ggaacctgcg   14220
ggggctgtgg ggcgtgaagg cgcccaccgg cgaccgggcg acggtgtcca gcctgctgac   14280
gcccaactcg cgcctgctgc tgctgctgat cgcgccgttc acggacagcg gcagcgtgtc   14340
ccgggacacc tacctgggc acctgctgac cctgtaccgc gaggccatcg ggcaggcgca   14400
ggtggacgag cacaccttcc aggagatcag cagcgtgagc cgcgccgctgg ggcaggagga   14460
cacgagcagc ctggaggcga ctctgaacta cctgctgacc aaccggcggc agaagattcc   14520
ctcgctgcac agcctgacct ccgaggagga gcgcatcttg cgctacgtgc agcagagcgt   14580
gagcctgaac ctgatgcgcg acggggtgac gcccagcgtg gcgctggaca tgaccgcgcg   14640
caacatggaa ccgggcatgt acgccgccgc ccggccttac atcaaccgtc tgatggacta   14700
cctgcatcgc gcggcggccg tgaaccccga gtactttacc aacgccatcc tgaacccgca   14760
ctggctcccg ccgcccgggt tctacagcgg gggcttcgag gtcccggaga ccaacgatgg   14820
cttcctgtgg gacgacatgg acgacagcgt gttctccccg cggccgcagg cgctggcgga   14880
agcgtccctg ctgcgtccca agaaggagga ggaggaggag gcgagtcgcc gccgcggcag   14940
cagcggcgtg gcttctctgt ccgagctggg ggcggcagcc gccgcgcgcc ccgggtccct   15000
gggcggcagc ccctttccga gcctggtggg gtctctgcac agcgagcgca ccacccgccc   15060
tcggctgctg ggcgaggacg agtacctgaa taactccctg ctgcagccgg tgcgggagaa   15120
aaacctgcct cccgccttcc ccaacaacgg gatagagagc ctggtggaca agatgagcag   15180
atggaagacc tatgcgcagg agcacaggga cgcgcctggc ctccggccgc ccacgcgcg   15240
ccagcgccac gaccgcagc ggggggctggt gtgggatgac gaggactccg cggacgatag   15300
cagcgtgctg gacctgggag ggagcggcaa cccgttcgcg cacctgcgcc cccgcctggg   15360
gaggatgttt taaaaaaaaa aaaaaaangc aagaagcatg atgcaaaaat taaataaaac   15420
tcaccaaggc catggcgacc gagcgttggt ttcttgtgtt cccttcagta tcgggcgcag   15480
ggcgatgtac caggagggac ctcctcccctc ttacgagagc gtggtgggcg cggcggcggc   15540
ggcgccctct tctcccttg cgtcgcagct gctggagccg ccgtacgtgc ctccgcgcta   15600
cctgcggcct acggggggga gaaacagcat ccgttactcg gagctggcgc ccctgttcga   15660
caccacccgg gtgtacctgg tggacaacaa gtccggccgc gtggcctccc tgaactacca   15720
gaacgaccac agcaattttt tgaccacggt catccagaac aatgactaca gcccgagcga   15780
ggccagcacc cagaccatca atctggatga ccggtcgcac tggggcggcg acctgaaaac   15840
catcctgcac accaacatgc ccaacgtgaa cgagttcatg ttcaccaata agttcaaggc   15900
gcgggtgatg gtgtcgcgct cgcacaccaa ggaagacggg gtggagctga agtacgagtg   15960
ggtggagttc gagctgccag agggcaacta ctccgagacc atgaccattg acctgatgaa   16020
caacgcgatc gtggagcact atctgaaagt gggcaggcag aacggggtcc tggagagcga   16080
catcgggtc aagttcgaca ccaggaactt ccgcctgggg ctggaccccg tgaccgggct   16140
ggttatgccc gggtgtaca ccaacgaggc cttccatccc acatcatcct tgtgcccgg   16200
ctgcgggtg gacttcactt acagccgcct gagcaacctc ctgggcatcc gcaagcggca   16260
gcccttccag gagggcttca ggatcaccta cgaggacctg gaggggggca acatcccgc   16320
gctcctcgat gtgaggcct accaggatag cttgaaggaa aatgaggcgg acaggagga   16380
taccgccccc gccgcctccg ccgccgccga gcagggcgag gatgctgctg acaccgccgg   16440
cgcggacggg gcagaggccg accccgctat ggtggtggag gctcccgagc aggaggagga   16500
catgaatgac agtgcggtgc gcggagacac cttcgtcacc cggggggagg aaaagcaagc   16560
ggaggccgag gccgcggccg aggaaaagca actggcggca gcagcggcgg cggcggcgtt   16620
ggccgcgcg gaggctgagt ctgaggggac caagcccgcc aaggagccg tgattaagcc   16680
cctgaccgaa gatagcaaga gcgcagtta caacctgctc aaggacagca ccaacaccgg   16740
gtaccgcagc tggtacctgg cctacaacta cggcgacccg tcgacggggg tgcgctcctg   16800
gaccctgctg tgcacgccgg acgtgacctg cggctcggag caggtgtact ggtcgctgcc   16860
cgacatgatg caagacccg tgaccttccg ctccacgcgg caggtcagca acttcccggt   16920
ggtgggcgag gagctgctgc ccgtgcactc caagagcttc tacaacgacc aggccgtcta   16980
ctcccagctc atccgccagt tcacctctct gacccacgtg ttcaatcgct tcctgagaa   17040
ccagattctg cgcgccccgc cgccccccac catcaccacc gtcagtgaaa acgttcctgc   17100
tctcacagat cacgggacgc taccgctgcg caacagcatc ggaggagtcc agcgagtgac   17160
cgttactgac gccagacgcc gcacctgccc ctacgtttac aaggccttgg gcatagtctc   17220
gccgcgctgc ctttccagcc gcactttttg agcaacacca ccatcatgtc catcctgatc   17280
tcacccagca ataactccgg ctgggactg ctgcgcgcgc ccagcaagat gttcggaggg   17340
gcgaggaagc gttccgagca gcaccccgtg gcgtgcgcg ggcacttccg cgccccctgg   17400
ggagcgcaca aacgcggccg cgcggggcgc accaccgtgg acgacgccat cgactcggtg   17460
gtggagcagg cgcgcaacta caggcccgcg gtctctaccg tggacgcggc catccagacc   17520
gtggtgcgga gcgcgaacaa gtgaagagcc gtgaagaggc cgtggccgc   17580
cgccaccgcc gccgacccgg ggccgccgcc aaacgcgccg ccgcggccct gcttcgccgg   17640
gccaagcgca cggccgccgg ccgccatg agggccgcgc gccgcttggc cgccggcatc   17700
accgccgcca ccatgccccc ccgtacccga agacgcgcgg ccgccgccgc cgccgccgcc   17760
atcagtgaca tggccagcag gcgccggggc aacgtgtact gggtgcgcga ctcggtgacc   17820
ggcacgcgcg tgcccgtgcg cttccgcccc ccgcggactt gagatgatgt gaaaaaacaa   17880
```

```
cactgagtct cctgctgttg tgtgtatccc agcggcggcg gcgcgcgcag cgtcatgtcc  17940
aagcgcaaaa tcaaagaaga gatgctccag gtcgtcgcgc cggagatcta tgggcccccg  18000
aagaaggaag agcaggattc gaagcccgc aagataaagc gggtcaaaaa gaaaagaaa    18060
gatgatgacg atgccgatgg ggaggtggag ttcctgcgcg ccacggcgcc caggcgcccg  18120
gtgcagtgga agggccggcg cgtaaagcgc gtcctgccgc ggtgcaccgc ggtggtcttc  18180
acgcccggcg agcgctccac ccggacttc aagcgcgtct atgacgaggt gtacggcgac   18240
gaagacctgc tggagcaggc caacgagcgc ttcggagagt ttgcttacgg gaagcgtcag  18300
cgggcgctgg ggaaggagga cctgctggcg ctgccgctgg accagggcaa ccccacccc   18360
agtctgaagc ccgtgaccct gcagcaggtg ctgccgagca gcgcaccctc cgaggcgaag  18420
cggggtctga agcgcgaggg cggcgacctg gcgcccaccg tgcagctcat ggtgcccaag  18480
cggcagaggc tggaggatgt gctggagaaa atgaaagtag accccggtct gcagccggac  18540
atcagggtcc gccccatcaa gcaggtggcg ccgggcctcg gcgtgcagac cgtggacgtg  18600
gtcatcccca ccggcaactc ccccgccgcc gccaccacta ccgctgcctc cacggacatg  18660
gagacacaga ccgatcccgc cgcagccgca gccgcagccg gcgcgcgcag ctcctcggcg  18720
gaggtgcaga cggacccctg gctgccgccg gcgatgtcag ctccccgcgc cgtcgcgggg  18780
cgcaggaagt acggcgccgc caacgcgctc ctgcccgagt acgccttgca tccttccatc  18840
gcgcccaccc ccggctaccg aggctatacc taccgcccgc gaagagccaa gggttccacc  18900
cgccgtcccc gccgacgcgc cgccgccacc acccgcgcgc gccgccgcag acgcagccc   18960
gcactggctc cagtctccgt gaggaaagtg gcgcgcgacg gacacaccct ggtgctgccc  19020
agggcgcgct accaccccag catcgtttaa aagcctgttg tggttcttgc agatatggcc  19080
ctcacttgcc gcctccgttt cccggtgccg ggataccgag gaggaagatc gcgccgcagg  19140
aggggtctgg ccggccgcgg cctgagcgga ggcagccgcc ggcgcaccg gcgggcgacgc  19200
gccaccagcc gacgcatgcg cggcggggtg ctgcccctgt taatccccct gatcgccgcg  19260
gcgatcggcg ccgtgcccgg gatcgcctcc gtggccttgc aagcgtccca gaggcattga  19320
cagacttgca aacttgcaaa tatggaaaaa aaaccccaa taaaaagtc tagactctca   19380
cgctcgcttg gtcctgtgac tattttgtag aatggaagac atcaactttg cgtcgctgca  19440
cccgcgtcac ggctcgcgcc cgttcctggg acactggaac gatatcggca ccagcaacat  19500
gagcggtggc gccttcagtt ggggctctct gtggagcggc attaaaagta tcgggtctgc  19560
cgttaaaaat tacggctccc gggcctgaa cagcagcacg ggccagatgt tgagagacaa    19620
gttgaaagag cagaacttcc agcagaaggt ggtggagggc ctggcctccg gcatcaaccg  19680
ggtggtggac ctggccaacc aggccgtgca gaataagatc aacagcagac tggaccccg   19740
gccgccggtg gaggaggtgc cgccggccgct ggagacggtg tccccgatg ggcgtggcga   19800
gaagcgcccg cggcccgata gggaagagac cactctggtc acgcagaccg atgagccgcc  19860
cccgtatgag gaggccctga agcaaggtct gcccaccacg cggcccatcg cgccgccgac  19920
caccggggtg gtgggccgcc acacccccgc cacgctggac ttgcctccgc ccgccgatgt  19980
gccgcagcag cagaaggcgg cacagccggg cccgcccgcg accgcctccc gttcctccgc  20040
cggtcctctg cgccgcgcgg ccagcggccc ccgcggggg gtcgcgaggc acggcaactg    20100
gcagagcacg ctgaacagca tcgtgggtct gggggtgcgg tccgtgaagc gccgccgatg  20160
ctactgaata gcttagctaa cgtgttgtat gtgtgtatgc ccctatgtc gccgccagag   20220
gagctgctga gtcgccgccg ttcgcgcgcc caccaccacc gccactccgc ccctcaagat  20280
ggcgacccca tcgatgatgc cgcagtggtc gtacatgcac atctcgggcc aggacgcctc  20340
ggagtacctg agcccgggc tggtgcagtt cgcccgcgcc accgagagct acttcagcct   20400
gagtaacaag tttaggaacc ccacggtggc gcccacgcac gatgtgacca ccgaccggtc  20460
tcagcgcctg acgctgcggt tcattcccgt ggaccgcgag gacaccgcgt actcgtacaa  20520
ggcgcggttc accctggccg tgggcgacaa ccgcgtgctg gacatggcct ccacctactt  20580
tgacatccgg ggggtgctgg accggggtcc cactttcaag ccctactctg gcaccgccta  20640
caactccctg ccccccaagg gcgctcccaa ctcctgcgag tgggagcaag aggaaactca  20700
ggcagttgaa gaagcagcag aagaggaaga agaagatgct gacggtcaag ctgaggaaga  20760
gcaagcagct accaaaaaga ctcatgtata tgctcaggct ccccttttctg gcgaaaaat   20820
tagtaaagat ggtctgcaaa taggaacgga cgctacagct acagaacaaa aacctattta  20880
tgcagaccct acattccagc ccgaaacccca aatcgggggaa tcccagtgga atgaggcaga  20940
tgctacagtc gccggcggta gagtgctaaa gaaatctact cccatgaaac catgctatgg  21000
ttcctatgca agacccacaa atgctaatgg aggtcagggt gtactaacgg caaatgccca  21060
gggacagcta gaatctcagg ttgaaatgca attcttttca acttctgaaa cgcccgtaa   21120
cgaggctaac aacattcagc ccaaattggt gctgtatagt gaggatgtgc acatggagac  21180
cccggatacg cacctttctt acaagcccgc aaaaagcgat gacaattcaa aaatcatgct  21240
gggtcagcag tccatgccca acagacctaa ttacatcggc ttcagagaca cttctatcgg  21300
cctcatgtat tacaatagca ctggcaacat gggagtgctt gcaggtcagg cctctcagtt  21360
gaatgcagtg gtggacttgc aagacagaaa cacagaactg tcctaccagc tcttgcttga  21420
ttccatgggt gacagaacca gatacttttc catgtggaat caggcagtgg acagttatga  21480
cccagatgtt agaattattg aaaatcatgg aactgaagac gagctcccca ctattgttt   21540
ccctctgggg ggcataggggg taactgacac ttaccaggct gttaaaacca acaatggcaa  21600
taacgggggc caggtgactt ggacaaaaga tgaaactttt gcagatcgca atgaaatagg   21660
ggtggggaaac aatttcgcta tggagatcaa cctcagtgcc aactgtgga gaaactttcct  21720
gtactccaac gtgcgcgtgt acctaccaga caagcttaag tacaaccct ccaatgtgga    21780
catctctgac aaccccaaca cctacgatta catgaacaag cgagtggtgg ccccggggct  21840
ggtggactgc tacatcaacc tgggcgcgcg ctggtcgctg gactacatgg acaacgtcaa  21900
cccctttcaac caccaccgca atgcgggcct gcgctaccgc tccatgctcc tgggcaacgg  21960
gcgctacgtg cccttccaca tccaggtgcc ccagaagttc tttgccatca agaaccttcct  22020
cctcctgccg ggctcctaca cctacgagtg gaacttcagg aaggatgtca acatggtcct  22080
ccagagctct ctgggtaacg atctcaggg ggacggggcc agcatcaagt tcgagagcat   22140
ctgcctctac gccaccttct tcccccatggc ccacaacacg gcctcacgc tcgaggccat   22200
gctcaggaac gacaccaacg accagtcctt caatgactac ctctccgccg ccaacatgct  22260
ctacccccata ccgcccaacg ccaccaacgt cctcaacctcc atccctctgc gcaactggga  22320
ggccttccgc ggctgggcct tcacccgcct caagaccaag agacccccct cctgggctc    22380
gggattcgac ccctactaca cctactcggg ctccattccc tacctggacg gcaccttcta  22440
cctcaaccac actttcaaga aggtctcggt caccttcgac tcctcgggtca gctgccggg   22500
caacgaccgt ctgctcaccc caacgagtt cgagatcaag cgctcggtcg acggggaggg  22560
ctacaacgtg gcccagtgca acatgaccaa ggactggttc ctggtccaga tgctggccaa  22620
```

```
ctacaacatc ggctaccagg gcttctacat cccagagagc tacaaggaca ggatgtactc 22680
cttcttcagg aacttccagc ccatgagccg gcaggtggtg gaccagacca agtacaagga 22740
ctaccaggag gtgggcatca tccaccagca caacaactcg ggcttcgtgg gctacctcgc 22800
ccccaccatg cgcgagggac aggcctaccc cgccaacttc ccctatccgc tcataggcaa 22860
gaccgcggtc gacagcatca cccagaaaaa gttcctctgc gaccgcaccc tctggcgcat 22920
cccctctcc agcaacttca tgtccatggg tgcgctctcg gacctgggcc agaacttgct 22980
ctacgccaac tccgcccacg ccctcgacat gaccttcgag gtcgacccca tggacgagcc 23040
caccctctc tatgttctgt tcgaagtctt tgacgtggtc cgggtccacc agccgcaccg 23100
cggcgtcatc gagaccgtgt acctgcgtac gcccttctcg gccggcaacg ccaccaccta 23160
aagaagcaag ccgcagtcat cgccgcctgc atgccgtcgg gttccaccga gcaagagctc 23220
agggccatcg tcagagacct gggatgcggg ccctattttt tgggcacctt cgacaagcgc 23280
ttccctggct ttgtctcccc acacaagctg gcctgcgcca tcgtcaacac ggccggccgc 23340
gagaccgggg gcgtgcactg gctggccttc gcctggaacc cgcgctccaa aacatgcttc 23400
ctctttgacc ccttcggctt ttcggaccag cggctcaagc aaatctacga gttcgagtac 23460
gagggcttgc tgcgtcgcag cgccatcgcc tcctcgcccg accgctgcgt cacccctcgaa 23520
aagtccaccc agaccgtgca ggggcccgac tcggccgcct gcggtctctt ctgctgcatg 23580
tttctgcacg cctttgtgca ctggcctcag agtcccatgg accgcaaccc caccatgaac 23640
ttgctgacgg gggtgcccaa ctccatgctc cagagccccc aggtcgagcc caccctgcgc 23700
cgcaaccagg agcagctcta cagcttcctg gagcgccact cgccttactt ccgccgccac 23760
agcgcacaga tcaggagggc cacctccttg tgccacttgc aagagatgca agaagggtaa 23820
taacgatgta cacactttt ttctcaataa atggcatctt tttatttata caagctctct 23880
ggggtattca tttcccacca ccacccgccg ttgtcgcgac ctggcctcat ttagaaatcg 23940
aaagggttct gccgggagtc gccgtgcgcc acgggcaggg acacgttgcg atactggtag 24000
cgggtgcccc acttgaactc gggcaccacc aggcgaggca gctcggggaa gttttcgctc 24060
cacaggctgc gggtcagcac cagcgcgttc atcaggtcgg gcgccgagat cttgaagtcg 24120
cagttggggc cgccgccctg cgccgcccgag ttgcggtaca ccgggtttga gcactggaac 24180
accaacagcg ccgggtgctt cacgctggcc agcacgctgc ggtcggagat cagctcggcg 24240
tccaggtcct ccgcgttgct cagcgcgaac gggtcatct tgggcacttg ccgccccagg 24300
aagggcgcgt gccccggttt cgagttgcag tcgcagcgca gcgggatcag caggtgcccg 24360
tgcccgact ggcgcgttggg gtacagcgcg cgcatgaagg cctgcatctg gcggaaggcc 24420
atctgggcct tggcgccctc cgagaagaac atgccgcagg acttgcccga gaactggttt 24480
gcgggggcagc tggcgtcgtg caggcagcag cgcgcgtcgg tgttggcgat ctgcaccacg 24540
ttgcgccccc accggttctt cacgatcttg gccttggacg attgctcctt cagcgcgcgc 24600
tgcccgttct cgctggtcac atccatctcg atcacatgtt ccttgttcac catgctgctg 24660
ccgtgcagac acttcagctc gccctccgtc tcggtgcagc ggtgctgcca cagcgcgcag 24720
cccgtgggct cgaaagactt gtaggtcacc tccgcgaagg actgcaggta ccctgcaaa 24780
aagcggccca tcatggtcac gaaggtcttg ttgctgctga aggtcagctg cagcccgcgg 24840
tgctcctcgt tcagccaggt cttgcacacg gccgccagcg cctccacctg gtcgggcagc 24900
atcttgaagt tcaccttcag ctcattctcc acgtggtact tgtccatcag cgtgcgcgcc 24960
gcctccatgc ccttctccca ggccgacacc agcggcaggc tcacggggtt cttcaccatc 25020
accgtggccg ccgcctccgc cgcgcttctcg ctttccgccc cgctgttctc ttcctcttcc 25080
tcctcttcct cgccgccgcc cactcgcagc ccccgcacca cggggtcgtc ttcctgcagg 25140
cgctgcacct tcgcgcttgcc gttgcgcccc tgcttgatgc gcacgggcgg gttgctgaag 25200
cccaccatca ccagcgcggc ctcttcttgc tcgtcctcgc tgtccagaat gacctccggg 25260
gagggggggt tggtcatcct cagtaccgag gcacgcttct ttttcttcct ggggggcgttc 25320
gccagctccg cggctgcggc cgctgccgag gtcgaaggcc gagggctggg cgtgcgcggc 25380
accagcgcgt cctgcgagcc gtcctcgtcc tcctcggact cgagacggag gcgggcccgc 25440
ttcttcgggg gcgcgcgggg cggcggaggc ggcggcggcg acggagacgg ggacgagaca 25500
tcgtccaggg tgggtggacg gcgggccgcg ccgcgtccgc gctcggggggt ggtctcgcgc 25560
tggtcctctt cccgactggc catctcccac tgctccttct cctataggca gaaagagatc 25620
atggagtctc tcatgcgagt cgagaaggag gaggacagcc taaccgcccc ctctgagccc 25680
tccaccaccg ccgccaccac cgccaatgcc gccgcggacg acgcgcccac cgagaccacc 25740
gccagtacca ccctcccag cgacgcaccc ccgtcgaga atgaagtgct gatcgagcag 25800
gacccggggtt ttgtgagcgg agaggaggat gaggtggatg agaaggagaa ggaggaggtc 25860
gccgcctcag tgcaaaaga ggataaaaag caagaccagg acgacgcaga taaggatgag 25920
acagcagtcg ggcgggggaa cggaagccat gatgctgatg acgctacct agacgtggga 25980
gacgacgtgc tgcttaagca cctgcaccgc cagtgcgtca tcgtctgcga cgcgctgcag 26040
gagcgctgcg aagtgcccct ggacgtgcgg gaggtcagcc gcgcctacga gcggcacctc 26100
ttcgcgccgc acgtgccccc caagcgccgg gagaacgcca cctgcgagcc caacccgcgt 26160
ctcaacttct acccggtctt cgcggtaccc gaggtgctgg ccacctacca catctttttc 26220
caaaactgca agatcccccct ctcctgccgc gccaaccgca cccgcgccga caaaccctg 26280
accctgcggc agggcgccca catacctgat atcgcctctc tggaggaagt gcccaagatc 26340
ttcgagggtc tcggtcgcga cgagaaacgg gcggcgaacg ctctgcacgg agacagcgaa 26400
aacgagagtc actcgggggt gctggtggag ctcgagggcg acaacgcgcg cctggccgta 26460
ctcaagcgca gcatagaggt cacccacttt gcctacccgg cgctcaacct gcccccaag 26520
gtcatgagtg tggtcatggg cgagctcatc atgcgccgcg cccagcccct ggccgcggat 26580
gcaaacttgc aagagtcctc cgaggaaggc ctgcccgcgg tcagcgacga gcagctggcg 26640
cgctggctgg agacccgcga ccccgcgcag ctggaggagc ggcgcaagct catgatggcc 26700
gcggtgctgg tcaccgtgga gctcgagtgt ctgcagcgct tcttcgcgga cccagagatg 26760
cagcgcaagc tcgaggagac cctgcactac accttccgcc agggctacgt gcgccaggcc 26820
tgcaagatct ccaacgtgga gctctgcaac ctggtctcct acctgggcat cctgcacgag 26880
aaccgcctcg gcagaacgt cctgcactcc accctcaaag gggaggcgcg ccgcgactac 26940
atccgcgact gcgcctacct cttcctctgc tacacctggg acaggccat gggggtctgg 27000
cagcagtgcc tggaggaacg caacctcaag gagctggaaa agctcctcga gcgcaccctc 27060
agggacctct ggacgggctt caacgagcgc tcggtggccg ccgcgctggc ggacatcatc 27120
tttcccgagc gcctgctcaa gaccctgcag cagggcctgc ccgacttcac cagccagagc 27180
atgctgcaga acttcaggac tttcatcctg gagcgctcgg gcatcctgcc ggccacttgc 27240
tgcgcgctgc ccagcgactt cgtgcccatc aagtacaggg agtgcccgcc gccgctctgg 27300
ggccactgct acctcttcca gctggccaac tacctcgcct accactcgga cctcatggaa 27360
```

```
gacgtgagcg gcgagggcct gctcgagtgc cactgccgct gcaacctctg cacgccccac  27420
cgctctctag tctgcaaccc gcagctgctc agcgagagtc agattatcgg taccttcgag  27480
ctgcagggtc cctcgcctga cgagaagtcc gcggctccag ggctgaaact cactccgggg  27540
ctgtggactt ccgcctacct acgcaaattt gtacctgagg actaccacgc ccacgagatc  27600
aggttctacg aagaccaatc ccgcccgccc aaggcggagc tcaccgcctg cgtcatcacc  27660
caggggcaca tcctgggcca attgcaagcc atcaacaaag cccgccgaga gttcttgctc  27720
aaaaagggtc gggggtgta cctgaccccc cagtccggcg aggagctaaa cccgctaccc  27780
ccgccgccgc cccagcagcg ggaccttgct tcccaggatg gcacccagaa agaagcagca  27840
gccgccgccg ccgccgcagc catacatgct tctggaggaa gaggaggagg actgggacag  27900
tcaggcagag gaggtttcgg acgaggagca ggaggagatg atggaagact gggaggagga  27960
cagcagccta gacgaggaag cttcagaggc cgaagaggtg gcagacgcaa caccatcgcc  28020
ctcggtcgca gccccctcgc cggggcccct gaaatcctcc gaacccagca ccagcgctat  28080
aacctccgct cctccggcgc cggcgccacc cgcccgcaga cccaaccgta gatgggacac  28140
cacaggaacc ggggtcggta agtccaagtg cccgccgccg ccccgccagc agcagcagca  28200
gcagcgccag ggctaccgct cgtggcgcgg gcacaagaac gccatagtcg cctgcttgca  28260
agactgcggg ggcaacatct cttcgcccg ccgcttcctg ctattccacc acggggtcgc  28320
cttcccccgc aatgtcctgc attactaccg tcatctctac agccctact gcagcggcga  28380
cccagaggcg gcagcggcag ccacagggc gaccaccacc taggaagata tcctccgcga  28440
gcaagacagc ggcagcagcg gccaggagac ccgcggcagc agcggcggga gcggtgggcg  28500
cactgcgcct ctcgcccaac gaaccctct cgacccggga gctcagacac aggatcttcc  28560
ccactttgta tgccatcttc caacagagca gaggccagga gcaggagctg aaaataaaaa  28620
acagatctct gcgctccctc caaccgcagct tctgtatca caaaagcgaa gatcagcttc  28680
ggcgcacgct ggaggacgcg gaggcactct tcagcaaata ctgcgcgctc actcttaaag  28740
actagctccg cgcccttctc gaatttaggc gggagaaaac tacgtcatcg ccggcgccg  28800
cccagcccgc ccagccgaga tgagcaaaga gattcccacg ccatacatgt ggagctacca  28860
gccgcagatg ggactcgcgg cgggagcggc ccaggactac tccaccccga tgaactacat  28920
gagcgcggga ccccacatga tctcacaggt caacggatc cgcgcccagc gaaaccaaat  28980
actgctggaa caggcggcca tcaccgccac gccccgccat aatctcaacc cccgaaattg  29040
gcccgccgcc ctcgtgtacc aggaaacccc ctccgccacc accgtactac ttccgcgtga  29100
cgcccagccg gaagtccaga tgactaactc aggggcgaag ctcgcgggcg gctttcgtca  29160
cggggcgcgg ccgctccgac caggtataag acacctgatg atcagaggcc gaggtatcca  29220
gctcaacgac gagtcggtga gctcttcgct cggtctccgt ccggacggaa ctttccagct  29280
cgccggatcc ggccgctctt cgttcacgcc ccgccaggcg tacctgactc tgcagacctc  29340
gtcctcggag ccccgctccg gcggcatcgg aaccctccag ttcgtggagg agttcgtgcc  29400
ctcggtctac ttcaacccct tctcgggacc tacccgacc agttcattcc  29460
gaactttgac gcggtgaagg actcggcgga cggctacgac tgaatgtcag gtgtcgaggc  29520
agagcagctt cgcctgagac acctcgagca ctgccgccgc cacaagtgct cgcccgcgg  29580
ttctggtgag ttctgctact ttcagctacc cgaggagcat accgagggc cggcgcacgg  29640
cgtccgcctg accacccagg gcgaggttac ctgttccctc atccgggagt ttaccctccg  29700
tccccctgcta gtggagcggg agcgggggtcc ctgtgtccta actatcgcct gcaactgccc  29760
taaccctgga ttacatcaag atctttgctg tcatctctgt gctgagttta ataaacgctg  29820
agatcagaat ctactgggc tcctgtcgcc atcctgaa cgccaccgtc ttcacccacc  29880
ccgaccagga ccaggcgaac ctcacctgcg gtctgcatcg gagggccaag aagtacctca  29940
cctggtactt caacggcacc cccttgtgg tttacaacag cttcgacggg gacggagtct  30000
ccctgaaaga ccagctctcc ggtctcagct actccatcca caagaacacc ccctccaac  30060
tcttccctcc ctacctgccg ggaacctacg agtgcgtcac cggccgctgc acccacctca  30120
cccgcctgat cgtaaaccag agctttccgg gaacagataa ctccctcttc cccagaaacag  30180
gaggtgagct caggaaactc cccgggacc agggcggaga cgtaccttcg acccttgtgg  30240
ggttaggatt ttttattacc gggttgctgg ctctttttaat caaagttttcc ttgagattg  30300
ttctttcctt ctacgtgtat gaacacctca acctccaata actctaccct ttcttcggaa  30360
tcaggtgact tctctgaaat cgggcttggt gtgctgctta ctctgttgat ttttttcctt  30420
atcatactca gccttctgtg cctcaggctc gccgctgct gcgcacacat ctatatctac  30480
tgctggttgc tcaagtgcag gggtcgccac ccaagatgaa caggtacatg gtcctatcga  30540
tcctaggcct gctggccctg gcggcctgca gcgccgccaa aaaagagatt acctttgagg  30600
agcccgcttg caatgtaact ttcaagcccg agggtgacca atgcaccacc ctcgtcaaat  30660
gcgttaccaa tcatgagagg ctgcgcatcg actacaaaaa caaaactggc cagtttgcgg  30720
tctatagtgt gtttacgccc ggagaccct ctaactactc tgtcaccgtc ttccagggcg  30780
gacagtctaa gatattcaat tacactttcc ctttttatga gttatgcgat gcggtcatgt  30840
acatgtcaaa acagtacaac ctgtggcctc cctctcccca ggcgtgtgtg gaaaatactg  30900
ggtcttactg ctgtatggct ttcgcaatca ctacgctcga tctaatctgc acggtgctat  30960
acataaaatt caggcagagg cgaatcttta tcgatgaaaa gaaatgcct tgatcgctaa  31020
caccggcttt ctatctgcag aatgaatgca atcacctccc tactaatcac caccaccctc  31080
cttgcgattg cccatgggtt gacacgaatc gaagtgccag tggggtccaa tgtcaccatg  31140
gtgggccccg ccggcaaatc caccctcatg tgggaaaaat ttgtccgcaa tcaatgggtt  31200
catttctgct ctaaccgaat cagtatcaag cccagagcca tctgcgatgg gcaaaatcta  31260
actctgatca atgtgcaaat gatggatgct gggtactatt acgggcagcg gggagaaatc  31320
attaattact ggcgaccca caaggactac atgctgcatg tagtcgaggc acttccact  31380
accccccca ctaccacctc tccaccacc accaccacta ctactactact tactactact  31440
actactacta ccactaccgc tgccgcat cccgcaaaa gcaccatgat tagcacaaag  31500
cccctcgtg ctcactccca cgccggcggg cccatcggtg cgacctcaga aaccaccgag  31560
ctttgcttct gccaatgcac taacgccagc gctcatgaac tgttcgacct ggagaatgag  31620
gatgtccagc agagctccgc ttgcctgacc caggaggctg tggagccgt tgccctgaag  31680
cagatcggtg attcaataat tgactcttct tctttttgcca ctcccgaata ccctcccgat  31740
tctacttttcc acatcacggg taccaaagac cctaacctct ctttctacct gatgctgctg  31800
ctctgtatct ctgtggtctc ttccgcgctg atgttactgg ggatgttctg ctgcctgatc  31860
tgccgcagaa agagaaaagc tcgctctcag ggccaaccac tgatgccctt ccctacccc  31920
ccggattttg cagataacaa gatatgagct cgctgctgac actaaccgct ttactagcct  31980
gcgctctaac ccttgtcgct tgcgactcga gattccacaa tgtcacagct gtggcaggag  32040
aaaatgttac tttcaactcc acggccgata cccagtggtc gtgagtggc tcaggtagct  32100
```

```
acttaactat ctgcaatagc tccacttccc ccggcatatc cccaaccaag taccaatgca   32160
atgccagcct gttcaccctc atcaacgctt ccacctggaa caatggactc tatgtaggct   32220
atgtacccct tggtgggcaa ggaaagaccc acgcttacaa cctggaagtt cgccagccca   32280
gaaccactac ccaagcttct cccaccacca ccaccaccac caccatcacc agcagcagca   32340
gcagcagcag ccacagcagc agcagcagat tattgacttt ggttttggcc agctcatctg   32400
ccgctaccca ggccatctac agctctgtgc ccgaaaccac tcagatccac cgcccagaaa   32460
cgaccaccgc caccaccgcta cacacctcca gcgatcagat gccgaccaac atcacccccct   32520
tggctcttca aatgggactt acaagcccca ctccaaaacc agtggatgcg ccgaggtct   32580
ccgccctcgt caatgactgg gcggggctgg gaatgtggtg gttcgccata ggcatgatgg   32640
cgctctgcct gcttctgctc tggctcatct gctgcctcca ccgcaggcga gccagacccc   32700
ccatctatag acccatcatt gtcctgaacc ccgataatga tgggatccat agattggatg   32760
gcctgaaaaa cctactttt tcttttacag tatgataaat tgagacatgc ctcgcatttt   32820
cttgtacatg ttccttctcc cacctttct ggggtgttct acgctggccg ctgtgtctca   32880
cctggaggta gactgcctct cacccttcac tgtctacctg ctttacggat tggtcaccct   32940
cactctcatc tgcagcctaa tcacagtaat catcgccttc atccagtgca ttgattacat   33000
ctgtgtgcgc ctcgcatact tcagacacca cccgcagtac cgagacagga acattgccca   33060
acttctaaga ctgctctaat catgcataag actgtgatct gccttctgat cctctgcatc   33120
ctgcccaccc tcacctcctg ccagtacacc acaaaatctc cgcgcaaaag acatgcctcc   33180
tgccgcttca cccaactgtg gaatataccc aaatgctaca acgaaaagag cgagctctcc   33240
gaagcttggc tgtatggggt catctgtgtc ttagttttct gcagcactgt ctttgccctc   33300
ataatctacc cctactttga tttgggatgg aacgcgatcg atgccatgaa ttaccccacc   33360
tttcccgcac ccgagataat tccactgcga caagttgtcc cgttgtcgt taatcaacgc   33420
ccccatccc ctacgcccac tgaaatcagc tactttaacc taacaggcgg agatgactga   33480
cgccctagat ctagaaatgg acggcatcag taccgagcag cgtctcctag agaggcgcag   33540
gcaggcggct gagcaagagc gcctcaatca ggagctccga gatctcgtta acctgcacca   33600
gtgcaaaaga ggcatctttt gtctggtaaa gcaggccaaa gtcacctacg agaagaccgg   33660
caacagccac cgcctcagtt acaaattgcc cacccagccg cagaagctgg tgctcatggt   33720
gggtgagaat cccatcaccg tcacccagca ctcggtagag accgaggggt gtctgcactc   33780
cccctgtcgg ggtccagaag acctctgcac cctggtaaag accctgtgcg gtctcagaga   33840
tttagtcccc tttaactaat caaacactgg aatcaataaa aagaatcact tacttaaaat   33900
cagacagcag gtctctgtcc agtttattca gcagcacctc cttcccctcc tcccaactct   33960
ggtactccaa acgccttctg gcggcaaact tcctccacac cctgaaggga atgtcagatt   34020
cttgctcctg tccctccgca cccactatct tcatgttgtt gcagatgaag cgcaccaaaa   34080
cgtctgacga gagcttcaac cccgtgtacc cctatgacac ggaaagcggc cctccctccg   34140
tcccttttcct caccccctccc ttcgtgtctc ccgatggatt ccaagaaagt cccccccggg   34200
tcctgtctct gaacctggcc gagccctggg tcacttccca cggcatgctc gccctgaaaa   34260
tgggaagtgg cctctccctg gacgacgctg gcaacctcac ctctcaagat atcaccaccg   34320
ctagccctcc cctcaaaaaa accaagacca acctcagccc agaaacctca tcccccctaa   34380
ctgtgagcac ctcaggcgcc ctcaccgtag cagccgccgc tccctgccg gtggccggca   34440
cctccctcac catgcaatca gaggcccccc tgacagtaca ggatgcaaaa ctcaccctgg   34500
ccaccaaagg ccccctgacc gtgtctgaag gcaaactggc cttgcaaaca tcggcccgc   34560
tgacggccgc tgacagcagc accctcacag tcagtgccac accaccccctt agcacaagca   34620
atggcagctt gggtattgac atgcaagccc ccatttacac caccaatgga aaactaggac   34680
ttaacttttgg cgctcccctg catgtggtag acagcctaaa tgcactgact gtagttactg   34740
gccaaggtct tacgataaac ggaacagccc tacaaactag agtctcaggt gccctcaact   34800
atgacacatc aggaaaccta gaattgagag ctgcaggggg tatgcgagtt gatgcaaatg   34860
gtcaacttat ccttgatgta gcttacccat ttgatgcaca aaacaatctc agccttaggc   34920
ttggacaggg acccctgttt gttaactctg cccacaactt ggatgttaac tacaacagag   34980
gcctctacct gttcacatct ggaaatacca aaaagctaga agttaatatc aaaacagcca   35040
agggtctcat ttatgatgac actgctatag caatcaatgc gggtgatggg ctacagtttg   35100
actcaggctc agatacaaat ccattaaaaa ctaaacttgg attaggactg gattatgact   35160
ccagcagagc cataattgct aaactgggaa ctggcctaag cttttgacaac acaggtgcca   35220
tcacagtagg caacaaaaat gatgacaagc ttaccttgtg gaccacacca gacccatccc   35280
ctaactgtag aatctattca gagaaagatg ctaaattcac acttgttttg actaaatgcg   35340
gcagtcaggt gttggccagc gttttctgtt tatctgtaaa aggtagcctt gcgcccatca   35400
gtggcacagt aactagtgct cagattgtcc tcagatttga tgaaaatgga gttctactaa   35460
gcaattcttc ccttgaccct caatactgga actacagaaa aggtgacctt acagagggca   35520
ctgcatatac caacgcagtg ggatttatgc ccaacctcac agcatcccca aaaacacaga   35580
gccaaactgc taaaagcaac attgtaagtc aggtttactt gaatgggac aaatccaaac   35640
ccatgaccct caccattacc ctcaatgaaa taatgaaac aggagatgcc acagtaagca   35700
cttactccat gtcattctca tggaactgga atggaagtaa ttacattaat gaaacgttcc   35760
aaaccaactc cttcaccttc tcctacatcg cccaagaata aaaagcatga cgctgttgat   35820
ttgattcaat gtgtttctgt tttatttca agcacaacaa aatcattcaa gtcattcttc   35880
catcttagct taatagacac agtagcttaa tagacccagt agtgcaaagc cccattctag   35940
cttataacta gtgagaagt actcgcctac atgggggtag agtcataatc gtgcatcagg   36000
ataggcggt ggtgctgcag cagcgcgcga ataaactgct gccgccgccg ctccgtcctg   36060
caggaataca acatgcagt ggtctcctca gcgatgattc gcaccgcccg cagcataagg   36120
cgccttgtcc tccgggcaca gcagccacc ctgatctcca ttaaatcagc acagtaactg   36180
cagcacagca ccacaatatt gttcaaaatc ccacagtgca aggcgctgta tccaaagtc   36240
atggcgggga ccacagaacc cacgtggcca tcataccaca agcgcaggta gattaagtgg   36300
cgacccctca taaacacgct ggacataaac attacctctt ttggcatgtt gtaattcacc   36360
acctcccggt accatataaa cctctgatta aacatggcgc catccaccac catcctaaac   36420
cagctggcca aaacctgccc gccggctata cactgcaggg aaccgggact ggaacaatga   36480
gagggagag cccaggactc gtaaccatgg atcatcatgc tcgtcatgat atcaatgttg   36540
gcacaacaca ggcacacgtg catacacttc ctcaggatta caagctcctc ccgcgttaga   36600
accatatccc agggaacaac ccattcctga atcagcgtaa atcccacact gcaggtaagaa   36660
cctcgcacgt aactcacgtt gtgcattgtc aaagtgttac attcgggcag cagcggatga   36720
tcctccagta tggtagcgcg ggtttctgtc tcaaaaggag gtagacgatc cctactgtac   36780
ggagtgcgcc gagacaaccg agatcgtgtt ggtcgtagtg tcatgccaaa tggaacgccg   36840
```

```
gacgtagtca tatttcctga agtcttagat ctctcaacgc agcaccagca ccaacacttc   36900
gcagtgtaaa aggccaagtg ccgagagagt atatatagga ataaaaagtg acgtaaacgg   36960
gcaaagtcca aaaaacgccc agaaaaaccg cacgcgaacc tacgcccga aacgaaagcc    37020
aaaaaacact agacactccc ttccggcgtc aacttccgct ttcccacgct acgtcacttg   37080
ccccagtcaa acaaactaca tatcccgaac ttccaagtcg ccacgcccaa aacaccgcct   37140
acacctcccc gcccgccggc ccgcccccaa acccgcctcc cgccccgcgc ccgccccgc    37200
gccgccatc tcattatcat attggcttca atccaaaata aggtatatta ttgatgatgg    37260
tttaaacgga tcctctagag tcgacctgca ggcatgcaag cttgagtata accccttgc    37320
ggccgcccgg gccgtcgacc aattctcatg tttgacagct tatcatcgaa tttctgccat   37380
tcatccgctt attatcactt attcaggcgt agcaaccagg cgtttaaggg caccaataac   37440
tgccttaaaa aaattacgcc ccgccctgcc actcatcgca gtactgttgt aattcattaa   37500
gcattctgcc gacatggaag ccatcacaaa cggcatgatg aacctgaatc gccagcggca   37560
tcagcacctt gtcgccttgc gtataatatt tgcccatggt gaaaacgggg gcgaagaagt   37620
tgtccatatt ggccacgttt aaatcaaaac tggtgaaact cacccaggga ttggctgaga   37680
cgaaaaacat attctcaata aacccttag ggaaataggc caggttttca ccgtaacacg    37740
ccacatcttg cgaatatatg tgtagaaact gccggaaatc gtcgtggtat tcactccaga   37800
gcgatgaaaa cgtttcagtt tgctcatgga aaacggtgta acaagggtga acactatccc   37860
atatccaccag ctcaccgtct ttcattgcca tacggaatcc gcgatgagca ttcatcaggc   37920
gggcaagaat gtgaataaag gccggataaa acttgtgctt attttctctt acggtcttta   37980
aaaaggccgt aatatccagc tgaacggtct ggttataggt acattgagca actgactgaa   38040
atgcctcaaa atgttcttta cgatgccatt gggatatatc aacggtggta tatccagtga   38100
ttttttctc cattttagct tccttagctc ctgaaaatct cgataactca aaaaatacgc    38160
ccggtagtga tcttatttca ttatggtgaa agttggaacc tcttacgtgc cgatcaacgt   38220
ctcatttcg ccaaaagttg gcccagggct tccggtatc aacagggaca ccaggattta    38280
tttattctgc gaagtgatct tccgtcacag gtatttattc gcgataagct catggagcgg   38340
cgtaaccgtc gcacaggaag gacagaaaa gcgcggatcg ggaagtgac ggacagaacg     38400
gtcaggacct ggattgggga ggcggttgcc gccgctgctg ctgacggtgt gacgttctct   38460
gttccggtca caccacatac gttccgccat tcctatgcga tgcacatgct gtatgccggt   38520
ataccgctga aagttctgca aagcctgatg ggacataagt ccatcagttc aacggaagtc   38580
tacacgaagg tttttgcgct ggatgtggct gcccggcacc gggtgcagtt tgcgatgccg   38640
gagtctgatg cggttgcgat gctgaaacaa ttatcctgag aataaatgcc ttggccttta   38700
tatgaaatg tggaactgag tggatatgct gttttttgtct gttaaacaga gaagctggct    38760
gttatccact gagaagcgaa cgaaacagtc gggaaaatct cccattatcg tagagatccg   38820
cattattaat ctcaggagcc tgtgtagcgt ttataggaag tagtgttctg tcatgatgcc   38880
tgcaagcggt aacgaaaacg atttgaatat gccttcagga acaatagaaa tcttcgtgcg   38940
gtgttacgtt gaagtggagc ggattatgtc agcaatggac agaacaacct aatgaacaca   39000
gaaccatgat gtggtctgtc cttttacagc cagtagtgct cgccgcagtc gagcgacagg   39060
gcgaagccct cgagtgagcg aggaagcacc agggaacagc acttatatat tctgcttaca   39120
cacgatgcct gaaaaaactt cccttgggt tatccactta tccacgggga tattttata    39180
attatttttt ttatagtttt tagatcttct tttttagagc gccttgtagg cctttatcca   39240
tgctggttct agagaaggtg ttgtgacaaa ttgcccttc agtgtgacaa atcccctca     39300
aatgacagtc ctgtctgtga caaattgccc ttaaccctgt gacaaattgc cctcagaaga   39360
agcttttttt tcacaaagtt atccctgctt attgactctt tttttatttag tgtgacaatc   39420
taaaaacttg tcacacttca catggatctg tcatggcgga aacagcggtt atcaatcaca   39480
agaaacgtaa aaatagcccg cgaatcgtcc agtcaaacga cctcactgag gcggcatata   39540
gtctctcccg ggatcaaaaa cgtatgctgt atctgttcgt tgaccagatc agaaaatctg   39600
atggcacccct acaggaacat gacggtatct gcgagatcca tgttgctaaa tatgctgaaa   39660
tattcggatt gacctctgcg gaagccagta aggatatacg gcaggcattg aagagtttcg   39720
cggggaagga agtggttttt tatcgccctg aagaggatgc cggcgatgaa aaaggctatg   39780
aatctttcc ttgtttatc aaacgtgcgc acagtccatc cagagggctt tacagtgtac    39840
atatcaaccc atatctcatt cccttcttta tcgggttaca gaaccggttt acgcagtttc   39900
ggcttagtga aacaaaagaa atcaccaatc cgtatgccat gcgtttatac gaatccctgt   39960
gtcagtatcg taagccggat ggctcaggca tcgtctctct gaaaatcgac tggatcatag   40020
agcgttacca gctgcctcaa agttaccagc gtatgcctga cttccgccgc cgcttcctgc   40080
aggtctgtgt taatgagatc aacagcagaa ctccaatgcc cctctcatac attgagaaaa   40140
agaaaggccg ccagacgact catatcgtat tttccttccg cgatatcact tccatgacga   40200
caggatagtc tgagggttat ctgtcacaga tttgagggtg gttcgtcaca tttgttctga   40260
cctactgagg gtaatttgtc acagttttgc tgtttccttc agcctgcatg gattttctca   40320
tactttttga actgtaattt ttaaggaagc caaatttgag ggcagtttgt cacagttgat   40380
ttccttctct ttcccttcgt catgtgacct gatatcgggg gttagttcgt catcattgat   40440
gaggggttgat tatcacagtt tattactctg aattggctat ccgcgtgtgt acctctacct   40500
ggagttttc ccacggtgga tatttcttct tgcgctgagc gtaagagcta tctgacagaa    40560
cagttcttct ttgcttcctc gccagttcgc tcgctatgct cggttacacg gctgcggcga   40620
gcgctagtga taataagtga ctgaggtatg tgctcttctt atctccttt gtagtgttgg    40680
tcttatttta aacaactttg cggttttttg atgacttgt gattttgttg ttgctttgca    40740
gtaaattgca agatttaata aaaaaacgca aagcaatgat taaggatgt tcagaatgaa    40800
actcatggaa acacttaacc agtgcataaa cgctggtcat gaaatgacga aggctatcgc   40860
cattgcacag tttaatgatg acagcccgga agcgaggaaa ataacccggc gctgagagaa   40920
aggtgaagca gcggatttag ttggggtttc ttctcaggct atcagatg ccgagaaagc     40980
agggcgacta ccgcacccgg atatggaaat tcgaggacgg gttgagcaac gtgttggtta   41040
tacaattgaa caaattaatc atatgcgtga tgtgtttggt acgcgattgc gacgtggtga   41100
agacgtattt ccaccggtga tcggggttgc tgcccataaa ggtggcgttt acaaaacctc   41160
agtttctgtt catcttgctc aggatctggc tctgaagggg ctacgtgttt gctcgtgga    41220
aagcgac ccgcaagggaa cagcctcaat gatccatcat atcttcatat                41280
tcatgcagaa gacactctcc tgcctttcta tcttggggaa aaggacgatg tcacttatgc   41340
aataaagccc acttgctggc cggggcttga cattattcct tcctgtcgg ctctgcaccg    41400
tattgaaact gagttaatgg gcaaatttga tgaaggtaaa ctgcccaccg atccacacct   41460
gatgctccga ctgccattg aaactgttgc tcatgactat gatgtcatag ttattgacag    41520
cgcgcctaac ctgggtatcg gcacgattaa tgtcgtatgt gctgctgatg tgctgattgt   41580
```

```
tcccacgcct gctgagttgt ttgactacac ctccgcactg cagttttttcg atatgcttcg   41640
tgatctgctc aagaacgttg atcttaaagg gttcgagcct gatgtacgta ttttgcttac   41700
caaatacagc aatagtaatg gctctcagtc cccgtggatg gaggagcaaa ttcgggatgc   41760
ctggggaagc atggttctaa aaaatgttgt acgtgaaacg gatgaagttg gtaaaggtca   41820
gatccggatg agaactgttt ttgaacaggc cattgatcaa cgctcttcaa ctggtgcctg   41880
gagaaatgct cttctatttt gggaacctgt ctgcaatgaa attttcgatc gtctgattaa   41940
accacgctgg gagattagat aatgaagcgt gcgcctgtta ttccaaaaca tacgctcaat   42000
actcaaccgt tgaagatac  ttcgttatcg acaccagctg ccccgatggt ggattcgtta   42060
attgcgccg  taggagtaat ggctcgcggt aatgccatta ctttgcctgt atgtggtcgg   42120
gatgtgaagt ttactcttga agtgctccgg ggtgatagtg ttgagaagac ctctccggta   42180
tggtcaggta atgaacgtga ccaggagctg cttactgagg acgcactgga tgatctcatc   42240
ccttctttc  tactgactgg tcaacagaca ccggcgttcg gtcgaagagt atctggtgtc   42300
atagaaattg ccgatgggag tcgccgtcgt aaagctgctg cacttaccga aagtgattat   42360
cgtgttctgg ttggcgagct ggatgatgag cagatggctg cattatccag attgggtaac   42420
gattatcgcc caacaagtgc ttatgaacgt ggtcagcgtt atgcaagccg attgcagaat   42480
gaatttgctg gaaatatttc tgcgctggct gatgcggaaa atatttcacg taagattatt   42540
acccgctgta tcaacaccgc caaattgcct aaatcagttg ttgctctttt ttctcacccc   42600
ggtgaactat ctgcccggtc aggtgatgca cttcaaaaag cctttacaga taaagaggaa   42660
ttacttaagc agcaggcatc taaccttcat gagcagaaaa aagctggggt gatatttgaa   42720
gctgaagaag ttatcactct tttaacttct gtgcttaaaa cgtcatctgc atcaagaact   42780
agtttaagct cacgacatca gtttgctcct ggagcgacag tattgtataa gggcgataaa   42840
atggtgctta acctggacag gtctcgtgtt ccaactggat gtatagagaa aattgaggcc   42900
attcttaagg aacttgaaaa gccagcaccc tgatgcgacc acgttttagt ctacgtttat   42960
ctgtctttac ttaatgtcct ttgttacagg ccagaaagca taactggcct gaatattctc   43020
tctgggccca ctgttccact tgtatcgtcg gtctgataat cagactggga ccacggtccc   43080
actcgtatcg tcggtctgat tattagtctg ggaccacgt cccactcgta tcgtcggtct   43140
gattattagt ctgggaccac ggtcccactc gtatcgtcgg tctgataatc agactgggac   43200
cacggtccca ctcgtatcgt cggtctgatt attagtctgg gaccatggtc ccactcgtat   43260
cgtcggtctg attattagtc tgggaccacg gtcccactcg tatcgtcggt ctgattatta   43320
gtctgaaacc acggtcccac tcgtatcgtc ggtctgatta ttagtctggg accacggtcc   43380
cactcgtatc gtcggtctga ttattagtct gggaccacga tcccactcgt gttgtcggtc   43440
tgattatcgg tctgggacca cggtcccact tgtattgtcg atcagactat cagcgtgaga   43500
ctacgattcc atcaatgcct gtcaagggca agtattgaca tgtcgtcgta acctgtgaaa   43560
cggagtaacc tcggtgtgcg gttgtatgcc tgctgtggat tgctgctgtg tcctgcttat   43620
ccacaacatt ttgcgcacgg ttatgtggac aaaatacctg gttacccagg ccgtgccggc   43680
acgctcggta cccggggatc ctcgtttaaa c                                 43711

SEQ ID NO: 53           moltype = DNA  length = 41545
FEATURE                 Location/Qualifiers
misc_difference         16144
                        note = modified_base - a, c, t, g, unknown or other
misc_feature            1..41545
                        note = Description of Artificial Sequence: Synthetic
                         polynucleotide
source                  1..41545
                        mol_type = other DNA
                        organism = synthetic construct
SEQUENCE: 53
catcatcaat aatatacctt attttggatt gaagccaata tgataatgag atgggcggcg     60
cggggcgggg cgcggggcgg gaggcgggtt tgggggcggg ccggcgggcg gggcggtgtg    120
gcggaagttg actttgtaag tgtggcggat gtgacttgct agtgccgggc gcggtaaaag    180
tgacgttttc cgtgcgcgac aacgcccccg ggaagtgaca ttttttcccgc ggttttttacc    240
ggatgttgta gtgaatttgg gcgtaaccaa gtaagatttg gccatttttcg cgggaaaact    300
gaaacgggga agtgaaatct gattaattt  gcgttagtca taccgcgtaa tatttgtcta    360
gggccgaggg acttttggcg attacgtgga ggactcgcc  aggtgttttt tgaggtgaat    420
ttccgcgttc cgggtcaaag tctgcgtttt attattatag gatatcccat tgcatacgtt    480
gtatccatat cataatatgt acatttatat tggctcatgt ccaacattac cgccatgttg    540
acattgatta ttgactagtt attaatagta atcaattacg gggtcattag ttcatagccc    600
atatatggag ttccgcgtta cataacttac ggtaaatggc ccgcctggct gaccgcccaa    660
cgaccccccgc ccattgacgt caataatgac gtatgttccc atagtaacgc caatagggac    720
tttccattga cgtcaatggg tggagtattt acgtaaact  gcccacttgg cagtacatca    780
agtgtatcat atgccaagta cgccccctat tgacgtcaat gacggtaaat ggcccgcctg    840
gcattatgcc cagtacatga ccttatggga ctttcctact tggcagtaca tctacgtatt    900
agtcatcgct attaccatgt tgatgcggtt ttggcagtac atcaatgggc gtggatagcg    960
gtttgactca cggggatttc caagtctcca ccccattgac gtcaatggga gtttgttttg   1020
gcaccaaaat caacgggact ttccaaaatg tcgtaacaac tccgccccat tgacgcaaat   1080
gggcggtagg cgtgtacggt gggaggtcta tataagcaga gctctcccta tcagtgatag   1140
agatctccct atcagtgata gagatcgtcg acgagctcgt ttagtgaacc gtcagatcgc   1200
ctggagacgc catccacgct gttttgacct ccatagaaga ccgggggacc gatccagcct   1260
ccgcggccgg gaacggtgca ttggaacgcg gattccccgt gccaagagtg atcttccg     1320
tttatctagg taccagatat cgccaccatg tccgaggact ttctgattct gatcgccatc   1380
ctggtgatcg tgattctcgt gggcacaatc acaaccctgg tgggcgccat cggcggcatt   1440
agggccagga ggagcttcct cttcattttgc atcttcttcc tgttcctctc cctcttcctg   1500
acaatcctgg ccctgctgtg gggcttcagc tggctcctgg tggtcctgtt ctgg          1560
gtgctctgga tggtcatcct cattctgctg ctgctggtgt accctattcc tcaccaccccc   1620
ctgcccacct ccctcaggtt tagaatgaag cagagggtga gcagcgaccc cacaggttct   1680
gacagaagcc ctcagggcag ccataatagc ctgaactccc ccgatgagga ggaccccaag   1740
gatgacacca gcaacctctc tgtcaacatg accagggggc gacctcccgt caatggacag   1800
ctcctcggac aacatgctca atgcccccct cactatccct gctgccatat tcagcatccc   1860
```

```
gacggagagg attccgatgg agacgatggc aagtcctggg gcgatgccgg agaggaagac   1920
aatgcccta  acgaccctaa caccgccagc accagagagt ccatttacga ggacctcaga   1980
tacccacaa  gggacgccaa tggcgagtat gagaacgtgg gataccccc  tagggacgga   2040
gatgcccctc ataggctcgg agagcctgtg tatgacgatg tggagcaagc caccgctaac   2100
gaggtgagaa tctcccctct gttcagactg ccctacggaa gcgttttcgg acctggcccc   2160
cagcctggac ccattctgga gagctccaca tggggctttc tggtcttcac acagacctcc   2220
ctgttcgccg acgacattgc cgacgctatt agggactact gcacaaccca ccctggcccc   2280
acaaggaaca cccaggtggt cctcatgaac ttcgagggca gcggagtgcc cctgcctatg   2340
ttttttcccc ctggagagga gacagaagag cagagagagg gcgatagagc tagcgactcc   2400
gacgagtccg aagacgctca gatcctgacc gtgttctgcc tgttttgcca gtggacactc   2460
tttatctgcc tgggaatcag gatgatctgt aactggaggg gcaaactcac caggatcatc   2520
tgcctgaagt tctgcctcta cggactgatt ccgcctcccc tgtccttcgg ctggtacgct   2580
ttttctgaagg aagtgaccct ccccaccaca gccaccgttg atcctaggca actccccctg   2640
ttcctcttca tcctgagctc cgtgctggtg attctcgcca tcatgatgga gtttcaaaca   2700
tcctccagcc tcttcgctgc tctgttcgtg attatcgccg gaatgctgtg cgtcacagtg   2760
ggcgtgattt ttctgctggc tggcgtcaag cctctcctga gcggcatgat ctgcgcctcc   2820
ggcatcacaa tgctcgtgct cggcgtcgtg ctgctggtgg tgtgcaccag agatgagcac   2880
gctatttccg ccagccacca tgctagcgat ggctccgtga atcagcagaa ggaaaatcag   2940
ccccagaccc tggaggaatg caagacagat caggagagga agaggtacag gaacaggctg   3000
gcctccagga ggtgtagagc taagttcagg aaccagctgg aacatttag  gacagtcgcc   3060
gctgctaaga cagaggagaa caacaggctc agggtgctca tcaggcagat gtgtcctaca   3120
ctggacgtgg aatccatcgt cccctccacc tccgccggct accacgagcc tctgaatcac   3180
ctgacccaca gccccagccc ttgtcatcac agggatgaac cccctcccag aagcccagc    3240
cctcaaccca ccgtctccga gcagtcccag cagtccccca ggcagcagag ccctcaaggc   3300
acatcccagg gttctacaag acctcaggtg cctggaggcg ccaccaccag aaaaagaggc   3360
ggcgtgagag gccaacctgc caagtgtcac ggcaagtaca ccacaaccgc cgagggactg   3420
accgctctcc tgaataggag gcacagcccc aggacatcca acgagggcag gtggatgaat   3480
ggagtcatgg ctgtgaacct ctccaaatgg ccccctgtaca gcctgaggag agccctggcc   3540
ctcgccatgg ctcctagaag gaggctctcc ggccctccct ggctgacagt gctgctgctg   3600
ctgtccacac tgagcgtggc cgcccctgct attctcttcc tgattttcag cgccggcgcc   3660
accattagca cagaagccag cctgctggtc ctgctcctgc tgtttgtgac cctgctgctg   3720
cctctcctgt cctccaacgg actccagctc cctgccgccc tgattctgat ccagtgtttc   3780
ctcctggccg ctgattatct cgcctacctg attctgccta ccattatgcc caggggcaga   3840
agcacaggaa ggaagggcag ggaagacaga aaagagagga gcagatcccc tctcagagct   3900
cctggcggtt ctgatggacc cagcacaagg gctggctgtg gagccggacc ctgtcagctg   3960
agcagcccca tcgccggaaa caacggcaat gaaggcggcg agggcgacga ctacaagagc   4020
tggaggaagc ccgaggaaga ggacaacggc cccaatgacc ccaataccaa caacaggatt   4080
gaggatggag acggcgacga cggaaaatcc tggaggaatc ctgaggagga ggataacaga   4140
aagcaggaca ggctgggcac caagccttc  atggacctcg acggaaccgg cggaggcgga   4200
ggctacagcc agatggtccc tatcgccacc gccccggaa  gcggccacgc cgctacctat   4260
caggatctcc aggccgcccc ttacatcatc tggcctctcc agaccgattg ccagcctgtg   4320
gctaccacct tcgcctcccc cggacagatc cagtggtata aagcgccgt  cccccagccc   4380
acagagcatt gctcccagtt tacaaacgct cccaccgtca accagcagca gcctattagc   4440
caacccagc  ccgaaaatcc ccctgctttc acctttaccc agcccgcttc catcattccc   4500
ggcgtcatta gcgcctccaa cctgaacgtg agcgcttccc ctatcatccc tagcgaccat   4560
gtcctcccca tcattacctc cgtgaccagc ctcgcccaac ctaataacat ggccggccac   4620
tggtatgaga gcgtgattcc cggcgtgttc ctctgcccca tgatcctccc ttccctgttc   4680
tggatttgct ccctgctgac cttcctggtg ggccacggag ccaatattgt gagcgccgtc   4740
ctgttcctcg tgctggcttg gtgtctcctc attgccaact ggaacgtgac aagagaggac   4800
ttcgtgtccg gcaggagaag ctccatgagc agcctgtccg tggccgcttc caccgccaca   4860
gccatgttcg ccagcttcct caccctgagc tttgatggct tgggcctgct gctgttttgc   4920
accgccctgg tgatccagac aatttacgtg ctgtatctgg tggtcatgga gatcaccgtg   4980
tggatcatga tgtttaggta tctccacttt tggatcaccc tgctgttcct gctgagcccc   5040
attattctct ccgtcgcctg tctcatcatc caatcctccg ccctgctgat cgaggctgtg   5100
tgctcacca  ccatcacagt cctggccatt ttttctgtggc tccctcctca aggcgctgag   5160
gccgatctcg gcaccgccct gctgattctg aataccgccc tgtgcctggt cgtgctgatc   5220
ctgaccgcta tccctacatg atgatgagcg gccgcgatct gctgtgcctt ctagttgcca   5280
gccatctgtt gtttgcccct cccccgtgcc ttccttgacc ctggaaggtg ccactcccac   5340
tgtccttttcc taataaaatg aggaaattgc atcgcattgt ctgagtaggt gtcattctat   5400
tctgggggggt ggggtggggc aggacagcaa ggggaggatt tgggaagaca ataggcaggga   5460
tgctgggggat gcgtgggggct ctatggccga tcagcgatcc ctgaggtggg tgagtgggcg   5520
tggcctgggg tggtcatgaa aatatataag ttgggggtct tagggtctct ttatttgtgt   5580
tgcagagacc gccggagcca tgagcgggag cagcagcagc agcagtagca gcagcgcctt   5640
ggatgggaga atcgtgagcc cttatttgac acgcgggata cccactggg  ccgggggtcg   5700
tcagaatgtg atgggctcca gcatcgacgg ccgaccgtc  ctgcccgcaa attccgccac   5760
gctgacctat gcgaccgtcg cggggacgcc gttggacgcc accgccgccg ccgccgccac   5820
cgcagccgcc tcggccgtgc gcagcctggc cacggacttt gcattcctgg accactggcc   5880
gacagggcgc acttctcggg ccgctgctgc cgccgttcgc gatgacaagc tgaccgccct   5940
gctggcgcag ttggatgcgc ttactcggga actggtgcag ctttctcagc aggtcatgsc   6000
cctgcgccag caggtctcct ccctgcaagc tggcgggaat gcttctccca caaatgccgt   6060
taagataaa  taaaccaga ctcgtttgg  attaaagaaa agtagcaagt gcattgctct   6120
cttattttca taattttccg cgcgcgatag gccctagacc agcgttctcg gtcgttgagg   6180
gtgcggtgta tcttctccag gacgtggtag aggtggctct ggacgttgag atacatgggc   6240
atgagccgga cccggggggtg gaggtagcac cactgcagac cttcatgctc cgggggtgtg   6300
ttgtagatga tccagtcgta gcaggagcgc tgggcatgga gcctaaaaat gtccttcagc   6360
agcaggccga tggccagggg gaggcccttg tgtaagtgt  ttacaaaacg gttaagttgg   6420
gaagggtgca ttcggggaga gatgatgtgc atcttggact gtattttag  attggcgatg   6480
tttccgccca gatcccttct gggattcatg ttgtgcagga ccaccagtac agtgtatccg   6540
gtgcacttgg ggaatttgtc atgcagctta gagggaaaag cgtggaagaa cttggagacg   6600
```

```
cctttgtggc ctcccagatt ttccatgcat tcgtccatga tgatggcaat gggcccgcgg   6660
gaggcagctt gggcaaagat atttctgggg tcgctgacgt cgtagttgtg ttccagggtg   6720
aggtcgtcat aggccatttt tacaaagcgc gggcggaggg tgcccgactg ggggatgatg   6780
gtccctctg gccctgggc gtagttgccc tcgcagatct gcatttccca ggccttaatc    6840
tcggaggggg gaatcatatc cacctgcggg gcgatgaaga aaacggtttc cggagccggg   6900
gagattaact gggatgagag caggtttcta agcagctgtg attttccaca accggtgggc   6960
ccataaataa cacctataac cggttgcagc tggtagttta gagagctgca gctgccgtcg   7020
tcccggagga ggggggccac ctcgttgagc atgtccctga cgcgcatgtt ctccccgacc   7080
agatccgcca gaaggcgctc gccgcccagg gacagcagct cttgcaagga agcaaagttt   7140
ttcagcggct tgaggccgtc cgccgtgggc atgtttttca gggtctggct cagcagctcc   7200
aggcggtccc agagctcggt gacgtgctct acggcatctc tatccagcat atctcctcgt   7260
ttcgcgggtt ggggcgactt tcgctgtagg gcaccaagcg gtggtcgtcc agcgggcca    7320
gagtcatgtc cttccatggg cgcagggtcc tcgtcagggt ggtctgggtc acggtgaagg   7380
ggtgcgctcc gggctgagcg cttgccaagg tgcgcttgag gctggttctg ctggtgctga   7440
agcgctgccg gtcttcgccc tgcgcgtcgg ccaggtagca tttgaccatg gtgtcatagt   7500
ccagcccctc cgcggcgtgt cccttggcgc gcagcttgcc cttggaggtg gcgccgcacg   7560
aggggcagag caggctcttg agcgcgtaga gcttgggggc gaggaagacc gattcggggg   7620
agtaggcgtc cgcgccgcag accccgcaca cggtctcgca ctccaccagc caggtgagct   7680
cggggcgcgc cgggtcaaaa accaggtttc ccccatgctt tttgatgcgt ttcttacctc   7740
gggtctccat gaggtggtgt ccccgctcgg tgacgaagag gctgtccgtg tctccgtaga   7800
ccgacttgag gggtctttc tccagggggg tccctcggtc ttcctcgtag aggaactcgg    7860
accactctga gacgaaggcc cgcgtccagg ccaggacgaa ggaggctatg tgggaggggt   7920
agcggtcgtt gtccactagg gggtccacct tctccaaggt gtgaagacac atgtcgcttt   7980
cctcggcgtc caggaaggtg attggcttgt aggtgtaggc cacgtgaccg ggggttcctg   8040
acgggggggt ataaaagggg gtgggggcgc gctcgtcgtc actctcttcc gcatcgctgt   8100
ctgcgagggc cagctgctgg ggtgagtatt ccctctcgaa ggcggcgcatg acctccgctga  8160
tgaggttgtc agtttccaaa aacgaggagg atttgatgtt cacctgtccc gaggtgatac   8220
ctttgagggt acccgcgtcc atctggtcag aaaaacacgat ctttttattg tccagcttgg   8280
tggcgaacga cccgtagagg gcgttggaga gcagcttggc gatggagcgc agggtctggt   8340
tcttgtccct gtcggcgcgc tccttggccg cgatgttgga ctgcacgtac tcgcgcgcga   8400
cgcagcgcca ctcggggaag acggtggtgc gctcgtcggg caccaggcgc acgcgccagc   8460
cgcggttgtg cagggtgacc aggtccacgt tggtggcgac ctccgcgcgc aggcgctcgt   8520
tggtccagca gagacggccg cccttgcgcg agcagaaggg gggcaggggg tcgagctggg   8580
tctcgtccgg ggggtccgcg tccacggtga aaacccggg gcgcaggccg gcgtcgaagt    8640
agtctatctt gcaaccttgc atgtcgcagcg cctgctgcca gtcgcgggcg gcgagcgcgc   8700
gctcgtaggg gttgagcggc gggccccagg gcatgggtg ggtgagtgcg gaggcgtaca    8760
tgccgcagat gtcatagacg tagagggggct cccgcaggac cccgatgtag gtgggggtagc   8820
agcggccgcc gcggatgctg gcgcgcacgt agtcatacag ctcgtgcgag ggggcgagga   8880
ggtcgggggcc caggttggtg cgggcggggc gctccgcgcg gaagcgatc tgcctgaaga    8940
tggcatgcga gttggaagag atggtgggc gctggaagac gttgaagctg gcgtcctgca    9000
ggccgacggc gtcgcgcacg aaggaggcgt aggagtcgcg cagcttgtgt accagctcgg   9060
cggtgacctg cacgtcgagc gcgcagtagt cgagggtctc gcggatgatg tcatatttag   9120
cctgccccctt cttttttccac agctcgccgt tgaggacaaa ctcttcgcgg tctttccagt   9180
actcttggat cgggaaaccg tccggttccg aacggtaaga gcctagcatg tagaactggt   9240
tgacggcctg gtaggcgcag cagcccttct ccacggggag ggcgtaggcc tgcgcggcct   9300
tgcggagcga ggtgtgggtc agggcgaagg tgtccctgac catgactttg aggtactggt   9360
gcttgaagtc ggagtcgtcg cagccgcccc gctcccaaga cgagaagtcg gtgcgcttct   9420
tggagcgggg gttgggcaga gcgaaggtga catcgttgaa gaggattttg cccgcgcggg   9480
gcatgaagtt gcgggtgatg cggaagggcc ccggcacttc agagcggttg ttgatgacct   9540
gggcggcgag cacgatctcg tcgaagccgt tgatgttgtg gcccacgatg tagagttcca   9600
ggaagcgggg ccggcccttt acggtgggca gcttcttttag ctcttcgtag gtgagctcct   9660
cgggcgaggc gaggccgtgc tcggccaggg cccagtccgc gaggtgcggg ttgtctctga   9720
ggaaggactt ccagaggtcg cgggccagga ggggtctgcag gcggtctctg aaggtcctga   9780
actggcggcc cacggccatt ttttcggggg tgatgcagta aaaggtgagg gggtcttgct   9840
gccagcggtc ccagtcgagc tgcagggcga ggtcgcgcgc ggcggtgacc aggcgctcgt   9900
cgccccccgaa tttcatgacc agcatgaagg gcacgagctg ctttccgaag gcccccatcc   9960
aagtgtaggt ctctacatcg taggtgacaa agaggcgctc cgtgcgagga tgcgagccga   10020
tcgggaagaa ctggatctcc cgccaccagt tggaggagtg gctgttgatg tggtggaagt   10080
agaagtcccg tcgccgggcc gaacactcgt gctggcttt gtaaaagcga gcgcagtact    10140
ggcagcgctg cacgggctgt acctcatgca cgagatgcaa ctttcgcccg cgcacgagga   10200
agccgagggg aaatctgagc ccccccgcctg gctcgcggca tggctggttc tcttctactt   10260
tggatgcgtg tccgtctccg tctgctcct cgaggggtgt tacggtggag cggaccacca    10320
cgccgcgcga gccgcaggtc cagatatcgg cgcgcggcgg tcggagtttg atgacgacat   10380
cgcgcagctg ggagctgtcc atggtctgga gctcccgcgg cggcgggga tcagccggga    10440
gttcttgcag gttcacctcg cagagtcggg ccagggcgcg gggcaggtct aggtggtacc   10500
tgatctctag gggcgtgttg gtggcggcgt cgatggcttg caggagcccg cagccccggg   10560
gggcgacgac ggtgccccgc ggggtggtgg tggtggtggc ggtgcagctc agaagcggtg   10620
ccgcggggcgg gccccggag gtagggggggg ctccggtccc gcgggcaggg gcggcagcgg   10680
cacgtcggtg tggagcgcgg gcaggagttg gtgctgtgag cgggaggttgc tggcgaaggc   10740
gacgacgcgg cggttgatct cctgatctg gcgcctctgc gtgaagacga cgggcccggt    10800
gagcttgaac ctgaaagaga gttgacagag atcaatctcg gtgtcattga ccgcggcctg   10860
gcgcaggatc tcctgcacgt ctcccgagtt gtcttggtag gcgatctcgg ccatgaactg   10920
ctcgatctct tcctcctgga ggtctccgcg tccgcgcgt tccacggtgg ccgccaggtc    10980
gttggagatg cgcccatga gctgcgagaa gggagttgagt ccgccctcgt tccagactcg   11040
gctgtagacc acgccccct ggtcatcgcg ggcgcgcatg accacctgcg cgaggttgag    11100
ctccacgtgc cgcgcgaaga cggcgtagtt gcgcagacgc tggaagaggt agttgagggt   11160
ggtggcggtg tgctcggcca cgaagaagtt catgacccag cggcgcaacg tggattcgtt   11220
gatgtccccc aaggcctcca gccgttccat ggcctcgtag aagtcacgg cgaagttgaa    11280
aaactgggag ttgcgcgccg acacggtcaa ctcctcctcc agaagacgga tgagctcggc   11340
```

```
gacggtgtcg cgcacctcgc gctcgaaggc tatggggatc tcttcctccg ctagcatcac   11400
cacctcctcc tcttcctcct cttctggcac ttccatgatg gcttcctcct cttcggggg    11460
tggcggcggc ggcggtgggg gaggggggcgc tctgcgccgg cggcggcgca ccgggaggcg   11520
gtccacgaag cgcgcgatca tctccccgcg gcggcggcgc atggtctcgg tgacggcgcg   11580
gccgttctcc cggggggcgca gttggaagac gccgccggac atctggtgct ggggcgggtg   11640
gccgtgaggc agcgagacgg cgctgacgat gcatctcaac aattgctgcg taggtacgcc   11700
gccgagggac ctgagggagt ccatatccac cggatccgaa aacctttcga ggaaggcgtc   11760
taaccagtcg cagtcgcaag gtaggctgag caccgtggcg ggcggcgggg ggtgggggga   11820
gtgtctggcg gaggtgctgc tgatgatgta attgaagtag gcggacttga cacggcggah   11880
ggtcgacagg agcaccatgt ccttgggtcc ggcctgctgg atgcggaggc ggtcggctat   11940
gccccaggct tcgttctggc atcggcgcag gtccttgtag tagtcttgca tgagcctttc   12000
caccggcacc tcttctcctt cctcttctgc ttcttccatg tctgcttcgg ccctggggcg   12060
gcgccgcgcc ccctgccc ccatgcgcgt gacccgaac ccctgagcg gttggagcag       12120
ggcagtgcg gcgacgacgc gctcggccag gatggcctgc tgcacctgcg tgagggtggt    12180
ttggaagtca tccaagtcca cgaagcggtg gtaggcgccc gtgttgatgg tgtaggtgca   12240
gttggccatg acggaccagt tgacggtctg gtgcccggt tgcgacatct cggtgtacct    12300
gagtcgcgag taggcgcggg agtcgaagac gtagtcgttg caagtccgca ccaggtactg   12360
gtagcccacc aggaagtgcg gcggcggctg gcggtagagg ggcagcgca gggtggcggg    12420
ggctccgggg gccaggtctt ccagcatgag gcggtggtag gcgtagatgt acctggacat   12480
ccaggtgata cccgcggcgg tggtggaggc gcgcggggaag tcgcgcaccc ggttccagat  12540
gttgcgcagg gcagaaaagt gctccatggt aggcgtgctc tgtccagtca gacgcgcgca   12600
gtcgttgata ctctagacca gggaaaacga aagccggcac tc ttccgtggtc            12660
tggtgaatag atcgcaaggg tatcatggcg gagggcctcg gttcgagccc cgggtccggg   12720
ccggacggtc cgccatgatc cacgcggtta ccgcccgcgt gtcgaaccca ggtgtgcgac   12780
gtcagacaac ggtggagtgt tccttttggc gttttttctgg ccgggcgccg cgccgcgta   12840
agagactaag ccgcgaaagc gaaagcagta agtggctcgc tccccgtagc cggagggatc   12900
cttgctaagg gttgcgttgc ggcgaacccc ggttcgaatc ccgtactcgg gccggccgga   12960
cccgcggcta aggtgttgga ttggcctccc cctcgtataa agaccccgct tcggattga    13020
ctccggacac ggggacgagc ccctttttatt tttgctttcc ccagatgcat ccggtgctgc  13080
ggcagatgcg ccccccgccc cagcagcagc aacaacacca gcaagagcgg cagcaacagc   13140
agcgggagtc atgcagggcc ccctcaccca ccctcggcgg gccggccacc tcggcgtccg   13200
cggccgtgtc tggcgcctgc ggcggcggcg ggggcccggc tgacgacccc gaggagcccc   13260
cgcggcgcag ggcagacac tacctggacc tggaggaggg cgagggcctg gcgcggctgg   13320
gggcgccgtc tcccgagcgc caccccgggg tgcagctgaa gcgcgactcg cgcgaggcgt   13380
acgtgcctcg gcagaacctg ttcagggacc gcgcgggcga gagatgcgag              13440
acaggaggtt cagcgcaggg cgggagctgc ggcaggggct gaaccgcgag cggctgctgc   13500
gcgaggagga ctttgagccc gacgcgcgga cggggatcag ccccgcgcgc gcgcacgtgg   13560
cggccgccga cctggtgacg gcgtacgagc agacggtgaa ccaggagatc aacttccaaa   13620
agagtttcaa caaccacgtg cgcacgcgtg tggcgcgca ggaggtgacc atcgggctga   13680
tgcacctgtg ggactttgta agcgcgctgg tgcagaaccc caacagcaag cctctgacgg   13740
cgcagctgtt cctgatagtg cagcacagca gggacaacga ggcgtttagg gacgcgctgc   13800
tgaacatcac cgagcccgag ggtcggtggc tgctggacct gattaacatc ctgcagagca   13860
tagtggtgca ggagcgcagc ctgagcctgg ccgacaaggt ggcgccatc aactactcga   13920
tgctgagcct gggcaagttt tacgcgcgca agatctacca gacgccgtac gtgcccatag   13980
acaaggaggt gaagatcgac ggttttttaca tgcgcatggc gctgaaggtg ctcaccctga   14040
gcgacgacct gggcgtgtac cgcaacgagc gcatccacaa ggccgtgagc gtgagccggc   14100
ggcgcgact gagcgaccgc gagctgatgc acagcctgca gcgggcgctg gggcggcggg   14160
gcagcggcga caggagggcgc gagtcctact tcgatgcggg ggcggacctg cgctgggcgc   14220
ccagccggcg ggccctggag gccgggggg tccgcgagga ctatgacgag gacggcgagg    14280
aggatgagga gtacgagcta gaggagggcg agtacctgga ctaaaccgcg ggtggtgttt   14340
ccggtagatg caagacccga acgtggtgga cccggccgtg cgggcggctc tgcagagcca   14400
gccgtccggc cttaactcct cagacgactg gcgacaggtc atggaccgca tcatgtcgct   14460
gacggcgcgt aacccggacg cgttccggca gcagccgcag gccaacaggc tctccgccat   14520
cctggaggcg gtggtgcctg cgcgctcgaa cccaccgcac gagaaggtgc tggccatagt   14580
gaacgcctg gccgagaaca gggccatccg cccggacgga gccgggctgg tgtacgacgc   14640
gctgctgcag cgcgtggccc gctacaacag cggcaacgtg cagaccaacc tggaccggct   14700
ggtgggggac gtgcgcgagg cggtggcgca gcgcgagcgc gcggatcggc agggcaacct   14760
gggctccatg gtgcgctga atgccttcct gagcacgcag ccggccaacg tgccgcgggg    14820
gcaggaagac tacaccaact ttgtgagcgc gctcggctag atggtgaccg agacccccca   14880
gagcgaggtg taccagtcgg gccggactact cttcttccaa accagcagac agggcctgca   14940
gacggtgaac ctgagccagg cttttcaagaa cctgcggggg ctgtgggcg tgaaggcgcc    15000
caccggcgac cgggcgacgg tgtccagcct gctgacgccc aactcgcgcc tgctgctgct   15060
gctgatcgcg ccgttcacgg acagcggcag cgtgtcccgg gacacctacc tggggcacct   15120
gctgaccctg taccgcaggg ccatcgggca ggcgcaggtg gagcagcaca ccttccagga   15180
gatcaccagc gtgagccgcg cgctggggca ggaggacacg agcagcctgg aggcgactct   15240
gaactacctg ctgaccaacc ggcggcagaa gattccctcg ctgcacagcc tgacctccga   15300
ggaggagcgc atcttcgcgct acgtgcagca gagcgtgagc ctgaacctga tgcgcgacgg   15360
ggtgacgccc agcgtggcgc tggacatgac cgcgcgcaac atggaaccgg gcatgtacgc   15420
cgcgcacga ccttacgatca ggacctgat ggactacctg catccgcgtg aa              15480
ccccgagtac tttaccaacg ccatcctgaa cccgcactgg ctcccgcgc ccgggttcta    15540
cagcgggggc ttcgaggtcc cggagaccaa cgatggcttc ctgtgggacg acatggacga   15600
cagcgtgttc tccccgcggc cgcaggcgct ggcggaagcg tccctgctgc gtccaagaa    15660
ggaggaggag gaggaggcga gtcgccgccg cggcagcagc ggcgtggctt ctctgtccga   15720
gctgggggcg gcagccgcg cgccgccgg gtccctggcg cagcagcgct ttccgagcct     15780
ggtgggtgtct ctgcacagcg agcgcaccac ccgcctcgg ctgctgggcg aggacgagta   15840
cctgaataac tccctgctgc agcggtgcg ggagaaaaac ctgcctccg ccttcccaa      15900
caacgggata gagagcctgg tggacaagat gagcagatgg aagacctatg cgcaggagca   15960
cagggacgcg cctgcgctcc ggccgcccac gcggcgccag cgcacgacc ggcagcgggg    16020
gctggtgtgg gatgacgagg actccgcgga cgatagcagc gtgctggacc tgggagggag   16080
```

```
cggcaacccg ttcgcgcacc tgcgcccccg cctggggagg atgttttaaa aaaaaaaaaa   16140
aaangcaaga agcatgatgc aaaaattaaa taaaactcac caaggccatg gcgaccgagc   16200
gttggtttct tgtgttccct tcagtatgcg gcgcgcggcg atgtaccagg agggacctcc   16260
tccctcttac gagagcgtgg tgggcgcggc ggcggcggcg ccctcttctc cctttgcgtc   16320
gcagctgctg gagccgccgt acgtgcctcc gcgctacctg cggcctaccg ggggagaaa    16380
cagcatccgt tactcggagc tggcgcccct gttcgacacc acccgggtgt acctggtgga   16440
caacaagtcg gcggacgtgg cctccctgaa ctaccagaac gaccacagca atttttgac    16500
cacggtcatc cagaacaatg actacagccc gagcgaggcc agcacccaga ccatcaatct   16560
ggatgaccgg tcgcactggg gcggcgacct gaaaaccatc ctgcacacca acatgcccaa   16620
cgtgaacgag ttcatgttca ccaataagtt caaggcgcgg gtgatggtgt cgcgctcgca   16680
caccaaggaa gaccgggtgg agctgaagta cgagtgggtg gagttcgagc tgccagaggg   16740
caactactcc gagaccatga ccattgacct gatgaacaac gcgatcgtgg agcactatct   16800
gaaagtgggc aggcagaacg gggtcctgga gagcgacatc ggggtcaagt tcgacaccag   16860
gaacttccgc ctgggggctgg accccgtgac cgggctggtt atgcccgggg tgtacaccaa   16920
cgaggccttc catcccgaca tcatcctgct gcccggctgc ggggtggact tcacttacag   16980
ccgcctgagc aacctcctgg gcatccgcaa gcggcagccc ttccaggagg gcttcaggat   17040
cacctacgag gacctggagg ggggcaacat ccccgcgctc ctcgatgtgg aggcctacca   17100
ggatagcttg aaggaaaatg aggcgggaca ggaggatacc gcccccgccg cctccgccgc   17160
cgccgagcag ggcgaggatg ctgctgacac cgcggccgcg gacggggcag aggccgaccc   17220
cgctatggtg gtgagggctc ccgagcagga ggaggacatg aatgacagtg cggtgcgcgg   17280
agacaccttc gtcacccggg gggaggaaaa gcaagcggag gccgaggccg cggccgagga   17340
aaagcaactg gcggcagcag gcggccggcc ggcgttggcc cggcggaggg ctgagtctga   17400
ggggaccaag cccgccaagg agcccgtgat taagcccctg accgaagata gcaagaagcg   17460
cagttacaac ctgctcaagg acagcaccaa caccgcgtac cgcagctggt acctggccta   17520
caactacggc gacccgtcga cggggggtgcg ctcctggacc ctgctgtgca cgccggacgt   17580
gacctgcgac tcggagcagg tgtactggtc gctgcccgac atgatgcaag acccgtgac    17640
cttccgctcc acgcggcagg tcagcaactt cccggtggtg ggcgccgagc tgctgcccgt   17700
gcactccaag agcttctaca acgaccaggc cgtctactcc cagctcatcc gccagttcac   17760
ctctctgacc cacgtgttca atcgctttcc tgagaaccag attctggcgc gcccgcccgc   17820
ccccaccatc accaccgtca gtgaaaacgt tcctgctctc acagatcacg ggacgctacc   17880
gctgcgcaac agcatcggag gagtccagcg agtgaccgtt actgacgcca gacgccgcac   17940
ctgcccctac gttacaagg ccttgggcat agtctcgccg cgcgtccttt ccagccgcac    18000
tttttgagca acaccaccat catgtccatc ctgatctcac ccagcaataa ctccggctgg   18060
ggactgctgc gcgcgcccag caagatgttc ggaggggcga ggaagcgttc cgagcagcac   18120
cccgtgcggc tgccgcgggca cttccgcgcc ccctgggagg cgcacaaacg cggccgcgcg   18180
gggcgcacca ccgtggacga cgccatcgac tcggtggtgg agcaggcgcg caactacagg   18240
cccgcggtct ctaccgtgga cgcggccatc cagaccgtgg tgcggggcgc gcggcggtac   18300
gccaagctga agagccgccg gaagcgcgtg gcccgccgcc accgccgccg acccggggcc    18360
gccgcaaac gcgccgccgc ggccctgctt cgccgggcca agccacggg ccgccgccgcgta    18420
gccatgaggg ccgcgcgccg cttggccgcc ggcatcaccg ccgccaccat ggccccccgt   18480
acccgaagac gcgcggccgc cgccgccgcc gccgccatca gtgacatggc cagcaggcgc   18540
cggggcaacg tgtactgggt gcgcgactcg gtgaccggca cgcgcgtgcc cgtgcgcttc   18600
cgcccccccgc ggacttgaga tgatgtgaaa aacaacact gagtctcctg ctgttgtgtg    18660
tatccccagc gcggcggcgc gcgcagcgtc atgtccaagc gcaaaatcaa agaagagatg   18720
ctccaggtcg tcgcgccgga gatctatggg ccccccgaaga aggaagagca ggattcgaag   18780
ccccgcaaga taaagcgggt caaaagaaa aagaaagatg atgacgatgc cgatggggag    18840
gtggagttcc tgcgcgccac ggcgcccagg cgccgggtgc agtggaaggg ccggcgcgta   18900
aagcgcgtcc tgcgcccccgg caccgcggtg gtcttcacgc ccggcgagcg ctccacccgg   18960
actttcaagc gcgtctatga cgaggtgtac ggcgacgaaa acctgctgga gcaggccaac   19020
gagcgcttcg gagagtttgc ttacgggaag cgtcagcggg cgctggggaa ggaggacctg   19080
ctggcgctgc cgctggacca gggcaaccc acccccagtc tgaagcccgt gacccctgag    19140
caggtgctgc cgagcagcgc accctccgag gcgaagcggg gtctgaagcg cgagggcggc   19200
gacctggcgc ccaccgtgca gctcatggtg cccaagcggc agaggctgga ggatgtgctg   19260
gagaaaatga aagtagaccc cggtctgcag ccggacatca gggtccgccc catcaagcag   19320
gtggcgcccg gcctcggcgt gcagaccgtg gacgtggtca tccccaccgg caactccccg   19380
gccgccgcca ccactaccgc tgcctccacg gacatggaga cacagaccga tcccgccgca   19440
gccgcagccg cagccgccgc cgcgacctcc tcgcggaggg tgcagacgga cccctggctg    19500
ccgcggcgca tgtcagctcc ccgcgcgcgt gcgggggcgca ggaagtacgg cgccgccaac   19560
gcgctcctgc ccgagtacgc cttgcatcct tccatcgcgc ccacccccgg ctaccgaggc   19620
tataccctacc gcccgcgaag agccaagggt tccacccgcc gtcccgccgc acgcgccgcc   19680
gccaccaccc gccgccgccg ccgcagacgc cagcccgcac tggctccagt ctccgtgagg   19740
aaaagtggcgc gcgacggaca cacccctgtg ctgcccaggg cgcgctacca ccccagcatc   19800
gtttaaaagc ctgttgtggt tcttgcagat atggccctca cttgccgcct ccgttccccg    19860
gtgccgggat accgaggagg aagatcgcgc cgcaggaggg gtctggccgg ccgcggccctg   19920
agcggaggca gccgccgcgc gcaccggcgg cgacgccgcca ccagccgacg catgcgcggc     19980
ggggtgctgc ccctgttaat ccccctgatc gccgcggcga tcggcgccgt gcccgggatc   20040
gcctccgtgg ccttgcaagc gtcccagagg cattgacaga cttgcaaact tgcaaatatg   20100
gaaaaaaaaa cccaataaaa aaagtctaga ctctcacgct cgcttggtcc tgtgactatt   20160
ttgtagaatg gaagacatca actttcgtc gctggcccccg cgtcacggct cgcgcccgtt    20220
cctgggacac tggaacgata tcggcaccag caacatgagc ggtggcgcct tcagttgggg   20280
ctctctgtgg agcggcatta aaagtatcgg gtctgccgtt aaaaattacg gctcccgggc   20340
ctggaacagc agcacgggcc agatgttgag agacaagttg aaagagcaga acttccagca   20400
gaaggtggtg gagggcctgg cctccggcat caacggggtg gtggacctgg ccaaccagcc   20460
cgtgcagaat aagatcaaca gcagactgga ccccccggag aagtgccgcc                20520
ggcgctggag acggtgtccc ccgatggcg tggcagaag cgcccggcc ccgatagga      20580
agagaccact ctggtcacgc agaccgatga gccgcccccg tatgaggagg ccctgaagca   20640
aggtctgccc accacgcggc ccatcgcgcc catggccacc ggggtggtgg gccgccacac   20700
ccccgccacg ctggacttgc ctccgcccgc cgatgtgccg cagcagcaga aggcggcaca   20760
gccgggcccg ccgcgaccg cctcccgttc ctccgccggt cctctgcgcc gcgcggccag   20820
```

```
cggcccccgc gggggggtcg cgaggcacgg caactggcag agcacgctga acagcatcgt   20880
gggtctgggg gtgcggtccg tgaagcgccg ccgatgctac tgaatagctt agctaacgtg   20940
ttgtatgtgt gtatgcgccc tatgtcgccg ccagaggagc tgctgagtcg ccgccgttcg   21000
cgcgcccacc accaccgcca ctccgcccct caagatggcg accccatcga tgatgccgca   21060
gtggtcgtac atgcacatct cgggccagga cgcctgagcc tacctgagcc ccgggctggt   21120
gcagttcgcc cgcgccaccg agagctactt cagcctgagt aacaagttta ggaaccccac   21180
ggtggcgccc acgcacgatg tgaccaccga ccggtctcag cgcctgacgc tgcggttcat   21240
tcccgtggac cgcgaggaca ccgcgtactc gtacaaggcg cggttcaccc tggccgtggg   21300
cgacaaccgc gtgctggaca tggcctccac ctactttgac atccgcgggg tgctggaccg   21360
gggtcccact ttcaagccct actctgcac cgcctacaac tccctgcccc ccaagggcgc   21420
tcccaactcc tgcgagtggg agcaagagga aactcaggca gttgaagaag cagcagaaga   21480
ggaagaagaa gatgctgacg gtcaagctga ggaagagcaa gcagctacca aaaagactca   21540
tgtatatgct caggctcccc tttctggcga aaaaattagt aaagatggtc tgcaaatagg   21600
aacggacgct acagctacag aacaaaaacc tatttatgca gaccctacat tccagcccga   21660
accccaaatc ggggagtccc agtggaatga ggcagatgct acagtcgccg cggtagagt   21720
gctaaagaaa tctactccca tgaaaccatg ctatggttcc tatgcaagac ccacaaatgc   21780
taatggaggt cagggtgtac taacggcaaa tgcccaggga cagctagaat ctcaggttga   21840
aatgcaattc ttttcaactt ctgaaaacgc ccgtaacgag gctaacaaca ttcagcccaa   21900
attggtgctg tatagtgagg atgtgcacat ggagaccccg gatacgcacc tttcttacaa   21960
gcccgcaaaa agcgatgaca attcaaaaat catgctgggt cagcagtcca tgcccaacag   22020
acctaattac atcggcttca gagacaactt tatcggcctc atgtattaca atagcactgg   22080
caacatggga gtgcttgcag gtcaggcctc tcagttgaca cagtggtgg acttgcaaga   22140
cagaaacaca gaactgtcct accagctctt gcttgattcc atgggtgaca gaaccagata   22200
cttttccatg tggaatcagg cagtggacag ttatgcccca gatgttagaa ttattgaaaa   22260
tcatggaact gaagacgagc tccccaacta ttgtttccct ctgggtggca tagggggtaac   22320
tgacacttac caggctgtta aaaccaacaa tggcaataac agggggccagg tgacttggac   22380
aaaagatgaa acttttgcag atcgcaatga aataggggtg ggaaacaatt tcgctatgga   22440
gatcaacctc agtgccaacc tgtgagagaa cttcctgtac tccaacgtgg cgctgtacct   22500
accagacaag cttaagtaca accccctccaa tgtggacatc tctgacaacc ccaacaccta   22560
cgattacatg aacaagcgag tggtggcccc ggggctggtg gactgctaca tcaacctggg   22620
cgcgcgctgg tcgctggact acatggacaa cgtcaaccag ttcaaccacc accgcaatgc   22680
gggcctgcgc taccgctcca tgctcctggg caacgggcgc tacgtgccct tccacatcca   22740
ggtgccccaa aagttctttg ccatcaagaa cctcctcctc ctgccgggct cctacaccta   22800
cgagtggaac ttcaggaagg atgtcaacat ggtcctccag agctctctgg gtaacgatct   22860
cagggtggac ggggccagca tcaagttcga gagcatctgc ctctacgcca ccttcttccc   22920
catgcccac aacacggcct ccacgctcga ggccatgctc aggaacgaca ccaacgacca   22980
gtccttcaat gactacctct ccgccgcaa catgctctac cccatacccg ccaacgccac   23040
caacgtcccc atctccatcc cctcgcgcaa ctgggcggcc ttccgcggct gggccttcac   23100
ccgcctcaag accaaggaga cccctcctt gggctcggga ttcgacccct actacacta   23160
ctcgggctcc attccctacc tggacgggac cttctacctc aaccacactt tcaagaaggt   23220
ctcggtcacc ttcgactcct cggtcagctg gccgggcaac gaccgtctgc tcaccccaa   23280
cgagttcgag atcaagcgct cggtcgacgg ggagggctac aacgtggccc agtgcaacat   23340
gaccaaggac tggttcctgg tccagatgct ggccaactac aacatcggct accgggcttc  23400
ctacatccca gagagctaca aggacaggat gtactccttc tcaggaact tccagccat    23460
gagccggcag gtggtggacc agaccaagta caaggactac caggaggtgg gcatcatcca   23520
ccagcacaac aactcgggct tcgtgggcta cctcgccccc accatgcgcg agggacaggc   23580
ctaccccgcc aactcccct atcgctcat aggcaagacc gcggtcgaca gcatcaccca   23640
gaaaaagttc ctctgcgacc gcaccctctg gcgcatcccc ttctccagca acttcatgtc   23700
catgggtgcg ctctcggacc tgggccagaa cttgctctac gccaactccg cccacgccct   23760
cgacatgacc ttcgaggtcg accccatgga cgagcccacc cttctctatg ttctgttcga   23820
agtcttttga gtggtccggg tccaccagcc gcaccgccgc gtcatcgaga ccgtgtacct   23880
gcgtacgccc ttctcggccg gcaacgccac cacctaaaga agcaagccgc agtcatcgcc   23940
gcctgcatgc cgtcgggttc caccgagcaa gagctcaggg ccatcgtcag agacctggga   24000
tgcgggccct atttttttggg caccttcgac aagcgcttcc ctggctttgt ctcccccacac   24060
aagctgccct gcgccatcgt caacacggcc ggccgcgaga ccgggggcgt gcactggctg   24120
gccttcgcct ggaacccgcg ctccaaaaca tgcttcctct tgacccctt cggcttttcg   24180
gaccagcggc tcaagcaaat ctacgagttc gagtacgagg cttgctgcg tcgcagcgcc   24240
atcgcctcct cgcccgaccg ctgcgtcacc ctcgaaagt ccaccagac cgtgcagggg   24300
cccgactcgg ccgcctgcgg tctcttctgc tgcatgtttc tgcacgcctt tgtgcactgg   24360
cctcagagtc ccatgcaccg caacccccacc atgaacttgc tgacggggt gcccaactcc   24420
atgctccaga gccccaggt cgagcccacc ctgcgccgca accaggagca gctctacagc   24480
ttcctggagc gccactcgcc ttacttccgc cgccacagcg cacagatcag gagggccacc   24540
tccttctgcc acttgcaaga gatgcaagaa gggtaataac gatgtacaca ctttttttct   24600
caataaatgg catcttttta tttatacaag ctctctgggta tattcatttc ccaccaccac   24660
ccgccgttgt cgccatctgg ctctatttag aaatcgaaag ggttctgccg ggagtcgccg   24720
tgcgccacgg gcaggacac gttgcgatac tggtagcggg tgcccacttt gaactcgggc   24780
accaccaggc gaggcagctc ggggaagttt tcgctccaca ggctgcgggt cagcaccagc   24840
gcgttcatca ggtcgggcgc cgagatcttg aagtcgcagt tggggccgcc gcctgcgcg   24900
cgcagttgc ggtacaccgg gttgcagcac tggaacacca acagcgccgg gtgcttcacg   24960
ctggccagca cgctgcgtc ggagatcagc tcggcgtcca ggtcctccgc gttgctcagc   25020
gcgaacgggg tcatcttggg cacttgccgc cccaggaagg gcgcgtgccc cggtttcgag   25080
ttgcagtcgc agcgcagcgg gatcagcagg tgcccgtgcc cggactcggc gttggggtac   25140
agcgcgcgca tgaaggcctg catctggcgg aaggccatct gggccttggc gccctccgag   25200
aagaacatgc gcaggacatt gcccgaagac tggtttggcg gcagctggc gtcgtgcagg   25260
cagcagcgcg cgtcggtgtt ggcgatctgc accacgttgc gccccaccg gttcttcacg   25320
atcttggcct tggacgattg ctccttcagc gcgcgctgcc cgttctcgct ggtcacatcc   25380
atctcgatca catgttcctt gttcaccatg ctgctgccgt gcagacactt cagctcgccc   25440
tccgtctcgg tgcagcggtg ctgccacagc gcgcagcccg tgggctcgaa agacttgtag   25500
gtcacctccg cgaaggactg caggtacccc tgcaaaaagc ggcccatcat ggtcacgaag   25560
```

```
gtcttgttgc tgctgaaggt cagctgcagc ccgcggtgct cctcgttcag ccaggtcttg   25620
cacacggccg ccagcgcctc cacctggtcg ggcagcatct tgaagttcac cttcagctca   25680
ttctccacgt ggtacttgtc catcagcgtg cgcgccgcct ccatgccctt ctcccaggcc   25740
gacaccagcg gcaggctcac gggttcttc accatcaccg tggccgccgc ctccgccgcg   25800
ctttcgcttt cgccccgct gttctcttcc tcttcctcct cttcctcgcc gccgccact    25860
cgcagccccc gcaccacggg gtcgtcttcc tgcaggcgct gcaccttgcg cttgccgttg   25920
cgccctgct tgatgcgcac gggcggttg ctgaagccca ccatcaccag cgcggcctct    25980
tcttgctcgt cctcgctgtc cagaatgacc tccggggagg gggggttggt catcctcagt   26040
accgaggcac gcttctttt cttcctgggg gcgttcgcca gctccgcgc tgcggccgct    26100
gccgaggtcg aaggccgagg gctgggcgtg cgcggcacca gcgcgtcctg cgagccgtcc   26160
tcgtcctcct cggactcgag acggaggcgg gcccgcttct tcggggcgcg gcggggcggc   26220
ggaggcggcg gcggcgacgg agacggggac gagacatcgt ccagggtggg tggacggcgg   26280
gccgcgccgc gtccgcgctc gggggtggtc tcgcgctggt cctcttcccg actggccatc   26340
tcccactgct ccttctccta taggcagaaa gagatcatgt agtctctcat gcgagtcgag   26400
aaggaggagg acagcctaac cgccccctct gagccctcca ccaccgccgc caccaccgcc   26460
aatgccgccg cggacgacgc gcccaccgag accaccgcca gtaccaccct cccagcgac    26520
gcaccccgc tcgagaatga agtgctgatc gagcaggacc cgggttttgt gagcggagag    26580
gaggatgagg tggatgagaa ggagaaggag gaggtcgccg cctcagtgcc aaaagaggat   26640
aaaaagcaag accaggacga cgcagataag gatgagacag cagtcgggcg ggggaacgga   26700
agccatgatg ctgatgacgg ctacctagac gtgggagacg acgtgctgct taagcacctg   26760
caccgccagt gcgtcatcgt ctgcgacgcg ctgcaggagc gctgcgaagt gccctggac    26820
gtggcgagg tcagccgcgc ctacgagcgg cacctcttcg cgccgcacgt gcccccaag    26880
cgccgggaga acggcacctg cgagcccaac ccgtctca acttctaccc ggtcttcgcg     26940
gtacccgagg tgctggccac ctaccacatc ttttccaaa actgcaagat ccccctctcc   27000
tgccgcgcca accgcacccg cgccgacaaa accctgaccc tgcggcaggg cgcccacata   27060
cctgatatcg cctctctgga ggaagtgccc aagatctcgg agggtctcgg tcgcgacgag   27120
aaacgggcgg cgaacgctct gcacggagac agcgaaaacg agagtcactc ggggtgctg   27180
gtggagctcg agggcgacaa cgcgcgcctg gccgtactca agcgcagcat agaggtcacc   27240
cactttgcct acccggcgct caacctgccc cccaaggtca tgagtgtggt catgggcgag   27300
ctcatcatgc gccgcgccca gccctgcc gcggatgcaa acttgcaaga gtcctccag     27360
gaaggcctgc ccgcggtcag cgacgagcag ctggcgcgct ggctggagac ccgcgacccc   27420
gcgcagctgg aggagcggcg caagctcatg atggccgcgg tgctggtcac cgtggagctc   27480
gagtgtctgc agcgcttctt cgcggacccc gagatgcagc gcaagctcga ggagaccctg   27540
cactacacct tccgccaggg ctacgtcgcg caggcctgca agatctccaa cgtggagctc   27600
tgcaacctgg tctcctacct gggcatcctg cacgagaacc gcctcgggca gaacgtcctg   27660
cactccaccc tcaaagggga ggcgcgccgc gactacatcc gcgactgcgc ctacctcttc   27720
ctctgctaca cctggcagac ggccatgggg gtctggcagc agtgcctgga ggagcgcaac   27780
ctcaaggagc tggaaaagct cctcaagcgc accctcaggg acctggac gggcttcaac    27840
gagcgctcgg tggccgccgc gctggcggac atcatctttc ccgagcgcct gctcaagacc   27900
ctgcagcagg gcctgcccga cttcaccagc cagagcatgc tgcagaactt caggactttc   27960
atcctggagc gctcgggcat cctgccgcc acttgctgcg cgctgcccag cgacttcgtg    28020
cccatcaagt acagggagtg cccgccgccg ctctggggcc actgctacct cttccagctg   28080
gccaactacc tcgcctacca ctcggacctc atggaagacg tgagcggcga gggcctgctc   28140
gagtgccact gccgctgcaa cctctgcacg ccccaccgct ctctagtctg caacccgcag   28200
ctgctcagcg agagtcagat tatcggtacc ttcgagctgc agggtccctc gcctgacgag   28260
aagtccgcgc ctccagggct gaaactcact ccggggctgt ggacttccgc ctacctacgc   28320
aaatttgtac ctgaggacta tcacgcccac gagatcaagt tctacgaaga ccaatccgc    28380
ccgcccaagg cggagctcac cgcctgcgtc atcacccagg ggcacatcct gggccaattg   28440
caagccatca acaaagcccg ccgagagttc ttgctgaaaa agggtcgggg ggtgtacctg   28500
gaccccagt ccggcgagga gctaaacccg ctaccccgc cgccgcccca gcagcgggac     28560
cttgcttccc aggatggcac ccagaaagaa gcagcagccg ccgccgccg cgcagccata   28620
catgcttctg gaggaagagg aggaggactg ggacagtcag gcagaggagg tttcggacga   28680
ggagcaggag gagatgatgg aagactggga ggaggacagc agcctagacg aggaagcttc   28740
agaggccgaa gaggtggcag acgcaacacc atcgccctcg gtcgcagccc cctcgccggg   28800
gcccctgaaa tcctccgaac ccagcaccag cgctataacc tccgctcctc cggcgccggc   28860
gccaccgcc cgcagaccca accgtagatg ggacaccaca ggaaccgggg tcggtaagtc   28920
caagtgccg ccgccgccac cgcagcagca gcagcagcag cgccagggct accgctcgtg    28980
gcgcgggcac aagaacgcca tagtcgcctg cttgcaagac tgcgggggca acatctcttt   29040
cgcccgccgc ttcctgctat tccaccacgg ggtcgccttt ccccgcaatg tcctgcatta   29100
ctaccgtcat ctctacagcc cctactgcag cggcgaccca gaggcggcag cggcagccac   29160
agcggcgacc accacctagg aagatatcct ccgcgggcaa gacagcggca gcagcggcca   29220
ggagacccgc ggcagcagcg gcgggagcgg tgggcgcact gcgcctctcg cccaacgaac   29280
ccctctcgac ccgggagctc agacacagga tcttccccac tttgtatgcc atcttccaac   29340
agagcagagg ccaggagcag gagctgaaaa taaaaaacag atctctgcac tccctcaccc   29400
gcagctgtct gtatcacaaa agcgaagatc agcttcggcg cacgctggag gacgcggagg   29460
cactcttcag caaatactgc gcgctcactc ttaaagacta gctccgcgcc cttctcgaat   29520
ttaggcggga gaaactacg tcatcgcggg ccgccgccca gccgcccag ccgagatgag    29580
caaagagatt cccacgccat acatgtggag ctaccaccg cagatgggac tcgcggcggg   29640
agcgcccag gactactcca cccgcatgaa ctacatgagc gcgggacccc acatgatctc   29700
acaggtcaac gggatccgcg cccagcgaaa ccaaatactg ctggaacagg cggccatcac   29760
cgccacgccc cgccataatc tcaacccccg aaattggccc gccgccctcg tgtaccagga   29820
aaccccctcc gccaccaccg tactacttcc gcgtgacgcc caggccgaag tccagatgac   29880
taactcaggg gcgcagctcg cgggcggctt tcgtcacggg gcgcggccgc tccgaccagg   29940
tataagacac ctgatgatca gaggcgagg tatccgcatc aacgacgagt cggtgagctc   30000
ttcgctcggt ctccgtccgg acggaacttt ccagctcgcc ggatccggcc gctcttcgtt   30060
cacgccccgc caggcgtacc tgactctgca gacctcgtcc tcggagcccc gctccggcgg   30120
catcggaacc ctccagttcg tggaggagtt cgtgccctcg gtctacttca cccccttctc   30180
gggacctccc ggacgctacc ccgaccagtt cattccgaac tttgacgcgg tgaaggactc   30240
ggcggacggc tacgactgaa tgtcaggtgt cgaggcagag cagcttcgcc tgagacacct   30300
```

```
cgagcactgc cgccgccaca agtgcttcgc ccgcggttct ggtgagttct gctactttca   30360
gctacccgag gagcataccg aggggccggc gcacggcgtc cgcctgacca cccagggcga   30420
ggttacctgt tccctcatcc gggagtttac cctccgtccc ctgctagtgg agcgggagcg   30480
gggtccctgt gtcctaacta tcgcctgcaa ctgccctaac cctggattac atcaagatct   30540
ttgctgtcat ctctgtgctg agtttaataa acgctgagat cagaatctac tgggatttag   30600
tccccttttaa ctaatcaaac actggaatca ataaaaagaa tcacttactt aaaatcagac   30660
agcaggtctc tgtccagttt attcagcagc acctccttcc cctcctccca actctggtac   30720
tccaaacgcc ttctggcggc aaacttcctc cacaccctga agggaatgtc agattcttgc   30780
tcctgtccct ccgcacccac tatcttcatg ttgttgcaga tgaagcgcac caaaacgtct   30840
gacgagagct tcaacccccgt gtaccctat gacacggaaa gcggccctcc ctccgtccct   30900
ttcctcaccc ctcccttcgt gtctcccgat ggattccaag aaagtccccc cggggtcctg   30960
tctctgaacc tggccgagcc cctggtcact tccacggca tgctcgccct gaaaatggga   31020
agtggcctct ccctggacga cgctggcaac ctccctctc aagatatcac caccgctagc   31080
cctcccctca aaaaaaccaa gaccaacctc agcctagaaa cctcatcccc cctaactgtg   31140
agcacctcag gcgcccctcac cgtagcagcc gccgctcccc tggcggtggc cggcacctcc   31200
ctcaccatgc aatcagaggc ccccctgaca gtacaggatg caaaactcac cctggccacc   31260
aaaggcccccc tgaccgtgtc tgaaggcaaa ctggccttgc aaacatcggc cccgctgacg   31320
gccgctgaca gcagcaccct cacagtcagt gccacaccac cccttagcac aagcaatggc   31380
agcttgggta ttgacatgca agcccccatt tacaccacca atggaaaact aggacttaac   31440
tttggcgctc ccctgcatgt ggtagacagc ctaaatgcac tgactgtagt tactggccaa   31500
ggtcttacga taaacggaac agcctacaa actagagtct caggtgccct caactatgac   31560
acatcaggaa acctagaatt gagagctgca ggggtgatgc gagttgatgc aaatggtcaa   31620
cttatccttg atgtagctta cccatttgat gcacaaaaca atctcagcct taggcttgga   31680
cagggacccc tgtttgttaa ctctgcccac aacttggatg ttaactacaa cagaggcctc   31740
tacctgttca catctggaaa taccaaaaag ctagaagtta atatcaaaac agccaagggt   31800
ctcatttatg atgacactgc tatagcaatc aatgcggtatg atgggctaca gtttgactca   31860
ggctcagata caaatccatt aaaaactaaa cttggattag gactggatta tgactccagc   31920
agagccataa ttgctaaact gggaactggc ctaagctttg acaacacagg tgccatcaca   31980
gtaggcaaca aaaatgatga caagcttacc ttgtggacca caccagaccc atcccctaac   32040
tgtagaatct attcagagaa agatgctaaa ttcacactt ttttgactaa atgcggcagt   32100
caggtgttgg ccagcgtttc tgttttatct gtaaaaggta gccttgcgcc catcagtggc   32160
acagtaacta gtgctcagat tgtcctcaga tttgatgaaa atggagtct actaagcaat   32220
tcttcccttg accctcaata ctggaactac agaaaaggtg accttacaga gggcactgca   32280
tataccaacg cagtgggatt tatgcccaac ctcacagcat acccaaaaac acagagccaa   32340
actgctaaaa gcaacattgt aagtcaggtt tacttgaatg gggacaaatc caaacccatg   32400
accctcacca ttaccctcaa tggaactaat gaaacaggag atgccacagt aagcacttac   32460
tccatgtcat tctcatggaa ctggaatgga agtaattaca ttaatgaaac gttccaaacc   32520
aactccttca ccttctccta catcgcccaa gaataaaaag catgacgctg ttgatttgat   32580
tcaatgtgtt tctgttttat tttcaagcac aacaaaatca ttcaagtcat tcttccatct   32640
tagcttaata gacacagtag cttaatagac ccagtagtgc aaagccccat tctagcttat   32700
aactagtgga gaagtactcg cctacatggg ggtagagtca taatcgtgca tcaggatagg   32760
gcggtggtgc tgcagcagcg cgcgaataaa ctgctgccgc cgccgctccg tcctgcagga   32820
atacaacatg cagtggtct cctcagcgat gattcgcacc gcagca taaggcgcct   32880
tgtcctccgg gcacagcagc gcaccctgat ctcacttaaa tcagcacagt aactgcagca   32940
cagcaccaca atattgttca aaatcccaca gtgcaaggcg ctgtatccaa agctcatggc   33000
ggggaccaca gaacccacgt ggccatcata ccacaagcgc aggtagatta agtggcgacc   33060
cctcataaac acgctggaca taaacattac ctcttttgga tgttgtaat tcaccacctc   33120
ccggtaccat ataaacctct gattaaacat ggcgccatcc accaccatcc taaaccagct   33180
ggccaaaacc tgcccgccgg ctatacactg cagggaaccg ggactggaac aatgacagtg   33240
gagagcccag gactcgtaac catggatcat catgctcgtc atgatatcaa tgttggcaca   33300
acacaggcac acgtgcatac acttcctcag gattacaagc tcctcccgcg ttagaaccat   33360
atcccaggga acaacccatt cctgaatcag cgtaaatccc acactgcagg gaagacctcg   33420
cacgtaactc acgttgtgca ttgtcaaagt gttacattcg ggcagcagcg gatgatcctc   33480
cagtatggta gcgcgggttt ctgtctcaaa aggaggtaga cgatcccctac tgtacggagt   33540
gcgccgagac aaccgagatc gtgttggtcg tagtgtcatg ccaaatggaa cgccggacgt   33600
agtcatattt cctgaagtct tagatctctc aacgcagcac cagcaccaac acttcgcagt   33660
gtaaaaggcc aagtgccgag agagtatata taggaataaa aagtgacgta aacgggcaaa   33720
gtccaaaaaa cgcccagaaa aaccgcacgc gaacctacgc cccgaaacga aagccaaaaa   33780
acactagaca ctcccttccg gcgtcaactt ccgctttccc acgctacgtc acttgcccca   33840
gtcaaacaaa ctacatatcc cgaacttcca agtcgccacg cccaaaaacac cgcctacacc   33900
tccccgcccg ccggccgcc cccaaacccg cctcccgccc cgcgcccgc ccgcgccgc   33960
ccatctcatt atcatattgg cttcaatcca aaataaggta tattattgat gatggtttaa   34020
acggatcctc tagagtcgac ctgcaggcat gcaagcttga gtattctata gtgtcaccta   34080
aatagcttgg cgtaatcatg gtcatagctg tttcctgtgt gaaattgtta tccgctcaca   34140
attccacaca acatacgagc cggaagcata aagtgtaaag cctggggtgc ctaatgagtg   34200
agctaactca cattaattgc gttgcgctca ctgcccgctt tccagtcggg aaacctgtcg   34260
tgccagctgc attaatgaat cggccaacgc gaacccttg cggccgcccg gccgtcgac   34320
caattctcat gtttgacagc ttatcatcga atttctgcca ttcatccgct tattatcact   34380
tattcaggcg tagcaaccag gcgtttaagg gcaccaataa ctgccttaaa aaaattacgc   34440
cccgccctgc cactcatcgc agtactgttg taattcatta agcattctgc cgacatggaa   34500
gccatcacaa acggcatgat gaacctgaat cgccagcggc atcagcacct tgtcgccttg   34560
cgtataatat ttgcccatgg tgaaacgggg gcgaagaag ttgtccatat tggccacgtt   34620
taaatcaaaa ctggtgaaac tcacccaggg attggctgag acgaaaaaca tattctcaat   34680
aaacccttta gggaaatagg ccaggttttc accacatctt gcgaatatat   34740
gtgtagaaac tgccgaaat cgtcgtggta ttcactccag agcgatgaaa acgtttcagt   34800
ttgctcatgg aaaacggtgt aacaggggtg aacactatcc catatcacca gctcaccgtc   34860
tttcattgcc atacggaatt ccggatgagc attcatcagg cggcaagaa tgtgaataaa   34920
ggccggataa aacttgtgct tatttttctt tacggtcttt aaaaaggccg taatatccag   34980
ctgaacggtc tggttatagg tacattgagc aactgactga aatgcctcaa aatgttcttt   35040
```

```
acgatgccat tgggatatat caacggtggt atatccagtg attttttttct ccattttagc   35100
ttccttagct cctgaaaatc tcgataactc aaaaaatacg cccggtagtg atcttatttc   35160
attatggtga aagttggaac ctcttacgtg ccgatcaacg tctcattttc gccaaaagtt   35220
ggcccagggc ttcccggtat caacaggac accaggattt atttattctg cgaagtgatc   35280
ttccgtcaca ggtatttatt cgcgataagc tcatggacgg gcgtaaccgt cgcacaggaa   35340
ggacagagaa agcgcggatc tgggaagtga cggacagaac ggtcaggacc tggattgggg   35400
aggcggttgc cgccgctgct gctgacggtg tgacgttctc tgttccggtc acaccacata   35460
cgttccgcca ttcctatgcg atgcacatgc tgtatgccgg tataccgctg aaagttctgc   35520
aaagcctgat gggacataag tccatcagtt caacggaagt ctacacgaag gttttttgcgc   35580
tggatgtggc tgcccggcac cgggtgcagt ttgcgatgcc ggagtctgat gcggttgcga   35640
tgctgaaaca attatcctga gaataaatgc cttggccttt atatggaaat gtggaactga   35700
gtggatatgc tgttttttgtc tgttaaacag agaagctggc tgttatccac tgagaagcga   35760
acgaaacagt cgggaaaatc tcccattatc gtagagatcc gcattattaa tctcaggagc   35820
ctgtgtagcg tttataggaa gtagtgttct gtcatgatgc ctgcaagcgg taacgaaaac   35880
gatttgaata tgccttcagg aacaatagaa atcttcgtgc ggtgttacgt tgaagtggag   35940
cggattatgt cagcaatgga cagaacaacc taatgaacac agaaccatga tgtggtctgt   36000
cctttttacag ccagtagtgc tcgccgcagt cgagcgacag ggcgaagccc tcgagtgagc   36060
gaggaagcac cagggaacag cacttatata ttctgcttac acacgatgcc tgaaaaaact   36120
tcccttgggg ttatccactt atccacgggg atatttttat aattatttttt tttatagttt   36180
ttagatcttc ttttttagag cgccttgtag gcctttatcc atgctggttc tagagaaggt   36240
gttgtgacaa attgcccttt cagtgtgaca aatcaccctc aaatgacagt cctgtctgtg   36300
acaaattgcc cttaaccctg tgacaaattg ccctcagaag aagctgtttt ttcacaaagt   36360
tatccctgct tattgactct ttttttattta gtgtgacaat ctaaaaactt gtcacacttc   36420
acatggatcc gtcatggcgg aaacagcggt tatcaatcac aagaaacgta aaaatagccc   36480
gcgaatcgtc cagtcaaacg acctcactga ggcggcatat agtctctccc gggatcaaaa   36540
acgtatgctg tatctgttcg ttgaccagat cagaaaatct gatggcaccc tacaggaaca   36600
tgacggtatc tgcgagatcc atgttgctaa atatgctgaa atattcggat tgacctctgc   36660
ggaagccagt aaggatatac ggcaggcatt gaagagtttc gcggggaagg aagtggtttt   36720
ttatcgccct gaagaggatg ccggcgatga aaaaggctat gaatcttttc cttggtttat   36780
caaacgtgcg cacagtccat ccagagggct ttacagtgta catatcaacc catatctca   36840
tcccttcttt atcgggttac agaaccggtt tacgcagttt cggcttagtg aaacaaaaga   36900
aatcaccaat ccgtatgcca tgcgtttata cgaatccctg tgtcagtatc gtaagccgga   36960
tggctcaggc atcgtctctc tgaaaatcga ctggatcata gagcgttacc agctgcctca   37020
aagttaccag cgtatgcctg acttccgccg ccgcttcctg caggtctgtg ttaatgagat   37080
caacagcaga actccaatgc gcctctcata cattgaagaa aagaaggcc gccagacgac   37140
tcatatcgta ttttccttcc gcgatatcac ttccatgacg acaggatagt ctgagggtta   37200
tctgtcacag atttgagggt ggttcgtcac atttgttctg acctactgag ggtaatttgt   37260
cacagttttg ctgtttcctt cagcctgcat ggatttttctc atactttttg aactgtaatt   37320
tttaaggaag ccaaatttga gggcagtttg tcacagtttga tttccttctc tttcccttcg   37380
tcatgtgacc tgatatcggg ggttagttcg tcatcattga tgaggggttga ttatcacagt   37440
ttattactct gaattggcta tccgcgtgtg tacctctacc tggagttttt cccacggtgg   37500
atatttcttc ttgcgctgag cgtaagagct atctgacaga acagttcttc tttgcttcct   37560
cgccagttcg ctcgctatgc tcggttacac ggctgcgcgg agcgctagtg ataataagtg   37620
actgaggtat gtgctcttct tatctccttt tgtagtgttg ctcttatttt aaacaacttt   37680
gcggtttttt gatgactttg cgattttgtt gttgctttgc agtaaattgc aagatttaat   37740
aaaaaaacgc aaagcaatga ttaaggatg ttcagaatga aactcatgga aacacttaac   37800
cagtgcataa acgctggtca tgaaatgacg aaggctatcg ccattgcaca gtttaatgat   37860
gacagcccgg aagcgaggaa aataacccgg cgctgagaaa taggtgaagc agcggattta   37920
gttgggggttt cttctcaggc tatcagagat gccgagaaag cagggcgact accgcacccg   37980
gatatggaaa ttcgaggacg ggttgagcaa cgtgttggtt atacaattga acaaattaat   38040
catatgcgtg atgtgtttgg tacgcgattg cgacgtgctg aagacgtatt tccaccggtg   38100
atcgggggttg ctgccataaa aggtggcgtt tacaaaacct cagtttctgt tcatcttgct   38160
caggatctgg ctctgaaggg gctacgtgtt ttgctcgtgg aagtaacga ccccagggga   38220
acagcctcaa tgtatcacgg atgggtacca gatcttcata ttcatgcaga agacactctc   38280
ctgccttttct atcttggga aaggacgat gtcacttatg caataaagcc cacttgctgg   38340
ccggggcttg acattattcc ttcctgtctg gctctgcacc gtattgaaac tgagttaatg   38400
ggcaaatttg atgaaggtaa actgcccacc gatccacacc tgatgctccg actgccatt   38460
gaaactgttg ctcatgacta tgatgtcata gttattgaca gcgcgcctaa cctgggtatc   38520
ggcacgatta atgtcgtatg tgctgctgat gtgctgattg ttcccacgcc tgctgagttg   38580
tttgactaca cctccgcact gcagttttttc gatatgcttc gtgatctgct caagaacgtg   38640
gatcttaaag ggttcgagcc tgatgtacgt atttttgctta ccaaatacag caatagtaat   38700
ggctctcagt ccccgtggat ggaggagcaa attcggatg cctggggaag catggttcta   38760
aaaaatgttg tacgtgaaac ggatgaagtt ggtaaaggtc agatccggat gagaactgtt   38820
tttgaacagg ccattgatca acgctcttca actggtgcct ggaaaaatgc tcttttcatt   38880
tgggaacctg tctgcaatga aattttcgat cgtctgatta accacgctg ggagattaga   38940
taatgaagcg tgcgcctgtt attccaaaac atacgctcaa tactcaaccg gttgaagata   39000
cttcgttatc gacaccagct gccccgatgg tggattcgtt aattgcgcgc gtaggagtaa   39060
tggctcgcgg taatgccatt actttgcctg tatgtggtcg ggatgtgaag tttactcttg   39120
aagtgctccg gggtgatagt gttgagaaga cctctcgggt atggtcaggt aatgaacgtg   39180
accaggagct gcttactgag gacgcactgg atgatctcat cccttctttt ctactgactg   39240
gtcaacagac accggcgttc ggtcgaagag tatctggtgt catagaaatt gccgatggga   39300
gtcgccgtca taaagctgct gcacttaccg aaagtgatta tcgtgttctg ttggcgagc   39360
tggatgatga gcagatggct gcattatcca gattgggtaa cgattatcgc ccaacaaagtg   39420
cttatgacag tggtcagcgt tatcaagcc gattgcagaa gttggaatatt   39480
ctgcgctgcg tgatgcggaa aatatttcac gtaagattat tacccgctgt atcaacaccg   39540
ccaaattgcc taaatcagtt gttgctcttt tttctcaccc cggtgaacta tctgcccggt   39600
caggtgatgc acttcaaaaa gcctttacag ataaagagga attacttaag cagcaggcat   39660
ctaaccttca tgagcagaaa aaagctgggg tgatatttga agctgaagaa gttatcactc   39720
ttttaacttc tgtgcttaaa acgtcatctg catcaagaac tagtttaagc tcacgacatc   39780
```

```
agtttgctcc tggagcgaca gtattgtata agggcgataa aatggtgctt aacctggaca    39840
ggtctcgtgt tccaactgag tgtatagaga aaattgaggc cattcttaag gaacttgaaa    39900
agccagcacc ctgatgcgac cacgttttag tctacgttta tctgtcttta cttaatgtcc    39960
tttgttacag gccagaaagc ataactggcc tgaatattct ctctgggccc actgttccac    40020
ttgtatcgtc ggtctgataa tcagactggg accacggtcc cactcgtatc gtcggtctga    40080
ttattagtct gggaccacgg tcccactcgt atcgtcggtc tgattattag tctgggacca    40140
cggtcccact cgtatcgtcg gtctgataat cagactggga ccacggtccc actcgtatcg    40200
tcggtctgat tattagtctg ggaccatggt cccactcgta tcgtcggtct gattattagt    40260
ctgggaccac ggtcccactc gtatcgtcgg tctgattatt agtctggaac cacgtcccca    40320
ctcgtatcgt cggtctgatt attagtctgg gaccacggtc ccactcgtat cgtcggtctg    40380
attattagtc tgggaccacg atcccactcg tgttgtcggt ctgattatcg gtctgggacc    40440
acggtcccac ttgtattgtc gatcagacta tcagcgtgag actacgattc catcaatgcc    40500
tgtcaagggc aagtattgac atgtcgtcgt aacctgtaga acggagtaac ctcggtgtgc    40560
ggttgtatgc ctgctgtgga ttgctgctgt gtcctgctta tccacaacat tttgcgcacg    40620
gttatgtgga caaaatacct ggttacccag gccgtgccgg cacgttaacc gggctgcatc    40680
cgatgcaagt gtgtcgctgt cgacgagctc gcgagctcgg acatgaggtt gccccgtatt    40740
cagtgtcgct gatttgtatt gtctgaagtt gttttttacgt taagttgatg cagatcaatt    40800
aatacgatac ctgcgtcata attgattatt tgacgtgtt tgatggcctc cagcacgtt    40860
gtgatatgta gatgataatc attatcactt tacgggtcct ttccggtgat ccgacaggtt    40920
acggggcggc gacctcgcgg gttttcgcta tttatgaaaa ttttccggtt taaggcgttt    40980
ccgttcttct tcgtcataac ttaatgtttt tatttaaaat accctctgaa aagaaaggaa    41040
acgacaggtg ctgaaagcga gcttttttggc ctctgtcgtt tcctttctct gtttttgtcc    41100
gtggaatgaa caatgaagt ccgagctcat cgctaatgaa ttcgtatagc atacattata    41160
cgaagttata ttcgatgcgg ccgcaagggg ttcgcgtcag cgggtgttgg cgggtgtcgg    41220
ggctggctta actatgcggc atcagagcag attgtactga gagtgcacca tatgcggtgt    41280
gaaataccgc acagatgcgt aaggagaaaa taccgcatca ggcgccattc gccattcagg    41340
ctgcgcaact gttgggaagg gcgatcggtg cgggcctctt cgctattacg ccagctggcg    41400
aaagggggat gtgctgcaag gcgattaagt tgggtaacgc cagggttttc ccagtcacga    41460
cgttgtaaaa cgacggccag tgaattgtaa tacgactcac tataggcga attcgagctc    41520
ggtacccggg gatcctcgtt taaac                                         41545

SEQ ID NO: 54          moltype = DNA   length = 42220
FEATURE                Location/Qualifiers
misc_difference        16789
                       note = modified_base - a, c, t, g, unknown or other
misc_feature           1..42220
                       note = Description of Artificial Sequence: Synthetic
                        polynucleotide
source                 1..42220
                       mol_type = other DNA
                       organism = synthetic construct
SEQUENCE: 54
catcatcaat aatataccttatttttggatt gaagccaata tgataatgag atgggcggcg    60
cggggcgggg cgcggggcgg gaggcgggtt tggggggcggg ccggcgggcg gggcggtgtg    120
gcggaagtgg actttgtaag tgtggcggat gtgacttgct agtgccgggc gcggtaaaag    180
tgacgttttc cgtgcgcgac aacgccccg ggaagtgaca tttttcccgc ggttttacc    240
ggatgttgta gtgaatttgg gcgtaaccaa gtaagatttg gccattttcg cgggaaaact    300
gaaacgggga agtgaaatct gattaatttt gcgttagtca taccgcgtaa tatttgtcta    360
gggccgaggg acttttggccg attacgtgga ggactcgccc aggtgttttt tgaggtgaat    420
ttccgcgttc cgggtcaaag tctgcgtttt attattatag gatatcccat tgcatacgtt    480
gtatccatat cataatatgt acatttatat tggctcatat ccaacattac cgccatgttg    540
acattgatta ttgactagtt attaatagta atcaattacg gggtcattag ttcatagccc    600
atatatggag ttccgcgtta cataacttac ggtaaatggc ccgcctggct gaccgcccaa    660
cgaccccgc ccattgacgt caataatgac gtatgttccc atagtaacgc caatagggac    720
tttccattga cgtcaatggg tggagtattt acggtaaact gcccacttgg cagtacatca    780
agtgtatcat atgccaagta cgccccctat tgacgtcaat gacggtaaat ggcccgcctg    840
gcattatgcc cagtacatga ccttatggga ctttcctact tggcagtaca tctacgtatt    900
agtcatcgct attaccatgg tgatgcggtt ttggcagtac atcaatgggc gtggatagcg    960
gtttgactca cggggatttc caagtctcca ccccattgac gtcaatggga gtttgttttg    1020
gcaccaaaat caacgggact ttccaaaatg tcgtaacaac tccgccccat tgacgcaaat    1080
gggcggtagg cgtgtacggt gggaggtcta tataagcaga gctctcccta tcagtgatag    1140
agatctccct atcagtgata gagatcgtcg acgagctcgt ttagtgaacc gtcagatcgc    1200
ctggagacgc catccacgct gttttgacct ccatagaaga caccgggacc gatccagcct    1260
ccgcgggggc gaacggtgca ttggaacgcg gattcccgtg ccaagagtg agatcttccg    1320
tttatctagg taccagatat cgccaccatg gacgaccagc gggacctgat cagcaacaac    1380
gagcagctgc ccatgctggg ccagaggcct ggcgccctg agcaagtg tagcagaggc    1440
gccgtgtaca ccgtgttcag catcctggtg gccctgctgc tggccggaca ggccaccacc    1500
gcctactttc tgtatcagca gcagggacgg ctggacaagc tgaccgtgac cagccagaac    1560
ctgcagctgg aaaacctgcg gatgaagctg cccaagcctg ccaagcccct gagccagatg    1620
agaatggcca cccccctgct gatgcaggcc ctgcctatgg ccggcctgcc cagaaacccc    1680
atgcagaacg ccaccaagca cggcaacatg accgaggacc acgtgatgca tctgctgctg    1740
aacgccgacc cctgaaggt gtaccccca ctgaagggca gcctgagcga gaacctgaag    1800
cacctgaaga cacaccatgga aaccatggac tggaaggtgt cgagagctg gctgcaccac    1860
tggctgtgt tcgagatgag caagcacagc ctggaacagc aggccgcctcc    1920
aaagagagc tggaactgga agatcccagc agcggcctgg gcgtgaccaa gcaggatctg    1980
ggccccgtgg ctatgtccga ggactttctg attctgatcg ccatcctggt gatcgtgatt    2040
ctcgtgggca caatcacaac cctggtgggc gccatcggcg cattagggc caggaggagc    2100
ttcctctcca tttgcatctt cttcctgttc ctctccctct tcctgacaat cctcgccctg    2160
ctgctgggct tcagctggct cctgctgtg gccatccgt tctgggtgct ctggctggtc    2220
```

```
atcctcattc tgctgctgct ggtgtaccct attcctcacc accccctgcc cacctccctc  2280
aggtttagaa tgaagcagag ggtgagcagc gaccccacag gttctgacag aagccctcag  2340
ggcagccata atagcctgaa ctcccccgat gaggaggacc ccaaggatga caccaagcaa  2400
cctctgtgca acatgaccca gggcggacct cccgtcaatg acagctcct cggacaacat  2460
gctcaatgcc cccctcacta tccctgctgc catattcagc atcccgacgg agaggattcc  2520
gatggagacg atggcaagtc ctggggcgat gccggagagg aagacaatgg ccctaacgac  2580
cctaacaccg ccagcaccag agagtccatt tacgaggacc tcagataccc cacaagggac  2640
gccaatggcg agtatgagaa cgtgggatac cccctaggg acggagatgc ccctcatagg  2700
ctcggagagc ctgtgtatga cgatgtggag caagccaccg ctaacgaggt gagaatctcc  2760
cctctgttca gactgcccta cggaagcgct ttcggacctg gccccagcc tggacccatt  2820
ctggagagct ccacatgggg ctttctggtc ttcacacaga cctccctgtt cgccgacgac  2880
attgccgacg ctattaggga ctactgcaca acccaccctg gcccacaag gaacacccag  2940
gtggtcctca tgaacttcga gggcagcgga gtgcccctgc ctatgttttt tcccccctgga 3000
gaggagacag aagagcagag agagggcgat agagctagcg actccgacga gtccgaagac  3060
gctcagatcc tgaccgtgtt ctgcctgttt tgccagtgga cactctttat ctgcctggga  3120
atcaggatga tctgtaactg gaggggcaaa ctcaccagga tcatctgcct gaagttctgc  3180
ctctacggac tgatttccgc ctccctgtcc ttcggctggt acgcttttct gaaggaagtg  3240
accctcccca ccacagccac cgttgatcct aggcaactcc ccctgttcct cttcatcctg  3300
agctccgtgc tggtgattct cgccatcatg atggagtttc aaacatcctc cagcctcttc  3360
gctgctctgt tcgtgattat cgccggaatg ctgtgcgtca cagtgggcgt gattttttctg 3420
ctggctggcg tcaagcctct cctgagcggc atgatctgcg cctccggcat cacaatgctc  3480
gtgctcggac tcgtgctgct ggtggtgtgc accagagatg agcacgctat ttccgccagc  3540
caccatgcta gcgatggctc cgtgaatcag cagaaggaaa atcagcccca gaccctggag  3600
gaatgcaaga cagatcagga gaggaagagg tacaggaaca ggctggcctc caggaggtgt  3660
agagctaagt tcaggaacca gctggaacat tttaggacag tcgccgctgc taagacagag  3720
gagaacaaca ggctcagggt gctcatcagg cagatgtgtc ctacactgga ctgtgaatcc  3780
atcgtcccct ccacctccgc cggctaccac gagcctctga atcacctgac ccacagcccc  3840
agcccttgtc atcacaggga tgaaccccce tccagaagcc ccagccctca acccaccgtc  3900
tccgagcagt cccagcagtc ccccaggcag cagagccctc aaggcacatc ccagggttct  3960
acaagacctc aggtgcctgg aggcgccacc accagaaaa gaggcggcgt ggagaggccaa 4020
cctgccaagt gtcacggcaa gtacaccaca accgccgagg gactgaccgc tctcctgaat  4080
aggaggcaca gccccaggac atccaacgag ggcaggtgga tgaatggagt catggctgtg  4140
aacctctcca aatggcccct gtacagcctg aggagagccc tggccctcgc catggctcct  4200
agaaggaggc tctccggccc tccctggctg acagtgctgc tgctgctgtc cacactgagc  4260
gtggccgccc tgctgattct cttcctgatt ttcagcgccg gcgccaccat tagcacagaa  4320
gccagcctgc tggtcctgct cctgctgttt gtgaccctgc tgctgcctct cctgtcctcc  4380
aacgactcc agctccctgc cgccctgatt ctgatccagt gtttcctcct ggccgctgat  4440
tatctcgcct acctgattct gcctaccatt atgcccaggg gcagaagcac aggaaggaag  4500
ggcagggaca cagagaaaga gaggacagaa tccccctctca gagctcctgg cggttctgat  4560
ggacccagca caagggctgg ctgtggagcc ggaccctgtc agctgagcgg ccccatcgcc  4620
ggaaacaacg gcaatgaagg cggcgagggc gacgactaca agagctggag gaagcccgag  4680
gaagaggaca acggccccaa tgaccccaat accaacaaca ggattgagga tggagacggc  4740
gacgacggaa aatcctgag gaataatcctgag gaggaggata acagaaagca gacaggctgg 4800
ggcaccaagc ctttcatgga cctcgacgga accgccggag gcgagggcta cagccagatg  4860
gtccctatcg ccaccgcccc cggaagcggc cacgccgcta cctatcagga tctccaggcc  4920
gccccttaca tcatctggcc tctccagacc gattgccagc tgtggctac caccttcgcc  4980
tcccccggac agatccagtg gtatacaagc gccgtcccc agcccacaga gcattgctcc  5040
cagtttacaa acgctcccac cgtcaaccag cagcagccta ttagccaacc ccagcccgaa  5100
aatcccctg cttccacctt tacccagccc gcttccatca ttcccggcgt cattagcgcc  5160
tccaacctga acgtgagcgc ttcccctatc atccctagcg accatgtcct cccccatcatt  5220
acctccgtga ccagcctcgc ccaacctaat aacatggccg gccactgta tgagagcgtg  5280
attcccggcc tgttcctctg ccccctgatc ctccttccc tgttctggat ttgctccctg 5340
ctgaccttcc tggtgggcca cggagccaat attgtgagcg ccgtcctgtt cctcgtgctg  5400
gcttggtgtc tcctcattgc caactggaac gtgacaagag aggacttcgt gtccggcagg  5460
agaagctcca tgagcagcct gtccgtggcc gcttccaccg ccacagccat gttcgccagc  5520
ttcctcaccc tgagctttga tggcctgggc ctgctgctgt ttggcaccgc cctggtgatc  5580
cagacaattt acgtgctgta tctggtggtc atggagatca ccgtgtggat catgatgttt  5640
aggtatctcc acttttggat caccctgctg ttcctgctga gcccattat tctctccgtc  5700
gcctgtctca tcatccaatc ctccgccctg ctgatcgagg ctgggtcgt caccaccatc  5760
acagtcctgg ccatttttct gtggctccct cctcaaggcg ctgaggccga tctcggcacc  5820
gccctgctga ttctgaatac cgcctgtgcc ctggtcgtgc tgatcctgac cgctatccct  5880
acatgatgat gagcggccgc gatctgctgt gccttctagt tgccagccat ctgttgtttg  5940
cccctcccc gtgccttcct tgaccctgga aggtgccact cccactgtcc tttcctaata  6000
aaatgaggaa attgcatcgc attgtctgag taggtgtcat tctattctgg ggggtggggt  6060
ggggcaggac agcaagggg aggattggga agacaatagc aggcatgctg gggatgcggt  6120
gggctctatg gccgatcagc gatcgctgag gtgggtgagt gggcgtggcc tggggtggtc  6180
atgaaaatat ataagttggg ggtcttaggg tctctttatt tgtgttgcag agaccgccgg  6240
agccatgagc gggagcagca gcagcagcag tagcagcagc gccttggatg gcagcatcgt  6300
gagcccttat ttgacgacgc ggatgcccca ctggggcagg gtgcgtcaga atgtgatggg  6360
ctccagcatc gacggccgac ccgtcctgcc cgcaaattcc gccacgctga cctatgcgac  6420
cgtcgcgggg acgccgttgg acgccaccgc cgccgccgcc gccaccgcag ccgcctcggc  6480
cgtgcgcagc ctgccacgg actttgcatt cctgggacca ctggcgacag ggctacttc  6540
tcgggccgct gctgccgccg ttcgcgatga caagctgacc gccctgctgg cgcagttgga  6600
tgcgcttact cggaactgg tgaccttcc tcagcaggt atgccctgcc gccagcaggt  6660
ctcctccctg caagctggcg ggaatgcttc tcccacaaat gccgtttaag ataaatttaaa  6720
ccagactctg tttggattaa agaaaagtag caagtgcatt gctctcttta ttcataatt  6780
ttccgcgcgc gataggccct agaccagcgt tctcggtcgt tgagggtgcg gtgtatcttc  6840
tccaggacgt ggtagaggtg gctctggacg ttgatataca tgggcatgag cccgtcccgg  6900
gggtggaggt agcaccactg cagagcttca tgctccgggg tggtgttgta gatgatccag  6960
```

```
tcgtagcagg agcgctgggc atggtgccta aaaatgtcct tcagcagcag gccgatggcc    7020
aggggggaggc ccttggtgta agtgtttaca aaacgttaa gttgggaagg gtgcattcgg    7080
ggagagatga tgtgcatctt ggactgtatt tttagattgg cgatgtttcc gcccagatcc    7140
cttctgggat tcatgttgtg caggaccacc agtacagtgt atccggtgca cttggggaat    7200
ttgtcatgca gcttagaggg aaaagcgtgg aagaacttgg agacgccttt gtggcctccc    7260
agattttcca tgcattcgtc catgatgatg gcaatgggcc cgcgggaggc agcttgggca    7320
aagatatttc tggggtcgct gacgtcgtag ttgtgttcca gggtgaggtc gtcataggcc    7380
attttttacaa agcgcgggcg gagggtgccc gactggggga tgatggtccc ctctggccct    7440
ggggcgtagt tgccctcgca gatctgcatt tcccaggcct taatctcgga gggggggaatc    7500
atatccacct gcggggcgat gaagaaaacg gtttccggga ccggggagat taactgggat    7560
gagagcaggt ttcaagcag ctgtgatttt ccacaaccgg tgggcccata aataacacct    7620
ataaccggtt gcagctggta gtttagagag ctgcagctgc cgtcgtcccg gaggaggggg    7680
gccacctcgt tgagcatgtc cctgacgcgc atgttctccc cgaccagatc cgccagaagg    7740
cgctcgccgc ccagggacag cagctcttgc aaggaagcaa agttttttcag cggcttgagg    7800
ccgtccgccg tgggcatgtt tttcagggtc tggctcagca gctccaggcg gtcccagagc    7860
tcggtgacgt gctctacggc atctctatcc agcatatctc ctcgtttcgc gggttggggc    7920
gactttcgct gtagggcacc aagcggtggt cgtccagcgg ggccagagtc atgtccttcc    7980
atggggcgcag ggtcctcgtc aggggtgtct gggtcacggt gaagggtgc gctccgggct    8040
gagcgcttgc caaggtgcgc ttgaggctgg ttctgctggt gctgaagcgc tgccggtctt    8100
cgccctgcgc gtcggccagg tagcatttga ccatggtgtc atagtccagc ccctccgcgg    8160
cgtgtcccctt ggcgcgcagc ttgcccttgg aggtggcgcc gcacgagggg cagagcaggc    8220
tcttgagcgc gtagagcttg ggggcgagga agaccgatgg ggctccgcgc    8280
cgcagacccc gcacacggtc tcgcactcca ccagccaggt gagctcgggg cgcgccgggt    8340
caaaaaccag gttcccccca tgcttttttga tgcgtttctt acctcgggtc tccatgaggt    8400
ggtgtccccg ctcggtgacg aagaggctgt ccgtgtctcc gtagaccgac ttgagggtgc    8460
ttttctccag ggggtccct cggtcttcct cgtagagcga ctccgaccac tctgagacga    8520
aggcccgcgt ccaggccagg acgaaggagg ctatgtggga ggggtagcgg tcgttgtcca    8580
ctaggggtc caccttctcc aagtgtgaa gacacatgtc gccttcctcg gcgtccagga    8640
aggtgattgg cttgtaggtg taggccacgt gaccgggggt tcctgacggg ggggtataaa    8700
aggggggtggg ggcgcgctcg tcgtcactct cttccgcatc gctgtctgcg agggccagct    8760
gctggggtga gtattccctc tcgaaggcgg gcatgacctc cgcgctgagg ttgtcagttt    8820
ccaaaaacga ggaggatttg atgttcacct gtcccgaggt gataccttg agggtacccg    8880
cgtccatctg gtcagaaaac acgatctttt tattgtccag cttggtggcg aacgacccgt    8940
agagggcgtt ggagagcagc ttggcgatgg agcgcagggt ctggttcttg tccctgtcgg    9000
cgcgctcctt ggccggcgatg ttgagctgca cgtactccgc cgcgacgcag cgccactcgg    9060
ggaagacggt ggtgcgctcg tcgggcacca ggcgcacgtg ccagccgcgg ttgtgcaggg    9120
tgaccaggtc cacgctggtg gcgacctcgc cgcgcaggcg ctcgttggtc cagcagagac    9180
ggccgccctt cgcgcagcag aagggggggca ggggtcgag ctgggtctcg tccggggggt    9240
ccgcgtccac ggtgaaaacc ccggggcgca ggccgcgtc gaagtagtct atcttgcaac    9300
cttgcatgtc cagcgcctgc tgccagtcgc gggcggcgag cgcgcgctcg taggggttga    9360
gcggcgggcc ccagggcatg gggtgggtga gtgcggaggc gtacatgccg cagatgtcat    9420
agacgtagag gggctcccgc aggaccccga tgtaggtggg gtagcagcgg ccgccgcgga    9480
tgctgcgcgg cacgtagtca tacagctcgt gcgagggggc gaggaggtcg ggcccaggt    9540
tggtgcgggc ggggcgctcc gcgcggaaga cgatctgcct gaagatggca tgcgagttgg    9600
aagagatggt ggggcgctgg aagacgttga agctggcgtc ctgcaggccg acggcgtcgc    9660
gcacgaagga ggcgtaggag tcgcgcagct tgtgtaccag ctcggcggtg acctgcacgt    9720
ccagcgcgca gtagtcgagg gtctcgcgga tgatgtcata tttagcctgc ccctttcttt    9780
tccacagctc gcgttgagg acaaactctt cgcggtcttt ccagtactct tggatcggga    9840
aaccgtccgg ttccgaacgg taagagccta gcatgtagaa ctggttgacg gcctggtagg    9900
cgcagcagcc cttctccacg gggagggcgt aggcctgcgc ggccttgcgg agcgaggtgt    9960
gggtcgggc gaaggtgtcc ctgaccatga cttttgaggta ctggtgcttg aagtcggagt   10020
cgtcgcagcc gccccgctcc cagagcgaga agtcggtgcg cttcttggag cggggggttgg   10080
gcagagcgaa ggtgacatcg ttgaagagga ttttgccccgc gcggggcatg aagttgcggg   10140
tgatgcggaa gggccccggc acttcagagc ggttgttgat gacctgggcg gcgagcacga   10200
tctcgtcgaa gccgttgatg ttgtggccca cgatgtagag ttccaggaag cggggccggc   10260
cctttacggt gggcagcttc tttagctctt cgtaggtagg ctcctcgggc gaggcgaggc   10320
cgtgctcggc cagggcccag tccgcgaggt gcgggttgtc tctgaggaag gacttccaga   10380
ggtcgcgggc caggagggtc tgcaggcggt ctctgaaggt cctgaactgg cggcccacgg   10440
ccatttttttc gggggtgatg cagtagaagg tgaggggggtc ttgctgccag cggtcccagt   10500
cgagctgcag ggcgaggtcg cgcgcggcgg tgaccaggcg ctcgtcgccc ccgaatttca   10560
tgaccagcat gaagggcacg agctgctttc cgaaggcccc catccaagtg taggtctcta   10620
catctaggt gacaaagagg cgctccgtgc gaggatgcga gccgatcggg aagaactgga   10680
tctcccgcca ccagttggag gagtggctgt tgatgtggtg gaagtagaag tcccgtcgcc   10740
gggccgaaca ctcgtgctgg ctttttgtaaa agcgacgcga gtactggcag cgctgcacgg   10800
gctgtacctc atgcacgaga tgcacctttc gcccgcgcac gaggaagccg aggggaaatc   10860
tgagcccccc gcctggctcg cggcatggct ggttctcttc tactttggat gcgtgtccgt   10920
ctccgtctgg ctcctcgagg ggtgttacgg tggagcggac caccacgccg cgcgagccgc   10980
aggtccagat atcggcgcgc ggcggtcgga gtttgatgac gacatcgcgc agctgggagc   11040
tgtccatggt ctggagctcc cgcgggcgcg gcaggtcagc cgggagttct tgcaggttca   11100
cctcgcagag tcgggccagg gcgcggggca ggtctaggtg gtacctgatc tctaggggcg   11160
tgttggtggc ggcgtcgatg gcttgcagga gcccgcagcc ccgggggggcg acgacggtgc   11220
cccgcgggggt ggtggtggtg gtggcggtgc agctcagaaa cggtgccgcg gcgggccccc   11280
cggaggtagg gggggctccg gtcccgcggg caggggcgga agcggcacgt cggcgtggag   11340
cgcaggcagg agttggtgct gtgccgacga gttgctggga aaggcgacga cgcggcggtt   11400
gatctcctgg atctggcgcc tctgcgtgaa gacgacgggc ccggtgagct tgaacctgaa   11460
agagagttcg acagaatcaa tctccgtgtc attgaccgcg gcctggcgca ggatctcctg   11520
cacgtctccc gagttgtctt ggtaggcgat ctcggccatg aactgctcga tctcttcctc   11580
ctggaggtct ccgcgtccgg cgcgttccac ggtggccgcg aggtcgttgg agatgcgccc   11640
catgagctgc gagaaggcgt tgagtccgcc ctcgttccag actcggctgt agaccacgcc   11700
```

```
ccctggtca tcgcgggcgc gcatgaccac ctgcgcgagg ttgagctcca cgtgccgcgc  11760
gaagacggcg tagttgcgca gacgctggaa gaggtagttg agggtggtgg cggtgtgctc  11820
ggccacgaag aagttcatga cccagcggcg caacgtggat tcgttgatgt cccccaaggc  11880
ctccagccgt tccatggcct cgtagaagtc cacggcgaag ttgaaaaact gggagttgcg  11940
cgccgacacg gtcaactcct cctccagaag acggatgagc tcggcgacgg tgtcgcgcac  12000
ctcgcgctcg aaggctatgg ggatctcttc ctccgctagc atcaccacct cctcctcttc  12060
ctcctcttct ggcacttcca tgatggcttc ctcctcttcg gggggtggcg gcggcggcgg  12120
tgggggaggg ggcgctctgc gccggcggcg gcgcaccggg aggcggtcca cgaagcgcgc  12180
gatcatctcc ccgcggcggc ggcgcatggt ctcggtgacg gcgcggccgt tctcccgggg  12240
gcgcagttgg aagacgccgc cggacatctg gtgctgggcg gggtggccgt gaggcagcga  12300
gacggcgctg acgatgcatc tcaacaattg ctgcgtaggt acgccgccga gggacctgag  12360
ggagtccata tccaccggat ccgaaaaacct ttcgaggaag gcgtctaacc agtcgcagtc  12420
gcaaggtagg ctgagcaccg tggcgggcgg cggggggtgg ggggagtgtc tggcggaggt  12480
gctgctgatg atgtaattga agtaggcgga cttgacacgg cggatggtcg acaggagcac  12540
catgtccttg ggtccggcct gctggatgcg gaggcggtcg gctatgcccc aggcttcgtt  12600
ctggcatcgg cgcaggtcct tgtagtagtc ttgcatgagc ctttccaccg gcacctcttc  12660
tccttcctct tctgcttctt ccatgtctgc ttcggccctg gggcggcgcc gcgcccccct  12720
gcccccatg cgcgtgaccc cgaacccct gagcggttgg agcagggcca ggtcggcgac  12780
gacgcgctcg gccaggatgg cctgctgcac ctgcgtgagg gtggtttgga agtcatccaa  12840
gtccacgaag cggtggtagg cgcccgtgtt gatggtgtag gtgcagttgg ccatgacgga  12900
ccagttgacg gtctggtggc ccggttgcga catctcggtg tacctgagtc gcgagtaggc  12960
gcgggagtcg aagactagt cgttgcaagt ccgcaccaag tactggtagc ccaccaggaa  13020
gtgcggcggc ggctggcggt agaggggcca gcgcagggtg gcgggggctc cggggggcca  13080
gtcttccagc atgaggcgt ggtaggcgta gatgtacctg gacatccagg tgatacccgc  13140
ggcggtggtg gaggcgcgcg ggaagtcgcg caccggtc cagatgttgc gcaggggcag  13200
aaagtgctc atggtaggcg tgctctgtcc agtcagacgc gcgcagtcgt tgatactcta  13260
gaccagggaa aacgaaagcc ggtcagcggg cactcttccg tggtctggtg aatagatcgc  13320
aaggggtatca tggcggaggg cctcggttcg agccccgggt ccgggccgga cggtccgcca  13380
tgatccacgc ggttaccgcc cgcgtgtcga acccaggtgt gcgacgtcag acaacgtgg  13440
agtgttccttt ttggcgtttt tctggccggg cgccggcgcc gctaagaga ctaagccgcg  13500
aaagcgaaag cagtaagtgg ctcgctcccc gtagccggag ggatccttgc taagggttgc  13560
gttgcggcga accccggttc gaatcccgta tcgggccgg ccggaccgc ggctaaggtg  13620
ttggattggc ctccccctcg tataaagacc ccgcttgcgg attgactccg gacacgggga  13680
cgagccctt ttatttttgc tttcccccaga tgcatccggt gctgcggcag atgcgccccc  13740
cgccccagca gcagcaacaa caccagcaag agcggcagca acagcagcgg gagtcatgca  13800
gggccccctc acccacctc ggcgggccgg ccacctcggc gtccgcgcc gtgtctggcg  13860
cctgcgcgg cggcgggggg ccggctgacg accccgagga gccccgcgg cgcagggcca  13920
gacactacct ggacctggag gagggcgagg gcctggcgcg gctgggggcg ccgtctcccg  13980
agcgccaccc gcgggtgcag ctgaagcgcg actcgcggcg ggctacgtg cctcggcaga  14040
acctgttcag ggaccgcgcg ggcgaggagc ccgaggagat gcgggacagg aggttcagcg  14100
cagggcggga gctgcggcag gggctgaacc gcgagcggct gctgcgcgag gaggactttg  14160
agcccgacgc gcggacgggg atcagccccg cgcgcgcgca cgtggcggcc gccgacctgg  14220
tgacgcgta cgagcagacg gtgaaccagg agatcaactt ccaaaagagt ttcaacaacc  14280
acgtgcgcac gctggtggcg cgcgaggagg tgaccatcgg gctgatgcac ctgtgggact  14340
ttgtaagcgc gctggtgcag aaccccaaca gcaagcctct gacggcgcag ctgttcctga  14400
tagtgcagca cagcagggac aacgaggcgt ttagggacgc gctgctgaac atcaccgagc  14460
ccgaggtgtcg gtgctgctg gacctgatta acatcctgca ggacatagtg gtgcaggagc  14520
gcagcctgag cctggccgac aaggtggcgg ccatcaacta ctcgatgctg agcctgggca  14580
agttttacgc gcgcaagatc taccagacgc cgtacgtgcc catagacaag gaggtgaaga  14640
tcgacggttt ttacatgcgc atggcgctga aggtgctcac cctgagcgac gacctgggcg  14700
tgtaccgcaa cgagcgcatc cacaaggccg tgagcgtgaa ccggccgcgc gagctgagcg  14760
accgcgagct gatgcacagc ctgcagcggg cgctggcggg cgccggcagc ggcgacaggg  14820
aggcggagtc ctacttcgat gcggggggcgg acctgcgctg ggcgcccagc cggcgggccc  14880
tggaggccgc ggggtccgc gaggactatg acgaggacgg cgaggaggat gaggagtacg  14940
agctagagga gggcgagtac ctggactaaa ccgcgggtgg tgtttccggt agatgcaaga  15000
cccgaacgtg gtggacccgg cgctgcgggc ggctctgcag agccagccgt ccggccttaa  15060
ctcctcagac gactggcgac aggtcatgga ccgcatcatg tcgctgacgg cgcgtaaccc  15120
ggacgcgttc cggcagcagc cgcaggccaa caggctctcc gccatcctgg aggcggtggt  15180
gcctgcgcgc tcgaacccca cgcacgagaa ggtgctggcc atagtgaacg cgctggccga  15240
gaacagggcc atccgccgg acgaggccgg gctggtgtac gacgcgctgc tgcagcgcgt  15300
ggcccgctac aacagcggca acgtgcagac caacctggac cggctggtgg ggacgtgcg  15360
cgaggcggtg gcgcagcgcg agcgcgcgga tcggcagggc aacctgggct ccatggtggc  15420
gctgaatgcc ttcctgagca cgcagccggc caacgtgccg cgggggcagg aagactacac  15480
caacttttgtg agcgcgctgc ggctgatggt gaccgagacc cccagacgg aggtgtacca  15540
gtcgggcccg gactacttct tccagaccag cagacagggc ctgcagacgg tgaacctgag  15600
ccaggctttc aagaacctgc ggggggctgtg gggcgtgaag gcgcccaccg cgacccgggc  15660
gacggtgtcc agcctgctga cgcccaactc gcgcctgctg ctgctgctga tcgcgccgtt  15720
cacggacagc ggcagcgtgt cccgggacac ctacctgggg cacctgctga ccctgtaccg  15780
cgaggccatc gggcaggcgc aggtggacga gcacaccttc caggagatca ccagcgtgag  15840
ccgcgcgctg gggcaggagg acacgagcag cctggaggcg actctgaact acctgctgac  15900
caaccggcgg cagaagattc cctcgctgca cagcctgacc tccgaggagg agcgcatctt  15960
gcgctacgtg cagcagagcg tgagcctgaa cctgatgcgc gacgggggtga cgcccagcgt  16020
ggcgctggac atgaccgcgc gcaacatgga accgggcatg tacgccgcgc accggcctta  16080
catcaaccgc ctgatggact gcttcatcg cgccgccgcg agtacttttac  16140
caacgccatc ctgaacccgc actggctccc gccgccgggg ttctacagcg ggggcttcga  16200
ggtcccggag accaacaatg gcttcctgtg ggacgacatg gacgacagcg tgttctcccc  16260
gcggccgcag cgctggcgg aagcgtccct gctgcgtccc aagaaggagg aggaggagga  16320
ggcgagtcgc cgccgcggca gcagcggcgt ggcttctctg tccgagctgg gggcggcagc  16380
cgccgcgcgc cccgggtccc tgggcggcag cccctttccg agcctggtgg ggtctctgca  16440
```

```
cagcgagcgc accacccgcc ctcggctgct gggcgaggac gagtacctga ataactccct   16500
gctgcagccg gtgcgggaga aaaacctgcc tcccgcctto cccaacaacg ggatagagag   16560
cctggtggac aagatgagca gatggaagac ctatgcgcag gagcacaggg acgcgcctgc   16620
gctccggccg cccacgcggc gccagcgcca cgaccggcag cggggctgg tgtgggatga    16680
cgaggactcc gcggacgata gcagcgtgct ggacctggca gggagcggca acccgttcgc   16740
gcacctgcgc ccccgcctgg ggaggatgtt taaaaaaaa aaaaaaaang caagaagcat    16800
gatgcaaaaa ttaaataaaa ctcaccaagg ccatggcgac cgagcgttgg tttcttgtgt   16860
tcccttcagt atgcgcgcg cggcgatgta ccaggaggga cctcctccct cttacgagag    16920
cgtggtgggc gcggcggcgg cggcgccctc ttctccctt gcgtcgcagc tgctggagcc    16980
gccgtacgtg cctccgcgct acctgcggcc tacggggggg agaaacagca tccgttactc   17040
ggagctggcg ccctgttcg acaccacccg ggtgtacctg gtggacaaca agtcggcgga    17100
cgtgcctcc ctgaactacc agaacgacca cagcaatttt ttgaccacgg tcatccagaa    17160
caatgactac agcccgagcg aggccagcac ccagaccatc aatctggatg accggtcgca   17220
ctgggggcgg gacctgaaaa ccatcctgca caccaacatg cccaacgtga acgagttcat   17280
gttcaccaat aagttcaagg cgcgggtgat ggtgtcgcgc tcgcacacca aggaagaccg   17340
ggtggagctg aagtacgagt gggtggagtt cgagctgcca gagggcaact actccgagac   17400
catgaccatt gacctgatga caacgcgat cgtgagcac tatctgaaag tgggcaggca     17460
gaacggggtc ctggagagcg acatcggggt caagttcgac accaggaact tccgcctggg   17520
gctggacccc gtgaccgggc tggttatgcc cggggtgtac accaacgagg ccttccatcc   17580
cgacatcatc ctgctgcccg gctgcgggg ggacttcact tacagccgcc tgagcaacct    17640
cctgggcatc cgcaagcggc agcccttcca ggagggcttc aggatcacct acgaggacct   17700
ggagggggac aacatcccg cgctcctcga tgtggaggcc taccaggata cgttgaagga    17760
aaatgaggcg ggacaggagg ataccgcccc cgccgcctcc gccgcgccg agcagggcga    17820
ggatgctgct gacaccgcgg ccgcggacgg ggcagaggcc gaccccgcta tggtggtgga   17880
ggctcccgag caggaggagg acatgaatga cagtgcggtg cgcggagaca ccttcgtcac   17940
ccggggggag gaaaagcaag cggaggccga gccgcggcc gaggaaaagc aactgggcac    18000
agcagcggcg gcggcggcgt tggccgcggc ggaggctgag tctgagggga ccaagcccgc   18060
caaggagccc gtgattaagc ccctgaccga agatagcaag aagcgcagtt acaacctgct   18120
caaggacagc accaacaccg cgtaccgcag ctggtacctg gcctacaact acggcgaccc   18180
gtcgacgggg gtgcgctcct ggaccctgct gtgcacgccg gacgtgacct gcggctcgga   18240
gcaggtgtac tggtcgctgc ccgacatgat gcaagacccc gtgaccttcc gctccacgcg   18300
gcaggtcagc aacttcccgg tggtgggcgc cgagctgctg cccgtgcact ccaagagctt   18360
ctacaacgac caggccgtct actcccagct catccgccag ttcacctctc tgacccacgt   18420
gttcaatcgc tttcctgaga accagattct ggcgcgcccg cccgccccca ccatcaccac   18480
cgtcagtgaa aacgttcctg ctctcacaga tcacggaacg ctaccgctgc gcaacagcat   18540
cggaggagtc cagcgagtga ccgttactga cgccagacgc cgcacctgcc cctacgttta   18600
caaggccttg ggcatagtct cgccgcgcgt cctttccagc cgcactttt gagcaacacc    18660
accatcatgt ccatcctgat ctcacccagc aataactccg gctggggact gctgcgcgcg   18720
cccagcaaga tgttcggagg ggcgaggaag cgttccgagc agcaccccgt gcgcgtgcgg   18780
gggcacttcc gcgccccctg gggagcgcac aaacgcggcc gcgcggggcg caccaccgtg   18840
gacgacgcca tcgactcggt ggtggagcag gcgcgcaact acaggccgc ggtctctacc     18900
gtggacgcgg ccatccagac cgtggtgcgg ggcgcgcggc ggtacgccaa gctgaagagc   18960
cgccggaagc gcgtggcccg ccgccaccgc cgccgaccg cgccgcgcgc caaacgcgcg     19020
gccgcggccc tgcttcgccc ggccaagcgc acgggccgcc gcgccgccat gaggccgcg     19080
cgccgcttgg ccgccggcat caccgccgcc accatggccc cccgtacccg aagacgcgcg   19140
gccgccgccg ccgccgccgc catcagtgac atggccagca ggcgccgggg caacgtgtac   19200
tgggtgcgcg actcggtgac cggcacgcgc gtgcccgtgc gcttccgccc cccgcggact   19260
tgagatgatg tgaaaaaaca acactgagtc tcctgctgtt gtgtgtatcc cagccggcggc  19320
ggcgcgcgca gcgtcatgtc caagcgcaaa atcaaagaag agatgctcca ggtcgtcgcg   19380
ccggagatct atgggccccc gaagaaggaa gagcaggatt cgaagccccg caagataaag   19440
cgggtcaaaa agaaaaagaa agatgatgac gatgccagcg gggaggtgga gttcctgcgc   19500
gccacgcgc ccaggcgccc ggtgcagtgg aagggccggc gcgtaaagcg cgtcctgcgc    19560
cccggcaccg cggtggtctt cacgcccggc gagcgctcca cccggacttt caagcgcgtc   19620
tatgacgagg tgtacggcga cgaagacctg ctggagcagg ccaacgagcg cttcggagag   19680
tttgcttacg ggaagcgtca gcgggcgctt gggaaggagg acctgctggc gctgccgctg   19740
gaccagggca acccccacccc cagtctgaag cccgtgaccc tgcagcaggt gctgccgagc   19800
agcgcaccct ccgaggcgaa gcggggtctg aagcgctgag gcggcgacct ggcgcccacc   19860
gtgcagctca tggtgcccaa gcggcagagg ctggaggatg tgctggagaa aatgaaagta   19920
gacccccggtc tgcagccgga catcagggtc cgcccccatca agcaggtggc gccgggcctg   19980
ggcgtgcaga ccgtggacgt ggtcatcccc accggcaact ccccccgccgc cgccaccact   20040
accgctgcct ccacggacat ggagacacag accgatcccg ccgcagccgc agccgcagcc   20100
gccgccgcga cctcctcggc ggaggtgcag acggacccct ggctgccgcc ggcgatgtca   20160
gctcccgcg cgcgtcgcgg gcgcaggaag tacgcgccgc caacgcgct cctgcccgag    20220
tacgccttgc atccttccat cgcgcccacc cccggctacc gaggtgtatac ctaccgcccg   20280
cgaagagcca agggttccac ccgccgtccc cgccgacgcg ccgccgccac caccgccgcc   20340
cgccgccgca gacgccagcc gcactggct ccagtctccg tgaggaaagt ggcgcgcgac     20400
ggacacaccc tggtgctgcc cagggcgcgc taccacccca gcatcgtttta aaagcctgtt   20460
gtggttcttg cagatatggc cctcacttgc cgcctccgtt tcccggtgcc gggatacccga   20520
ggaggaagat cgcgccgcag gagggtctg gccggccggg gcctgagccgg aggcagccgc    20580
cgcgcgcacc ggcggcgacg cgccaccagc cgacgcatgc gcgcggggt gctgcccctg     20640
ttaatccccc tgatcgccgc ggcgatcggc gccgtgcccg ggatcgcctc cgtgccttg     20700
caagcgtccc agaggcattg acagacttgc aaacttgcaa atatgcaaaa aaaacccca     20760
ataaaaaagt ctagactctc acgctcgctt ggtcctgtga ctattttgta gaatggaaga   20820
catcaactt gcgtcgctgg cccccgcgtca ccgtcctgg gacactggaa                 20880
cgatatcggc accagcaaca tgagcggtgg cgccttcagt tgggggctctc tgtgcgagcg  20940
cattaaaagt atcgggtctg ccgttaaaaa ttacggctcc cggcctgga acagcagcac     21000
gggccagatg ttgagagaca gttgaaagaa gcagaacttc cagcagaagg tggtggaggg   21060
cctgcctcc ggcatcaacg gggtggtgga cctgccaac caggccgtgc agaataagat     21120
caacagcaga ctgaccccccc ggccgccggt ggaggaggtg ccgccggcgc tggagacggt   21180
```

```
gtcccccgat gggcgtggcg agaagcgccc gcggcccgat agggaagaga ccactctggt   21240
cacgcagacc gatgagccgc ccccgtatga ggaggccctg aagcaaggtc tgcccaccac   21300
gcggcccatc gcgcccatgg ccaccggggt ggtgggccgc cacaccccg ccacgctgga    21360
cttgcctccg cccgccgatg tgccgcagca gcagaaggcg gcacagccgg gcccgcccgc   21420
gaccgcctcc cgttcctccg ccggtcctct gcgccgccgg gccagcggcc cccgcggggg   21480
ggtcgcgagg cacggcaact ggcagagcac gctgaacagc atcgtgggtc tgggggtgcg   21540
gtccgtgaag cgccgccgat gctactgaat agcttagcta acgtgttgta tgtgtgtatg   21600
cgccctatgt cgccgccaga ggagctgctg agtcgccgcc gttcgcgcgc ccaccaccac   21660
cgccactccg cccctcaaga tggcgacccc atcgatgatg ccgcagtggt cgtacatgca   21720
catctcgggc caggacgcct cggagtacct gagccccggg ctggtgcagt tcgcccgcgc   21780
caccgagagc tacttcagcc tgagtaacaa gtttaggaac cccacggtgg cgcccacgca   21840
cgatgtgacc accgaccggt ctcagcgcct gacgctgcgg ttcattcccg tggaccgcga   21900
ggacaccgcg tactcgtaca aggcgcggtt cacccctggc gtgggcgaca accgcgtgct   21960
ggacatggcc tccacctact ttgacatccg cggggtgctg gaccggggtc ccactttcaa   22020
gccctactct ggcaccgcct acaactccct ggccccccaag ggcgctccca actcctgcga   22080
gtgggagcaa gaggaaactc aggcagttga agaagcagca gaagaggaag aagaagatgc   22140
tgacggtcaa gctgaggaag agcaagcagc taccaaaaag actcatgtat atgctcaggc   22200
tccccttct ggcgaaaaaa ttagtaaaga tggtctgcaa ataggaacgg acgctacagc    22260
tacagaacaa aaacctattt atgcagaccc tacattccaa cccgaacccc aaatcgggga   22320
gtcccagtgg aatgaggcag atgctacagt cgccggcggt agagtgctaa agaaatctac   22380
tcccatgaaa ccatgctatg gttcctatgc aagacccaca aatgctaatg gaggtcaggg   22440
tgtactaacg gcaaatgccc agggacagct agaatctcag gttgaaatgc aattctttc    22500
aacttctgaa aacgcccgta acgaggctaa caacattcag cccaaattgg tgctgtatag   22560
tgaggatgtg cacatggaga cccccggatac gcacctttct tacaagcccg caaaaagcga   22620
tgacaattca aaaatcatgc tgggtcagca gtccatgccc aacagaccta attacatcgg   22680
cttcagagac aactttatcg gcctcatgta ttacaatagc actggcaaca tgggagtgct   22740
tgcaggtcag gcctctcagt tgaatgcagt ggtggacttg caagacagaa acacagaact   22800
gtcctaccag ctcttgcttg attccatggg tgacagaacc agatactttt ccatgtggaa   22860
tcaggcagtg gacagttatg acccagatgt tagaattatt gaaaatcatg gaactgaaga   22920
cgagctcccc aactattgtt tccctctggg tggcataggg gtaactgaca cttaccaggc   22980
tgttaaaacc aacaatggca ataacgtgggg ccaggtgact tggacaaaag atgaaacttt   23040
tgcagatcgc aatgaaatag gggtgggaaa caatttcgct atggagatca acctcagtgc   23100
caacctgtgg agaaacttcc tgtactccaa cgtggcgctg tacctaccag acaagcttaa   23160
gtacaacccc tccaatgtgg acatctctga caaccccaac acctacgatt acatgaacaa   23220
gcgagtggtg gccccggggc tggtggactg ctacatcaac ctgggcgcgc gctggtcgct   23280
ggactacatg gacaacgtca acccttcaa ccaccaccgc aatgcgggcc tgcgctaccg    23340
ctccatgctc ctgggcaacg ggcgctacgt gccttccac atccaggtgc cccagaagtt    23400
ctttgccatc aagaacctcc tcctcctgcc gggctcctac acctacgagt ggaacttcag   23460
gaaggatgtc aacatggtcc tccagagctc tctgggtaac gatctcaggg tggacggggc   23520
cagcatcaag ttcgagagca tctgcctcta cgccaccttc ttccccatgg cccacaacac   23580
ggcctccacg ctcgaggcca tgctcaggaa cgacaccaac gaccagtcct tcaatgacta   23640
cctctccgcc gccaacatgc tctacccat acccgccaac gccaccaacg tccccatctc    23700
catccctcg cgcaactggg cggccttccg cggctggcc ttcacccgcc tcaagaccaa     23760
ggagaccccc tccctgggct cgggattcga cccctactac acctactcgg gctccattcc   23820
ctacctggac ggcaccttct acctcaacca cactttcaag aaggtctcgg tcaccttcga   23880
ctcctcggtc agctggccgg gcaacgaccg tctgctcacc cccaacgagt cgagatcaa    23940
gcgctcggtc gacaggtgagg gctacaacgt ggcccagtgc aacatgacca aggactggtt   24000
cctggtccag atgctggcca actacaacat cggctaccag ggcttctaca tcccagagag   24060
ctacaaggac aggatgtact ccttcttcag gaacttccag cccatgagcc ggcaggtggt   24120
ggaccagacc aagtacaagg actaccagga ggtgggcatc atccaccagc acaacaactc   24180
gggcttcgtg ggctacctcg cccccaccat gcgcgaggga caggcctacc cgccaactt    24240
ccccctatcc gctcataggca agaccgcggt cgacagcatc acccagaaaa agttcctctg   24300
cgaccgcacc ctctgcgcca tccccttctc cagcaacttc atgtccatgg gtgcgctctc   24360
ggacctgggc cagaacttgc tctacgccaa ctccgcccac gccctcgaca tgaccttcga   24420
ggtcgacccc atggacgagc ccaccctttct ctatgttctg ttcgaagtct ttgacgtggt   24480
ccgggtccac cagccgcacc gcggcgtcat cgagaccgtg tacctgcgta cgcccttctc   24540
ggccggcaac gccaccacct aaagaagcaa gccgcagtca tcgccgcctg catgcgtcg    24600
ggttccaccg agcaagagct cagggccatc gtcagagacc tgggatgcgg gccctatttt   24660
ttgggcacct tcgacaagcg cttccctggc tttgtctccc cacacaagct ggctgcgcc    24720
atcgtcaaca cggccggccg cgagaccggg ggcgtgcact ggctggcctt cgcctggaac   24780
ccgcgctcca aaacatgctt cctctttgac cccttcggct tttcggacca gcggctcaag   24840
caaatctacg agttcgagta cgagggcttg ctgcgtcgca gcgccatcgc ctcctcgccc   24900
gaccgctgcg tcacctcga aaagtccacc cagaccgtgc aggggcccga ctcggccgcc    24960
tgcggtctct tctgctgcat gtttctgcac gcctttgtgc actggcctca gagtcccatg   25020
gaccgcaacc ccaccatgaa cttgctgacg ggggtgccca actccatgct ccagagcccc   25080
caggtcgagc ccaccctgcg ccgcaaccag gagcagctct acagcttcct ggagcgccac   25140
tcgccttact tccgccgcca cagcgcacag atcaggaggg ccacctcctt ctgccacttg   25200
caagagatgc aagaagggta ataacgatgt acacactttt tttctcaata aatggcatct   25260
ttttatttat acaagctctc tggggtattc atttccccac accaccgcc gttgtccaca    25320
tctggctcta tttagaaatc gaaagggttc tgccggagtc gccgtgcgc acgggcagg     25380
gacacgttgc gatactggta gcgggtgccc cacttgaact cggcaccac caggcgaggc    25440
agctcgggga agttttcgct ccacaggctg cgggtcagca ccagcgcgtt catcaggtcg   25500
ggcgccgaga tcttgaagtc gcagttgggg ccgccgccct gcgcgcgcga gttgcggtac   25560
accggggttgc agcactggaa caccaacagc gccgggtgcc tggccagcacgctg         25620
cggtcggaga tcagctcggc gtccaggtcc tccgcgttgc tcagcgcgaa cggggtcatc   25680
ttgggcactt gccgccccag gaagggcgcg tgccccggtt tcgagttgca gtcgcagcgc   25740
agcgggatca gcaggtgccc gtgcccggac tcggcgttgg ggtacagcgc gcgcatgaag   25800
gcctgcatct ggcggaaggc catctgggcc ttggcgcccc ccgagaagaa catgccgcag   25860
gacttgcccg agaactggtt tgcggggcag ctggcgtcgt gcaggcagca gcgcgcgtcg   25920
```

```
gtgttggcga tctgcaccac gttgcgcccc caccggttct tcacgatctt ggccttggac    25980
gattgctcct tcagcgcgcg ctgcccgttc tcgctggtca catccatctc gatcacatgt    26040
tccttgttca ccatgctgct gccgtgcaga cacttcagct cgccctccgt ctcggtgcag    26100
cggtgctgcc acagcgcgca gcccgtgggc tcgaaagact tgtaggtcac ctccgcgaag    26160
gactgcaggt acccctgcaa aaagcggccc atcatgatca cgaaggtctt gttgctgctg    26220
aaggtcagct gcagcccgcg gtgctcctcg ttcagccagg tcttgcacac ggccgccagc    26280
gcctccacct ggtcgggcag catcttgaag ttcaccttca gctcattctc cacgtggtac    26340
ttgtccatca gcgtgcgcgc cgcctccatg cccttctccc aggccgacac cagcggcagg    26400
ctcacggggt tcttcaccat caccgtggcc gccgcctccg ccgcgctttc gctttccgcc    26460
ccgctgttct cttcctcttc ctcctcttcc tcgccgccgc ccactcgcag ccccccgcacc   26520
acggggtcgt cttcctgcag gcgctgcacc ttgcgcttgc cgttgcgccc ctgcttgatg    26580
cgcacgggcg ggttgctgaa gcccaccatc accagcgcgg cctcttcttg ctcgtcctcg    26640
ctgtccagaa tgacctccgg ggagggggggg ttggtcatcc tcagtaccga ggcacgcttc    26700
tttttcttcc tggggggcgtt cgccagctcc gcggctgcgg ccgctgccga ggtcgaaggc    26760
cgagggctgg gcgtgcgcgg caccagcgcg tcctgcgagc cgtcctcgtc ctcctcggac    26820
tcgagacgga ggcgggcccg cttcttcggg ggcgcgcggg gcggcggagg cggcggcggc    26880
gacggagacg gggacgagac atcgtccagg gtgggtggac ggcgggccgc gccgcgtccg    26940
cgctcggggg tggtctcgcg ctggtcctct tcccgactgg ccatctccca ctgctccttc    27000
tcctataggc agaaagagat catggagtct ctcatgcgag tcgagaagga ggaggacagc    27060
ctaaccgccc cctctgagcc ctccaccacc gccgccacca ccgccaatgc cgccgcggac    27120
gacgcgccca ccgagaccac cgccagtacc accctcccca gcgacgcacc cccgctcgag    27180
aatgaagtgc tgatcgagca ggacccgggt ttttgtgagcg gaggaggagga tgaggtgagt    27240
gagaaggaga aggaggaggt cgccgcctca gtgccaaaag aggataaaaa gcaagaccag    27300
gacgacgcag ataaggatga cacagcagtc gggcggggga acggaagcca tgatgctgat    27360
gacggctacc tagacgtggg agacgacgtg ctgcttaagc acctgcaccg ccagtgcgtc    27420
atcgtctgcg acgcgctgca ggagcgctgc gaagtgcccc tggacgtggc ggaggtcagc    27480
cgcgcctacg agcggcacct cttcgcgccg cacgtgcccc ccaagcgccg ggagaacggc    27540
acctgcgagc ccaacccgcg tctcaacttc tacccggtct tcgcggtacc cgaggtgctg    27600
gccacctacc acatctttttt ccaaaactgc aagatccccc tctcctgccg cgccaaccgc    27660
acccgcgccg acaaaaccct gaccctgcgg cagggcgccg acatacctga tatcgcctct    27720
ctggaggaag tgcccaagat cttcgagggt ctcggtcgcg acgagaaacg ggcggcgaac    27780
gctctgcacg gagacagcga aaacgagagt cactcggggg tgctggtgga gctcgagggc    27840
gacaacgcgc gcctggccgt actcaagcgc agcatagagg tcacccactt tgcctacccg    27900
gcgctcaacc tgccccccaa ggtcatgagt gtggtcatgg gcgagctcat catgcgccgc    27960
gcccagcccc tggccgccgga tgcaaacttg caagagtcct ccgaggaagg cctgcccgcg    28020
gtcagcgacg agcagctggc gcgctggctg gagacccgcg accccgcgca ctgcgaggag    28080
cggcgcaagc tcatgatggc cgcggtgctg gtcaccgtgg agctcgagtg tctgcagcgc    28140
ttcttcgcgg accccgagat gcagcgcaag ctcgaggaga ccctgcacta caccttccgc    28200
cagggctacg tgccgcaggc ctgcaagatc tccaacgtgg agctctgcaa cctggtctcc    28260
tacctgggca tcctgcacga gaaccgcctc gggcagaacg tcctgcactc caccctcaaa    28320
ggggaggcgc gccgcgacta catccgcgac tgcgcctacc tcttcctctg ctacacctgg    28380
cagacgccca tgggggtctg gcagcagtgc ctggaggagc gcaacctcaa ggagctggaa    28440
aagctcctca agcgcaccct cagggacctc tggacgggct tcaacgaccg ctcggtggcc    28500
gccgcgctgg cggacatcat ctttcccgag cgcctgctca agaccctgca caggggcctg    28560
cccgacttca ccagccagag catgctgcag aacttcagga cttttcatcct ggagcgctcg    28620
ggcatcctgc cggccacttg ctgcgcgctg cccagcgact tcgtgcccat caagtacagg    28680
gagtgcccgc ccgcgctctg gggccactgc tacctcttcc agctggccaa ctacctcgcc    28740
taccactcgg acctcatgga agacgtgagc ggcgagggcc tgctcgagtg ccactgccgc    28800
tgcaacctct gcacgcccca ccgctctcta gtctgcaacc cgcagctgct cagcgagagt    28860
cagattatcg gtaccttcga gctgcagggt ccctcgcctg acgagaagtc cgcggctcca    28920
gggctgaaac tcactccggg gctgtggact tccgcctacc tacgcaaatt tgtacctgga    28980
gactaccacg cccacgagat caggttctac gaagaccaat cccgcccgcc caaggcggag    29040
ctcaccgcct gcgtcatcac ccaggggcac atcctgggcc aattgcaagc catcaacaaa    29100
gcccgccgag agttcttgct gaaaaagggt cgggggggtgt acctgacccc cagtccggc    29160
gaggagctaa acccgctacc cccgccgccg ccccagcagc gggaccttgc ttcccaggat    29220
ggcacccaga aagaagcagc agccgccgcc gccgccgcag ccatacatgc ttctggagga    29280
agaggaggag gactgggaca gtcaggcaga ggaggtttcg gacgaggagc aggaggagat    29340
gatggaagac tgggaggagg acagcagcct agacgaggaa gcttcagagg ccgaagaggt    29400
ggcagacgca acaccatcgc cctcggtcgc agccccctcg ccggggcccc tgaaatcctc    29460
cgaacccagc accagcgcta taacctccgc tcctccggcg ccggcgccac ccgcccgcag    29520
acccaaccgt agatgggaca ccacaggaac cgggtcggt aagtccaagt gcccgccgcc    29580
gccaccgcag cagcagcagc agcagcgcca gggctaccgc tcgtggcgcg ggcacaagaa    29640
cgccatagtc gcctgcttgc aagactgcgg gggcaacatc tctttcgccc gccgcttcct    29700
gctattccac cacggggtcg ccttttcccg caatgtgtca cattactacc gtcatctcta    29760
cagccctac tgcagcggcg acccagaggc ggcagcgca gccacagcgg cgaccaccac     29820
ctaggaagat atcctccgcg ggcaagacag cggcagcagc ggccaggaga cccgcggcag    29880
cagcggcggg agcggtgggc gcactgcgcc tctcgcccaa cgaaccctc tcgacccggg    29940
agctcagaca caggatcttc cccactttgt atgccatctt ccaacagagc agaggccagg    30000
agcaggagct gaaaataaaa aacagatctc tgcgctccct cacccgcagc tgtctgtatc    30060
acaaaagcga agatcagctt cggcgcacgc tggaggacgc ggaggcactc ttcagcaaat    30120
actgcgcgct cactcttaaa gactagctcc gcgcccttct cgaatttagg cgggagaaaa    30180
ctacgtcatc gccggccgcc gcccagcccg cccagccgga atgagcaaag agattcccac    30240
gccatacatg tggagctacc agccgcagat gggactcgcg gcgggagcgg cccaggacta    30300
ctcacccgg atgaactaca tgagcgcggg accccacatg atctcacagg tcaacgggat    30360
ccgcgcccag cgaaaccaaa tactgctgga acaggcggcc atcaccgcca cgccccgcca    30420
taatctcaac ccccgaaatt ggcccgccgc cctcgtgtac caggaaaccc cctccgccac    30480
caccgtacta cttccgcgtg acgcccaggc cgaagtccag atgactaact cagggggcgca    30540
gctcgcgggc ggctttcgtc acggggcgcg ccgctccga ccaggtataa gacacctgat    30600
gatcagaggc cgaggtatcc agctcaacga cgagtcggtg agctcttcgc tcggtctccg    30660
```

```
tccggacgga actttccagc tcgccggatc cggccgctct tcgttcacgc cccgccaggc   30720
gtacctgact ctgcagacct cgtcctcgga gccccgctcc ggcggcatcg gaaccctcca   30780
gttcgtggag gagttcgtgc cctcggtcta cttcaacccc ttctcgggac ctccccggacg  30840
ctaccccgac cagttcattc cgaactttga cgcggtgaag gactcggcgg acggctacga   30900
ctgaatgtca ggtgtcgagg cagagcagct tcgcctgaga cacctcgagc actgccgccg   30960
ccacaagtgc ttcgcccgcg gttctggtga gttctgctac tttcagctac ccgaggagca   31020
taccgagggg ccggcgcacg gcgtccgcct gaccacccag ggcgaggtta cctgttccct   31080
catccggag tttaccctcc gtccctgct agtggagcgg gagcgggtc cctgtgtcct   31140
aactatcgcc tgcaactgcc ctaaccctgg attacatcaa gatctttgct gtcatctctg   31200
tgctgagttt aataaacgct gagatcagaa tctactggga tttagtcccc tttaactaat   31260
caaacactgg aatcaataaa aagaatcact tacttaaaat cagacagcag gtctctgtcc   31320
agtttattca gcagcacctc cttccccctcc tcccaactct ggtactccaa acgcttctg   31380
gcggcaaact tcctccacac cctgaaggga atgtcagatt cttgctcctg tccctccgca   31440
cccactatct tcatgttgtt gcagatgaag cgcaccaaaa cgtctgacga gagcttcaac   31500
cccgtgtacc cctatgacac ggaaagcggc cctcccccg tccctttcct caccccctccc  31560
ttcgtgtctc ccgatggatt ccaagaaagt cccccccgggg tcctgtctct gaacctggcc   31620
gagccctgg tcacttccca cggcatgctc gccctgaaaa tgggaagtgg cctctcccctg   31680
gacgacgctg gcaacctcac ctctcaagat atcaccaccg ctagccctcc cctcaaaaaa   31740
accaagacca acctcagcct agaaacctca tccccccctaa ctgtgagcac ctcaggcgcc   31800
ctcaccgtag cagccgccgc tcccctggcg gtggccggca cctccctcac catgcaatca   31860
gaggccccccc tgacagtaca ggatgcaaaa ctcaccctgg ccaccaaagg cccccctgacc  31920
gtgtctgaag gcaaactggc cttgcaaaca tcggccccgc tgacagcagc   31980
accctcacag tcagtgccac accacccctt agcacaagca atggcagctt gggtattgac   32040
atgcaagccc ccatttacac caccaatgga aaactaggac ttaactttgg cgctcccctg   32100
catgtggtag acagcctaaa tgcactgact gtagttactg gccaaggtct tacgataaac   32160
ggaacagccc tacaaactag agtctcaggt gccctcaact atgcacatc aggaaaccta   32220
gaattgagag ctgcagggg tatgcgagtt gatgcaaatg gtcaacttat ccttgatgta   32280
gcttacccat ttgatgcaca aaacaatctc agccttaggc ttggacaggg acccctgtt    32340
gttaactctg cccacaactt ggatgttaac tacaacagag gcctctacct gttcacatct   32400
ggaaatacca aaaagctaga agttaatatc aaaacagcca agggtctcat ttatgatgac   32460
actgctatag caatcaatgc gggtgatggg ctacagtttg actcaggctc agatacaaat   32520
ccattaaaaaa ctaaacttgg attaggactg gattatgact ccagcagagc cataattgct   32580
aaaactggaa ctggcctaag ctttgacaac acaggtgcca tcacagtagg caacaaaaat   32640
gatgcaaagc ttaccttgtg gaccacacca gacccatccc ctaactgtag aatctattca   32700
gagaaagatg ctaaattcac acttgttttg actaaatgcg gcagtcaggt gttggccagc   32760
gttctgttt tatctgtaaa aggtagcctt gcgcccatca gtggcacagt aactagtgct   32820
cagattgtcc tcagatttga tgaaaatgga gttctactaa gcaattcttc ccttgaccct   32880
caatactgga actacagaaa aggtgacctt acagagggca ctgcatatac caacgcagtg   32940
ggatttatgc ccaacctcac agcatcccca aaaacacaga gccaaactgc taaaagcact   33000
attgtaagtc aggtttactt gaatggggac aaatccaaac ccatgaccct caccattacc   33060
ctcaatggaa ctaatgaaac aggagatgcc acagtaagca cttaccccat gtcattctca   33120
tggaactgga atggaagtaa ttacattaat gaaacgttcc aaaccaactc cttcaccttc   33180
tcctacatcg cccaagaata aaaagcatga cgctgttgat ttgattcaat gtgttttcgt   33240
ttttatttttca agcacaacaa aatcattcaa gtcattcttc catcttagct taatagacac   33300
agtagcttaa tagaccccagt agtgcaaagc cccattctag cttataacta gtggagaagt   33360
actcgcctac atggggggtag agtcataatc gtgcatcagg ataggcggt ggtgctgcag   33420
cagcgcgcgg ataaactgct gccgccgccga ctccgtcctg caggaataca acatggcagt   33480
ggtctcctca gcgatgattc gcaccgcccg cagcataagg cgccttgtcc tccgggcaca   33540
gcagcgcacc ctgatctcac ttaaatcagc acagtaactg cagcacagca ccacaatatt   33600
gttcaaaatc ccacagtgca aggcgctgta tccaaagctc atggcgggga ccacagaacc   33660
cacgtggcca tcataccaca agcgcaggta gattaagtgg cgaccccta taaacacgct   33720
ggacataaac attacctctt ttggcatgtt gtaattcacc acctcccggt accatataaa   33780
cctctgatta aacatggcgc catccaccac catcctaaac cagctggcca aaacctgccc   33840
gccggctata cactgcaggg aaccgggact ggaacaatga cagtggagag cccaggactc   33900
gtaaccatgg atcatcatgc tcgtcatgat atcaatgttg gcacaacaca ggcacacgtg   33960
catacacttc ctcaggatta caagctcctc ccgcgttaga accatatccc agggaacaac   34020
ccattcctga atcagcgtaa atcccacact gcagggaaga cctcgcacgt aactcacgtt   34080
gtgcattgtc aaagtgttac attcgggcag cagcggatga tcctccagta tggtagcgcg   34140
ggtttctgtc tcaaaaggag gtagacgatc cctactgtac ggagtgcgcc gagacaaccg   34200
agatcgtgtt ggtcgtagtg tcatgccaaa tggaacgccg gacgtagtca tatttcctga   34260
agtcttagat ctctcaacgc agcaccagca ccaaacacttc gcagtgtaaa aggcaagtg    34320
ccgagagagt atatatagga ataaaaagtg acgtaaacgg gcaaagtcca aaaaacgccc   34380
agaaaaaccg cacgcgaacc tacgccccga aacgaaagcc aaaaaacact agacactccc   34440
ttccggcgtc aacttccgct ttcccacgct acgtcacttg cccagtcaa acaaactaca    34500
tatcccgaac ttccagtcg ccacgcccaa aacaccgcct acacctcccc gcccgccggc    34560
ccgcccccaa acccgcctcc cgcccgcgc ccgcccgc gccgccatc tcattatcat      34620
attggcttca atccaaaata aggtatatta ttgatgatgc tttaaacgga tcctctagag   34680
tcgacctgca ggcatgcaag cttgagtatt ctatagtgtc acctaaatag cttggcgtaa   34740
tcatggtcat agctgtttcc tgtgtgaaat tgttatccgc tcacaattcc acacaacata   34800
cgagccggaa gcataaagtg taaagcctgg ggtgcctaat gagtgagcta actcacatta   34860
attgcgttgc gctcactgcc cgctttccag tcgggaaacc tgtcgtgcca gctgcattaa   34920
tgaatcggcc aacgcgaacc ccttgcgccg cccgggccg tcgaccaatt ctcatgtttg   34980
acagcttatc atcgaatttc tgccattcat ccgcttatta tcacttattc agtcggtac    35040
ccgggggatc tcgtttaaac aggctagca accaggcgtt taagggcacc aataactgcc   35100
ttaaaaaaat tacgccccgc cctgccactc atcgcagtac tgttgtaatt cattaagcat   35160
tctgccgaca tggaagccat cacaaacggc atgatgaacc tgaatcgcca gcggcatcag   35220
caccttgtcg ccttgcgtat aatatttgcc catggtgaaa acgggggcga agaagttgtc   35280
catattggcc acgtttaaat caaaactggt gaaactcacc cagggattgg ctgagacgaa   35340
aaacatattc tcaataaacc ctttagggaa ataggccagg ttttcaccgt aacacgccac   35400
```

```
atcttgcgaa tatatgtgta gaaactgccg gaaatcgtcg tggtattcac tccagagcga  35460
tgaaaacgtt tcagtttgct catggaaaac ggtgtaacaa gggtgaacac tatcccatat  35520
caccagctca ccgtctttca ttgccatacg gaattccgga tgagcattca tcaggcgggc  35580
aagaatgtga ataaaggccg gataaaactt gtgcttattt ttctttacgg tctttaaaaa  35640
ggccgtaata tccagctgaa cggtctggtt ataggtacat tgaccaactg actgaaatgc  35700
ctcaaaatgt tctttacgat gccattggga tatatcaacg gtggtatatc cagtgattt  35760
tttctccatt ttagcttcct tagctcctga aaatctcgat aactcaaaaa atacgcccgg  35820
tagtgatctt atttcattat ggtgaaagtt ggaacctctt acgtgccgat caacgtctca  35880
ttttcgccaa aagttggccc agggcttccc ggtatcaaca gggacaccag gatttattta  35940
ttctgcgaag tgatcttccg tcacaggtat ttattcgcga taagctcatg gagcggcgta  36000
accgtcgcac aggaaggaca gagaaagcgc ggatctggga agtgacggac agaacggtca  36060
ggacctggat tggggaggcg gttgccgccg ctgctgctga cggtgtgacg ttctctgttc  36120
cggtcacacc acatacgttc cgccattcct atgcgatgca catgctgtat gccggtatac  36180
cgctgaaagt tctgcaaagc ctgatgggac ataagtccat cagttcaacg gaagtctaca  36240
cgaaggtttt tgcgctggat gtggctgccc ggcaccgggt gcagtttgcg atgccggagt  36300
ctgatgcggt tgcgatgctg aaacaattat cctgagaata aatgccttgg cctttatatg  36360
gaaatgtgga actgagtgga tatgctgttt ttgtctgtta aacagagaag ctggctgtta  36420
tccactgaga agcgaacgaa acagtcggga aaatctccca ttatcgtaga gatccgcatt  36480
attaatctca ggagcctgtg tagcgtttat aggaagtagt gttctgtcat gatgcctgca  36540
agcggtaacg aaaacgattt gaatatgcct tcaggaacaa tagaaatctt cgtgcggtgt  36600
tacgttgaag tggagcggat tatgtcagca atggacagaa caacctaatg aacacagaac  36660
catgatgtgg tctgtccttt tacagccagt agtgctcgcc ggagtcgagc gacagggcga  36720
agccctcgag tgagcgagga agcaccaggg aacagcactt atatattctg cttacacacg  36780
atgcctgaaa aaacttccct tggggttatc cacttatcca cggggatatt tttataatta  36840
ttttttttat agttttaga tcttcttttt tagagcgcct tgtaggcctt tatccatgct  36900
ggttctgaga aaggtgttgt gacaaattgc cctttcagtg tacaaatca ccctcaaatg  36960
acagtcctgt ctgtgacaaa ttgccctaa ccctgtgaca aattgccctc agaagaagct  37020
gttttttcac aaagttatcc ctgcttattg actcttttt atttagtgtg acaatctaaa  37080
aacttgtcac acttcacatg gatctgtcat ggcggaaaca gcggttatca atcacaagaa  37140
acgtaaaaat agcccgcgaa tcgtccagtc aaacgacctc actgaggcgg catatagtct  37200
ctcccgggat caaaaacgta tgctgtatct gttcgttgac cagatcagaa aatctgatgg  37260
caccctacag gaacatgacg gtatctgcga gatccatgtt gctaaatatg ctgaaatatt  37320
cggattgacc tctgcggaag ccagtaagga tatacggcag gcattgaaga gtttcgcggg  37380
gaaggaagtg gttttttatc gccctgaaga ggatgccggc ggtgaaaaag gctatgaatc  37440
ttttccttgg tttatcaaac gtgcgcacag tccatccaga gggctttaca gtgtacatat  37500
caacccatat ctcattccct tctttatcgg gttacagaac cggttacgc agtttcggct  37560
tagtgaaaca aaagaaatca ccaatccgta tgccatgcgt ttatacgaat ccctgtgtca  37620
gtatcgtaag ccggatggct caggcatcgt ctctctgaaa atcgactgga tcatagagcg  37680
ttaccagctg cctcaaagtt accagcgtat gcctgacttc ggccgccgct tcctgcaggt  37740
ctgtgttaat gagatcaaca gcagaactcc aatgcgcctc tcatacattg agaaaaagaa  37800
aggccgccag acgactcata tcgtattttc cttccgcgat atcacttcca tgacgacagg  37860
atagtctgag ggttatctgt cacagatttg agggtggttc gtcacatttg ttctgaccta  37920
ctgagggtaa tttgtcacag ttttgctgtt tccttcgtgc tgcatggatt ttctcatact  37980
ttttgaactg taatttttaa ggaagccaaa tttgagggca gtttgtcaca gttgatttcc  38040
ttctcttttcc cttcgtcatg tgacctgata tcgggggtta gttcgtcatc attgatgagg  38100
gttgattatc acagtttatt actctgaatt ggctatccgc gtgtgtacct ctacctggag  38160
tttttcccac ggtggatatt tcttcttgcg ctgagcgtaa gagctatctg acagaacagt  38220
tcttctttgc ttcctcgcca gttcgctcgc tatgctcggt tacacggctg cggcgagcgc  38280
tagtgataat aagtgactga ggtatgtgct cttcttatct ccttttgtag tgttgctctt  38340
attttaaaca actttgcggt ttttttgatga cttttgcgatt ttgttgttgc tttgcagtaa  38400
attgcaagat ttaataaaaa aacgcaaagc aatgattaaa ggatgttcag aatgaaactc  38460
atggaaacac ttaaccagtg cataaacgct ggtcatgaaa tgacgaaggc tatcgccatt  38520
gcacagttta atgatgacag cccggaagcg aggaaaataa cccggcgctg gagaataggt  38580
gaagcagcgg atttagttgg ggtttcttct caggctatca gagatgccga aaagcaggg  38640
cgactaccgc acccggatat ggaaattcga ggacgggttg agcaacgtgt tggttataca  38700
attgaacaaa ttaatcatat gcgtgatgtg tttggtacgc gattgcgacg tgctgaagac  38760
gtatttccac cggtgatcgg ggttgctgcc cataaaggtg gcgttacaa aacctcagtt  38820
tctgttcatc ttgctcagga tctggctctg aaggggctac gtgttttgct cgtggaaggt  38880
aacgaccccc agggaacagc ctcaatgtat cacggatggg taccagatct tcatattcat  38940
gcagaagaca ctctcctgcc tttctatctt ggggaaaagg acgatgtcac ttatgcaata  39000
aagcccactt gctggccggg gcttgacatt attccttcct gtctggctct gcaccgtatt  39060
gaaactgagt taatgggcaa atttgatgaa ggtaaactgc ccaccgatcc acacctgatg  39120
ctccgactgg ccattgaaac tgttgctcat gactatgatg tcatagttat tgacagcgcg  39180
cctaacctgg gtatcggcac gattaatgtc gtatgtcgtc ctgatgtgcc gattgttccc  39240
acgcctgctg agttgtttga ctacacctcc gcactgcagt ttttcgatat gcttcgtgat  39300
ctgctcaaga acgttgatct aaagggttc gagcctgatg tacgtatttt gcttaccaaa  39360
tacagcaata gtaatggctc tcagtccccg tggatggagg agcaaattcg ggatgcctgg  39420
ggaagcatgg ttctaaaaaa tgttgtacgt gaaacggatg aagttggtaa aggtcagatc  39480
cggatgagaa ctgttttga acaggccatt gatcaacgct cttcaactgg tgcctggaga  39540
aatgctcttt ctatttggga acctgtctgc aatgaaattt tcgatcgtct gattaaacca  39600
cgctgggaga ttagataatg aagcgtgcgc ctgttattcc aaaacatacg ctcaatactc  39660
aaccggttga agatacttcg ttatcgacac cagctgcccc gatggtggat tcgttaattg  39720
cgcgcgtagg agtaatggct cgcggtaatg ccattacttt gcctgtatgt ggtcgggatg  39780
tgaagttac tcttgaagtg ctccggggtg atagtgttga gaagacctcc gggtatggt  39840
caggtaatga acgtgaccag gagctgctta ctgaggacgc actggatgat ctcatcccctt  39900
cttttctact gactggtcaa cagacaccgg cgttcggtcg aagagtatct ggtgtcatag  39960
aaattgccga tgggagtcgc cgtcgtaaag ctgctgcact taccgaaagt gattatcgtg  40020
ttctggtttgg cgagctggat gatgagcaga tggctgcatt atccagattg ggtaacgatt  40080
atcgcccaac aagtgcttat gaacgtggtc agcgttatgc aagccgattg cagaatgaat  40140
```

-continued

```
ttgctggaaa tatttctgcg ctggctgatg cggaaaatat ttcacgtaag attattaccc    40200
gctgtatcaa caccgccaaa ttgcctaaat cagttgttgc tcttttttct cacccggtg     40260
aactatctgc ccggtcaggt gatgcacttc aaaaagcctt tacagataaa gaggaattac    40320
ttaagcagca ggcatctaac cttcatgagc agaaaaaagc tggggtgata tttgaagctg    40380
aagaagttat cactcttttta acttctgtgc ttaaaacgtc atctgcatca agaactagtt   40440
taagctcacg acatcagttt gctcctggag cgacagtatt gtataagggc gataaaatgg    40500
tgcttaacct ggacaggtct cgtgttccaa ctgagtgtat agagaaaatt gaggccattc    40560
ttaaggaact tgaaaagcca gcaccctgat gcgaccacgt tttagtctac gtttatctgt    40620
ctttacttaa tgtcctttgt tacaggccag aaagcataac tggcctgaat attctctctg    40680
ggcccactgt tccacttgta tcgtcggtct gataatcaga ctgggaccac ggtcccactc    40740
gtatcgtcgg tctgattatt agtctgggac cacggtccca ctcgtatcgt cggtctgatt    40800
attagtctgg gaccacggtc ccactcgtat cgtcggtctg ataatcagac tgggaccacg    40860
gtcccactcg tatcgtcggt ctgattatta gtctgggacc atggtcccac tcgtatcgtc    40920
ggtctgatta ttagtctggg accacggtcc cactcgtatc gtcggtctga ttattagtct    40980
ggaaccacgg tcccactcgt atcgtcggtc tgattattag tctgggacca cggtcccact    41040
cgtatcgtcg gtctgattat tagtctggga ccacgatccc actcgtgttg tcggtctgat    41100
tatcggtctg ggaccacggt cccacttgta ttgtcgatca gactatcagc gtgagactac    41160
gattccatca atgcctgtca agggcaagta ttgacatgtc gtcgtaacct gtagaacgga    41220
gtaacctcgg tgtgcggttg tatgcctgct gtggattgct gctgtgtcct gcttatccac    41280
aacattttgc gcacggttat gtggacaaaa tacctggtta cccaggccgt gccggcacgt    41340
taaccgggct gcatccgatg caagtgtgtc gctgtcgacg agctcgcgag ctcggacatg    41400
aggttgcccc gtattcagtg tcgctgattt gtattgtctg aagttgtttt tacgttaagt    41460
tgatgcagat caattaatac gatacctgcg tcataattga ttatttgacg tggtttgatg    41520
gcctccacgc acgttgtgat atgtagatga taatcattat cactttacgg gtcctttccg    41580
gtgatccgac aggttacggg gcggcgacct cgcgggtttt cgctatttat gaaaattttc    41640
cggtttaagg cgtttccgtt cttcttcgtc ataacttaat gtttttattt aaaataccct    41700
ctgaaaagaa aggaaacgac aggtgctgaa agcgagcttt ttggcctctg tcgtttcctt    41760
tctctgtttt tgtccgtgga atgaacaatg gaagtccgag ctcatcgcta ataacttcgt    41820
atagcataca ttatacgaag ttatattcga tgcggccgca aggggttcgc gtcagcgggt    41880
gttggcgggt gtcggggctg gcttaactat gcggcatcag agcagattgt actgagagtg    41940
caccatatgc ggtgtgaaat accgcacaga tgcgtaagga gaaataccg catcaggcgc    42000
cattcgccat tcaggctgcg caactgttgg gaagggcgat cggtgcgggc ctcttcgcta    42060
ttacgccagc tggcgaaagg gggatgtgct gcaaggcgat taagttgggt aacgccaggg    42120
ttttcccagt cacgacgttg taaaacgacg gccagtgaat tgtaatacga ctcactatag    42180
ggcgaattcg agctcggtac ccggggatcc tcgtttaaac                         42220
```

UNITED STATES PATENT AND TRADEMARK OFFICE
CERTIFICATE OF CORRECTION

| | | |
|---|---|---|
| PATENT NO. | : 12,264,179 B2 | Page 1 of 1 |
| APPLICATION NO. | : 18/358350 | |
| DATED | : April 1, 2025 | |
| INVENTOR(S) | : Stefania Capone et al. | |

It is certified that error appears in the above-identified patent and that said Letters Patent is hereby corrected as shown below:

In the Claims

In Claim 5, at Column 153, Lines 18 and 19, please replace "(1) a third EBNA3A fragment consisting of SEQ ID NO: 16;" with -- (l) a third EBNA3A fragment consisting of SEQ ID NO: 16; --.

In Claim 5, at Column 153, Lines 24 and 25, please replace "(0) a sixth EBNA3A fragment consisting of SEQ ID NO: 19;" with -- (o) a sixth EBNA3A fragment consisting of SEQ ID NO: 19; --.

Signed and Sealed this
Twentieth Day of May, 2025

Coke Morgan Stewart
*Acting Director of the United States Patent and Trademark Office*